US008263085B2

(12) United States Patent
Silverman et al.

(10) Patent No.: US 8,263,085 B2
(45) Date of Patent: Sep. 11, 2012

(54) GAMMARETROVIRUS ASSOCIATED WITH CANCER

(75) Inventors: Robert H. Silverman, Beachwood, OH (US); Eric A. Klein, Shaker Heights, OH (US); Graham Casey, Pasadena, CA (US); Joseph DeRisi, San Francisco, CA (US); Don Ganem, San Francisco, CA (US)

(73) Assignees: The Cleveland Clinic Foundation, Cleveland, OH (US); The Regents of the University of California, Oakland, CA (US)

( * ) Notice: Subject to any disclaimer, the term of this patent is extended or adjusted under 35 U.S.C. 154(b) by 1004 days.

(21) Appl. No.: 11/903,756

(22) Filed: Sep. 24, 2007

(65) Prior Publication Data

US 2010/0166797 A1    Jul. 1, 2010

Related U.S. Application Data

(63) Continuation of application No. PCT/US2006/013167, filed on Apr. 7, 2006.

(60) Provisional application No. 60/751,809, filed on Dec. 19, 2005, provisional application No. 60/669,473, filed on Apr. 7, 2005.

(51) Int. Cl.
*A61K 39/21* (2006.01)
*C12N 5/071* (2010.01)
*C12N 7/00* (2006.01)
(52) U.S. Cl. .................... 424/207.1; 536/23.72
(58) Field of Classification Search .............. None
See application file for complete search history.

(56) References Cited

U.S. PATENT DOCUMENTS

| 2010/0184015 A1 | 7/2010 | Silverman et al. |
| 2011/0135674 A1 | 6/2011 | Qiu et al. |
| 2011/0151431 A1 | 6/2011 | Mikovits et al. |

FOREIGN PATENT DOCUMENTS

| EP | 0464533 A1 | 1/1992 |
| EP | 1882032 | 1/2008 |
| WO | WO 2004/037972 | 12/2002 |
| WO | WO 2006/110589 | 10/2006 |
| WO | WO 2010/075414 A2 | 7/2010 |
| WO | WO 2010/148323 A2 | 12/2010 |

OTHER PUBLICATIONS

Antoine, M., et al., "Envelope Protein", EBI Accession No. UNIPROT:Q9WLJ4 (1999), retrieved on line at www.ebi.ac.uk/cgi-bin/dgfetch on Feb. 5, 2010.
Antoine, M., et al., Envelope and Long Terminal Repeat Sequences of an Infectious Murine Leukemia Virus from a Human SCLC Cell Line: Implications for Gene Transfer, *Virus Genes*, 17:157-168 (1998).

Battini, J.-L., et al., "Receptor Choice Determinants in the Envelope Glycoproteins of Amphotropic, Xenotropic, and Polytropic Murine Leukemia Viruses", *J Virol.*, 66(3):1468-1475 (Mar. 1992).
Battini, J.-L., et al., "A Human Cell-Surface Receptor for Xenotropic and Polytropic Murine Leukemia Viruses: Possible Role in G Protein-Coupled Signal Transduction", *Proc. Natl. Acad. Sci. USA*, 96: 1385-1390 (Feb. 1999).
Behera, A.K., et al., "2'-5' Oligoadenylate Synthetase Plays a Critical Role in Interferon-γ Inhibition of Respiratory Syncytial Virus Infection of Human Epithelial Cells", *J. Biol. Chem.*, 277(28):25601-25608 (2002).
Berlioz, C., and Darlix, J.-L., "An Internal Ribosomal Entry Mechanism Promotes Translation of Murine Leukemia Virus *gag* Polyprotein Precursors", *J. Virol.*, 69(4): 2214-2222 (Apr. 1995).
Brightman B.K., et al., "Preleukemic Hematopoietic Hyperplasia Induced by Moloney Murine Leukemia Virus is an Indirect Consequence of Viral Infection", *J. Virol.*, 64(9):4582-4584 (Sep. 1990).
Carpten, J., et al., "Germline Mutations in the Ribonuclease L Gene in Families Showing Linkage with HPC1", *Nature Genetics*, 30:181-184 (Feb. 2002).
Carter B.S., et al., "Mendelian Inheritance of Familial Prostate Cancer", *Proc. Natl. Acad Sci.*, 89(8):3367-3371 (Apr. 1992).
Casey, G., et al., "RNASEL Arg462Gln Variant is Implicated in Up to 13% of Prostate Cancer Cases", *Nat. Genet.*, 32(4):581-583 (Dec. 2002; online Nov. 4, 2002).
Cho, B.C., et al., "Frequent Disruption of the N*f*1 Gene by a Novel Murine AIDS Virus-Related Provirus in BXH-2 Murine Myeloid Lymphomas", *J. Virol.*, 69(11):7138-7146 (Nov. 1995).
Clark, S.P. and Mak, T.W., "Complete Nucleotide Sequence of an Infectious Clone of Friend Spleen Focus-Forming Provirus: gp55 is an Envelope Fusion Glycoprotein", *Proc. Natl. Acad. Sci. USA*, 80:5037-5041 (Aug. 1983).
Clemens, M.J. and Williams B.R.G., "Inhibition of Cell-Free Protein Synthesis by pppA$2'$ p$^{5'}$ A$^{2'}$ p$^{5'}$ A: A Novel Oligonucleotide Sythesized by Interferon-Treated L Cell Extracts", *Cell*, 13(3):565-572 (Mar. 1978).
Das, D., et al., "Detection and Expression of Human BK Virus Sequences in Neoplastic Prostate Tissues", *Oncogene*, 23(42)7031-7046 (2004).
Dong, B. and Silverman, R..H., "2-5A-Dependent RNase Molecules Dimerize During Activation by 2-5A", *J. Biol. Chem.*, 270(8):4133-4137 (Feb. 24, 1995).

(Continued)

*Primary Examiner* — Bao Li
(74) *Attorney, Agent, or Firm* — Hamilton, Brook, Smith & Reynolds, P.C.

(57) ABSTRACT

The present invention provides for isolated nucleic acid sequences encoding viruses; isolated polypeptides comprising amino acid sequences of the virus; vectors comprising the viral nucleic acid sequences; cells comprising the vectors; antibodies and antigen binding fragments thereof which have binding specificity for the virus; methods of detecting or screening for the virus (e.g., in an individual); methods of identifying agents that inhibit the virus; methods of inducing an immune response to the virus; methods of treating disease associated with the presence of XMRV in an individual (e.g., cancer such as prostate cancer); methods of detecting asymptomatic cancer (e.g., prostate cancer); methods of identifying an individual at risk for developing cancer (e.g., prostate cancer); and kits for detecting the virus.

6 Claims, 65 Drawing Sheets
(25 of 65 Drawing Sheet(s) Filed in Color)

OTHER PUBLICATIONS

Dong, X., et al., "Mutations in CHEK2 Associated with Prostate Cancer risk,", *Am. J. Hum. Genet.*, 72:270-280 (2003).

Downing, S.R., et al., "Mutations in Ribonuclease L Gene Do Not Occur at a Greater Frequency in Patients with Familial Prostate Cancer Compared with Patients with Sporadic Prostate Cancer", *Clin. Prostate Cancer*, 2(3):177-180 (Dec. 2003).

Edwards, S.M., et al., "Two Percent of Men with Early-Onset Prostate Cancer Harbor Germline Mutations in the *BRCA2* Gene", *Am. J. Hum. Genet.*, 72: 1-12 (2003).

Eisen, M.B., et al., "Cluster Analysis and Display of Genome-Wide Expression Patterns," *PNAS*, 95: 14863-14868 (Dec. 1998).

Fass D., et al., "Structure of a Murine Leukemia Virus Receptor-Binding Glycoprotein at 2.0 Angstrom Resolution", *Science*, 277(5332):1662-1666 (Sep. 12, 1997).

Flodstrom-Tullberg, M., et al., "RNase L and Double-Stranded RNA-Dependent Protein Kinase Exert Completmentary Roles in Isleet Cell Defense During Coxsackievirus Infection", *J. Immunol.*, 174:1171-1177 (2005).

Friedman, R.M., and Ramseur, J,M., "Inhibition of Murine Leukemia Virus Production in Chronically Infected AKR Cells: A Novel Effect of Interferon", *Proc. Natl. Acad. Sci. USA*, 71(9):3542-3544 (Sep. 1974).

Hanger, J.J., et al., "The Necleotide Sequence of Koala (*Phascolarctos cinereus*) Retrovirus: A Novel Type C Endogenous Virus Related to Gibbon Ape Leukemia Virus", *J. Virol.*, 74(9):4264-4272 (May 2000).

Hassel, B.A., et al., "A dominant Negative Mutant of 2-5A-Dependent RNase Suppresses Antiproliferative and Antiviral Effects of Interferon", *EMBO J.*, 12(8):3297-3304 (1993).

Hayes, R.B., et al., "Sexual Behaviour, STDs and Risks for Prostate Cancer", *Br. J. Cancer*, 82(3):718-725 (2000).

Herr, W., "Nucleotide Sequence of AKV Murine Leukemia Virus", *J. Virol.*, 49(2): 471-478 (1984).

Iordanov, M.S., et al., "Activation of p38 Mitogen-Activated Protein Kinase and c-Jun $NH_2$-Terminal Kinase by Double-Stranded RNA and Encephalomyocarditis Virus: Involvement of RNase L, Protein Kinase R, and Alternative Pathways", *Mol. Cell Biol.*, 20(2):617-627 (Jan. 2000).

Itin, A. and Keshet, E., "Primer Binding Sites Corresponding to Several tRNA Species Are Present in DNAs of Different Members of the Same Retrovirus-Like Gene Family (VL30)", *J. Virol.*, 54(1):236-239 (Apr. 1985).

Kerr, I.M. and Brown, R.E., "pppA2' p5' A2' p5' A: An Inhibitor of Protein Synthesis Synthesized with an Enzyme Fraction from the Interferon-Treated Cells", *Proc. Natl. Acad. Sci. U S A*, 75(1):256-260 (Jan. 1978).

Khimani, A.H., et al., "Phylogenetic Relationship of the Complete Rauscher Murine Leukemia Virus Genome with Other Murine Leukemia Virus Genomes", *Virology*, 238: 64-67 (1997).

Kotar, K., et al., "The RNASEL 471 delAAAG Allele and Prostate Cancer in Ashkenazi Jewish Men", *J. Med. Genet.*, 40: e22 , pp. 1-3 (2003).

Lenz, J., et al., "Nucleotide Sequence of the Akv *env* Gene", *J. Virol.*, 42(2):519-529 (May 1982).

Li, G., et al., "An Apoptotic Signaling Pathway in the Interferon Antiviral Response Mediated by RNase L and c-Jun $NH_2$-terminal Kinase", *J. Biol. Chem.*, 279(2):1123-1131 (Jan. 9, 2004).

Lindmark, F., et al., "H6D Polymorphism in Macrophage-Inhibitory Cytokine-1 Gene Associated with Prostate Cancer", *J. Natl. Cancer Inst.*, 96(16):1248-1254 (Aug. 18, 2004).

Maitra, R.K. and Silverman, R.H., "Regulation of Human Immunodeficiency Virus Replication by 2',5'-Oligoadenylate-Dependent RNase L", *J. Virol.*, 72(2):1146-1152 (Feb. 1998).

Maitra, R.K., et al., "HIV-1 TAR RNA Has an Intrinsic Ability to Activate Interferon-Inducible Enzymes", *Virology*, 204(2):823-827 (1994).

Malathi, K., et al., "HPC1/RNASEL Mediates Apoptosis of Prostate Cancer Cells Treated with 2',5'-Oligoadenylates, Topoiisomerase I Inhibitors, and Tumor Necrosis Factor-RElated Apoptosis-Inducing Ligand", *Cancer Res.*, 64(24):9144-9151 (Dec. 15, 2004).

Marchesani, M., et al., "New Paraoxonase 1 Polymorphism 1102V and the Risk of Prostate Cancer in Finnish Men", *J. Natl. Cancer Inst.*, 95(11):812-818 (Jun. 4, 2003).

Martinand, C., et al., "RNase L Inhibitor Is Induced During Human Immunodeficiency Virus Type 1 Infection and Down Regulates the 2-5A/RNase L Pathway in Human T Cells", *J. Virol.*, 73(1):290-296 (Jan. 1999).

Multiple Authors, GenBank Accession No. AAC97875, retrieved on line at www.ncbi.nlm.nih.gov/protein/4049916 on Feb. 8, 2010.

Multiple Authors, GenBank Accession No. ACOL01001362, retrieved on line www.ncbi.nlm.nih.gov/nucore/239602885 on Feb. 8, 2010.

Multiple Authors, GenBank Accession No. ACOL01001500, retrieved on line at www.ncbi.nlm.nih.gov/nucore/239602738 on Feb. 8, 2010.

Multiple Authors, GenBank Accession No. ACOL01001501, retrieved on line at www.ncbi.nlm.nih.gov/nucore/239602737 on Feb. 8, 2010.

Multiple Authors, GenBank Accession No. ACOL01001702, retrieved on line at www.ncbi.nlm.nih.gov/nucore/239602524 on Feb. 8, 2010.

Multiple Authors, GenBank Accession No. ACOL01001819, retrieved on line at www.ncbi.nlm.nih.gov/nucore/239602399 on Feb. 8, 2010.

Multiple Authors, GenBank Accession No. ACOL01001885, retrieved on line at www.ncbi.nlm.nih.gov/nucore/239602328 on Feb. 8, 2010.

Multiple Authors, GenBank Accession No. AF151794, retrieved on line at www.ncbi.nlm.nih.gov/nucore/7145188 on Feb. 8, 2010.

Multiple Authors, GenBank Accession No. AF221065, retrieved on line at www.ncbi.nlm.nih.gov/nucore/11078528 on Feb. 8, 2010.

Multiple Authors, GenBank Accession No. DQ241301, retrieved on line at www.ncbi.nlm.nih.gov/nucore/82582295 on Feb. 8, 2010.

Multiple Authors, GenBank Accession No. DQ241302, retrieved on line at www.ncbi.nlm.nih.gov/nucore/82582299 on Feb. 8, 2010.

Multiple Authors, GenBank Accession No. U13776, retrieved on line at www.ncbi.nlm.nih.gov/nucore/535531 on Feb. 8, 2010.

Multiple Authors, GenBank Accession No. J01998, retrieved on line at www.ncbi.nlm.nih.gov/nucore/331993 on Feb. 8, 2010.

Multiple Authors, GenBank Accession No. K02730, retrieved on line at www.ncbi.nlm.nih.gov/nucore/332081 on Feb. 8, 2010.

Nelson, W.G., et al., "Mechanisms of Disease; Prostate Cancer", *N. Engl. J. Med.*, 349(4):366-381 (Jul. 24, 2003).

O'Neill, R.R., et al., "Envelope and Long Terminal Repeat Sequences of a Cloned Infectious NZB Xenotropic Murine Leukemia Virus", *J. Virol.*, 53(1):100-106 (Jan. 1985).

Ott, D. and Rein A., "Basis for Receptor Specificity of Nonecotropic Murine Leukemia Virus Surface Glycoprotein $gp70^{su}$", *J. Virol.*, 66(8):4632-4638 (Aug. 1992).

Perryman, S., et al., "Complete Nucleotide Sequence of Friend Murine Leukemia Virus, Strain FB29", *Nucleic Acids Res.*, 19(24): 6950 (Nov. 12, 1991).

Pitha, P.M., "Multiple Effects of Interferon on the Replication of Human Immunodeficiency Virus Type 1", *Antiviral Res.*, 24: 205-219 (1994).

Poli, G., et al., "Interferons in the Pathogenesis and Treatment of Human Immunodeficiency Virus Infection", *Antiviral Res.*, 24: 221-233 (1994).

Raisch, K.P., et al., "Constitutive Production of a Murine Retrovirus in the Human B-Lymphoblastoid Cell Line, DG-75", *Virology*, 250(1):135-139 (1998).

Raisch, K.P., et al., "Molecular Cloning, Complete Sequence, and Biological Characterization of a Xenotropic Murine Leukemia Virus Constitutively Released from the Human B-Lymphoblastoid Cell Line DG-75", *Virology*, 308(1):83-91 (2003).

Rennert, H., et al., "A Novel Founder Mutation in the RNASEL Gene, 471delAAAG, Is Associated with Prostate Cancer in Ashkenazi Jews" *Am. J. Hum. Genet.*, 71(4):981-984 (2002).

Rokman, A., et al., "Germline Alterations of the RNASEL Gene, a Candidate HPC1 Gene at 1q25, in Patients and Families with Prostate Cancer", *Am. J. Hum. Genet.*, 70(5):1299-1304 (2002).

Rusch, L., et al., "Caspase-Dependent Apoptosis by 2',5'-Oligadcnylate Activation of RNase L is Enhanced by IFN-β", *J. Interferon Cytokine Res.*, 20(12):1091-1100 (2000).

Ryman, K.D., et al., "Effects of PKR/RNase L-Dependent and Alternative Antiviral Pathways on Alphavirus Replication and Pathogenesis", *Viral Immunol.*, 15(1):53-76 (2002).

Schaffer, A.A., et al., "Improving the Accuracy of PSI-BLAST Protein Database Searches with Composition-Based Statistics and Other Refinements", *Nucleic Acids Res.*, 29(14):2994-3005 (2001).

Schroder, H.C., et al., "(2'-5')Oligoadenylate and Intracellular Immunity Against Retrovirus Infection", *Int. J. Biochem.*, 24(1):55-63 (1992).

Shinnick, T.M., et al., Nucleotide Sequence of Moloney Murine Leukaemia Virus, *Nature*, 293:543-548 (Oct. 15, 1981).

Sijts, E.J., et al., "Cloning of the MCF1233 Murine Leukemia Virus and Identification of Sequences Involved in Viral Tropism, Oncogenicity and T Cell Epitope Formation", *Virus Res.*, 34:339-349 (1994).

Silverman, R.H, "Implications for RNase L in Prostate Cancer Biology", *Biochemistry*, 42(7):1805-1812 (Feb. 25, 2003).

Smith, J.A., et al., "Involvement of the Interferon-Regulated Antiviral Proteins PKR and RNase L in Reovirus-Induced Shutoff of Cellular Translation", *J. Virol.*, 79(4):2240-2250 (Feb. 2005).

Tailor, C.S., et al., "Cloning and Characterization of a Cell Surface Receptor for Xenotropic and Polytropic Murine Leukemia Viruses", *Proc. Natl. Acad. Sci. USA*, 96:927-932 (Feb. 1999).

Tailor, C.S., et al., "Cell Surface Receptors for Gammaretroviruses" in *Cellular Factors Involved in Early Steps of Retroviral Replication*, Young, J.A.T. ed. (NY: Springer), *Curr Top Microbial Immunol.*, 281:29-106 (2003).

Urisman, A, et al., "E-Predict: A Computational Strategy for Species Identification Based on Observed DNA Microarray Hybridization Patterns", *Genome Biol.*, 6: R78 PLOS Pathogens (Aug. 30, 2005).

Urisman, A., et al., "Identification of a Novel Gammaretrovirus in Prostate Tumors of Patients Homozygous for R462Q RNASEL Variant" *PLoS Pathogens*, 2(3)e25:0211-0225 (Mar. 2006).

Wang, D, et al., "Viral Discovery and Sequence Recovery Using DNA Microarrays", *PLoS Biol.*, 1(2)e2:257-260 (2003).

Wang, D., et al., "Microarray-Based Detection and Genotyping of Viral Pathogens", *Proc. Natl. Acad. Sci. USA*, 99(24):15687-15692 (Nov. 26, 2002).

Wu, T., et al., "Rmcη2, a Xenotropic Provirus in the Asian Mouse Species Mus castaneus, Blocks Infection by Polytropic Mouse Gammaretroviruses.", *J. Virology*, 79(15): 9677-9684 (Aug. 2005).

Xiang, Y., et al., "Effects of RNase L Mutations Associated with Prostate Cancer on Apoptosis Induced by 2',5'-Oligoadenylates 1", *Cancer Res.*, 63(20):6795-6801 (Oct. 15, 2003).

Xu, J., et al., "Germline Mutations and Sequence Variants of the Macrophage Scavenger Receptor 1 Gene are Associated with Prostate Cancer Risk", *Nat. Genet.*, 32(2):321-325 (Oct. 2002).

Xu, J., et al., "Associations Between hOGGI Sequence Variants and Prostate Cancer Susceptibility[1]", *Cancer Res.*, 62:2253-2257 (Apr. 15, 2002).

Yang, Y.L., et al., "Receptors for Polytropic and Xenotropic Mouse Leukaemia Viruses Encoded by a Single Gene at Rmc1", *Nat. Genet.*, 21:216-219 (Feb. 1999).

Zambrano, A., et al., "Detection of Human Polyomaviruses and Papillomaviruses in Prostatic Tissue Reveals the Prostate as a Habitat for Multiple Viral Infections", *Prostate*, 53(4):263-276 (2002).

Zheng, S.L., et al., "Sequence Variants of Toll-Like Receptor 4 are Associated with Prostate Cancer Risk: Results from the Cancer Prostate in Sweden Study", *Cancer Res.*, 64:2918-2922 (Apr. 15, 2004).

Zhou, A., et al., "interferon Action and Apoptosis are Defective in Mice Devoid of 2',5'-Oligoadenylate-Dependent RNase L",. *Embo J.*, 16(21):6355-6363 (1997).

Zhou, A., et al., "Expression Cloning of 2-5A-Dependent RNAase: A Uniquely Regulated Mediator of Interferon Aciton", *Cell*, 72(5):753-765 (Mar. 12, 1993).

Zuker, M., et al., "Using Reliability Information to Annotate RNA Secondary Structures", *RNA*, 4(6):669-679 (1998).

Dong, B. et al., "An Infectious Retrovirus Susceptible to an IFN Antiviral Pathway from Human Prostate Tumors", *PNAS*, 104(5):1655-1660 (Jan. 30, 2007).

Multiple Authors, GenBank Accession No. DQ399707.1, retrieved on line at www.ncbi.nlm.nih.gov/nucore/DQ399707 on Mar. 11, 2010.

Silverman, R.H., "A Scientific Journey Through the 2-5A/RNase L System", *Cytokine & Growth Factor Reviews*, 18:381-388 (online Jul. 27, 2007).

Non-published application filed Dec. 22, 2009, entitled "Method for Detection of XMRV", U.S. Appl. No. 12/645,181.

Oct. 18, 2007, Notification Concerning Transmittal International Preliminary Report on Patentability, PCT/US2006/013167.

Nov. 8, 2006, Notification of Transmittal of the International Search Report and the Written Opinion of the International Search Authority, or Declaration, PCT/US2006/013167.

Mar. 18, 2009, Examination Report, 2006235266.

Aug. 28, 2009, Examination Report, 562221.

Non-published application filed Dec. 22, 2009, entitled "Method for Detection of XMRV", PCT/US2009/069244.

Nelson, W.G., et al., "Mechanisms of Disease. Prostate Cancer", *N. Engl. J. Med.*, 349(4):366-381 (Jul. 24, 2003).

Arnold, R.S., et al., "XMRV Infection in Prostate Cancer Patients: Novel Serologic Assay and Correlation with PCR and FISH", *Urology*, 75(4):755-761 (2010).

Barquinero, J., et al., "Retroviral Vectors: New Applications for an Old Tool", *Gene Ther.*, 11:S3-S9 (2004).

Battini, J-L., et al., "A Human Cell-Surface Receptor for Xenotropic and Polytropic Murine Leukemia Viruses: Possible Role in G Protein-Coupled Signal Transduction", *Proc. Natl. Acad. Sci. USA*, 96:1385-1390 (Feb. 1999).

Bhosle, S., et al., "Evaluation of Cellular Determinants Required for in vitro XMRV Entry of Human Prostate Cancer and Non-Cancerous Cells", *J. Viral.*, [Epub ahead of print, retrieved online at www.jvi.asm.org on May 25, 2010, pp. 1-28] (Apr. 21, 2010).

Bhowmick, N.A., et al., "Stromal Fibroblasts in Cancer Initiation and Progression", *Nature*, 432:332-337 (Nov. 18, 2004).

Carter, B.S., et al., "Hereditary prostate Cancer: Epidemiologic and Clinical Features", *J. Urol.*, 150:797-802 (Sep. 1993).

Castelli, J.C., et al,, "The Role of 2'-5' Oligoadenylate-Activated Ribonuclease L in Apoptosis", *Cell Death Differ.*, 5:313-320 (1998).

Cobbs, C.S., et al., "Human Cytomegalovirus Infection and Expression in Human Malignant Glioma", *Cancer Res.*, 62: 3347-3350 (Jun. 15, 2002).

Coffin, J.M. and Stoye, J.P., "A New Virus for Old Diseases?", *Science*, 326:530-531 (Oct. 23, 2009).

Courouce, A-M., et al., "Seroepidemiology of HTLV-I/II in Universal Screening of Blood Donations in France", *Aids* 7(6):841-847 (1993).

D'Arcy, F., et al., "No Evidence of XMRV in Irish Prostate Cancer Patients with R462Q Mutation", *Eur. Urol. Suppl.*, 7(3):271, Abstract 801 (2008).

De Marzo, A.M., et al., "Inflammation in Prostate Carcinogenesis", *Nat. Rev. Cancer*, 7:256-269 (Apr. 2007).

Demettre, E., et al., "Ribonuclease L Proteolysis in Peripheral Blood Mononuclear Cells of Chronic Fatigue Syndrome Patients", *J. Biol. Chem.*, 277(38):35746-35751 (Sep. 20, 2002).

Denner, J., "Detection of a Gammaretrovirus, XMRV in the Human Population: Open Questions and Implications for Xenotransplantation", *Retrovirology*, 7:16 (3 pgs) (2010).

Dennis, L.K. and Dawson, D.V., "Meta-Analysis of Measures of Sexual Activity and Prostate Cancer", *Epidemiology*, 13(1):72-79 (Jan. 2002).

Dennis, L.K., et al., "Epidemiologic Association Between Prostatitis and Prostate Cancer", *Urology*, 60(1):78-83 (2002).

Devanur, L.D., and Kerr, J.R. "Chronic Fatigue Syndrome", *J. Clin. Virol.*, 37:139-150 (2006).

Dong, B., et al., "An Infectious Retrovirus Susceptible to an IFN Antiviral Pathway from Human Prostate Tumors", *Proc. Natl. Acad. Sci. USA*, 104(5):1655-1660 (Jan. 30, 2007).

Dong, B. and Silverman, R.H., "Androgen Stimulates Transcription and Replication of Xenotropic Murine Leukemia Virus-Related Virus", *J. Virol.*, 84(3):1648-1651 (Feb. 2010, ahead of print Nov. 11, 2009).

Dong, B., et al., "A Natural Human Retrovirus Efficiently Complements Vectors Based on Murine Leukemia Virus", *PLoS ONE*, 3(9):e3144 (4 pgs) (Sep. 4, 2008).

Erlwein, O., et al., "Failure to Detect the Novel Retrovirus XMRV in Chronic Fatigue Syndrome", *PLoS ONE*, 5(1):e8519 (4 pgs) (Jan. 6, 2010).

Fan, H., "A New Human Retrovirus Associated with Prostate Cancer", *Proc. Natl. Acad. Sci. USA*, 104(5):1449-1450 (Jan. 30, 2007).

Feng, H., et al., "Clonal Integration of a Polyomavirus in Human Merkel Cell Carcinoma", *Science*, 319:1096-1100 (Feb. 22, 2008).

Fischer, N., et al., "Prevalence of Human Garnmaretrovirus XMRV in Sporadic Prostate Cancer", *J. Clin. Virol.*, 43:277-283 (2008).

Goff, S.P., "Retroviridae: The Retroviruses and Their Replication", In *Fields Virology*, Fifth Edition, vol. 2, D.M. Knipe, et al., eds. (Philadelphia, PA:Lippincott Williams & Wilkins), Chapter 55, pp. 1999-2069 (2007).

Groom, H.C.T., et al., "Absence of Xenotropic Murine Leukaemia Virus-Related Virus in UK Patients with Chronic Fatigue Syndrome", *Retrovirology*, 7:10 (10 pgs) (2010).

Groom, H.C.T., et al., "Susceptibility of Xenotropic Murine Leukemia Virus-Related Virus (XMRV) to Retroviral Restriction Factors," *Proc. Natl. Acad. Sci. USA*, 107(11):5166-5171 (Mar. 16, 2010).

Hohn, O., et al., "Lack of Evidence for Xenotropic Murine Leukemia Virus-Related Virus(XMRV) in German Prostate Cancer Patients", *Retrovirology*, 6:92 (11 pages) (Oct. 16, 2009).

Hong, S., et al., "Fibrils of Prostatic Acid Phosphatase Fragments Boost Infections by XMRV, a Human Retrovirus Associated with Prostate Cancer", *J. Virol.*, 83(14):6995-7003 (Jul. 2009).

Huang, W-Y., et al. "Sexually Transmissible Infections and Prostate Cancer Risk", *Cancer Epidemiol. Biomarkers Prev.*, 17(9):2374 2381 (Sep. 2008).

Kim, S., et al., "Integration Site Preference of Xenotropic Murine Leukemia Virus-Related Virus, a New Human Retrovirus Associated With Prostate Cancer", *J. Virol.*, 82(20):9964-9977 (Oct. 2008).

Kim, S., et al., "Fidelity of Target Site Duplication and Sequence Preference During Integration of Xenotropic Murine Leukemia Virus-Related Virus", *PLoS ONE*, 5(4):e10255 (6 pgs) (Apr. 2010).

Klein, E.A., et al., "Genetic Susceptibility and Oxidative Stress in Prostate Cancer: Integrated Model with Implications for Prevention", *Urology*, 68(6):1145-1151 (2006).

Knouf, E.C., et al., "Multiple Integrated Copies and High-Level Production of the Human Retrovirus XMRV (Xenotropic Murine Leukemia Virus-Related Virus) from 22Rv1 Prostate Carcinoma Cells", *J. Virol.*, 83(14):7353-7356 (Jul. 2009; ahead of print Apr. 29, 2009).

Li, H., and Tai, B.C., "RNASEL Gene Polymorphisms and the Risk of Prostate Cancer: A Meta-Analysis", *Clin. Cancer Res.*, 12(19):5713-5719 (Oct. 1, 2006).

Li, W-H., et al., "Evolutionary Analyses of the Human Genome", *Nature*, 409:847-849 (Feb. 15, 2001).

Lombardi, V.C., et al., "Detection of an Infectious Retrovirus, XMRV, in Blood Cells of Patients with Chronic Fatigue Syndrome", *Science*, 326:585-589 (Oct. 23, 2009).

Maier, C., et al., "Mutation Screening and Association Study of RNASEL as a Prostate Cancer Susceptibility Gene", *Br. J. Cancer*, 92(6):1159-1164 (online Feb. 15, 2005).

Mani, R.S., et al., "Induced Chromosomal Proximity and Gene Fusions in Prostate Cancer", *Science*, 326:1230 (Nov. 27, 2009).

McCormick, A.L., et al., "Quantification of Reverse Transcriptase in ALS and Elimination of a Novel Retroviral Candidate", *Neurology*, 70:278-283 (Jan. 22, 2008).

Metzger, M.J., et al., "The Prostate Cancer-Associated Human Retrovirus XMRV Lacks Direct Transforming Activity But Can Induce Low Rates of Transformation in Cultured Cells", *J. Virol.*, 84(4);1874-1880 (Feb. 2010; ahead of print Dec. 9, 2009).

Münch, J., et al., "Semen-Derived Amyloid Fibrils Drastically Enhance HIV Infection", *Cell*, 131:1059-1071 (Dec. 14, 2007).

Paprotka, T., et al., "Inhibition of Xenotropic Murine Leukemia Virus-Related Virus by APOBEC3 Proteins and Antiviral Drugs", *J. Virol.*, 84(11):5719-5729 (Jun. 2010; ahead of print Mar. 24, 2010).

Platz, E.A. and De Marzo, A.M., "Epidemiology of Inflammation and Prostate Cancer", *J. Urol.* 171:S36-S40 (Feb. 2004).

Proietti, F.A., et al., "Global Epidemiology of HTLV-I Infection and Associated Diseases", *Oncogene*, 24:6058-6068 (2005).

Putzi, M.J. and De Marzo, A.M., "Morphologic Transitions Between Proliferative Inflammatory Atrophy and High-Grade Prostatic Intraepithelial Neoplasia", *Urology*, 56(5):828-832(2000).

Qui, X., et al., "XMRV: Examination of Viral Kinetics, Tissue Tropism, and Serological Markers of Infection", Meeting Abstract: 17th Conference on Retroviruses and Opportunistic Infections (San Francisco, CA), Paper #151 [retrieved online http://www.retroconferenceorg/2010/Abstracts/39393htm] (Feb. 16-19, 2010).

Roan, N.R., et al., "The Cationic Properties of SEVI Underlie its Ability to Enhance HIV Infection", *J. Virol.*, 83(1):73-80 (Jan. 2009; ahead of print Oct. 22, 2008).

Rodriguez, J.J. and Goff, S.P., "Xenotropic Murine Leukemia Virus-Related Virus Establishes an Efficient Spreading Infection and Exhibits Enhanced Transcriptional Activity In Prostate Carcinoma Cells", *J. Virol.*, 84(5):2556-2562 (Mar. 2010; ahead of print Dec. 16, 2009).

Sakuma, R., et al., "Xenotropic Murine Leukemia Virus-Related Virus is Susceptible to AZT", *Virology*, 397:1-6 (online Dec. 2, 2009).

Schlaberg R., et al., "XMRV is Present in Malignant Prostatic Epithelium and is Associated with Prostate Cancer, Especially High-Grade Tumors", *Proc. Natl. Acad. Sci. USA*, 106(38):16351-16356 (Sep. 22, 2009).

Schlecht,-Louf, G., et al., "Retroviral Infection in vivo Requires an Immune Escape Virulence Factor Encrypted in the Envelope Protein of Oncoretroviruses", *Proc. Natl. Acad. Sci. USA*, 107(8):3782-3787 (Feb. 23, 2010).

Sfanos, K.S., et al., "A Molecular Analysis of Prokaryotic and Viral DNA Sequences in Prostate Tissue from Patients with Prostate Cancer Indicates the Presence of Multiple and Diverse Microorganisms", *Prostate*, 68:306-320 (2008).

Sfanos, K.S., et al., "Acute Inflammatory Proteins Constitute The Organic Matrix of Prostatic Corpora Amylacea and Calculi in Men with Prostate Cancer", *Proc. Nat. Acad. Sci. USA*, 106(9):3443-3448 (Mar. 3, 2009).

Sharma, P., et al., "Organ and Cell Lineage Dissemination of XMRV in Rhesus Macaques During Acute and Chronic Infection", Meeting Abstract: 17th Conference on Retroviruses and Opportunistic Infections (San Francisco, CA), Paper #150LB [retrieved online http://wwwretroconferenceorg/2010/Abstracts/39855htm] (Feb. 16-19, 2010).

Silverman, R.H., "Viral Encounters with 2',5'-Oligoadenylate Synthetase and RNase L During the Interferon Antiviral Response", *J. Virol.*, 81(23):12720-12729 (Dec. 2007, ahead of print Sep. 5, 2007).

Singh, I., et al., "Raltegravir is a Potent Inhibitor of XMRV, a Virus Implicated in Prostate Cancer and Chronic Fatigue Syndrome", *PLoS ONE*, 5(4):e9948 (7 pgs) (Apr. 1, 2010).

Stang, A., et al., "Unintended Spread of a Biosafety Level 2 Recombinant Retrovirus", *Retrovirology*, 6:86 (6 pgs) (Sep. 22, 2009).

Stieler, K., et al., "Host Range and Cellular Tropism of the Human Exogenous Gammaretrovirus XMRV", *Virology*, 399:23-30 (online Jan. 27, 2010).

Suhadolnik, R.J., et al., "Biochemical Evidence for a Novel Low Molecular Weight 2-5A-Dependent RNase L in Chronic Fatigue Syndrome", *J. Interferon Cytokine Res.*, 17:377-385 (1997).

Sutcliffe, S., et al,. "Sexually Transmitted Infections and Prostatic Inflammation/Cell Damage as Measured by Serum Prostate Specific Antigen Concentration", *J. Urol.*, 175:1937-1942 (May 2006).

Tlsty, T.D., and Hein, P.W., "Know Thy Neighbor: Stromal Cells Can Contribute Oncogenic Signals", *Curr. Opin. Genet. Dev.*, 11:54-59 (2001).

van Kuppeveld, F.J.M., et al., "Prevalence of Xenotropic Murine Leukaemia Virus-Related Virus in Patients with Chronic Fatigue Syndrome in the Netherlands: Retrospective Analysis of Samples from an Established Cohort", *BMJ*, 340:c1018 (6 pgs) (2010).

Voisset, C., et al., "Human RNA "Rumor" Viruses: the Search for Novel Human Retroviruses in Chronic Disease", *Microbiol. Mol. Biol. Rev.*, 72(1):157-196 (Mar. 2008).

Wiklund, F., et al., "Genetic Analysis of the *RNASEL* Gene in Hereditary, Familial, and Sporadic Prostate Cancer", *Clin. Cancer Res.*, 10:7150-7156 (Nov. 1, 2004).

Yan, Y., et al., "Six Host Range Variants of the Xenotropic/Polytropic Gammaretroviruses Define Determinants for Entry in the XPR1 Cell Surface Receptor", *Retrovirology*, 6:87 (11 pgs) (Oct. 7, 2009).

May 19, 2010, Invitation to Pay Additonal Fees and, Where Applicable, Protest Fee (Partial Search Report), PCT/US2009/069244.

Non-Published U.S. Appl. No. 61/347,185, filed May 21, 2011 entitled, Method of Detecting and Treating XMRV Infection. Inventor: Robert H. Silverman.

Aug. 16, 2010, International Search Report and Written Opinion, PCT/US2009/069244.

Nov. 29, 2010, Examination Response, Australian Patent Application No. 2006235266.

Dec. 10, 2010, Notice of Acceptance, 20066235266.

Feb. 9, 2011, Response to Official Action, 06749572.

Feb. 16, 2011, Response to Examiners Report, 562221.

May 26, 2011, Notice of Acceptance, 562221.

Erlwein, O., et al., "DNA Extraction Columns Contaminated With Murine Sequences," *PLOS One*, 6(8): 1-4 (2011).

Kenyon, J.C. and Lever, A.M., "XMRV, Prostate Cancer and Chronic Fatigue Syndrome," *British Medical Bulletin*, 98: 61-74 (2011).

Paprotka, T., et al., "Recombinant Origin of the Retrovirus XMRV",*Science*, 333: 97-101 (2011).

Switzer, W.M., et al., "No Association of Xenotropic Murine Leukemia Virus-Related Viruses With Prostate Cancer," *PLOS One*, 6(5): 1-9 (2011).

Onlamoon, N., et al., "Infection, Viral Dissemination, and Anitbody Responses of Rhesus Macaques Exposed to the Human Gammaretrovirus XMRV," *Journal of Virology*, 85(9): 4547-4557 (2011).

Pandhare-Dash, J., et al., "XMRV Accelerates Cellular Proliferation, Transformational Activity, and Invasivemenss of Prostate Cancer Cells by Downregulating p27 $K^{ip1}$," *The Prostate*, published online in Wiley Online Library, URL: www.wileyonlinelibrary.com, 12 pages (2011).

Nov. 3, 2011, Office Action Restriction Requirement for U.S. Appl. No. 12/645,181.

Dec. 1, 2011, Reply to Restriction Requirement filed, U.S. Appl. No. 12/645,181.

Dec. 13, 2011, Office Action, U.S. Appl. No. 12/645,181.

Apr. 1, 2011, Communication pursuant to Article 94(3) EPC., 06749572.1.

Jul. 7, 2011, Notification Concerning Transmittal of International Preliminary Report on Patentability., PCT/US2009/069244.

Aug. 12, 2011, Response to Official Action., 06749572.1.

Aug. 26, 2011, Communication pursuant to Article 94(3) EPC., 06749572.1.

Sep. 8, 2011, Office Action (translated)., 2008-505606.

Sep. 8, 2011, Communication pursuant to Rules 161(1) and 162 EPC., 09804357.3.

Aug. 30, 2011, Office Action., 2007-12361.

Aug. 3, 2010, Office Action, 06749572.1.

Furuta, R.A., et al., "The Prevalence of Xenotropic Murine Leukemia Virus-Related Virus in Healthy Blood Donors in Japan", Abstract presented at 2009 meeting on Retroviruses, Cold Spring Harbor Laboratories, p. 100 (May 18-May 23, 2009).

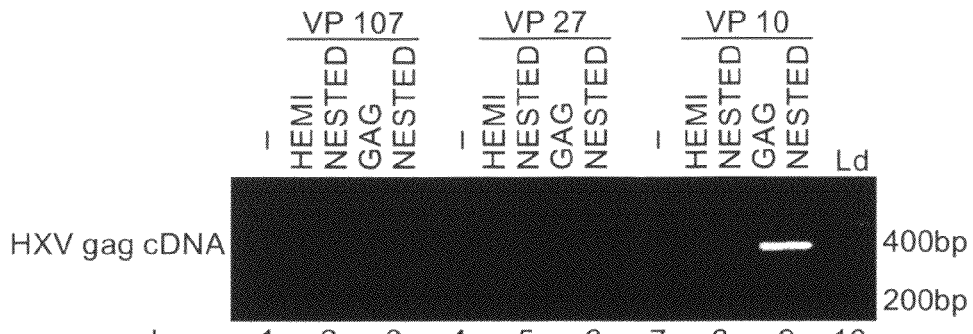
FIG. 6
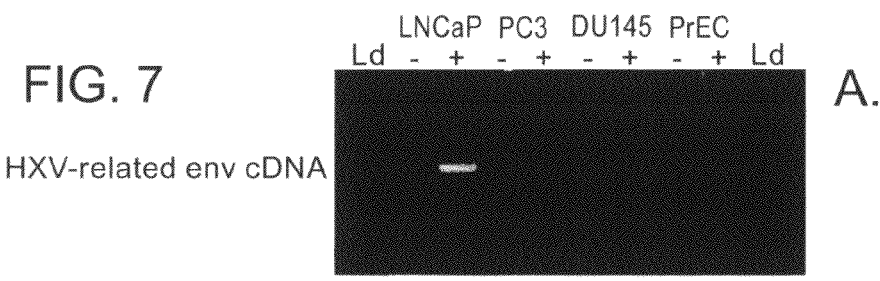
FIG. 7
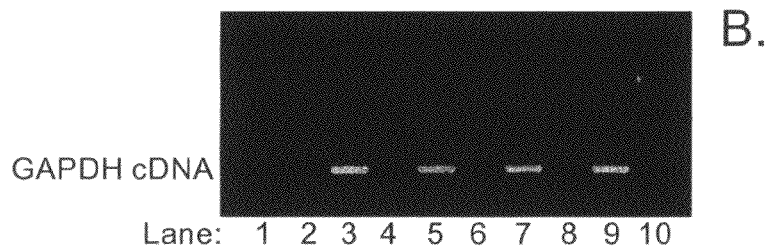
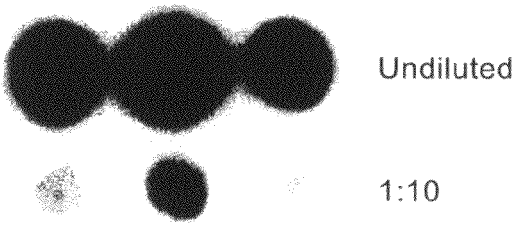
FIG. 8

HXV₃₅ Gag (SEQ ID NO: 3)

```
MGQTVTTPLS LTLQHWGDVQ RIASNQSVDV KKRRWVTF S
AEWPTFNVGW PQDGTFNLGV ISQVKSRVF  PGPHGHPDQV
PYIVTWEALA YDPPPWVKPF VSPKPPPLPT APVLPPGPSA
QPPSRSALYP ALTLSIKSKP PKPQVLPDSG GPLIDLLTED
PPPYGVQPSS SARENNEEEA ATTSEVSPPS P VSRLRGRR
DPPAADSTTS QAFPLR GGD GQLQYWPFSS SDLYNWKNNN
PSFSEDPGKL TALIESVLIT HQPTWDD QQ LLGTLLTGEE
KQRVLLEAGK AVRGNDGRPT QLPNEVNAAF PLERPDWDYT
TTEGRNHLVL YRQLLLAGLQ NAGRSPTNLA KVKGITQGPN
ESPSAFLERL KEAYRRYTPY DPEDPGQETN VS SFIWQSA
PDIGRKLERL EDLKSKTLGD LVREAEKIFN KRETPEEREE
RIRREIEEKE ERRRAEDEQR ERERDRRRHR E SKLLATVV
IGQRQDRQGG ERRRPQLDKD Q AY KEKGH WAKD PKKPR
GPRGPRPQTS LLTLGD
```

Antigenic Candidates:

DVKKRRWVTFCSAE      (SEQ ID NO: 7)

EAGKAVRGNDGRPTQL    (SEQ ID NO: 8)

KDCPKKPRGPRGPR      (SEQ ID NO: 9)

Hydropathy Plot

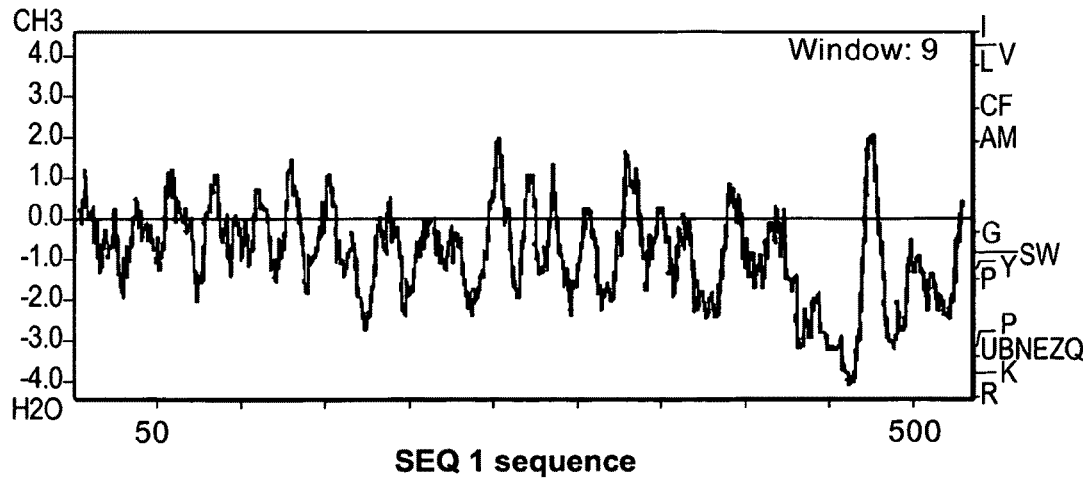

FIG. 11

FIG. 13 Amino acid sequence of HXV$_{35}$ (SEQ ID NO: 2)

MGQTVTTPLSLTLQHWGDVQRIASNQSVDVKKRRWVTFCSAEWPTFNVGW
PQDGTFNLGVISQVKSRVFCPGPHGHPDQVPYIVTWEALAYDPPPWVKPFVSP
KPPPLPTAPVLPPGPSAQPPSRSALYPALTLSIKSKPPKPQVLPDSGGPLIDLLTE
DPPPYGVQPSSSARENNEEEAATTSEVSPPSPMVSRLRGRRDPPAADSTTSQAF
PLRMGGDGQLQYWPPSSSDLYNWKNNNPSPSEDPGKLTALIESVLITHQPTW
DDCQQLLGTLLTGEEKQRVLLEAGKAVRGNDGRPTQLPNEVNAAFPLERPD
WDYTTTEGRNHLVLYRQLLLAGLQNAGRSPTNLAKVKGITQGPNESPSAFLE
RLKEAYRRYTPYDPEDPGQETNVSMSFIWQSAPDIGRKLERLEDLKSKTLGDL
VREAEKIFNKRETPEEREERIRREIEEKEERRRAEDEQRERERDRRRHREMSKL
LATVVIGQRQDRQGGERRRPQLDKDQCAYCKEKGHWAKDCPKKPRGPRGP
RPQTSLLTLGDGGQGQEPPPEPRITLKVGGQPVTFLVDTGAQHSVLTQNPGPL
SDKSAWVQGATGGKRYRWTTDRKVHLATGKVTHSFLHVPDCPYPLLGRDLL
TKLKAQIHFEGSGAQVVGPMGQPLQVLTLNIENKYRLHETSKEPDVPLGSTW
LSDFPQAWAETGGMGLAVRQAPLIIPLKATSTPVSIKQYPMSQEARLGIKPHIQ
RLLDQGILVPCQSPWNTPLLPVKKPGTNDYRPVQDLREVNKRVEDIHPTVPNP
YNLLSGLPPSHQWYTVLDLKDAFFCLRLHPTSQPLFAFEWRDPEMGISGQLT
WTRLPQGFKNSPTLFDEALHRDLADFRIQHPDLILLQYVDDLLLAATSEQDCQ
RGTRALLQTLGNLGYRASAKKAQICQKQVKYLGYLLKEGQRWLTEARKETV
MGQPTPKTPRQLREFLGTAGFCRLWIPGFAEMAAPLYPLTKTGTLFNWGPDQ
QKAYQEIKQALLTAPALGLPDLTKPFELFVDEKQGYAKGVLTQKLGPWRRPV
AYLSKKLDPVAAGWPPCLRMVAAIAVLTKDAGKLTMGQPLVILAPHAVEAL
VKQPPDRWLSNARMTHYQAMLLDTDRVQFGPVVALNPATLLPLPEKEAPHD
CLEILAETHGTRPDLTDQPIPDADYTWYTDGSSFLQEGQRRAGAAVTTETEVI
WARALPAGTSAQRAELIALTQALKMAEGKKLNVYTDSRYAFATAHVHGEIY
RRRGLLTSEGREIKNKNEILALLKALFLPKRLSIIHCPGHQKGNSAEARGNRM
ADQAAREAAMKAVLETSTLLIEDSTPYTPPHFHYTETDLKRLRELGATYNQT
KGYWVLQGKPVMPDQSVFELLDSLHRLTHPSPQKMKALLDREESPYYMLNR
DRTIQYVTETCTACAQVNASKAKIGAGVRVRGHRPGTHWEVDFTEVKPGLY
GYKYLLVFVDTFSGWVEAFPTKRETAKVVSKKLLEDIFPRFEMPQVLGSDNG
PAFASQVSQSVADLLGIDWKLHCAYKPQSSGQVERINKTIKETLTKLTLASGT
KDWVLLLPLALYRARNTPGPHGLTPYEILYGAPPPLVNFHNPEMSKLTNSPSL
QAHLQALQAVQQEVWKPLAAAYQDQLDQVIPHPFRVGDAVWVRRHQTKN
LEPRWKGPYTVLLTTPTALKVDGISAWIHAAHVKAATTPPAGTAWKVQRSQ
NPLKIRLTRGAPMESPAFSKPLKDKINPWGPLIIMGILVRAGASVQRDSPHQVF
NVTWKITNLMTGQTANATSLLGTMTDTFPKLYFDLCDLVGDNWDDPEPDIG
DGCRSPGGRKRTRLYDFYVCPGHTVLTGCGGPREGYCGKWGCETTGQAYW
KPSSSWDLISLKRGNTPKGQGPCFDSSVGSGSIQGATPGGRCNPLVLEFTDAG
KRASWDAPKTWGLRLYRSTGADPVTLFSLTRQVLNVGPRVPIGPNPVITEQLP
PSQPVQIMLPRPPRPPPSGAASMVPGAPPPSQQPGTGDRLLNLVEGAYQALNL
TSPDKTQECWLCLVSGPPYYEGVAVLGTYSNHTSAPANCSVTSQHKLTLSEV
TGQGLCIGAVPKTHQALCNTTQKTSDGSYYLASPAGTIWACSTGLTPCLSTTV
LNLTTDYCVLVELWPKVTYHSPNYVYGQFGKKTKYKREPVSLTLALLLGGL
TMGGIAAGVGTGTTALVATKQFEQLQAAIHTDLGALEKSVSALEKSLTSLSE
VVLQNRRGLDLLFLKEGGLCAALKKECCFYADHTGVVRDSMAKLRERLNQR
QKLFESGQGWFEGLFNRSPWFTTLISTIMGPLIVLLLILLFGPCILNRLVQFVKD
RISVVQALVLTQQYHQLKSIDPEEVESRE

FIG. 14 Amino Acid sequence of HXV$_{35}$ GAG (SEQ ID NO: 3):

MGQTVTTPLSLTLQHWGDVQRIASNQSVDVKKRRWVTFCSAEWPTFNVGW
PQDGTFNLGVISQVKSRVFCPGPHGHPDQVPYIVTWEALAYDPPPWVKPFVSP
KPPPLPTAPVLPPGPSAQPPSRSALYPALTLSIKSKPPKPQVLPDSGGPLIDLLTE
DPPPYGVQPSSSARENNEEEAATTSEVSPPSPMVSRLRGRRDPPAADSTTSQAF
PLRMGGDGQLQYWPFSSSDLYNWKNNNPSFSEDPGKLTALIESVLITHQPTW
DDCQQLLGTLLTGEEKQRVLLEAGKAVRGNDGRPTQLPNEVNAAFPLERPD
WDYTTTEGRNHLVLYRQLLLAGLQNAGRSPTNLAKVKGITQGPNESPSAFLE
RLKEAYRRYTPYDPEDPGQETNVSMSFIWQSAPDIGRKLERLEDLKSKTLGDL
VREAEKIFNKRETPEEREERIRREIEEKEERRAEDEQRERERDRRRHREMSKL
LATVVIGQRQDRQGGERRRPQLDKDQCAYCKEKGHWAKDCPKKPRGPRGP
RPQTSLLTLGD

FIG. 15 Amino Acid sequence of HXV$_{35}$ PRO-POL (SEQ ID NO: 4):

GGQGQEPPPEPRITLKVGGQPVTFLVDTGAQHSVLTQNPGPLSDKSAWVQGA
TGGKRYRWTTDRKVHLATGKVTHSFLHVPDCPYPLLGRDLLTKLKAQIHFEG
SGAQVVGPMGQPLQVLTLNIENKYRLHETSKEPDVPLGSTWLSDFPQAWAET
GGMGLAVRQAPLIIPLKATSTPVSIKQYPMSQEARLGIKPHIQRLLDQGILVPC
QSPWNTPLLPVKKPGTNDYRPVQDLREVNKRVEDIHPTVPNYNLLSGLPPSH
QWYTVLDLKDAFFCLRLHPTSQPLFAFEWRDPEMGISGQLTWTRLPQGFKNS
PTLFDEALHRDLADFRIQHPDLILLQYVDDLLLAATSEQDCQRGTRALLQTLG
NLGYRASAKKAQICQKQVKYLGYLLKEGQRWLTEARKETVMGQPTPKTPRQ
LREFLGTAGFCRLWIPGFAEMAAPLYPLTKTGTLFNWGPDQQKAYQEIKQAL
LTAPALGLPDLTKPFELFVDEKQGYAKGVLTQKLGPWRRPVAYLSKKLDPVA
AGWPPCLRMVAAIAVLTKDAGKLTMGQPLVILAPHAVEALVKQPPDRWLSN
ARMTHYQAMLLDTDRVQFGPVVALNPATLLPLPEKEAPHDCLEILAETHGTR
PDLTDQPIPDADYTWYTDGSSFLQEGQRRAGAAVTTETEVIWARALPAGTSA
QRAELIALTQALKMAEGKKLNVYTDSRYAFATAHVHGEIYRRRGLLTSEGRE
IKNKNEILALLKALFLPKRLSIIHCPGHQKGNSAEARGNRMADQAAREAAMK
AVLETSTLLIEDSTPYTPPHFHYTETDLKRLRELGATYNQTKGYWVLQGKPV
MPDQSVFELLDSLHRLTHPSPQKMKALLDREESPYYMLNRDRTIQYVTETCT
ACAQVNASKAKIGAGVRVRGHRPGTHWEVDFTEVKPGLYGYKYLLVFVDTF
SGWVEAFPTKRETAKVVSKKLLEDIFPRFEMPQVLGSDNGPAFASQVSQSVA
DLLGIDWKLHCAYKPQSSGQVERINKTIKETLTKLTLASGTKDWVLLLPLALY
RARNTPGPHGLTPYEILYGAPPPLVNFHNPEMSKLTNSPSLQAHLQALQAVQQ
EVWKPLAAAYQDQLDQPVIPHPFRVGDAVWVRRHQTKNLEPRWKGPYTVL
LTTPTALKVDGISAWIHAAHVKAATTPPAGTAWKVQRSQNPLKIRLTRGAP

FIG. 16 Amino acid sequence of HXV$_{35}$ ENV (SEQ ID NO: 5):

MESPAFSKPLKDKINPWGPLIIMGILVRAGASVQRDSPHQVFNVTWKITNLMT
GQTANATSLLGTMTDTFPKLYFDLCDLVGDNWDDPEPDIGDGCRSPGGRKRT
RLYDFYVCPGHTVLTGCGGPREGYCGKWGCETTGQAYWKPSSSWDLISLKR
GNTPKGQGPCFDSSVGSGSIQGATPGGRCNPLVLEFTDAGKRASWDAPKTWG
LRLYRSTGADPVTLFSLTRQVLNVGPRVPIGPNPVITEQLPPSQPVQIMLPRPPR
PPPSGAASMVPGAPPPSQQPGTGDRLLNLVEGAYQALNLTSPDKTQECWLCL
VSGPPYYEGVAVLGTYSNHTSAPANCSVTSQHKLTLSEVTGQGLCIGAVPKT
HQALCNTTQKTSDGSYYLASPAGTIWACSTGLTPCLSTTVLNLTTDYCVLVEL
WPKVTYHSPNYVYGQFGKKTKYKREPVSLTLALLLGGLTMGGIAAGVGTGT
TALVATKQFEQLQAAIHTDLGALEKSVSALEKSLTSLSEVVLQNRRGLDLLFL
KEGGLCAALKKECCFYADHTGVVRDSMAKLRERLNQRQKLFESGQGWFEG
LFNRSPWFTTLISTIMGPLIVLLLILLFGPCILNRLVQFVKDRISVVQALVLTQQ
YHQLKSIDPEEVESRE

FIG. 17 Sequence from LNCaP RNA RTPCR product. (7084-7750bp) (SEQ ID NO: 6)

aaaagagagcccggtgtcattaactctggccctgtctgttggggaggacttactatgggcggcatagctccaggagttggaa
cagggactacagccctagtggccaccaaacaattcgagcagctccaggcagccatacatacagaccttggggccttagaa
aaaatcagtcagtgccctagaaaagtctctgacctcgttgtctgaggtggtcctacagaaccggaggggattagatctactgt
tcctaaaagaaggaggattatgtgctgccctaaaagaagaatgctgtttttacgcggaccacactggcgtagtaagagatag
catggcaaagctaagagaaaggttaaaccagagacaaaaattgttcgaatcaggacaagggtggtttgagggactgtttaa
caggtccccatggttcacgaccctgatatccaccaccattatgggccctctgatagtactttattaatcctactttcggaccct
gtattctcaaccgcttggtccagtttgtaaaagacacagaatttcggtagtgcaggccctggttctgacccagcagtatcacc
aactcaaatcaatagatccagaagaagtggaatcacgtgaataaaagattttattcagtttccagaaagagggggggaatgaa
agaccccccataaggc

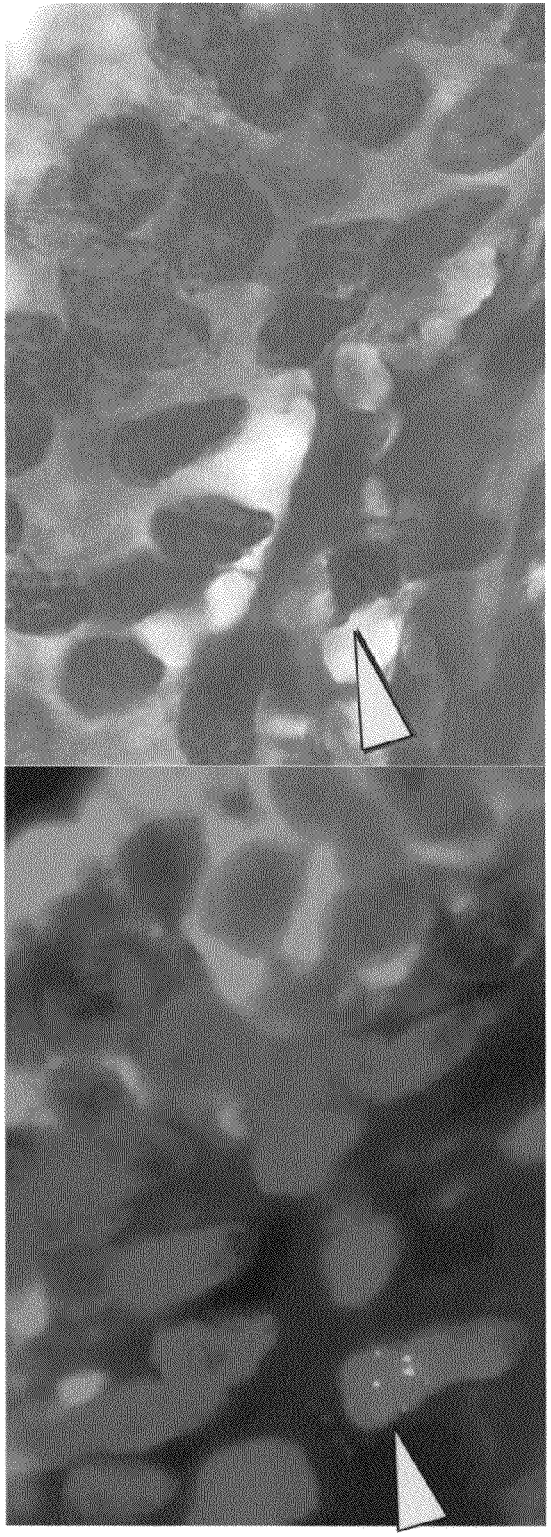

Homozygous R462Q RNase L Prostates are XMRV Positive by FISH

FIG. 18A

Analysis of prostate from patient VP62. Left Panel: Immunohistochemistry (IHC) (red) with a mouse anti-cytokeratin AE1/AE3 (20:1 mixture of AE1 to AE3) monoclonal Ab cocktail from Roche. The anti-keratin AE 1 Ab recognizes the 56.5, 50, 50', 48 and 40 kDa keratins of the acidic subfamily. The anti-keratin AE3 Ab recognizes all 6 members of the basic subfamily. The IHC (red) labels prostate epithelial cells. The green label is FISH for HXV35 env probe as described in the legend to FIG. 9. Blue is DAPI staining of nuclei. Right Panel: Hematoxylin and eosin staining.

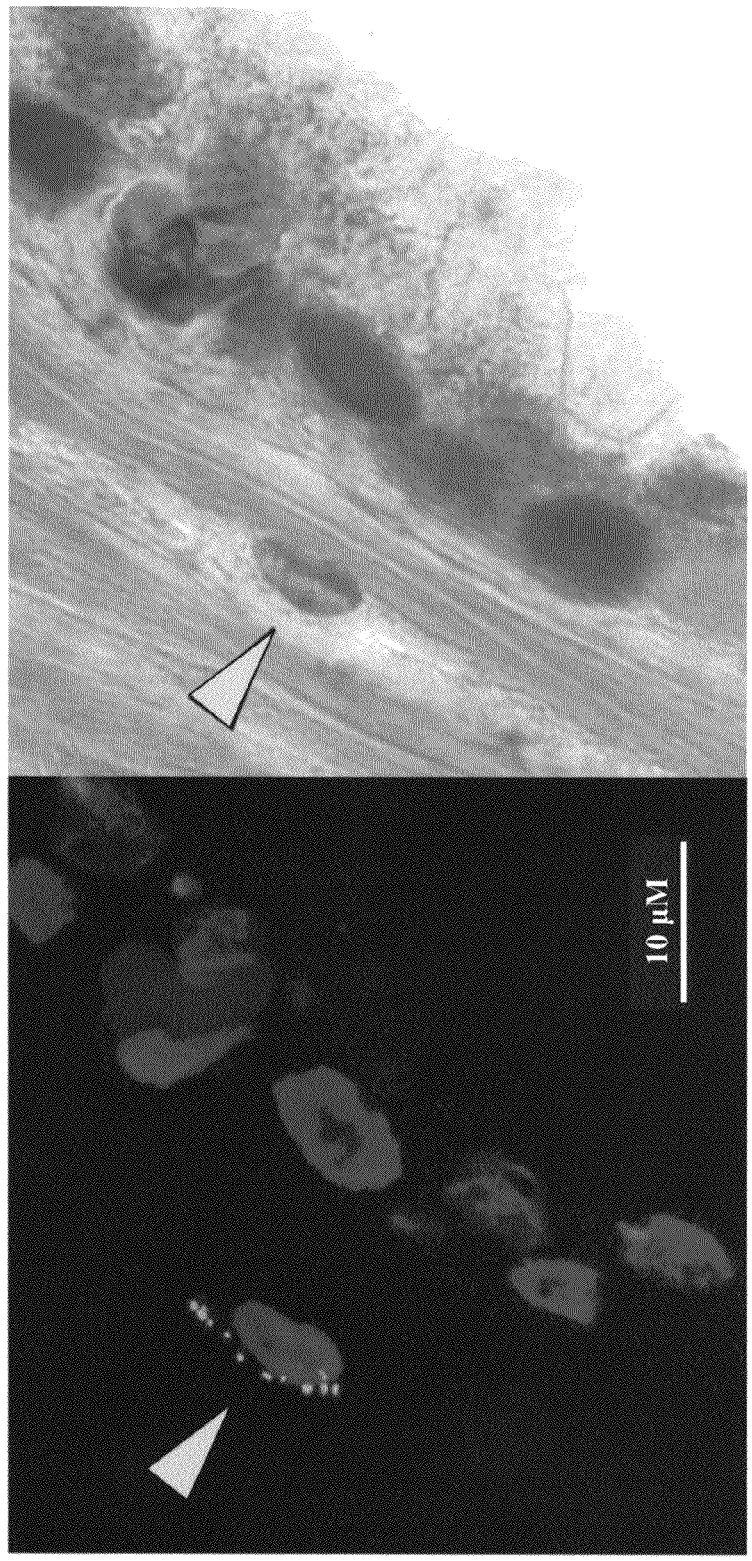

LNCaP Clone R is XMRV Positive by IHC with Antibody to p30 Capsid

LNCaP

LNCaP Clone R

Analysis of LNCaP, clone R. Right panel: immunohistochemistry with specific antiserum prepared in goats to Rauscher mouse Leukemia virus p30 protein (ATCC, catalog no. VR-1564AS-Gt) showing labeling of HXV gag protein plus DAPI (blue) staining of nuclei. Right panel: DAPI staining of nuclei.

LNCaP Clone R is XMRV Positive by FISH + IHC

Doubling labeling by IHC and FISH of HXV in LNCaP infected cells. Immunohistochemistry with specific antiserum prepared in goats to Rauscher mouse leukemia virus p30 protein (ATCC, catalog no. VR-1564AS-Gt) showing labeling of HXV gag protein plus DAPI (blue) staining of nuclei plus FISH labeling (green) of virus nucleic acid.

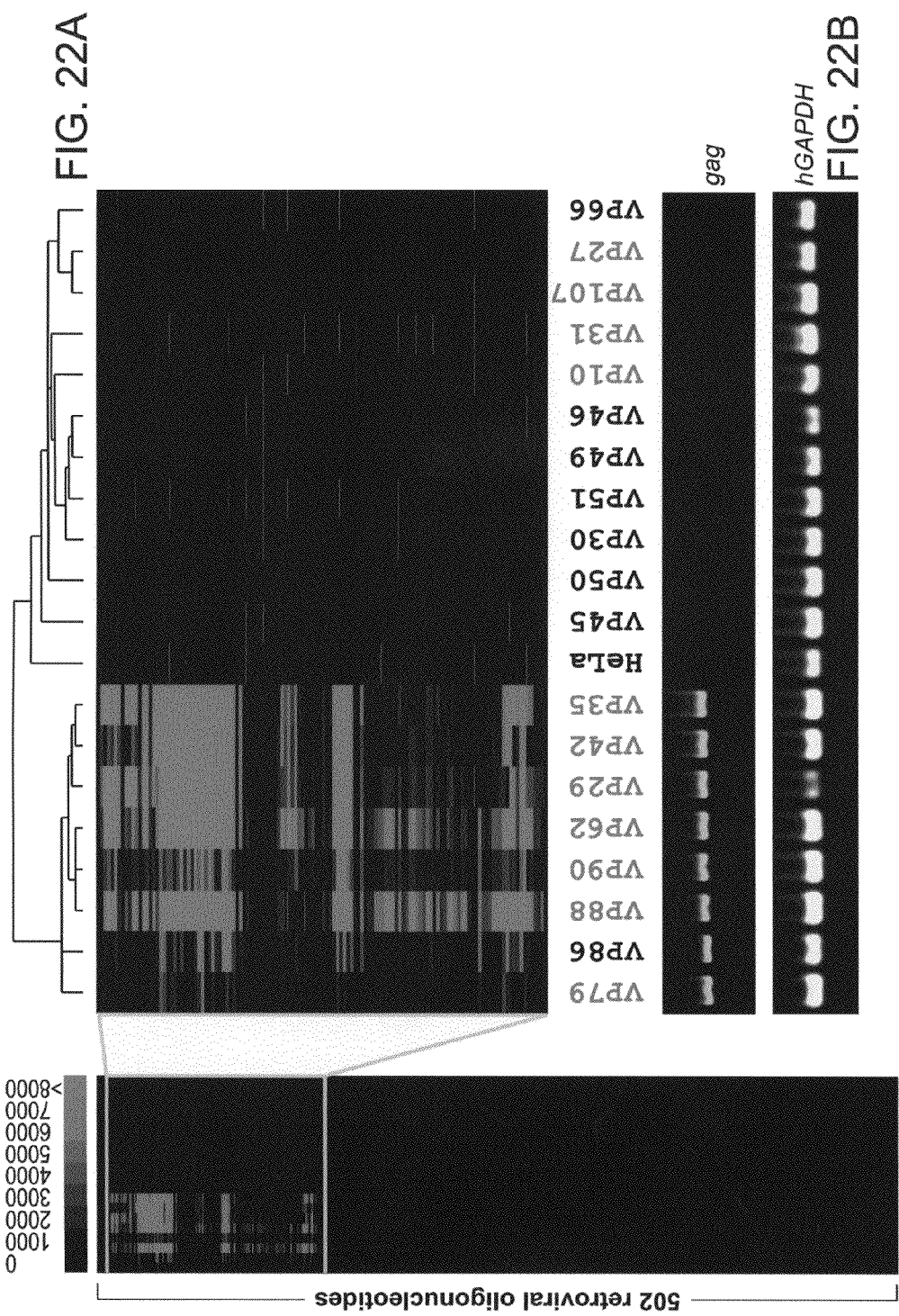

Complete genomes

FIG. 25

|  |  | VRA |  |  |
|---|---|---|---|---|
| (X) | VP35 | LCDLVG------CMIASGPPHWGIEYQAPYSSPPGPPCC

```
1    GCGCCAGTCATCCGATAGACTGAGTCGCCCGGGTACCCGTGTTCCCAATAAAGCCTTTG
R    ------------------------------------------------------------

61   CTGTTTGCATCCGAATCCGAAGCGTGGCCTCGCTGTTCCTTGGAGGGTCTCCTCAGAGTGATTGA
R    ---------->
U5                 -----

121  CTACCCCAGCTCGGGGGTCTTTCATTTGGGGGCTCGTCCGGGATTCGGAGACCCCCGCCCA
U5   ------------------------------------------------------------>
tRNA-Pro PBS

181  GGGACCACCGACCCACCGTCGGGAGGTAAGCCGGCGATCGTTTTGTCTTTGTCTCT
splice donor                    ------>

241  GTCTTTGTGCTGTGTGTGTGTGCCGGCATCTAATCCTCGCGCCTGCGTCTGAATCTGTA

301  CTAGTTAGCTAACTAGATCTGTATCTGGCGGTTCCGCGGAAGAACTGACGAGTTCGTATT
gl-Gag start                                              --->

361  CCCGGGCCGCAGCCCCAGGGAGACGTCCCAGCCCTCGGGGCCCGTTTTGTGGCCCATTC
                                                      ▽ 24 nt

421  TGTATCAGTTAACCTACCCGAGTCGGACTCTTTGGAGTGGCTTTGTTGGGGGACGAGAGA
```

FIG. 28A (continued)

```
481       CAGAGACACTTCCCGCCCCCGTCTGAATTTTTGCTTTCGGTTTTACGCCCGAAACCGCGCC

541       GCGGCGTCTGATTTGTTTTGTGTTCTTCTTCGTTCTTCGTTAGTTTTTCTTCTGTCTTTAAGT
GAG-OF primer ----------->

601       GTTCTCGAGATCATGGGACAGACCGTAACTACCCCTCTGAGTCTAACCTTGCAGCACTGG
Gag                      M  G  Q  T  V  T  T  P  L  S  L  T  L  Q  H  W
GAG-IF primer ----------->

661       GGAGATGTCCAGCGCATTGCATCCAACCAGTCTGTGGATGTCAAGAAGAGGCGCTGGGTT
Gag       G  D  V  Q  R  I  A  S  N  Q  S  V  D  V  K  K  R  R  W  V

721       ACCTTCTGTTCCGCCGAATGGCCAACTTTCAATGTAGGATGGCCTCAGGATGGTACTTTT
Gag       T  F  C  S  A  E  W  P  T  F  N  V  G  W  P  Q  D  G  T  F

781       AATTTAGGTGTGTTATCTCTCAGGTCAAGTCTAGAGTCTTTTGTCCTGGTCCCCACGGACAC
Gag       N  L  G  V  I  S  Q  V  K  S  R  V  F  C  P  G  P  H  G  H

841       CCGGATCAGGTCCCATATATCGTCACCTGGGAGGCACTTGCCTATGACCCCCCGTGG
Gag       P  D  Q  V  P  Y  I  V  T  W  E  A  L  A  Y  D  P  P  P  W

901       GTCAAACCGTTTGTCTCTCCTAAACCCCCTTTACCGACAGCTCCCGTCCTCCCGCCC
Gag       V  K  P  F  V  S  P  K  P  P  P  L  P  T  A  P  V  L  P  P
```

FIG. 28A (continued)

```
961   GGTCCTTCTGCGCAACCTCCGTCCCGATCTGCCCTTTACCCTGCCCTCTATA
Gag    G  P  S  A  Q  P  P  S  R  S  A  L  Y  P  A  L  T  L  S  I
GAG-IR primer                                   <-------------------

1021  AAGTCCAAACCTCCTAAGCCCCCAGTTCTCCCTGATAGCGGCGACCTCTCATTGACCTT
Gag    K  S  K  P  P  K  P  Q  V  L  P  D  S  G  G  P  L  I  D  L

1081  CTCACAGAGGATCCCCCGCCTACGGAGTACAACCTTCCTGCCAGGGAGAACAAT
Gag    L  T  E  D  P  P  P  Y  G  V  Q  P  S  S  A  R  E  N  N
GAG-OR primer                                          <-------

1141  GAAGAAGAGGCGGCCACCACCTCCGAGGTTTCCCCCCTTCTCCCATGGTGTCTCGACTG
Gag    E  E  E  A  T  T  S  E  V  S  P  P  S  P  M  V  S  R  L

1201  CGGGGAAGGAGAGACCCTCCCGCAGCGGACTCCACCAGGCATTCCCACTCCGC
Gag    R  G  R  R  D  P  P  A  A  D  S  T  T  S  Q  A  F  P  L  R

1261  ATGGGGGGAGATGGGCCAGCTTCAGTACTGGCCGTTTTCCCTCTGATTTATATAATTGG
Gag    M  G  G  D  G  Q  L  Q  Y  W  P  F  S  S  D  L  Y  N  W

1321  AAAAATAATAACCCTTCCTTTTCTGAAGATCCAGTAAAATTGACGGCCTTGATTGAGTCC
Gag    K  N  N  P  S  F  S  E  D  P  G  K  L  T  A  L  I  E  S
```

FIG. 28A (continued)

```
1381  GTCCTCATCACCCACCAGCCCACCTGGGACGACTGTCAGCAGTTGTTGGGACCCTGCTG
Gag    V  L  I  T  H  Q  P  T  W  D  D  C  Q  Q  L  L  G  T  L  L

1441  ACCGGAGAAGAAAAAGCAGCGGGTGCTCCTAGAGGCTGGAAAGGCAGTCCGGGCAATGAT
Gag    T  G  E  E  K  Q  R  V  L  L  E  A  G  K  A  V  R  G  N  D

1501  GGACGCCCCACTCAGTTGCCTAATGAAGTCAATGCTGCTTTTCCCCTTGAGCGCCCCGAT
Gag    G  R  P  T  Q  L  P  N  E  V  N  A  A  F  P  L  E  R  P  D

1561  TGGGATTACACCACTACAGAAGGTAGGAACCACCTAGTCCTCTACCGCCAGTTGCTCTTA
Gag    W  D  Y  T  T  E  G  R  N  H  L  V  L  Y  R  Q  L  L  L

1621  GCGGGTCTCCAAAACGCGGGAGCCCAGGAGCCCCACCAATTTGGCCAAGGTAAAAGGATAACC
Gag    A  G  L  Q  N  A  G  R  S  P  T  N  L  A  K  V  K  G  I  T

1681  CAGGGACCTAATGAGTCTCCCCTCAGCCCTTTTTAGAGAGACTCAAGGAGGCCTATCGCAGG
Gag    Q  G  P  N  E  S  P  S  A  F  L  E  R  L  K  E  A  Y  R  R

1741  TACACTCCTTATGACCCTGAGGACCCAGGGCAAGAACCAATGTGTCCATGTCATTCATC
Gag    Y  T  P  Y  D  P  E  D  P  G  Q  E  T  N  V  S  M  S  F  I

1801  TGGCAGTCTGCCCCCGGATATCGGGCGAAAGTTAGAGAGCGGAAAGATTTAAAGAGCAAG
Gag    W  Q  S  A  P  D  I  G  R  K  L  E  R  L  E  D  L  K  S  K
```

FIG. 28A (continued)

```
1861        ACCTTAGGAGACTTAGTGAGGAAGCTGAAAAGATCTTTAATAAGCGAGAAACCCGGAA
Gag          T  L  G  D  L  V  R  E  A  E  K  I  F  N  K  R  E  T  P  E

1921        GAAAGAGAGGAACGTATCAGGAGAGAAATAGAGGAAAAAGAAGAACGCCGTAGGGCAGAG
Gag          E  R  E  E  R  I  R  R  E  I  E  E  K  E  E  R  R  A  E

1981        GATGAGCAGAGAGAGAGGGACCCGCAGAAGACATAGAGAGATGAGCAAGTCTTG
Gag          D  E  Q  R  E  R  D  R  R  H  R  E  M  S  K  L  L

2041        GCCACTGTAGTTATTGGTCAGAGACAGGATAGACAGGGGGGAGAGCGGAGGAGGCCCAA
Gag          A  T  V  V  I  G  Q  R  Q  D  R  Q  G  G  E  R  R  R  P  Q

2101        CTTGATAAGGACCAATGCGCCTACTGCAAAGAAAAGGGACACTGGGCTAAGGACTGCCCA
Gag          L  D  K  D  Q  C  A  Y  C  K  E  K  G  H  W  A  K  D  C  P

2161        AAGAAGCCACGAGGGCCCCGAGGACCCGAGGCCCCAGACCTCCCTCCTGACCTTAGGTGAC
Gag          K  K  P  R  G  P  P  R  G  P  P  R  P  Q  T  S  L  L  T  L  G  D

2221        TAGGGAGGTCAGGGTCAGGAGCCCCCCCCTGAACCCAGGATAAACCCTCAAAGTCGGGGGG
Gag-Pro-Pol  *  G  G  Q  Q  E  P  P  P  P  P  R  I  T  L  K  V  G  G

2281        CAACCCGTCACCTTCCTGGTAGATACTGGGGCCCAACACTCCGTGCTGACCCAAAATCCT
Gag-Pro-Pol  Q  P  V  T  F  L  V  D  T  G  A  Q  H  S  V  L  T  Q  N  P
```

FIG. 28A (continued)

```
2341          GGACCCCTAAGTGACAAGTCTGCCTGGGTCCAAGGGCTACTGGAGGAAAGCGGTATCGC
Gag-Pro-Pol    G  P  L  S  D  K  S  A  W  V  Q  G  A  T  G  G  K  R  Y  R

2401          TGGACCACGGATCGCAAAGTACATCTGGCTAAGGTCACCCACTCTTTCCTCCAT
Gag-Pro-Pol    W  T  T  D  R  K  V  H  L  A  T  G  K  V  T  H  S  F  L  H

2461          GTACCAGAGACTGCCCCTATCCTCTGCTAGGAAGAGACTTGCTGACTAAACTAAAAGCCCAA
Gag-Pro-Pol    V  P  D  C  P  Y  P  L  L  G  R  D  L  L  T  K  L  K  A  Q

2521          ATCCACTTCGAGGGATCAGGAGCTCAGGTTGTGGGACCGATGGGACAGCCCTGCAAGTG
Gag-Pro-Pol    I  H  F  E  G  S  G  A  Q  V  V  G  P  M  G  Q  P  L  Q  V

2581          CTGACCCTAAACATAGAAAATAAGTATCGGCTACATGAGACCCTCAAAGAGCCAGATGTT
Gag-Pro-Pol    L  T  L  N  I  E  N  K  Y  R  L  H  E  T  S  K  E  P  D  V

2641          CCTCTAGGGTCCACATGGCTTTCTGATTTTCCCCAGGCCTGGGCGGAAACCGGGGGCATG
Gag-Pro-Pol    P  L  G  S  T  W  L  S  D  F  P  Q  A  W  A  E  T  G  G  M

2701          GGACTGGCAGTTCGCCAAGCTCCTCTGATCATACCTCTGAAGGCAACCTCTACCCCGTG
Gag-Pro-Pol    G  L  A  V  R  Q  A  P  L  I  I  P  L  K  A  T  S  T  P  V

2761          TCCATAAAACAATACCCCATGTCACAAGAAGCCAGACTGGGGATCAAGCCCCACATACAG
Gag-Pro-Pol    S  I  K  Q  Y  P  M  S  Q  E  A  R  L  G  I  K  P  H  I  Q
```

FIG. 28A (continued)

```
2821        AGGCTGTTGGACCAGGGAATACTGGTACCCTGCCAGTCCCCTGGAACACGCCCCTGCTA
Gag-Pro-Pol  R  L  L  D  Q  G  I  L  V  P  C  Q  S  P  W  N  T  P  L  L

2881        CCCGTTAAGAAACCAGGGACTAATGATTATAGGCCTGTGTCCAGGATCTGAGAGAAGTCAAC
Gag-Pro-Pol  P  V  K  K  P  G  T  N  D  Y  R  P  V  Q  D  L  R  E  V  N

2941        AAGCGGGTGGAAGACATCCACCCCACCGTGCCCAACCCTTACAACCTCTTGAGCGGGCTC
Gag-Pro-Pol  K  R  V  E  D  I  H  P  T  V  P  N  P  Y  N  L  L  S  G  L

3001        CCACCCGTCCCACCAGTGGTACACTGTGCTTGATTTAAAGGATGCCTTTTTCTGCCTGAGA
Gag-Pro-Pol  P  P  S  H  Q  W  Y  T  V  L  D  L  K  D  A  F  F  C  L  R

3061        CTCCACCCCCAGTCAGCCCTCTCTTCGCCCTTTGAGTGGAGAGATCCAGAGATGGGAATC
Gag-Pro-Pol  L  H  P  T  S  Q  P  L  F  A  F  E  W  R  D  P  E  M  G  I

3121        TCAGGACAACTGACCTGGACCAGACTCCCACAGGGTTTCAAAAACAGTCCCACCCTGTTT
Gag-Pro-Pol  S  G  Q  L  T  W  T  R  L  P  Q  G  F  K  N  S  P  T  L  F

3181        GATGAGGCACTGCACAGAGACCTAGCAGATTTCCGGATCCAGCACCCAGACTTGATCCTG
Gag-Pro-Pol  D  E  A  L  H  R  D  L  A  D  F  R  I  Q  H  P  D  L  I  L

3241        CTACAGTACGTGGATGACTTACTGCTGGCCGCCACTTCTGAGCAAGACTGCCAACGAGGT
Gag-Pro-Pol  L  Q  Y  V  D  D  L  L  L  A  A  T  S  E  Q  D  C  Q  R  G
```

FIG. 28A (continued)

```
3301        ACTCGGGGCCCTATTACAAACCCTAGGGAACCTCGGGTATCGGGCCTCGGCCAAGAAGCC
Gag-Pro-Pol  T  R  A  L  L  Q  T  L  G  N  L  G  Y  R  A  S  A  K  K  A

3361        CAAATTGCCAGAAACAGGTCAAGTATCTGGGGTATCTCCTAAAGAGGGACAGAGATGG
Gag-Pro-Pol  Q  I  C  Q  K  Q  V  K  Y  L  G  Y  L  L  K  E  G  Q  R  W

3421        CTGACTGAGGCCAGAAAAGAGACTGTGATGGGGCAGCCCACTCCGAAGACCCCTGACAA
Gag-Pro-Pol  L  T  E  A  R  K  E  T  V  M  G  Q  P  T  P  K  T  P  R  Q

3481        CTAAGGGAGTTCCTAGGGACGGCAGGCTTCTGTGCGCCTCTGGATCCCTGGGTTTGCAGAA
Gag-Pro-Pol  L  R  E  F  L  G  T  A  G  F  C  R  L  W  I  P  G  F  A  E

3541        ATGGCAGCCCCCCTTGTACCCTCTTACCAAAACGGGGACTCTGTTTAATTGGGGCCCAGAC
Gag-Pro-Pol  M  A  A  P  L  Y  P  L  T  K  T  G  T  L  F  N  W  G  P  D

3601        CAGCAAAAGGCCTATCAAGAAATCAAACAGGCTCTTCTAACTGCCCCGCCCTGGGATTG
Gag-Pro-Pol  Q  Q  K  A  Y  Q  E  I  K  Q  A  L  L  T  A  P  A  L  G  L

3661        CCAGATTTGACTAAGCCCTTTGAACTCTTTGTCGACGAGAAGCAGGGCTACGCCCAAAGGC
Gag-Pro-Pol  P  D  L  T  K  P  F  E  L  F  V  D  E  K  Q  G  Y  A  K  G

3721        GTCCTAACGCAAAAACTGGGACCTTGGCGTCGGCCTGTGGCCTACCTGTCCAAAAAGCTA
Gag-Pro-Pol  V  L  T  Q  K  L  G  P  W  R  R  P  V  A  Y  L  S  K  K  L
```

FIG. 28A (continued)

```
3781        GACCCAGTGGCAGCTGGGTGGCCCCCTTGCCTACGGATGGTAGCAGCCATTGCCGTTCTG
Gag-Pro-Pol  D   P   V   A   A   G   W   P   P   C   L   R   M   V   A   A   I   A   V   L

3841        ACAAAGGATGCAGGCAAGCTAACTATGGGACAGCCGCTAGTCATTCTGGCCCCCATGCG
Gag-Pro-Pol  T   K   D   A   G   K   L   T   M   G   Q   P   L   V   I   L   A   P   H   A

3901        GTAGAAGCACTGGTCAAACAACCCCCTGACCGTTGGCTATCCAATGCCCGCATGACCCAC
Gag-Pro-Pol  V   E   A   L   V   K   Q   P   P   D   R   W   L   S   N   A   R   M   T   H

3961        TATCAGGCAATGCTCCTGGATACAGACCGGGTTCAGTTCGGACCGGTGGTGGCCCTCAAC
Gag-Pro-Pol  Y   Q   A   M   L   L   D   T   D   R   V   Q   F   G   P   V   V   A   L   N

4021        CCGGCCACCCTGCTCCCCCTACCGGAAAAGGAAGCCCCCATGACTGCCTCGAGATCTTG
Gag-Pro-Pol  P   A   T   L   L   P   L   P   E   K   E   A   P   H   D   C   L   E   I   L

4081        GCTGAGACGCACGGAACCAGACCGGACCTCACGGACCCCATCCCAGACGCTGATTAC
Gag-Pro-Pol  A   E   T   H   G   T   R   P   D   L   T   D   Q   P   I   P   D   A   D   Y

4141        ACTTGGTACACAGATGGAAGCAGCTTCCTACAAGAAGGACAACGGAGAGCTGGAGCAGCG
Gag-Pro-Pol  T   W   Y   T   D   G   S   S   F   L   Q   E   G   Q   R   R   A   G   A   A

4201        GTGACTACTGAGACCGAGGTAATCTGGGCTCTGCCGGGGCTGGAACATCCGCCCAA
Gag-Pro-Pol  V   T   T   E   T   E   V   I   W   A   R   A   L   P   A   G   T   S   A   Q
```

FIG. 28A (continued)

```
4261  CGAGCCGAACTGATAGCACTCACCCAGCCTTAAAGATGGCAGAAGGTAAGAAGCTAAAT
Gag-Pro-Pol   R  A  E  L  I  A  L  T  Q  A  L  K  M  A  E  G  K  K  L  N

4321  GTTTACACTGATAGCCGCTATGCCTTCGCCACGGCCCATGTCCATGGAGAAATATATAGG
Gag-Pro-Pol   V  Y  T  D  S  R  Y  A  F  A  T  A  H  V  H  G  E  I  Y  R

4381  AGGCGAGGGTTGCTGACCTCAGAAGGCAGAGAAATTAAAAACAAGAGATCTTGGCC
Gag-Pro-Pol   R  R  G  L  L  T  S  E  G  R  E  I  K  N  E  I  L  A

4441  TTGCTAAAAGCTCTCTTTCTGCCCAAACGACTTAGTATAATTCACTGTCCAGGACATCAA
Gag-Pro-Pol   L  L  K  A  L  F  L  P  K  R  L  S  I  I  H  C  P  G  H  Q

4501  AAAGGAAACAGTGCTGAGGCCAGAGGCAACCGTATGGCAGATCAAGCAGCCCGAGAGGCA
Gag-Pro-Pol   K  G  N  S  A  E  A  R  G  N  R  M  A  D  Q  A  A  R  E  A

4561  GCCATGAAGGCAGTTCTAGAAAACCTCTACACTCCTCATAGAGACTCAACCCGTATACG
Gag-Pro-Pol   A  M  K  A  V  L  E  T  S  T  L  L  I  E  D  S  T  P  Y  T

4621  CCTCCCCATTTCCATTACACCGAAACAGATCTCAAAAGACTACGGGAACTGGGAGCCACC
Gag-Pro-Pol   P  P  H  F  H  Y  T  E  T  D  L  K  R  L  R  E  L  G  A  T

4681  TACAATCAGACAAAAGGATATTGGGTCCTACAAGGCAAACCTGTGATGCCCGATCAGTCC
Gag-Pro-Pol   Y  N  Q  T  K  G  Y  W  V  L  Q  G  K  P  V  M  P  D  Q  S
```

FIG. 28B

```
4741  GTGTTTGAACTGTTAGACTCCCTACACAGACTCACCCATCCGAGCCCTCAAAAGATGAAG
Gag-Pro-Pol   V  F  E  L  L  D  S  L  H  R  L  T  H  P  S  P  Q  K  M  K

4801  GCACTCCTCGACAGAGAAGAAAGCCCCTACTACATGTTAAACCGGGACAGAACTATCCAG
Gag-Pro-Pol   A  L  L  D  R  E  E  S  P  Y  Y  M  L  N  R  D  R  T  I  Q

4861  TATGTGACTGAGACCTGCACCGCCTGTGCCCAAGTAAATGCCAGCAAAGCCAAAATTGGG
Gag-Pro-Pol   Y  V  T  E  T  C  T  A  C  A  Q  V  N  A  S  K  A  K  I  G

4921  GCAGGGGTGCCAGTACGCGGAGACATCGGCCAGGCACCCATTGGGAAGTTGATTTCACGGAA
Gag-Pro-Pol   A  G  V  R  V  R  G  H  R  P  G  T  H  W  E  V  D  F  T  E

4981  GTAAAGCCAGGACTGTATGGGTACAAGTACCTCCTAGTGTTTGTAGACACCTTCTCTGGC
Gag-Pro-Pol   V  K  P  G  L  Y  G  Y  K  Y  L  L  V  F  V  D  T  F  S  G

5041  TGGGTAGAGGCATTCCCGACCAAGCGGGAAACTGCCAAGGTTGTGACCAAAAAGCTGTTA
Gag-Pro-Pol   W  V  E  A  F  P  T  K  R  E  T  A  K  V  V  T  K  K  L  L

5101  GAAGACATTTTTCCGAGAGATTTGGAATGCCGCAGGTATTGGGATCTGATAACGGGCCTGCC
Gag-Pro-Pol   E  D  I  F  P  R  F  G  M  P  Q  V  L  G  S  D  N  G  P  A

5161  TTCGCCTCCCAGTAAGTCAGTCAGTGGCCGATTTACTGGGATCGATTGGAAGTTACAT
Gag-Pro-Pol   F  A  S  Q  V  S  Q  S  V  A  D  L  L  G  I  D  W  K  L  H
```

FIG. 28B (continued)

```
5221         TGTGCTTATAGACCCCAGAGTTCAGGACAGGTAGAAAGAATGAATAGAACAATTAAGGAG
Gag-Pro-Pol   C  A  Y  R  P  Q  S  S  G  Q  V  E  R  M  N  R  T  I  K  E

5281         ACTTTGACCAAATTAACGCTTGCATCTGGCACTAGAGACTGGGTACTCCTACTCCCCTTA
Gag-Pro-Pol   T  L  T  K  L  T  L  A  S  G  T  R  D  W  V  L  L  L  P  L

5341         GCCCTCTACCGAGCCCGGAATACTCCGGGCCCCCACGGACTGACTCCGTATGAAATTCTG
Gag-Pro-Pol   A  L  Y  R  A  R  N  T  P  G  P  H  G  L  T  P  Y  E  I  L

5401         TATGGGGCACCCCCGCCCCCTTGTCAATTTTCATGATCCTGAAATGTCAAAGTTAACTAAT
Gag-Pro-Pol   Y  G  A  P  P  P  P  L  V  N  F  H  D  P  E  M  S  K  L  T  N

5461         AGTCCCTCTCTCCAAGCTCACTTACAGGCCCTCCAAGCAGTACAACAAGAGGTCTGGAAG
Gag-Pro-Pol   S  P  S  L  Q  A  H  L  Q  A  L  Q  A  V  Q  Q  E  V  W  K
splice accep                              ------->

5521         CCGCTGGCCGCTGCTTATCAGGACCAGCTAGATCAGCCAGTGATACCACACCCCTTCCGT
Gag-Pro-Pol   P  L  A  A  A  Y  Q  D  Q  L  D  Q  P  V  I  P  H  P  F  R

5581         GTCGGGTGACGCCGTGTGGGTACGCCGGCACCAGACTAAGAACTTAGAACCTCGCTGGAAA
Gag-Pro-Pol   V  G  D  A  V  W  V  R  R  H  Q  T  K  N  L  E  P  R  W  K
```

FIG. 28B (continued)

```
5641        GGACCCTACACCGTCCTGCTGACAACCCCACCGCTCTCAAAGTAGACGGCATCTCTGCG
Gag-Pro-Pol  G  P  Y  T  V  L  L  T  T  P  T  A  L  K  V  D  G  I  S  A

5701        TGGATACACGCCGCTCACGTAAAGGCGGACAACTCCTCCGGCCGGAACAGCATGGAAA
Gag-Pro-Pol  W  I  H  A  A  H  V  K  A  A  T  T  P  P  A  G  T  A  W  K
Env                                                                M  E

5761        GTCCAGCGTTCTCAAAACCCCTTAAAGATAAGATTAACCCGTGGGGCCCCCTGATAATTA
Gag-Pro-Pol  V  Q  R  S  Q  N  P  L  K  I  R  L  T  R  G  A  P  *
Env          S  P  A  F  S  K  P  L  K  D  K  I  N  P  W  G  P  L  I  I

5821        TGGGGATCTTGGTGTGAGGGCAGGAGCCTCAGTACAACGTGACAGCCCTCACCAGTCTTTA
Env          M  G  I  L  V  R  A  G  A  S  V  Q  R  D  S  P  H  Q  V  F

5881        ATGTCACTTGGAAAATTACCAACCTAATGACACAAACAGCTAATGCTACCTCCCCCTCC
Env          N  V  T  W  K  I  T  N  L  M  T  Q  T  A  N  A  T  S  L

5941        TGGGGACGATGACAGACACTTTCCCTAAACTATATTTGACTTGTGTGATTAGTTGGAG
Env          L  G  T  M  T  D  T  F  P  K  L  Y  F  D  L  C  D  L  V  G

6001        ACAACTGGGATGACCCGGAACCCGATATTGGAGATGGTTGCCGCTCTCCCGGGGAAGAA
Env          D  N  W  D  D  P  E  P  D  I  G  D  G  C  R  S  P  G  G  R
```

FIG. 28B (continued)

```
6061  AAAGGACAAGACTATATGATTTCTATGTTTGCCCGGTCATACTGTATTAACAGGGTGTG
Env    K  R  T  R  L  Y  D  F  Y  V  C  P  G  H  T  V  L  T  G  C

6121  GAGGGCCGAGAGAGGGCTACTGTGGCAAATGGGGATGTGAGACCACTGGACAGGCATACT
Env    G  G  P  R  E  G  Y  C  G  K  W  G  C  E  T  T  G  Q  A  Y

6181  GGAAGCCATCATCATCATGGGACCTAATTTCCCTTAAGCGAGGAAACACTCCTAAGGGTC
Env    W  K  P  S  S  S  W  D  L  I  S  L  K  R  G  N  T  P  K  G

6241  AGGGCCCCTGTTTTGATTCCTCAGTGGGCTCCGGTAGCATCCAGGGTGCCACACCGGGGG
Env    Q  G  P  C  F  D  S  S  V  G  S  G  S  I  Q  G  A  T  P  G

6301  GTCGATGCAACCCCCTAGTCCTAGAATTCACTGACGCGGGTAAAAAGGGCCAGCTGGATG
Env    G  R  C  N  P  L  V  L  E  F  T  D  A  G  K  R  A  S  W  D

6361  CCCCCAAAAACATGGGGACTAAGACTGTATCGATCCACTGGGCCGACCCGGTGACCCTGT
Env    A  P  K  T  W  G  L  R  L  Y  R  S  T  G  A  D  P  V  T  L

6421  TCTCTCTGACCCGCCCAGTCCTCAATGTAGGGCCCGCTCCCCATTGGGCCTAATCCCG
Env    F  S  L  T  R  Q  V  L  N  V  G  P  R  V  P  I  G  P  N  P

6481  TGATCACTGAACAGCTACCCCCCTCCCAACCCGTGCAGATCATGCTCCCCAGGCCTCCTC
Env    V  I  T  E  Q  L  P  P  S  Q  P  V  Q  I  M  L  P  R  P  P
```

FIG. 28B (continued)

```
6541  GTCCTCCTCCTTCAGGCGCGGCCTCTATGGTGCCTGGGCTCCCCGCCTTCTCAACAAC
Env    R  P  P  S  G  A  A  S  M  V  P  G  A  P  P  P  S  Q  Q

6601  CTGGGACGGGAGACAGGCTGCTAAACCTGGTAGAAGGAGCCTACCAAGCCCTCAACCTCA
Env    P  G  T  G  D  R  L  L  N  L  V  E  G  A  Y  Q  A  L  N  L

6661  CCAGTCCCGACAAAACCCAGGAGTGTGGCTGTGTCCTAGTATCGGGACCCCCCTACTACG
Env    T  S  P  D  K  T  Q  E  C  W  L  C  L  V  S  G  P  P  Y  Y

6721  AAGGGGTGGCCGTGCTAGGTACTTACTCCAACCATACCTCTGCCCCGGCTAACTGCTCCG
Env    E  G  V  A  V  L  G  T  Y  S  N  H  T  S  A  P  A  N  C  S

6781  TGACCTCCCAACAACAAGCTGACCCTGTCCGAAGTGACCGGACAGGGACTCTGCATAGGAG
Env    V  T  S  Q  H  K  L  T  L  S  E  V  T  G  Q  G  L  C  I  G

6841  CAGTTCCCAAAACCCATCAGGCCCTGTGTAATACCACCCAGAAGACGAGCGACGGGTCCT
Env    A  V  P  K  T  H  Q  A  L  C  N  T  T  Q  K  T  S  D  G  S

6901  ACTATTTGGCCTCTCCCGCCGGGACCATTTGGGCTTGCAGCACCGGGCTCACTCCCTGTC
Env    Y  Y  L  A  S  P  A  G  T  I  W  A  C  S  T  G  L  T  P  C

6961  TATCTACTACTGTGCTTAACTTAACCACTGATTACTGTGTCCTGGTTGAACTCTGGCCAA
Env    L  S  T  T  V  L  N  L  T  T  D  Y  C  V  L  V  E  L  W  P
```

FIG. 28B (continued)

```
7021  AGGTAACCTACCACTCCCCTAATTATGTTTATGGCCAGTTTGGAAAGAAAACTAAATATA
Env    K  V  T  Y  H  S  P  N  Y  V  Y  G  Q  F  G  K  K  T  K  Y

7081  AAAGAGAGCCGGTGTCATTAACTCTGGCCCTGCTGTTGGGAGGACTTACTATGGGCGGCA
Env    K  R  E  P  V  S  L  T  L  A  L  L  L  G  G  L  T  M  G  G

7141  TAGCTGCAGGAGTTGGAACAGGGACTACAGCCCTAGTGGCCACCAAACAATTCGAGCAGC
Env    I  A  A  G  V  G  T  G  T  T  A  L  V  A  T  K  Q  F  E  Q

7201  TCCAGGCAGCCATACATACAGACCCTTGGGGCCCTAGAAAAATCAGTCAGTGCCCTAGAA
Env    L  Q  A  A  I  H  T  D  L  G  A  L  E  K  S  V  S  A  L  E

7261  AGTCTCTGACCTCGTTGTCTGAGGTGGTCCTACAGAACCGGAGGGATTAGATCTACTGT
Env    K  S  L  T  S  L  S  E  V  V  L  Q  N  R  R  G  L  D  L  L

7321  TCCTAAAAGAAGGAGGATTATGTGCTGCCCTAAAAAAGAAAGATGCTGTTTTTACGCGGACC
Env    F  L  K  E  G  G  L  C  A  A  L  K  K  E  C  C  F  Y  A  D

7381  ACACTGGCGTAGTAAGAGATAGCATGGCAAAGCTAAGAGAAAGGTTAAACCAGAGACAAA
Env    H  T  G  V  V  R  D  S  M  A  K  L  R  E  R  L  N  Q  R  Q

7441  AATTGTTCGAATCAGGACAAGGGTGGTTTGAGGGACTGTTTAACAGGTCCCCATGGTTCA
Env    K  L  F  E  S  G  Q  G  W  F  E  G  L  F  N  R  S  P  W  F
```

FIG. 28B (continued)

```
7501  CGACCCTGATATCCACCATTATGGGCCCCTCTGATAGTACTTTTATTAATCCTACTCTTCG
Env    T  T  L  I  S  T  I  M  G  P  L  I  V  L  L  L  L  F

7561  GACCCTGTATTCTCAACCGCTTGGTCCAGTTTGTAAAAGACAGAATTTCGGTAGTGCAGG
Env    G  P  C  I  L  N  R  L  V  Q  F  V  K  D  R  I  S  V  V  Q

7621  CCCTGGTTCTGACCCAACAGTATCACCAACTCAAATCAATAGATCCAGAAGAAGTGGAAT
Env    A  L  V  L  T  Q  Q  Y  H  Q  L  K  S  I  D  P  E  E  V  E

7681  CACGTGAATAAAAAGATTTTATTCAGTTTCCAGAAAGAGGGGGAATGAAAGACCCCACCA
Env    S  R  E  *
U3    ------------------------------------------

7741  TAAGGCTTAGCACGCTAGCTACAGTAACGCCATTTTGCAAGGCATGGAAAAGTACCAGAG
U3    ------------------------------------------------------------

7801  CTGAGTTCTCAAAAGTTACAAGGAAGTTTAATTAAAGAATAAGGCTGAATAACACTGGGA
U3    ------------------------------------------------------------

7861  CAGGGGCCAAACAGGATATCTGTAGTCAGGCACCTGGGCCCCGGCTCAGGGCCAAGAACA
U3    ------------------------------------------------------------
GRE   ------------
```

FIG. 28B (continued)

```
7921  GATGGTCCTCAGATAAAGCGAAACTAACAACAGTTTCTGGAAAGTCCCACCTCAGTTTCA
U3    ||||||||||||||||||||||||||||||||||||||||||||||||||||||||||||
GRE          ------->

7981  AGTTCCCCAAAAGACCGGGAAATACCCCAAGCCTTATTTAAACTAACCAATCAGCTCGCT
U3    ||||||||||||||||||||||||||||||||||||||||||||||||||||||||||||
CAAT box                                       ------->

8041  TCTCGCTTCTGTACCCGCGCTTTTTGCTCCCCAGTCCTAGCCCTATAAAAAGGGGTAAG
U3    ||||||||||||||||||||||||||||||||||||||||||||||||||||||||||||
TATA box                                             ------->

8101  AACTCCACACTCGGGCGCCAGTCATCCGATAGACTGAGTCGCCCGGGTACCCGTGTTCC
U3    ||||||||||||||||||||||||||||||||||||||||||||||||||||||||||||
R     ------->

8161  CAATAAAGCCTTTTGCTGTTTGCAA
R     |||||||||||||||||||||||||
polyA signal  ------->
polyA site              >
```

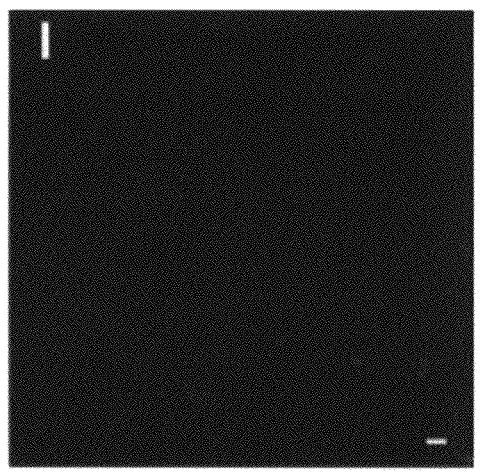 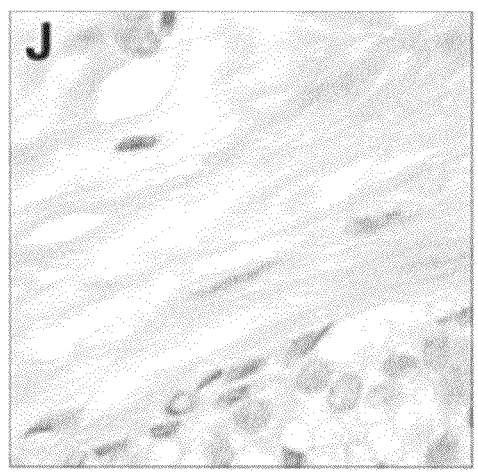
FIG. 33 (cont.)

Site 1  viral  GGGGGTCTTTCA GTTCTTGTGCTCTCTCAGAGGT  (SEQ ID NO: 31)
chromosome 10q11.22
FRMPD Site 2  viral  GGGGGTCTTTCA ACAAGAGCCCGGAATCGCCCGT  (SEQ ID NO: 32)
chromosome 7q22
MLL5

Site 3  viral  GGGGGTCTTTCA GTTGTATATTTCAACTGAAG  (SEQ ID NO: 33)
chromosome 7p15
GPNMB

FIG. 36C

GAMMARETROVIRUS ASSOCIATED WITH CANCER

RELATED APPLICATIONS

This application is a continuation of PCT/US2006/013167, filed Apr. 7, 2006, which claims the benefit of U.S. Provisional Application No. 60/669,473, filed on Apr. 7, 2005, and U.S. Provisional Application No. 60/751,809, filed on Dec. 19, 2005. The entire teachings of the above applications are incorporated herein by reference.

GOVERNMENT SUPPORT

The invention was supported, in whole or in part, by a grant NIH/NCI RO1 CA103943-01 from the National Institutes of Health. The Government has certain rights in the invention.

BACKGROUND OF THE INVENTION

Sexually transmitted diseases have increased in the last 30 years. Such diseases have been linked to cancers (e.g., prostate cancer). Carcinoma of the prostate is the second leading cause of cancer deaths in American men and the most frequent visceral cancer (Kumar, V., et al., S. L. (1997) in *Basic Pathology*, 6th ed., pp. 584-588, W.B. Saunders Co., Philadelphia Kumar et al, 1997). Among populations in the U.S., African Americans have the highest risk. The American Cancer Society estimated that there were about 190,000 new cases and 30,000 deaths from prostate cancer in the US in 2003. Genetics, aging, hormonal, and environmental risk factors all play roles in the pathogenesis of prostate cancer (Nelson W G., et al., *N Engl J Med,* 349(4):366-81, 2003).

A need exists for improved detection and treatment methods for such cancers.

SUMMARY OF THE INVENTION

The present invention is directed to an isolated xenotropic murine leukemia virus (MLV) related virus (XMRV) that can cause cancer in the individual. That is, the etiology of the cancer in the individual is a likely link to the presence of XMRV in the individual.

In one embodiment, the present invention is directed to an isolated XMRV present in a prostate tumor of an individual. In a particular embodiment, the XMRV is a human xenotropic virus (HXV). The individual can have a mutation in the hereditary prostate cancer-1 (HPC1) allele encoding an RNase L gene. In a particular, the mutation is a homozygous mutation (e.g., homozygous for the RNase L mutation R462Q).

In one embodiment, the isolated virus comprises a nucleic acid sequence having at least 94% identity to SEQ ID NO: 1 and a complement thereof. In a particular embodiment, the isolated virus comprises SEQ ID NO: 1 or a complement thereof.

In another embodiment, the invention is directed to an isolated virus comprising an amino acid sequence encoded by a nucleic acid sequence having at least 94% identity to SEQ ID NO: 1. For example, the isolated virus can comprise an amino acid sequence encoded by SEQ ID NO: 1.

The present invention is also directed to isolated peptides. In one embodiment, the invention pertains to an isolated virus comprising SEQ ID NO: 2. In particular embodiments, the isolated polypeptide comprises an amino acid sequence having at least 97% similarity to SEQ ID NO: 3, an amino acid sequence having at least 97% similarity to SEQ ID NO: 4 and/or an amino acid sequence having at least 94% similarity to SEQ ID NO: 5.

The present invention is also directed to a vector comprising one or more of the nucleic acid sequences described herein. The invention further encompasses a cell comprising the vectors. In addition, the invention comprises methods of producing XMRV. In one embodiment, the method comprises maintaining a cell transfected or infected with XMRV. The method can further comprise isolating XMRV produced by the cell (e.g., from a cell supernatant).

Also encompassed by the present invention is an antibody or antigen binding fragment thereof that specifically binds to a virus comprising an amino acid sequence encoded by a nucleic acid sequence having at least 94% identity to SEQ ID NO: 1. The antibody or antigen binding fragment can bind to a gag polypeptide (e.g., SEQ ID NO: 3), a pro-pol peptide (e.g., SEQ ID NO:4) and/or an env polypeptide (e.g., SEQ ID NO: 5) of the virus.

The present invention is also directed to methods of detecting XMRV. In one embodiment, detection of XRMV in an individual indicates that the individual has cancer or at risk of developing cancer (e.g., prostate cancer). The method can comprise detecting the XMRV in the individual by detecting a nucleic acid sequence that encodes all or a portion of the XMRV (e.g., a nucleic acid sequence having at least 94% identity to SEQ ID NO: 1 or a complement thereof). Alternatively, the method can comprise detecting the XMRV in the individual by detecting a polypeptide encoded by the XMRV (e.g., a gag polypeptide, a pol polypeptide, an env polypeptide and combinations thereof).

In another embodiment, the invention is directed to a method of detecting XMRV in a sample comprising contacting the sample with a nucleic acid sequence that hybridizes to all of a portion of an XMRV nucleic acid sequence under conditions in which a hybridization complex can occur between the nucleic acid sequence and the XMRV nucleic acid sequence. Whether the hybridization complex is present in the sample is determined, wherein if the hybridization complex is detected, then XMRV is in the sample.

In another embodiment, the invention relates to a method of detecting XMRV in a sample comprising contacting the sample with an antibody or antigen binding fragment thereof that specifically binds to an XMRV polypeptide under conditions in which a complex can occur between the antibody and the XMRV polypeptide. Whether the complex is present in the sample is determined, wherein if the complex is detected, then XMRV is in the sample.

The present invention is also directed to a method of identifying an agent that inhibits an XMRV comprising contacting the XMRV with an agent to be assessed. Whether XMRV is inhibited in the presence of the agent is determined, wherein if XMRV is inhibited in the presence of the agent, then the agent inhibits XMRV. In a particular embodiment, the activity of the XMRV in the presence of the agent is determined by measuring the ability of the XMRV to produce retroviral particles with reverse transcriptase activity.

Methods of inducing an immune response to an XMRV in an individual in need thereof is also encompassed by the present invention. The method can comprise administering to the individual an effective amount of an agent which induces an immune response to the XMRV in the individual upon administration. The agent can be a subunit of XMRV, an attenuated XMRV and combinations thereof.

The present invention is also directed to a method of treating a cancer (e.g., prostate cancer) in an individual wherein XMRV is present in the individual, such as in a tumor, comprising administering to the individual an effective amount of an agent that inhibits XMRV.

The present invention also pertains to a method of detecting asymptomatic (early stage) cancer (e.g., early stage prostate cancer) in an individual wherein XMRV is present in the prostate of the individual, comprising detecting the presence of an XMRV in the individual, wherein the presence of XMRV in the individual is indicative of early stage prostate cancer in the individual.

Also encompassed by the present invention is a method of identifying an individual at risk for developing cancer (e.g., prostate cancer), comprising detecting the presence of an XMRV in the individual, wherein the presence of XMRV in the individual is indicative of an individual at risk for developing prostate cancer.

The invention is also directed to kits for detecting the presence of XMRV in a sample. In one embodiment, the kit comprises a labeled moiety that detects XMRV in a sample (e.g., a nucleic acid sequence that hybridizes to all of a portion of an XMRV nucleic acid sequence; an antibody or antigen binding fragment thereof that specifically binds to XMRV).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is an agarose gel showing the presence of HXV RNA in human prostate cancer tissue as determined by RTPCR. Ethidium bromide stained 1% agarose gel electrophoresis of nested RT-PCR products. An HXV RNA was detected as a GAG-nested RT-PCR product in VP 10 (but not in VP 107 and VP27) prostate RNA samples, whereas only non-specific amplification products were observed in HEMI-nested lanes. Method: One μg DNase-treated total RNA, 1 uL of reverse primer (100 pmol), and 7.5 uL of $H_2O$ were used per reaction. Denaturation was at 65° C. for 5 min and the primers were annealed at room temperature for 5 min. Ten μl reaction mix (10× buffer (Stratascript) 2 μL, 12.5 mM dNTPs 0.84, H20 3.2 μL, 0.1 M DTT 2 μL, and RT 2 μL) were added and the sample was incubated at 42° C. for 1 hr. Two μL of each RT reaction was then used to seed the PCRs. All primers were at 100 pmol/uL. The PCR recipe for a 50 uL reaction is as follows: 10×PCR buffer (Stratascript) 5 μL, 50 mM $MgCl_2$ 2 μL, outside forward primer 0.5 μL, outside reverse primer 0.5 μL, 25 mM dNTPs 0.5 μL (or 1 μL of 12.5 mM), Taq DNA polymerase 0.5 μL (5 U/μL Invitrogen Inc.), $H_2O$ to 50:Ls. PCR parameters: denaturation at 94° C. for 2 min, [94° C. for 45 sec, outside primer annealing for 45 sec, 72° C. for 1.5 minutes]×30 cycles, followed by an elongation step at 72° C. for 7 min. One μl of the outside PCR was used to seed the inside PCR. The thermalcycling parameters for the inside PCR were exactly the same as the outside, with the exception of primer annealing temperatures. Ld=DNA ladder, −=w/o cDNA.

FIG. 7 is an agarose gel showing the presence of HXV-related RNA in LNCaP (clone R) cell line as determined by RT-PCR. Ethidium bromide stained 1% agarose gel electrophoresis of RT-PCR products. One μg of reverse transcribed (DNase-treated) total RNA from prostate cancer cell lines $LNCaP_R$, PC3, and DU 145 and normal prostate epithelial cell (PrEC) RNA were amplified by RT-PCR using primers specific to the viral env region (top) and GAPDH (bottom). Ld=DNA ladder, −without cDNA, +with cDNA.

FIG. 8 shows that LNCaP cells produce HXV-related virus as determined by reverse transcriptase assays. RT activity observed in virus infected LNCaP cell media at 2, 4 and 8 days of growth (twelve-hour exposure). Media from 2, 4 and 8 days was diluted 1:10 with fresh media before RT assay. Mock reactions containing no media were used as a negative control.

FIG. 11 shows the amino acid sequences of the $HXV_{35}$ gag peptide (SEQ ID NO: 3), the HXV gag peptides (SEQ ID NOS.: 7, 8, 9) used to raise antibody in rabbits and a hydropathy plot generated from HXV35 gag protein.

FIG. 13 shows the amino acid sequence of $HXV_{35}$ (SEQ ID NO: 2).

FIG. 14 shows that amino acid sequence of $HXV_{35}$ gag peptide (SEQ ID NO: 3).

FIG. 15 shows the amino acid sequence of the $HXV_{35}$ pro-pol peptide (SEQ ID NO: 4).

FIG. 16 shows the amino acid sequence of the $HXV_{35}$ env peptide (SEQ ID NO:5).

FIG. 17 is a partial nucleotide sequence of an HXV-LNCaP viral sequence, obtained as an RNA RTPCR product (7084-7750 bp) (SEQ ID NO:6) and which has 97% identity with the $HXV_{35}$ env nucleotide sequence and has 97.6% similarity with the $HXV_{35}$ env amino acid sequence, indicating that the HXV-LNCaP and the $HXV_{35}$ are variants of the same virus.

FIGS. 18A-18D show the immunohistochemical analysis of prostate from patient VP62 which indicates that homozygous R462Q RNase L prostates are XMRV positive by FISH. FIGS. 18A-18D, Left panel: Immunohistochemistry (1HC) (red) with a mouse anti-cytokeratin AE1/AE3 (20:1 mixture of AE1 to AE3) monoclonal Ab cocktail from Roche. The anti-keratin AE1 Ab recognizes the 56.5, 50, 50', 48 and 40 kDa keratins of the acidic subfamily. The anti-keratin AE3 Ab recognizes all 6 members of the basic subfamily. The IHC (red) labels prostate epithelial cells. The green label is FISH for $HXV_{35}$ env probe as described in the legend to FIG. 9. Blue is DAPI staining of nuclei. FIGS. 18A-18D, Right panel. Hematoxylin and eosin staining.

FIG. 19, Left panel: immunohistochemistry with specific antiserum prepared in goats to Rauscher mouse leukemia virus p30 protein (ATCC, catalog no. VR-1564AS-Gt) showing labeling of HXV gag protein plus DAPI (blue) staining of nuclei. Right panel: DAPI staining of nuclei.

FIGS. 22A-22B shows XMRV detection by DNA microarrays and RT-PCR. FIG. 22A shows Virochip hybridization patterns obtained for tumor samples from 19 patients. The samples (x axis) and the 502 retroviral oligonucleotides present on the microarray (y axis) were clustered using hierarchical clustering. The color bar indicates the range of observed hybridization intensities. The magnified view shows a selected cluster containing oligonucleotides with the strongest positive signal. Samples from patients with QQ RNASEL genotype are shown in red, and those from RQ and RR individuals as well as controls are in black. FIG. 22B shows results of nested RT-PCR specific for XMRV gag gene. Amplified gag PCR fragments along with the corresponding human GAPDH amplification controls were separated by gel electrophoresis using the same lane order as in the microarray cluster.

FIG. 23A is chematic map of the 8185 nt XMRV genome. LTR regions (R, U5, U3) are indicated with boxes. Predicted open reading frames encoding Gag, Gag-Pro-Pol, and Env polyproteins are labeled in green. The corresponding start and stop codons (AUG, UAG, UGA, UAA) as well as the alternative Gag start codon (CUG) are shown with their nucleotide positions. Similarly, splice donor (SD) and acceptor (SA) sites are shown and correspond to the spliced 3.2 Kb Env subgenomic RNA (wiggled line). FIG. 23B shows the cloning and sequencing of XMRV VP35 genome. Clones obtained by probe recovery from hybridizing microarray oligonucleotides (blue bars) or by PCR from tumor cDNA (black bars) were sequenced. Primers used to amplify individual clones (Table 10) were derived either from the genome of MTCR (black arrows) or from overlapping VP35 clones (blue arrows). FIG. 23C shows the genome sequence similarity plots comparing XMRV VP35 with XMRV VP42, MuLV DG-75, and MTCR. The pair-wise alignments were made using AVID (Bray, N., et al., *Genome Res.*, 13:97-102 (2003)), and plots were generated using mVISTA (Frazer, K A, et al., *Nucleic Acids Res.*, 32:W273-279 (2004)) with the default window size of 100 nucleotides. Y axis scale represents percent nucleotide identities from 50 to 100%.

FIG. 25 shows multiple-sequence alignment of protein sequences from XMRV and related MuLVs spanning SU glycoprotein variable regions (VRA and VRB) known to determine receptor specificity (Battini J L., et al., *J Virol* 66: 1468-1475; Tailor C S., et al., *Immunol* 281: 29-106). Env protein sequences from XMRV VP35 (SEQ ID NO.: 10) and VP42 (SEQ ID NO.: 11); MTCR (SEQ ID NO.: 14); MuLVs DG-75 (SEQ ID NO.: 12), NZB-9-1 (SEQ ID NO.: 13), MCF1233 (SEQ ID NO.: 15), Akv (SEQ ID NO.: 19), Moloney (SEQ ID NO.: 18), Friend (SEQ ID NO.: 16), and Rauscher (SEQ ID NO.: 17) were aligned using ClustalX with the default settings. Sequences are labeled as xenotropic (X), polytropic (P), or ecotropic (E) based on published experimental evidence (Raisch K P., et al., *Virology* 308: 83-91;, O'Neill R R., et al., *J Virol* 53: 100-106; Perryman S., et al., *Nucleic Acids Res* 19: 6950; Shinnick T M., et al., *Nature* 293: 543-548; Sijts E J., et al., *Virus Res* 34: 339-349, Khimani A H., et al., *Virology* 238: 64-67; Lenz J., et al., *J Virol* 42: 519-529). Variable regions VRA and VRB are shown as boxes. Nucleotide positions to the right of the alignment are relative to the Env start codon.

FIG. 26 shows multiple-sequence alignment of 5'gag leader nucleotide sequences from XMRV and related MuLVs. Sequences extending from the alternative CUG start codon to the AUG start codon of gag derived from XMRV VP35 (SEQ ID NO.: 20) and VP42 (SEQ ID NO.: 21); MTCR (SEQ ID NO.: 22), MuLVs DG-75, (SEQ ID NO.: 24), MCF1233, (SEQ ID NO.: 23) and Friend (SEQ ID NO.: 25) were aligned with ClustalX using the default settings. Predicted amino acid translation corresponding to the VP35 sequence is shown above the alignment; "*" indicates a stop. Nucleotide positions to the right of the alignment are relative to the C of the alternative CUG start codon.

FIG. 27A shows a phylogenetic tree based on the 380 nt XMRV gag RT-PCR fragment from the 9 positive tumor samples and the corresponding sequences from MTCR; and MuLVs DG-75, MCF1233, Akv, Moloney, Rauscher and Friend. The sequences were aligned using ClustalX, and the corresponding tree was generated using the neighbor joining method (see materials and methods). XMRV fragments from tumor samples are indicated in red. FIG. 27B sows a phylogenetic tree based on a 2500 nt pol PCR fragment from the 9 XMRV-positive tumor samples. PCR fragments were obtained using amplified cDNA as the template. The tree was constructed as described in FIG. 27A.

FIGS. 28A-28B shows the complete nucleotide sequence of XMRV VP35 (SEQ ID NO.: 26). Numbers to the left indicate nucleotide coordinates relative to the first nucleotide. Predicted open reading frames for Gag (SEQ ID NO.: 27); Gag-Pro-Pol (SEQ ID NO.: 28) and Env (SEQ ID NO.: 29) polyproteins are shown below the corresponding nucleotides. Characteristic 24-nt deletion in the 5' gag leader is indicated with a triangle. Other genome features as well as primers used in the nested gag RT-PCR are shown as arrows.

FIG. 34A shows RT-PCR results indicating the presence of a gammaretrovirus in LNCaP-R cells. PCR amplicons for a 700 bp env-LTR region are separated on a 1% agarose gel stained with ethidium bromide. Prostate cell lines used are indicated at the top. RT-PCR for the eighth exon of human GAPDH mRNA is included for comparison. FIG. 34B shows phylogenetic analysis of XMRV LNCaP-R based on complete genome sequences. Complete genomes of XMRV LNCaP-R; XMRV VP35 and VP42 (Urisman A., et al., *PLOS Pathogens*; MTCR; MuLVs DG-75, MCF1233, Akv, Moloney, Friend, and Rauscher; Feline leukemia virus (FLV); Koala retrovirus (KoRV); and Gibbon ape leukemia virus (GALV) were aligned with ClustalX using default settings. An unrooted neighbor-joining tree was generated (see Materials and Methods) based on the alignment. Bootstrap values (N=1000 trials) are indicated. MuLV genomes are labeled as xenotropic (X), polytropic (P), or ecotropic (E). FIG. 34C shows multiple-sequence alignment of 5'gag leader nucleotide sequences from XMRV-LNCaP RV and related MuLVs. Using default settings of ClustalX (Example 3, Materials and Methods) sequences extending from the alternative CUG start codon to the AUG start codon of gag derived from XMRV-LNCaP RV (SEQ ID NO.: 30), XMRV-VP35 (SEQ ID NO.: 20) and VP42 (SEQ ID NO.: 21), MTCR (SEQ ID NO.: 22), MuLVs DG-75 (SEQ ID NO.: 24), MCF1233 (SEQ ID NO.: 23), and Friend MuLV (SEQ ID NO.: 25) were aligned. Nucleotide positions to the right of the alignment are relative to the first position of the alternative CUG start codon. "*" above the aligned nucleotide sequences indicates a stop codon. FIG. 34D shows genome sequence similarity plots comparing XMRV-VP35, MTCR, MCF1233 and MuLV DG-75 relative to XMRV-LNCaP RV. The alignments were created using AVID (Bray N., et al., *Genome Res* 13: 97-102). Plots were visualized using VISTA (Frazer K A., et al., *Nucleic Acids Res* 32: W273-279) with the default window size of 100 nucleotides. Y axis scale represents percent nucleotide identities from 50 to 100%. Similarity plots are shown relative to the predicted open reading frames for XMRV LNCaP-R, which are represented as black bars.

FIG. 35A is a schematic map of the 8185 nt XMRV-LNCaP RV genome. LTR regions (R, U5, U3) are indicated with open boxes. Predicted open reading frames encoding Gag, Gag-Pro-Pol, and Env polyproteins are labeled in green. The nucleotide positions of the corresponding start and stop codons (AUG, UAG, UGA, UAA) as well as the alternative Gag start codon (CUG) are indicated. Similarly, splice donor (SD) and acceptor (SA) nucleotide positions corresponding to the spliced 3.2 kb env subgenomic RNA sites are shown. Northern Blot probes used in (FIG. 35B) are represented as black bars relative to the positon within the genome. FIG. 35B shows the presence of viral transcripts in the LNCaP-R cell line by Northern Blot analysis. Total RNA isolated from the cell lines LNCaP R, Raji, NIH3T3 and DU145 was separated on a 1.2% formaldehyde agarose gel, blotted and probed with radiolabeled DNA corresponding to nucleotide positions 7780-7991 within the LTR region (left). Position of the full length and spliced message are represented with an arrow. The blot was stripped (Material and Methods) and reprobed using a radiolabeled XMRV VP35 Gag probe (positions 603-957) capable of detecting only the full length transcript (right). Size markers to the left indicate the sizes of the human 18S ribosomal RNA (1.9 kb) and the 28S ribosomal RNA (5 kb). FIG. 35C shows the screening for the presence of LNCaP-RV in different cell lines with affinity purified polyclonal antibody against an XMRV VP35 Gag (NC) peptide (red) in LNCaP-R, LNCaP-FGC, DU145 and PC3 cells (as indicated). Nuclei were counterstained using DAPI. Immunofluorescence images were captured using a Texas Red filter. Bar shown in the panel is 30 μm.

FIGS. 36A-36C show the following. FIG. 36A shows viral integration sites in the LNCaP-R cell line. Southern blot of genomic DNA isolated from the human cell lines LNCaP-R, LNCaP-FGC, DU145 and the mouse cell line NIH3T3 digested with PstI and probed with radiolabeled probe derived from XMRV-VP35 U3 LTR region (nucleotide positions 7780-7991). Positions of molecular weight markers separated in a 0.8% agarose gel are indicated on the right. Multiple integration sites within the DNA of LNCaP-R cells are pointed out with arrows on the left. FIG. 36B shows ethidium bromide staining of the PstI digested genomic DNA in (FIG. 36A) shows relative amounts of genomic DNA loaded. FIG. 36C shows sequences of three different XMRV LNCaP-R integration sites (SEQ ID NOS.: 31, 32, 33). The sites were determined by a modified linker mediated PCR technique (see Example 3, Material and Methods). Viral sequences are boxed; above each sequence chromosome positions of the corresponding integration sites are indicated.

FIG. 37A shows reverse transcriptase assays using cell supernatants were performed in duplicate (−Virus) or in quadruplicate (+Virus) at the indicated times after infection. Autoradiograph of the reverse transcriptase assays spotted to DEAE paper is shown on the left. Quantitation of reverse transcriptase activity by phosphorimage analysis is shown on the right. FIG. 37B shows Northern Blot analysis of the mock (−) or LNCaP-RV (+) infected cell lines 24 hr after infection. Total RNA was extracted, separated on a 1.2% Formaldehyde gel, blotted and probed with a radiolabeled XMRV VP35 LTR probe (positions 7780-7991). Size markers to the left indicate the sizes of the human 18S ribosomal RNA (1.9 kb) and the 28S ribosomal RNA (5 kb). FIG. 37C shows Southern Blot analysis of the mock (−) or LNCaP-RV (+) infected cell lines 36 hr after infection. Genomic DNA of LNCaP-FGC and DU145 cells infected or mock infected was extracted (see Example 3, Material and Methods), digested with PstI, separated on a 0.8% Agarose-gel, blotted and probed with a radiolabeled XMRV VP35 U3 LTR probe (positions 7780-7991). Numerous de novo integration events are indicated by brackets to the left. NIH3T3 genomic DNA was used as a positive control. Molecular weight markers are shown on the right.

DETAILED DESCRIPTION OF THE INVENTION

Figure 1:
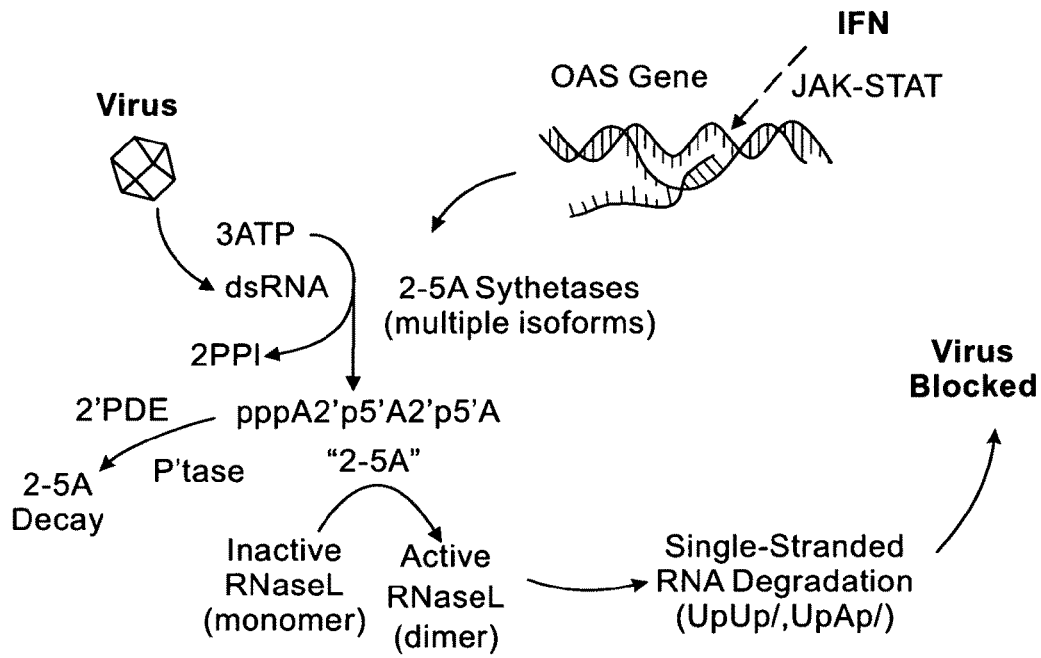
FIG. 1 is a schemtaic illustrating the role of the 2-5 A/RNase L system in the antiviral activity of interferons; 2'-PDE, 2',5'-phosphodiesterase; P'tase, 5'-phosphatase.

As described herein, the role of the antiviral enzyme, RNase L, in prostate tumor biology was investigated. A clinical study was performed in which 150 prostate cancer patients scheduled for prostatectomies were genotyped for the most common germline mutation in RNase L (R462Q). RNA isolated from the prostate tissues was processed for analysis on Virochips, a comprehensive DNA microarray of viral sequences. A novel gammaretrovirus related to xenotropic strains of murine leukemia virus (referred to herein as xenotropic murine leukemia virus (MLV) related virus (XMRV) was identified and cloned from patients homozygous for the RNase L mutation. In a particular embodiment, the XMRV is human xenotropic virus (HXV). HXV infection of the prostate was common in patients homozygous for the RNase L mutation R462Q (about 60% incidence), but relatively infrequent in heterozygous and in homozygous wild type patients (incidence of 10% or less). In situ methods confirmed the presence of HXV nucleic acid in prostates.

Accordingly, the present invention provides for isolated nucleic acid sequences encoding XMRV isolated polypeptides comprising amino acid sequences of XMRV; vectors comprising the viral nucleic acid sequences; cells comprising the vectors; antibodies and antigen binding fragments thereof which have binding specificity for XMRV; methods of producing XMRV; methods of detecting or screening for XMRV (e.g., in an individual); methods of identifying agents that inhibit XMRV; methods of inducing an immune response to XMRV; methods of treating disease associated with the presence of XMRV in an individual (e.g., cancer such as prostate cancer); methods of detecting asymptomatic cancer (e.g., prostate cancer); methods of identifying an individual at risk for developing cancer (e.g., prostate cancer); and kits for detecting the XMRV.

Carcinoma of the prostate is the second leading cause of cancer deaths in American men and the most frequent visceral cancer (Kumar, V., et al., *Basic Pathology*, 6th ed., pp. 584-588, W.B. Saunders Co., Philadelphia). Among populations in the U.S., African Americans have the highest risk. The American Cancer Society estimated that there were about 190,000 new cases and 30,000 deaths from prostate cancer in the US in 2003. Genetics, aging, hormonal, and environmental risk factors all play roles in the pathogenesis of prostate cancer (Nelson W G., et al., *N Engl J Med,* 349(4):366-81, 2003). Remarkably, men with three or more first-degree relatives with prostate cancer have an 11-fold increased risk compared with men that have no family history of the disease (Steinberg G D., et al., *Prostate,* 17(4):337-47, 1990). Segregation analysis supports the existence of rare autosomal dominant, highly penetrant gene(s) in hereditary prostate cancer (HPC) with early onset (Carter B S., et al., *Proc Natl Acad Sci,* 89(8):3367-71, 1992). Several different HPC genes are predicted to collectively account for about 43% of early onset (less than or equal to 55 years) disease and 9% of all cases of prostate cancer. These inherited prostate cancer susceptibility genes are believed to function at an early stage in the molecular pathogenesis of prostate cancer, during the progression of normal prostate epithelium to proliferative inflammatory atrophy (PIA) (Nelson W G., et al., *N Engl J Med,* 349(4):366-81, 2003). Chronic or recurrent microbial infections are suspected initiating events in PIA. PIA lesions, in turn, may be precursors of prostate intraepithelial neoplasia (PIN) and, after many years, lead to overt carcinoma and finally to metastatic cancer. The prostate has been suggested by others to be a resident organ for mutiple viral infections including the human BK polyomavirus (Das D., et al., *Oncogene,* 23(42):7031-46, 2004) and HPV (Zambrano A., et al., *Prostate,* 53(4):263-76, 2002). In addition, a large case-control study showed an association between prostate cancer frequency and a history of sexually transmitted diseases (Hayes R B., et al., *Br J Cancer,* 82(3):718-25, 2000). Interestingly, five candidate prostate cancer susceptibility alleles function in immunity and/or inflammation (HPC1/RNASEL, TLR4, MIC-1, MSR-1 and PON1) (Carpten, J., et al., *Nature Genetics* 30:181-4, 2002; Zheng S L., et al., *Cancer Res.* 64(8):2918-22, 2004; Lindmark F., et al., *J Natl Cancer Inst.* 96(16):1248-54, 2004; Xu, J., et al., *Nat. Genet.* 32(2):321-5, 2002; Marchesani M., et al., *J Natl Cancer Inst.* 95(11):812-8, 2003).

Figure 2:
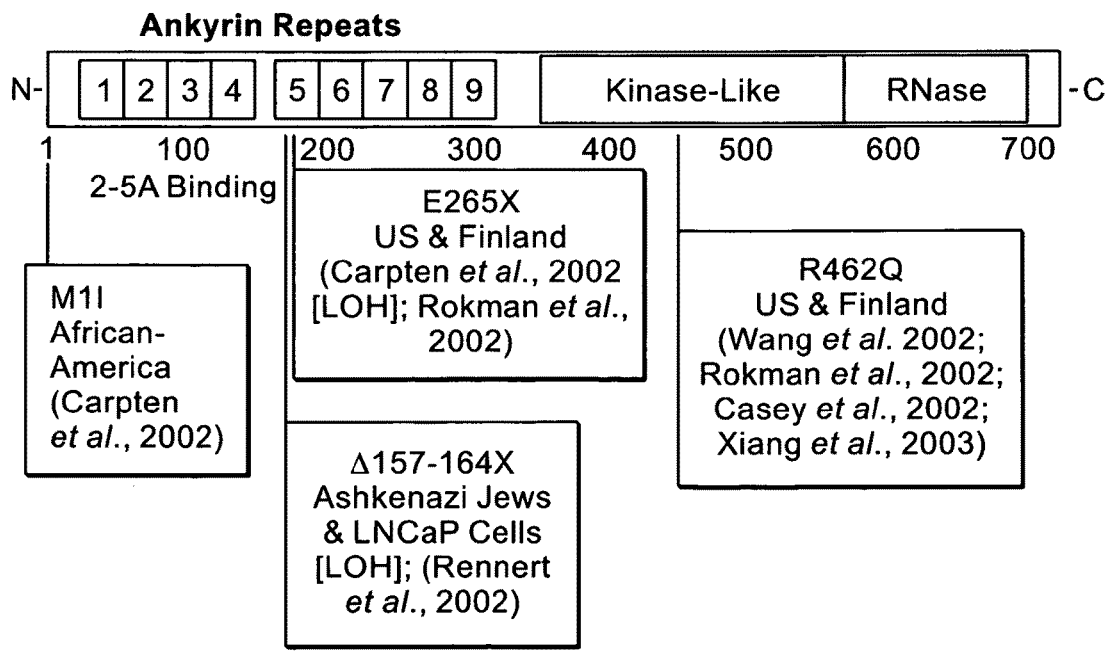
FIG. 2 is a schematic illustrating RNASEL mutations in different populations of prostate cancer cases aligned to the domain structure of RNase L; LOH, loss of heterozygosity (Carpten, J, et al., *Nature Genetics* 2002; 30:181-4; Rokman A., et al., *Am J Hum Genet.* 2002 May; 70(5):1299-304; Rennert, H., et al., *Am J Hum Genet.* 2002 October; 71(4): 981-4; Wang D., et al., *Proc Natl Acad Sci USA.* 2002 Nov. 26; 99(24):15687-92; Casey G., et al., *Nat. Genet.* 2002 December; 32(4):581-3; Xiang Y., et al., *Cancer Res.* 2003; 63(20): 6795-801).

HPC1, the prototype of the gene family, was linked to chromosome 1q24-25 in 1996 (Smith et al., 1996) and to the RNASEL gene at 1q25 in 2002 (Carpten, J., et al., *Nature Genetics* 30:181-4, 2002). HPCI/RNASEL encodes a regulated nuclease, RNase L, that functions in the interferon (IFN) antiviral response (Clemens M J, et al., *Cell* 13(3):565-72, 1979; Zhou A., et al., *Cell* 72(5):753-65, 1993; Hassel B A, et al., *EMBO J.* 12(8):3297-304, 1993). IFN treatment of cells induces a family of 2-5A synthetases that are stimulated by double stranded RNA to convert ATP to PPi and a series of short 2' to 5' linked oligoadenylates, collectively referred to as 2-5A (Kerr I M, et al., *Proc Natl Acad Sci USA.* 75(1):25660, 1978). (FIG. 1). The only well established function of 2-5A is activation of RNase L leading to inhibition of the replication of certain viruses, including Coxsackievirus (Flodstrom-Tullberg, M., et al., *J. Immunol.,* 174, 1171-1177, 2005). Upon binding 2-5A, RNase L converts from inactive monomers to active dimers (Dong B., et al., *J Biol. Chem.* 270(8): 4133-7, 1995). Sustained activation of RNase L by 2-5A binding leads to cleavage of 28S and 18S rRNA and to caspase-dependent apoptosis (Rusch L., et al., *J Interferon Cytokine Res.* 20(12):1091-100, 2000). RNase L-mediated apoptosis is accompanied by cytochrome C release from mitochondria and requires JNK and caspase-3 activity (Iordanov M S, et al., *Mol Cell Biol.* 20(2):617-27, 2000); Li G., et al., *J Biol. Chem.* 279(2):1123-31, 2004; Malathi K., et al., *Cancer Res.* 64(24):9144-51, 2004). Previously it has been demonstrated that activation of RNase L by 2-5A leads to apoptosis of late-stage human prostate cancer cell lines whereas naturally-occurring mutations in RNASEL allow cell survival (Xiang Y., et al., *Cancer Res.* 63(20):6795-801, 2003). Involvement of RNASEL/HPC1 in hereditary prostate cancer is supported by identification and association of different mutations (Mil, E265X, 471)AAAG, & R462Q) with disease onset and/or frequency (Carpten, et al., *Nature Genetics* 30:181-4, 2002; Rokman A., et al., *Am J Hum Genet.* 70(5):1299-304, 2002; Rennert H., et al., *Am J Hum Genet.* 71(4):981-4, 2002; Casey, G., et al., *Nat. Genet.* 32(4):581-3, 2002; Silverman, R. H, *Biochemistry* 72, 25; 42(7):1805-12., 2003) (FIG. 2). Functional or epidemiological data for a role of RNASEL in HPC have been observed in most, but not all studies (Downing S R., et al., *Clin Prostate Cancer* 2:177-80, 2003; Kotar K., et al., *J Med Genet.* 40: e22, 2003.

Recently the R462Q variant of RNASEL has been implicated in unselected (including both familial and non-familial) prostate cancer cases (Casey G., et al., *Nat. Genet.* 32(4):581-3, 2002). Interestingly, the R462Q variant of RNase L had about 3-fold reduced catalytic activity in vitro. The reduced ribonuclease activity of RNase L R462Q is due to a decreased capacity to dimerize into the active form of the enzyme (Xiang Y., et al., *Cancer Res.* 63(20):6795-80, 2003). An expanded study was performed on DNA isolated from 423 unselected prostate cancer cases and 454 unaffected sibling controls (Casey G., et al., *Nat. Genet.* 32(4):581-3, 2002). A significant association of the R462Q variant with cases was observed (P=0.011). The odds ratios indicated that carrying one copy of the R462Q variant gene increased risk of prostate cancer by about 1.5-fold, while having two variant alleles doubled the risk. On the other hand, another variant of RNase L, D541E, was not associated with increased risk of prostate cancer and did not affect RNase L activity. Results implicated R462Q in up to 13% of cases, which would make it the most prevalent genetic marker for prostate cancer (and possibly for any of the common cancers). Therefore, R462Q could be an important risk marker for prostate cancer in the general male population.

As described herein, viruses in tumor-bearing prostates were identified and compared to virus frequency in men with different RNASEL genotypes. Because inactivating mutations in RNase L are relatively rare, the studies focused on the missense variant R462Q. Traditional viral detection methods have several disadvantages including failure of some viruses to grow in cell culture, limits to the number of DNA sequences that can be simultaneously amplified by multiplex PCR, antibody availability and evolving viral serotypes. Therefore, to determine an association of certain viruses with prostate cancer, a microarray-based detection method (Virochip) was used for genotyping viral pathogens developed at UCSF by Drs. DeRisi and Ganem (Wang D., et al., *Proc Natl Acad Sci USA.* 99(24):15687-92, 2002; Wang D., et al., *Biol.* 1(2):E2. Epub, 2003). These microarrays contain long (70-mer) oligonucleotides that can detect and identify several hundred different types of viruses. Because the array contains highly conserved sequences within viral nucleic acids, it can detect viruses not explicitly represented. A novel gammaretrovirus related to xenotropic strains of murine leukemia virus (referred to herein as xenotropic murine leukemia virus (MLV) related virus (XMRV) was identified and cloned from patients homozygous for the RNase L mutation.

Accordingly, the present invention provides an isolated or recombinant xenotropic murine leukemia virus (MLV) related virus (XMRV). The present invention also relates to isolated or recombinant XMRV proviruses and retroviral particles (e.g., produced by cells infected with XMRV). In one embodiment, the XMRV virus is an isolated or recombinant human xenotropic virus (HXV).

The invention embodies virus deposited with the A.T.C.C., 10801 University Boulevard, Manassass, Va., 02110-2209 on Mar. 30, 2005, designated A.T.C.C. No. PTA-6650, or virus derived therefrom. The virus deposited with the A.T.C.C. is designated Human Xenotropic Virus (HXV)-LNCaP (HXV-LN) isolated from an LNCaP clone, animal (human). HXV is a retrovirus (gamma) related to murine leukemia virus (MLV), gag reacts with Rausher MLV P30 antibody (A.T.C.C. Accession No. VR-15645A-Gt) on Western blots. As indicated herein, the virus can be grown in cell lines LNCaP (A.T.C.C. Accession No. CRL-1740) and DU145 (A.T.C.C. Accession No. HTB-81). Cell line media and conditions for growth of the cell lines in which the virus can be grown include RPMI 1640 with O-Glucose 2.0 g/L, Glutamine (2.05 mM) 300 mg/L, Pyridoxine HCl 1.0 mg/L, sodium bicarbonate 2 g/L, fetal bovine serum (heat-inactivated) 10%, PEN/STREP 200 units, air, 95%: $CO_2$, 5%, 37° C. Infected cell (e.g., LNCaP cells) supernatant fluid can be centrifuged (e.g., at 12,000 g for 15 minutes) followed by filtration (e.g., through two successive 0.2 um filters).

Nucleic Acid Molecules

The present invention provides isolated XMRV nucleic acid molecules. By an "XMRV nucleic acid molecule" is meant a nucleic acid molecule that encodes an XMRV polypeptide. Such nucleic acid molecules include, for example, the XRMV nucleic acid molecule described in detail herein; an isolated nucleic acid comprising SEQ ID NO: 1; a complement of an isolated nucleic acid comprising SEQ ID NO: 1; an isolated nucleic acid encoding an XMRV polypeptide of SEQ ID NO: 2; a complement of an isolated nucleic acid encoding an XRMV polypeptide of SEQ ID NO: 2; a nucleic acid that is hybridizable under high stringency conditions to a nucleic acid molecule that encodes SEQ ID NO: 1 or a complement thereof; a nucleic acid molecule that is hybridizeable under high stringency conditions to a nucleic acid comprising SEQ ID NO: 1; and an isolated nucleic acid molecule that has at least 55%, 60%, 65%, 70%, 75%, 80%, 85%, 90%, 92, 94% 95%, 96%, 97%, 98% or 99% sequence identity with all or a portion of SEQ ID NO: 1, or a complement thereof. In one embodiment, the percent identity is determined over the full length of the XMRV nucleic acid molecule (e.g., the full length of SEQ ID NO:1). In another embodiment, the percent identity is determined over a portion of the XMRV nucleic acid molecule (e.g., the portion encoding the gag, pro-pol and/or env polypeptide of XMRV). For example, the isolated nucleic acid molecule can have at least 70%, 75%, 80%, 85%, 90%, 92%, 94%, 95%, 96%, 97%, 98% or 99% sequence identity with a portion of SEQ ID NO: 1 that encodes the pol polypeptide of an XMRV (e.g., SEQ ID NO:4).

The isolated nucleic acid molecules of the present invention can be RNA, for example, mRNA, or DNA, such as cDNA. DNA molecules can be double-stranded or single-stranded; single stranded RNA or DNA can be either the coding (sense) or non-coding (antisense) strand. The nucleic acid molecule can include all or a portion of the coding sequence of the gene and can further comprise additional non-coding sequences such as introns and non-coding 3' and 5' sequences (including regulatory sequences, for example). Additionally, the nucleic acid molecule can be fused to a marker sequence, for example, a sequence that encodes a polypeptide to assist in isolation or purification of the polypeptide. Such sequences include, but are not limited to, FLAG tags, as well as sequences that encode a glutathione-S-transferase (GST) fusion protein and those that encode a hemagglutinin A (HA) polypeptide marker from influenza.

An "isolated," "substantially pure," or "substantially pure and isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA or cDNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an isolated nucleic acid molecule comprises at least about 50%, 80%, 90%, 95%, 98% or 99% (on a molar basis) of all macromolecular species present.

The XMRV nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Therefore, recombinant DNA contained in a vector are included in the definition of "isolated" as used herein.

Isolated nucleotide molecules also include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded polypeptide, as probes for isolating homologous sequences (e.g., from other mammalian species) or for detecting expression of the gene in tissue (e.g., human tissue), such as by Northern blot analysis.

The present invention also pertains to variant XMRV nucleic acid molecules that are not necessarily found in nature but that encode an XMRV polypeptide. Thus, for example, DNA molecules that comprise a sequence that is different from a naturally-occurring XRMV nucleotide sequence but which, due to the degeneracy of the genetic code, encode an XMRV polypeptide of the present invention are also the subject of this invention.

The invention also encompasses XMRV nucleotide sequences encoding portions (fragments), or encoding variant polypeptides such as analogues or derivatives of an XMRV polypeptide. In one embodiment, a fragment of an XMRV nucleotide sequence comprises SEQ ID NO: 6. Such variants can be naturally-occurring, such as in the case of allelic variation or single nucleotide polymorphisms, or non-naturally-occurring, such as those induced by various mutagens and mutagenic processes. Intended variations include, but are not limited to, addition, deletion, and substitution of one or more nucleotides that can result in conservative or non-conservative amino acid changes, including additions and deletions. Preferably, the XMRV nucleotide (and/or resultant amino acid) changes are silent or conserved; that is, they do not alter the characteristics or activity of the XMRV polypeptide.

Other alterations of the XMRV nucleic acid molecules of the invention can include, for example, labeling, methylation, internucleotide modifications such as uncharged linkages (e.g., methyl phosphonates, phosphotriesters, phosphoamidates, and carbamates), charged linkages (e.g., phosphorothioates or phosphorodithioates), pendent moieties (e.g., polypeptides), intercalators (e.g., acridine or psoralen), chelators, alkylators, and modified linkages (e.g., alpha anomeric nucleic acids).

The invention also pertains to XMRV nucleic acid molecules that hybridize under high stringency hybridization conditions, such as for selective hybridization, to a nucleotide sequence described herein (e.g., nucleic acid molecules that specifically hybridize to a nucleotide sequence encoding XMRV polypeptides described herein, and, optionally, have an activity of the XMRV polypeptide). In one embodiment, the invention includes variants described herein that hybridize under high stringency hybridization conditions (e.g., for selective hybridization) to a nucleotide sequence comprising the nucleotide sequence of SEQ ID NO: 1, and the complement of SEQ ID NO: 1. In another embodiment, the invention includes variants described herein that hybridize under high stringency hybridization conditions (e.g., for selective hybridization) to a nucleotide sequence encoding an amino acid sequence of SEQ ID NO: 2. In a preferred embodiment, the variant that hybridizes under high stringency hybridizations encodes a polypeptide that has a biological activity of an XMRV polypeptide (e.g., ability to infect prostate tissue).

Activities of XMRV include the ability to infect a cell (e.g., a prostate cell), produce a provirus and produce retroviral particles.

Such nucleic acid molecules can be detected and/or isolated by specific hybridization (e.g., under high stringency conditions). "Stringency conditions" for hybridization is a term of art that refers to the incubation and wash conditions, e.g., conditions of temperature and buffer concentration, that permit hybridization of a particular nucleic acid to a second nucleic acid; the first nucleic acid may be perfectly (i.e., 100%) complementary to the second, or the first and second may share some degree of complementarity that is less than perfect (e.g., about or at least 70%, 75%, 85%, 94% 95%, 96%, 97%, 98%, 99%). For example, certain high stringency conditions can be used that distinguish perfectly complementary nucleic acids from those of less complementarity. "High stringency conditions," "moderate stringency conditions," and "low stringency conditions" for nucleic acid hybridizations are explained in Current Protocols in Molecular Biology (See Ausubel et al., supra, the entire teachings of which are incorporated by reference herein). The exact conditions that determine the stringency of hybridization depend not only on ionic strength (e.g., 0.2×SSC or 0.1×SSC), temperature (e.g., room temperature, 42° C. or 68° C.), and the concentration of destabilizing agents such as formamide or denaturing agents such as SDS, but also on factors such as the length of the nucleic acid sequence, base composition, percent mismatch between hybridizing sequences, and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 85%, at least about 90% or at least about 95% or more identical to each other remain hybridized to one another. By varying hybridization conditions from a level of stringency at which no hybridization occurs to a level at which hybridization is first observed, conditions that will allow a given sequence to hybridize (e.g., selectively) with the most similar sequences in the sample can be determined.

Exemplary hybridization conditions are described in Krause and Aaronson, Methods in Enzymology, 200:546-556 (1991), and also in Ausubel, et al., supra, which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in Tm of 17° C. Using these guidelines, the washing temperature can be determined empirically for high, moderate, or low stringency, depending on the level of mismatch sought.

For example, a low stringency wash can comprise washing in a solution containing 0.2×SSC/0.1% SDS for 10 minutes at room temperature; a moderate stringency wash can comprise washing in a prewarmed solution (42° C.) solution containing 0.2×SSC/0.1% SDS for 15 minutes at 42° C.; and a high stringency wash can comprise washing in prewarmed (68° C.) solution containing 0.1×SSC/0.1% SDS for 15 minutes at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

The present invention also provides isolated XMRV nucleic acid molecules that contain a fragment or portion that hybridizes under highly stringent conditions to a nucleotide sequence comprising a nucleotide sequence selected from SEQ ID NO: 1, and the complement of SEQ ID NO: 1, and also provides isolated nucleic acid molecules that contain a fragment or portion that hybridizes under highly stringent conditions to a nucleotide sequence encoding an amino acid sequence selected from SEQ ID NO: 2. The nucleic acid fragments of the invention are at least about 15, preferably, at least about 18, 20, 23, or 25 nucleotides, and can be 30, 40, 50, 100, 200 or more nucleotides in length. Fragments that are, for example, 30 or more nucleotides in length, that encode antigenic polypeptides described herein are particularly useful, such as for the generation of antibodies as described herein.

In a related aspect, the XMRV nucleic acid fragments of the invention are used as probes or primers in assays such as those described herein. "Probes" or "primers" are oligonucleotides that hybridize in a base-specific manner to a complementary strand of nucleic acid molecules. Such probes and primers include polypeptide nucleic acids, as described in Nielsen et al., Science, 254, 1497-1500 (1991). As also used herein, the term "primer" in particular refers to a single-stranded oligonucleotide that acts as a point of initiation of template-directed DNA synthesis using well-known methods (e.g., PCR, LCR) including, but not limited to those described herein.

Typically, a probe or primer comprises a region of nucleotide sequence that hybridizes to at least about 15, typically about 20-25, and more typically about 40, 50 or 75, consecutive nucleotides of a nucleic acid molecule comprising a contiguous nucleotide sequence selected from: SEQ ID NO: 1, the complement of SEQ ID NO: 1, and a sequence encoding an amino acid sequence of SEQ ID NO: 2.

In preferred embodiments, a probe or primer comprises 100 or fewer nucleotides, preferably, from 6 to 50 nucleotides, and more preferably, from 12 to 30 nucleotides. In other embodiments, the probe or primer is at least 70% identical to the contiguous nucleotide sequence or to the complement of the contiguous nucleotide sequence, preferably, at least 80% identical, more preferably, at least 90% identical, even more preferably, at least 95% identical, or even capable of selectively hybridizing to the contiguous nucleotide sequence or to the complement of the contiguous nucleotide sequence. Often, the probe or primer further comprises a label, e.g., radioisotope, fluorescent compound, enzyme, or enzyme co-factor.

The nucleic acid molecules of the invention such as those described above can be identified and isolated using standard molecular biology techniques and the sequence information provided in SEQ ID NO: 1, and/or SEQ ID NO: 2. For example, nucleic acid molecules can be amplified and isolated by the polymerase chain reaction using synthetic oligonucleotide primers designed based on one or more of the nucleic acid sequences provided above and/or the complement of those sequences. Or such nucleic acid molecules may be designed based on nucleotide sequences encoding the amino acid sequences provided in SEQ ID NO: 2. See generally PCR Technology: Principles and Applications for DNA Amplification (ed. H. A. Erlich, Freeman Press, NY, N.Y., (1992); PCR Protocols: A Guide to Methods and Applications (Eds. Innis et al., Academic Press, San Diego, Calif., (1990); Mattila et al., Nucleic Acids Res., 19: 4967 (1991); Eckert et al., PCR Methods and Applications, 1: 17 (1991); PCR (eds. McPherson et al., IRL Press, Oxford)); and U.S. Pat. No. 4,683,202. The nucleic acid molecules can be amplified using cDNA, mRNA, or genomic DNA as a template, cloned into an appropriate vector and characterized by DNA sequence analysis.

Suitable amplification methods include the ligase chain reaction (LCR) (See Wu and Wallace, Genomics, 4:560 (1989); and Landegren et al., Science, 241:1077 (1988)), transcription amplification (Kwoh et al., Proc. Natl. Acad. Sci. USA, 86:1173 (1989)), and self-sustained sequence replication (See Guatelli et al., Proc. Nat. Acad. Sci. USA, 87:1874 (1990)) and nucleic acid based sequence amplification (NASBA). The latter two amplification methods involve isothermal reactions based on isothermal transcription, that produce both single stranded RNA (ssRNA) and double stranded DNA (dsDNA) as the amplification products in a ratio of about 30 or 100 to 1, respectively.

The amplified DNA can be radiolabeled and used as a probe for screening a cDNA library, for example, one derived from human cells or any other desired cell type. Corresponding clones can be isolated, DNA can be obtained following in vivo excision, and the cloned insert can be sequenced in either or both orientations by art-recognized methods to identify the correct reading frame encoding a polypeptide of the appropriate molecular weight. For example, the direct analysis of the nucleotide sequence of nucleic acid molecules of the present invention can be accomplished using well-known methods that are commercially available. See, for example, Sambrook et al., Molecular Cloning, A Laboratory Manual (2nd Ed., CSHP, New York (1989)); and Zyskind et al., Recombinant DNA Laboratory Manual, (Acad. Press, (1988)). Using these or similar methods, the polypeptide and the DNA encoding the polypeptide can be isolated, sequenced, and further characterized.

Antisense and interfering RNA (e.g., siRNA; shRNA) nucleic acid molecules of the invention can be designed using the nucleotide sequence of SEQ ID NO: 1, and/or the complement of SEQ ID NO: 1, and/or a portion of those sequences, and/or the complement of those portions or sequences, and/or a sequence encoding the amino acid sequence of SEQ ID NO: 2, or encoding a portion of SEQ ID NO: 2. The methods are based on binding of a polynucleotide to a complementary DNA or RNA.

The antisense or interfering RNA of the invention comprise a sequence complementary to at least a portion of an RNA transcript of an informative gene. Absolute complementarity, although preferred, is not required. A sequence "complementary to at least a portion of an RNA," referred to herein, means a sequence having sufficient complementarity to be able to hybridize with the RNA, forming a stable duplex. The ability to hybridize will depend on both the degree of complementarity and the length of the RNA sequence. Generally, the larger the hybridizing nucleic acid, the more base mismatches with the RNA it may contain and still form a stable duplex. One skilled in the art can ascertain a tolerable degree of mismatch by use of standard procedures to determine the melting point of the hybridized complex.

In general, the isolated XMRV nucleic acid sequences of the invention can be used as to identify homologous viral sequence and to detect an XMRV in an individual or in a sample. The nucleic acid molecules of the present invention can also be used as therapeutic agents.

The XMRV nucleic acid molecules of the present invention can further be used to derive primers, to raise anti-polypeptide antibodies using DNA immunization techniques, and as an antigen to raise anti-DNA antibodies or elicit immune responses. Portions or fragments of the nucleotide sequences identified herein (and the corresponding complete gene sequences) can be used in numerous ways as polynucleotide reagents. The XMRV nucleotide sequences of the invention can be used to identify and express recombinant polypeptides for analysis, characterization, or therapeutic use, or as markers for tissues in which the corresponding polypeptide is expressed, either constitutively, during tissue differentiation, or in diseased states. The nucleic acid sequences can additionally be used as reagents in the screening and/or diagnostic assays described herein, and can also be included as components of kits (e.g., reagent kits) for use in the screening and/or diagnostic assays described herein.

Standard techniques, such as the polymerase chain reaction (PCR) and DNA hybridization, may be used to clone XMRV homologs in other species, for example, mammalian homologs (e.g., primate, feline, canine, rodent, ovine, bovine homologs). XMRV homologs may be readily identified using low-stringency DNA hybridization or low-stringency PCR with XMRV probes or primers. Degenerate primers encoding XMRV polypeptides may be used to clone XMRV homologs by RT-PCR.

Alternatively, additional XMRV homologs can be identified by utilizing consensus sequence information for XMRV polypeptides to search for similar polypeptides in other species. For example, polypeptide databases for other species can be searched for proteins with the XMRV domains characteristic of an XMRV nucleic acid molecule described herein. Candidate polypeptides containing such a motif can then be tested for their XMRV biological activities, using methods described herein.

Expression of the Nucleic Acid Molecules

Another aspect of the invention pertains to nucleic acid constructs containing an XMRV nucleic acid molecule, for example, one selected from the group consisting of SEQ ID NOs: 1 or 6, and the complement of any of SEQ ID NOs: 1 or 6 (or portions thereof). Yet another aspect of the invention pertains to XMRV nucleic acid constructs containing a nucleic acid molecule encoding the amino acid sequence of SEQ ID NO: 2 or portions of SEQ ID NO: 2 (e.g., SEQ ID NOs: 3, 4, 5). The constructs comprise a vector (e.g., an expression vector) into which a sequence of the invention has been inserted in a sense or antisense orientation.

One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences).

It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells, such as E. coli, insect cells (using baculovirus expression vectors), yeast cells or mammalian cells. Suitable host cells are discussed further in Goeddel, supra. Alternatively, the recombinant expression vector can be transcribed and translated in vitro, for example, using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., E. coli), insect cells, yeast, or mammalian cells (such as Chinese hamster ovary cells (CHO) or COS cells, human 293T cells, HeLa cells, NIH 3T3 cells, mouse erythroleukemia (MEL) cells, LNCaP cells, and DU145 cells). Other suitable host cells are known to those skilled in the art.

Vector DNA can be introduced into prokaryotic or eukaryotic cells via conventional transformation or transfection techniques. As used herein, the terms "infection", "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture, can be used to produce (i.e., express) an XMRV polypeptide of the invention. Accordingly, the invention further provides methods for producing an XMRV polypeptide using the host cells of the invention. In one embodiment, the method comprises culturing the host cell of invention (into which a recombinant expression vector encoding a polypeptide of the invention has been introduced) in a suitable medium such that the XMRV polypeptide is produced. In another embodiment, the method further comprises isolating the polypeptide from the medium or the host cell.

Polypeptides

The present invention features isolated or recombinant XMRV polypeptides, and fragments, derivatives, and variants thereof, as well as polypeptides encoded by nucleotide sequences described herein (e.g., other variants). As used herein, the term "polypeptide" refers to a polymer of amino acids, and not to a specific length; thus, peptides, oligopeptides, and proteins are included within the definition of a polypeptide.

As used herein, a polypeptide is said to be "isolated," "substantially pure," or "substantially pure and isolated" when it is substantially free of cellular material, when it is isolated from recombinant or non-recombinant cells, or free of chemical precursors or other chemicals when it is chemically synthesized. In addition, a polypeptide can be joined to another polypeptide with which it is not normally associated in a cell (e.g., in a "fusion protein") and still be "isolated," "substantially pure," or "substantially pure and isolated." An isolated, substantially pure, or substantially pure and isolated polypeptide may be obtained, for example, using affinity purification techniques described herein, as well as other techniques described herein and known to those skilled in the art.

By an "XMRV polypeptide" is meant a polypeptide having XMRV biological activity, for example, the ability to infect prostate cells. An XMRV polypeptide is also a polypeptide whose activity can be inhibited by molecules having XMRV inhibitory activity. Examples of XMRV polypeptides include a substantially pure polypeptide comprising or consisting of SEQ ID NO: 2; and a polypeptide having preferably at least 75%, 80%, 82%, 85%, 90%, 92%, 94%, 95%, 96%, 97%, 98% or 99% sequence identity to SEQ ID NO: 2, as determined using the BLAST program and parameters described herein. In another embodiment, examples of XMRV polypeptides include a substantially pure polypeptide comprising or consisting of SEQ ID NO: 2; and a polypeptide having preferably at least 75%, 80%, 82%, 85%, 90%, 92%, 94%, 95%, 96%, 97%, 98% or 99% sequence similarity to SEQ ID NO: 2, as determined using the BLAST program and parameters described herein.

A polypeptide of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, less than about 5%, or less than about 1% other proteins.

When a polypeptide is recombinantly produced, it can also be substantially free of culture medium, i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide of the invention comprises an amino acid sequence encoded by a nucleic acid molecule of SEQ ID NO: 1, and complements and portions thereof. The polypeptides of the invention also encompasses fragments and sequence variants (e.g., allelelic variants). Variants also encompass polypeptides derived from other organisms, but having substantial homology to a polypeptide encoded by a nucleic acid molecule comprising the nucleotide sequence of SEQ ID NO: 1, and complements and portions thereof, or having substantial homology to a polypeptide encoded by a nucleic acid molecule comprising the nucleotide sequence of SEQ ID NO: 1. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

As used herein, two polypeptides (or a region of the polypeptides) are substantially homologous or identical when the amino acid sequences are at least about 82%, 85%, 90%, 92%, 94%, 95%, 96%, 97%, 98% or 99% homologous or identical. A substantially identical or homologous amino acid sequence, according to the present invention, will be encoded by a nucleic acid molecule hybridizing to SEQ ID NO: 1, or a portion thereof, under stringent conditions as more particularly described herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of the XMRV amino acid or nucleotide sequence aligned for comparison purposes is at least 30%, 40%, 50%, 60%,70%, 80%, 85%, 90%, 92%, 94%, 95%, 96%, 97%, 98%, 99% or 100% of the length of the reference sequence, for example, those sequences provided in FIGS. 1 and 2. The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873-5877 (1993). Such an algorithm is incorporated into the BLASTN and BLASTX programs (version 2.2) as described in Schaffer et al., Nucleic Acids Res., 29:2994-3005 (2001). When utilizing BLAST and Gapped BLAST programs, the default parameters of the respective programs (e.g., BLASTN) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1. In another embodiment, the percent identity between two polypeptides or two polynucleotides is determined over the full-length of the polypeptide or polynucleotide of interest.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG sequence alignment software package (Accelrys, San Diego, Calif.). When utilizing the ALIGN program for comparing amino acid sequences, a PAM 120 weight residue table, a gap length penalty of 12, and a gap penalty of 4 can be used. Additional algorithms for sequence analysis are known in the art and include ADVANCE and ADAM as described in Torellis and Robotti, Comput. Appl. Biosci., 10: 3-5 (1994); and FASTA described in Pearson and Lipman, Proc. Natl. Acad. Sci. USA, 85: 2444-8 (1988).

In another embodiment, the percent identity between two amino acid sequences can be accomplished using the GAP program in the GCG software package using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package, using a gap weight of 50 and a length weight of 3.

The invention also encompasses XMRV polypeptides having a lower degree of identity but having sufficient similarity so as to perform one or more of the same functions performed by an XMRV polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247: 1306-1310 (1990).

A variant polypeptide can differ in amino acid sequence by one or more substitutions, deletions, insertions, inversions, fusions, and truncations or a combination of any of these. Further, variant polypeptides can be fully functional (e.g., ability to infect cells and produce progeny virus) or can lack function in one or more activities (e.g., ability to produce progeny virus). Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region.

Amino acids that are essential for function (e.g., infection) can be identified by methods known in the art, such as site-directed mutagenesis or alanine-scanning mutagenesis (Cunningham et al., Science, 244: 1081-1085 (1989)). The latter procedure introduces a single alanine mutation at each of the residues in the molecule (one mutation per molecule). The resulting mutant molecules are then tested for biological activity in vitro. Sites that are critical for polypeptide activity can also be determined by structural analysis, such as crystallization, nuclear magnetic resonance, or photoaffinity labeling (See Smith et al., J. Mol. Biol., 224: 899-904 (1992); and de Vos et al. Science, 255: 306-312 (1992)).

The invention also includes XMRV polypeptide fragments of the polypeptides of the invention. Fragments can be derived from a polypeptide comprising SEQ ID NO: 2, or from a polypeptide encoded by a nucleic acid molecule comprising SEQ ID NO: 1, or a portion thereof, complements thereof, or other variant thereof. The present invention also encompasses fragments of the variants of the polypeptides described herein. Useful fragments include those that retain one or more of the biological activities of the polypeptide, as well as fragments that can be used as an immunogen to generate polypeptide-specific antibodies. In particular embodiments, XMRV polypeptide fragments of the polypeptides of the invention comprise a gag polypeptide (e.g., SEQ ID NO:3), a pro-pol polypeptide (e.g., SEQ ID NO: 4), an env polypeptide (e.g., SEQ ID NO: 4) and combinations thereof.

Biologically active fragments include peptides that are, for example, 6, 9, 12, 15, 18, 20, 30, 40, 50, 60, 70, 80, 90, 100, or more amino acids in length.

Fragments can be discrete (not fused to other amino acids or polypeptides) or can be fused to one or more components of a polypeptide. Further, several fragments can be comprised within a single larger polypeptide. In one embodiment, a fragment designed for expression in a host can have heterologous pre- and pro-polypeptide regions fused to the amino terminus of the polypeptide fragment and an additional region fused to the carboxyl terminus of the fragment.

Standard molecular biology methods for generating polypeptide fragments are known in the art. Once the fragments are generated, they can be tested for biological activity, using, for example, any of the methods described herein.

The invention thus provides chimeric or fusion polypeptides. These comprise an XMRV polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment, the fusion polypeptide does not affect the function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example, β-galactosidase fusions, yeast two-hybrid GAL fusions, poly-His fusions, FLAG-tagged fusions and Ig fusions. Such fusion polypeptides can facilitate the purification of recombinant polypeptide. In certain host cells (e.g., mammalian host cells), expression and/or secretion of a polypeptide can be increased by using a heterologous signal sequence. Therefore, in another embodiment, the fusion polypeptide contains a heterologous signal sequence at its N-terminus.

EP-A 0464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. (See Bennett et al., Journal of Molecular Recognition, 8: 52-58 (1995) and Johanson et al., The Journal of Biological Chemistry, 270,16: 9459-9471 (1995)). Thus, this invention also encompasses soluble fusion polypeptides containing a polypeptide of the invention and various portions of the constant regions of heavy or light chains of immunoglobulins of various subclass (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., "Current Protocols in Molecular Biology," John Wiley & Sons, (1998), the entire teachings of which are incorporated by reference herein). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

The substantially pure, isolated, or substantially pure and isolated XMRV polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector is introduced into a host cell, and the polypeptide is expressed in the host cell. Alternatively, the cell can be infected with XMRV virus. The XMRV polypeptide can then be isolated from the cells or the supernatant of cells by an appropriate purification scheme using standard protein purification techniques.

In general, XMRV polypeptides of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the polypeptide or a molecule to which it binds (e.g., a receptor or a ligand) in biological fluids. The polypeptides can also be used as markers for cells or tissues in which the corresponding polypeptide is preferentially expressed, either constitutively, during tissue differentiation, or in a diseased state. The polypeptides can also be used to isolate a corresponding binding agent, and to screen for peptide or small molecule antagonists or agonists of the binding interaction. The polypeptides of the present invention can also be used as therapeutic agents.

Antibodies

Polyclonal and/or monoclonal antibodies that selectively bind all or a portion of an XMRV polypeptide, homologs and variants thereof are also provided. The invention provides antibodies to an XMRV polypeptide or polypeptide fragment of the invention, e.g., having an amino acid sequence encoded by SEQ ID NO: 2, or a portion thereof, or having an amino acid sequence encoded by a nucleic acid molecule comprising all or a portion of SEQ ID NO: 1, or another variant, or portion thereof.

The term "purified antibody" as used herein refers to immunoglobulin molecules and immunologically active portions of immunoglobulin molecules, i.e., molecules that contain an antigen binding site that selectively binds an antigen. A molecule that selectively binds to a polypeptide of the invention is a molecule that binds to that polypeptide or a fragment thereof, but does not substantially bind other molecules in a sample, e.g., a biological sample that naturally contains the polypeptide. Preferably the antibody is at least 60%, by weight, free from proteins and naturally occurring organic molecules with which it naturally associated. More preferably, the antibody preparation is at least 75% or 90%, and most preferably, 99%, by weight, antibody. Examples of immunologically active portions of immunoglobulin molecules include F(ab) and F(ab')2 fragments that can be generated by treating the antibody with an enzyme such as pepsin.

The invention provides polyclonal and monoclonal antibodies that selectively bind to an XMRV polypeptide of the invention. The term "monoclonal antibody" or "monoclonal antibody composition," as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., an XMRV polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from tissue, blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, Nature 256:495-497 (1975), the human B cell hybridoma technique (Kozbor et al., Immunol. Today 4:72 (1983)), the EBV-hybridoma technique (Cole et al., Monoclonal Antibodies and Cancer Therapy, Alan R. Liss, Inc., pp. 77-96 (1985)) or trioma techniques. The technology for producing hybridomas is well known (see generally Current Protocols in Immunology, Coligan et al., (eds.) John Wiley & Sons, Inc., New York, N.Y. (1994)). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., Nature, 266:55052 (1977); R. H. Kenneth, in Monoclonal Antibodies: A New Dimension In Biological Analyses, Plenum Publishing Corp., New York, N.Y. (1980); and Lerner, Yale J. Biol. Med. 54:387-402 (1981)). Moreover, the ordinarily skilled worker will appreciate that there are many variations of such methods that also would be useful.

In one alternative to preparing monoclonal antibody-secreting hybridomas, a monoclonal antibody to an XMRV polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9:1370-1372 (1991); Hay et al., Hum. Antibod. Hybridomas 3:81-85 (1992); Huse et al., Science 246: 1275-1281 (1989); and Griffiths et al., EMBO J. 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate an XMRV polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for an XMRV polypeptide of the invention can be used to detect the polypeptide (e.g., in a cellular lysate, cell supernatant, blood sample, or tissue sample).

The antibodies of the present invention can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferase, luciferin, green fluorescent protein, and aequorin, and examples of suitable radioactive material include, for example, $^{125}$I, $^{131}$I, $^{35}$S, $^{32}$P and $^{3}$H.

Retroviral Vectors

The XMRV of the present invention can also be used as an expression vector and/or targeting vector wherein a moiety is inserted into or attached to an XMRV using known methods, thereby producing a recombinant XMRV.

In one embodiment the moiety of interest is a nucleic acid which is introduced into the genome of an XMRV (e.g., using homologous recombination), thereby producing a recombinant XMRV, and the recombinant XMRV can express the moiety of interest. In addition, the recombinant XMRV can be used to deliver the moiety of interest to cells that are targeted by (can be infected by) XMRV (e.g., a prostate tumor cell) under conditions in which the nucleic acid is expressed in the targeted cell. The nucleic acid of interest can be, for example, a nucleic acid which encodes a marker (e.g., neomycin, ꓱ-galactosidase, green fluorescent protein) and/or a therapeutic agent (e.g., interferon, interleukin, antineoplastins, synthetic peptides) and can include regulatory sequences (e.g., promoters (constitutive, inducible), enhancers).

In particular embodiments, the XMRV is attenuated (e.g., avirulent). Attenuated XMRV can be obtained using known methods (e.g., serial passage). The genome of the XMRV can be modified wherein the gene coding for one or more or all of the viral proteins (e.g., gag, pol, env) have been replaced by a nucleic acid of interest, thereby producing an XMRV vector plasmid. In particular embodiments, one or more XMRV genes have been replaced, thereby producing a modified XMRV vector plasmid which cannot replicate. A packaging cell line that produces viral proteins but lacks the ability to produce replication competent virus can be used to package the modified XMRV into retroviral particles. The XMRV vector plasmid which includes the nucleic acid of interest can be transfected into the packaging cell line wherein the XMRV vector plasmid is transcribed and packaged into modified retroviral particles (recombinant retroviral particles). The modified retroviral particles can be used to infect cells targeted by XMRV and the nucleic acid of interest present in the XMRV vector plasmid can then be expressed in the infected cells. A cell infected with such a modified retroviral particle cannot produce new virus since one or more of the viral proteins are not present in the infected cells. However, the nucleic acid of interest is integrated into the infected cell's DNA and can now be expressed in the infected cell.

Diagnostic and Screening Assays

The present invention also pertains to diagnostic assays for assessing the presence of XMRV expression, or for assessing activity of XMRV polypeptides of the invention. In one embodiment, the assays are used in the context of a biological sample (e.g., blood, serum, cells, tissue) to thereby determine whether XMRV is present in an individual or a sample from an individual, or whether an individual is at risk for (has a predisposition for or a susceptibility to) developing cancer (e.g., a cancer that can develop due to transmission of XMRV (e.g., sexual transmission), such as prostate, cervical or ovarian cancer). The invention also provides for prognostic (or predictive) assays for determining whether an individual is susceptible to developing cancer. For example, the presence of XMRV in an individual could indicate that the individual has an increased risk of developing cancer. Such assays can be used for prognostic or predictive purpose to thereby prophylactically treat an individual prior to the onset of symptoms associated with cancer.

Another aspect of the invention pertains to assays for monitoring the influence of agents, or candidate compounds (e.g., drugs or other agents) on the nucleic acid molecule expression or biological activity of polypeptides of the invention, as well as to assays for identifying candidate compounds that bind to an XMRV polypeptide. These and other assays and agents are described in further detail in the following sections.

Diagnostic Assays

XMRV nucleic acid molecules, probes, primers, polypeptides, and antibodies to an XMRV polypeptide can be used in methods of diagnosis of a susceptibility to, or likelihood of an individual having cancer, as well as in kits useful for diagnosis of a susceptibility to cancer.

In one embodiment, the invention is directed to a method of diagnosing or detecting cancer (e.g., prostate cancer) using hybridization methods, such as Southern analysis, Northern analysis, or in situ hybridizations (see Ausubel, et al., supra). For example, a biological sample from a test subject (a "test sample") of DNA (e.g., cDNA) or RNA is obtained from an individual suspected of having, being susceptible to or predisposed for, cancer (the "test individual"). The test sample can be from any source that contains XMRV nucleic acid molecules such as a blood sample or a tissue sample. The DNA, RNA, or cDNA sample is then examined to determine whether an XMRV nucleic acid molecule is present. The presence of the XMRV nucleic acid can be indicated by hybridization of RNA or cDNA to a nucleic acid probe. A "nucleic acid probe," as used herein, can be a DNA probe or an RNA probe. The probe can be any of the nucleic acid molecules described above (e.g., the entire nucleic acid molecule, a fragment, a vector comprising the gene, a probe, or primer, etc.).

To detect XMRV nucleic acid a hybridization sample is formed by contacting the test sample which is suspected of containing XMRV nucleic acid, with at least one nucleic acid probe. A preferred probe is a labeled nucleic acid probe capable of hybridizing to XMRV nucleic acids described herein. The nucleic acid probe can be, for example, a full-length nucleic acid molecule, or a portion thereof, such as an oligonucleotide of at least 15, 30, 50, 100, 250, or 500 nucleotides in length and sufficient to specifically hybridize under stringent conditions to appropriate mRNA or genomic DNA. For example, the nucleic acid probe can be all or a portion of SEQ ID NO: 1, or the complement of SEQ ID NO: 1; or can be a nucleic acid molecule encoding all or a portion of SEQ ID NO: 2. Other suitable probes for use in the diagnostic assays of the invention are described above.

The hybridization sample is maintained under conditions that are sufficient to allow hybridization of the nucleic acid probe to XMRV nucleic acid. More than one nucleic acid probe can also be used concurrently in this method. Hybridization of any one of the nucleic acid probes is indicative of a susceptibility to, or likelihood of an individual having cancer (e.g., prostate cancer).

Hybridization can be detected using Southern blot analysis, Northern blot analysis, arrays of oligonucleotide probes that are complementary to target nucleic acid sequence segments from an individual. For example, in one embodiment, an oligonucleotide array can be used. Oligonucleotide arrays typically comprise a plurality of different oligonucleotide probes that are coupled to a surface of a substrate in different known locations. Oligonucleotide arrays include "Virochip" and "GENECHIPS™" (U.S. Pat. No. 5,143,854 and PCT patent publication Nos. WO 90/15070 and 92/10092). These arrays can generally be produced using mechanical synthesis methods or light directed synthesis methods that incorporate a combination of photolithographic methods and solid phase oligonucleotide synthesis methods. See Fodor et al., Science 251:767-777 (1991), U.S. Pat. No. 5,143,854; PCT Publication No. WO 90/15070; PCT Publication No. WO 92/10092, and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein.

Once an oligonucleotide array is prepared, a nucleic acid of interest is hybridized to the array and scanned for the target nucleic acid molecule. Hybridization and scanning are generally carried out by methods described herein and also in, e.g., PCT Publication Nos. WO 92/10092 and WO 95/11995, and U.S. Pat. No. 5,424,186, the entire teachings of which are incorporated by reference herein.

In addition, the level of XMRV nucleic acid can be detected using, for example, in situ hybridization techniques known to one skilled in the art, or by examining the level of expression, activity, and/or composition of an XMRV polypeptide, by a variety of methods, including enzyme linked immunosorbent assays (ELISAs), Western blots, immunoprecipitations, immunohistochemistry, and immunofluorescence. A test sample from an individual can also be assessed for the presence of an alteration in the level of an XMRV nucleic acid or in the expression and/or an alteration in composition of the polypeptide encoded by an XMRV nucleic acid.

Detection of XMRV in a sample can be compared with the expression or composition of an XMRV in a control sample. A control sample is a sample that corresponds to the test sample (e.g., is from the same type of cells), and is from an individual in which XMRV is not present.

Various means of examining expression or composition of an XMRV polypeptide can be used, including spectroscopy, colorimetry, electrophoresis, isoelectric focusing, and immunoassays such as immunoblotting (see also Ausubel et al., supra; particularly chapter 10). For example, in one embodiment, an antibody capable of binding to the polypeptide (e.g., as described above), preferably an antibody with a detectable label, can be used. Antibodies can be polyclonal, or more preferably, monoclonal. An intact antibody, or a fragment thereof (e.g., Fab or F(ab')2) can be used. The term "labeled," with regard to the antibody, is intended to encompass direct labeling of the antibody by coupling (i.e., physically linking) a detectable substance to the antibody, as well as indirect labeling of the antibody by reacting it with another reagent that is directly labeled. An example of indirect labeling is detection of a primary antibody using a fluorescently labeled secondary antibody.

Western blotting analysis, using an antibody as described above that specifically binds to an XMRV polypeptide can be used to identify the presence in a test sample of an XMRV polypeptide.

In one embodiment of this method, the level or amount of an XMRV polypeptide in a test sample is compared with the level or amount of an XMRV polypeptide in a control sample. A level or amount of the polypeptide in the test sample that is higher or lower than the level or amount of the polypeptide in the control sample, such that the difference is statistically significant, is indicative of an alteration in the expression of the XMRV polypeptide, and can be indicative of a susceptibility to cancer.

Kits (e.g., reagent kits) useful in the methods of diagnosis comprise components useful in any of the methods described herein, including, for example, hybridization probes or primers as described herein (e.g., labeled probes or primers), reagents for detection of labeled molecules, antibodies that bind to an XMRV polypeptide, means for amplification of nucleic acids comprising XMRV, or means for analyzing the nucleic acid sequence of XMRV, or for analyzing the amino acid sequence of an XMRV polypeptide, etc.

Screening Assays and Agents Identified

The invention provides methods (also referred to herein as "screening assays") for identifying the presence of a nucleic acid of the invention, as well as for identifying the presence of a polypeptide encoded by a nucleic acid of the invention. For example, the present invention provides for a method of screening and monitoring for the presence of XMRV in, for example, tissue, units of blood, plasma and/or platelets in a depository for such samples (e.g., a blood bank; an organ bank).

In one embodiment, the presence (or absence) of a nucleic acid molecule of interest (e.g., a nucleic acid that has significant homology with a nucleic acid of XMRV) in a sample can be assessed by contacting the sample with a nucleic acid comprising a nucleic acid of the invention (e.g., a nucleic acid having the sequence of SEQ ID NO: 1, or the complement thereof, or a nucleic acid encoding an amino acid having the sequence of SEQ ID NO: 2, or a fragment or variant of such nucleic acids), under stringent conditions as described above, and then assessing the sample for the presence (or absence) of hybridization. In a preferred embodiment, high stringency conditions are conditions appropriate for selective hybridization. In another embodiment, a sample containing the nucleic acid molecule of interest is contacted with a nucleic acid containing a contiguous nucleotide sequence (e.g., a primer or a probe as described above) that is at least partially complementary to a part of the nucleic acid molecule of interest (e.g., an XMRV nucleic acid), and the contacted sample is assessed for the presence or absence of hybridization. In a preferred embodiment, the nucleic acid containing a contiguous nucleotide sequence is completely complementary to a part of the nucleic acid molecule of XMRV.

In any of the above embodiments, all or a portion of the nucleic acid of interest can be subjected to amplification prior to performing the hybridization.

In another embodiment, the presence (or absence) of an XMRV polypeptide, such as a polypeptide of the invention or a fragment or variant thereof, in a sample can be assessed by contacting the sample with an antibody that specifically binds to the polypeptide of XMRV (e.g., an antibody such as those described above), and then assessing the sample for the presence (or absence) of binding of the antibody to the XMRV polypeptide.

In another embodiment, the invention provides methods for identifying agents or compounds (e.g., fusion proteins, polypeptides, peptidomimetics, prodrugs, receptors, binding agents, antibodies; small molecules or other drugs, or ribozymes) that alter or modulate (e.g., increase or decrease; enhance or inhibit) the activity of the polypeptides described herein, or that otherwise interact with the polypeptides herein. For example, such compounds can be compounds or agents that bind to polypeptides described herein; that have a stimulatory or inhibitory effect on, for example, the activity of the polypeptides of the invention; or that change (e.g., enhance or inhibit) the ability of the polypeptides of the invention to interact with molecules with which XMRV polypeptides normally interact (XMRV binding agents).

The candidate compound can cause an increase in the activity of the polypeptide. For example, the activity of the polypeptide can be increased by at least 1.5-fold to 2-fold, at least 3-fold, or, at least 5-fold, relative to the control. Alternatively, the polypeptide activity can be a decrease, for example, by at least 10%, at least 20%, 40%, 50%, or 75%, or by at least 90%, relative to the control.

In one embodiment, the invention provides assays for screening candidate compounds or test agents to identify compounds that bind to or modulate the activity of polypeptides described herein (or biologically active portion(s) thereof), as well as agents identifiable by the assays. As used herein, a "candidate compound" or "test agent" is a chemical molecule, be it naturally-occurring or artificially-derived, and includes, for example, peptides, proteins, synthesized molecules, for example, synthetic organic molecules, naturally-occurring molecule, for example, naturally occurring organic molecules, nucleic acid molecules, and components thereof.

In general, candidate compounds for uses in the present invention may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. For example, candidate compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des. 12: 145 (1997)). Furthermore, if desired, any library or compound is readily modified using standard chemical, physical, or biochemical methods.

If desired, compounds shown to be useful agents for treatment are chemically modified according to methods known in the art. Compounds identified as being of therapeutic value may be subsequently analyzed using animal models for diseases in which it is desirable to alter the activity or expression of the nucleic acids or polypeptides of the present invention.

In one embodiment to identify candidate compounds that alter the biological activity of an XMRV polypeptide, a cell, tissue, cell lysate, tissue lysate, or solution containing or expressing an XMRV polypeptide (e.g., SEQ ID NO: 2), can be contacted with a candidate compound to be tested under conditions suitable for XMRV infection of a cell. Methods for assessing viral infectivity are known in the art (e.g., assess the ability of the XMRV to produce retroviral particles with reverse transcriptase activity).

Alternatively, the XMRV nucleic acid molecule or polypeptide can be contacted directly with the candidate compound to be tested. The level (amount) of XMRV biological activity is assessed (e.g., either directly or indirectly), and is compared with the level of biological activity in a control. If the level of the biological activity in the presence of the candidate compound differs, by an amount that is statistically significant, from the level of the biological activity in the absence of the candidate compound, or in the presence of the candidate compound vehicle only, then the candidate compound is a compound that alters the biological activity of an XMRV polypeptide. For example, an increase in the level of an XMRV biological activity relative to a control, indicates that the candidate compound is a compound that enhances (is an agonist of) XMRV activity. Similarly, a decrease in the level of XMRV biological activity relative to a control, indicates that the candidate compound is a compound that inhibits (is an antagonist of) XMRV activity. In another embodiment, the level of biological activity of an XMRV polypeptide or derivative or fragment thereof in the presence of the candidate compound to be tested, is compared with a control level that has previously been established. A level of the biological activity in the presence of the candidate compound that differs from the control level by an amount that is statistically significant indicates that the compound alters XMRV biological activity.

The present invention also relates to an assay for identifying compounds that alter the expression of an XMRV nucleic acid molecule (e.g., antisense nucleic acids, interfering RNA (e.g., siRNA, shRNA), fusion proteins, polypeptides, peptidomimetics, prodrugs, receptors, binding agents, antibodies, small molecules or other drugs, or ribozymes) that alter (e.g., increase or decrease) expression (e.g., transcription or translation) of the nucleic acid molecule or that otherwise interact with the nucleic acids described herein, as well as compounds identifiable by the assays. For example, a solution containing a nucleic acid encoding an XMRV polypeptide can be contacted with a candidate compound to be tested. The level and/or pattern of XMRV expression is assessed, and is compared with the level and/or pattern of expression in a control. If the level and/or pattern in the presence of the candidate compound differs, by an amount or in a manner that is statistically significant, from the level and/or pattern in the absence of the candidate compound, or in the presence of the candidate compound vehicle only, then the candidate compound is a compound that alters the expression of XMRV.

This invention further pertains to novel compounds identified by the above-described screening assays. Accordingly, it is within the scope of this invention to further use a compound identified as described herein in an appropriate animal model. For example, a compound identified as described herein (e.g., an antibody) can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of novel compounds identified by the above-described screening assays for treatments as described herein. In addition, a compound identified as described herein can be used to alter activity of an XMRV polypeptide, or to alter expression of XMRV, by contacting the polypeptide or the nucleic acid molecule (or contacting a cell comprising the polypeptide or the nucleic acid molecule) with the compound identified as described herein.

Pharmaceutical Composition

The present invention also pertains to pharmaceutical compositions comprising nucleic acids described herein, particularly nucleotides encoding the polypeptides described herein; comprising polypeptides described herein (e.g., SEQ ID NO: 2, and/or variants thereof); and/or comprising a compound that alters (e.g., increases or decreases) XMRV expression or XMRV polypeptide activity as described herein. For instance, the compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compounds are administered in a therapeutically effective amount. The amount of compounds that will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of an angiogenic disease, a vascular disease, a heart disease, or a circulatory disease, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the compounds can be separated, mixed together in any combination, present in a single vial or tablet. Compounds assembled in a blister pack or other dispensing means is preferred. For the purpose of this invention, unit dosage is intended to mean a dosage that is dependent on the individual pharmacodynamics of each compound and administered in FDA approved dosages in standard time courses.

Methods of Therapy

The present invention also pertains to methods of treatment (prophylactic, diagnostic, and/or therapeutic) for a disease associated with XMRV, using an XMRV therapeutic compound. An "XMRV therapeutic compound" is a compound that inhibits XMRV polypeptide activity and/or XMRV nucleic acid molecule expression, as described herein (e.g., an agonist or antagonist). XMRV therapeutic compounds can inhibit XMRV polypeptide activity or nucleic acid molecule expression by a variety of means, such as, for example, by inducing an immune response to an XMRV, interfering with XMRV polypeptide activity (e.g., by binding to an XMRV polypeptide), or by downregulating expression of the XMRV nucleic acid molecule. In one embodiment, the XMRV therapeutic compound is a vaccine. Representative XMRV therapeutic compounds include the following: nucleic acids or fragments or derivatives thereof described herein, polypeptides described herein; peptidomimetics; fusion proteins or prodrugs thereof; antibodies; other small molecules; and other compounds that inhibit XMRV nucleic acid expression or polypeptide activity, for example, those compounds identified in the screening methods described herein. In particular embodiments, the inhibitors of XMRV are reverse transcriptase inhibitors (e.g., AZT, (zidovudine, Retrovir) and protease inhibitors. More than one XMRV therapeutic compound can be used concurrently, if desired.

The XMRV therapeutic compound that is a nucleic acid is used in the treatment of a disease associated with XMRV. In one embodiment, the disease is a cancer in which the etiology of the cancer is attributable to the presence of XMRV in an individual (e.g., prostate, cervical, uterine cancer). The term, "treatment" as used herein, refers not only to ameliorating symptoms associated with the disease, but also preventing or delaying the onset of the disease, inducing an immune response to the disease and also lessening the severity or frequency of symptoms of the disease. The therapy is designed to inhibit or downregulate activity of an XMRV polypeptide in an individual. For example, an XMRV therapeutic compound can be administered in order to downregulate or decrease the expression or availability of the XMRV nucleic acid molecule or variants thereof. In one embodiment, the invention is directed to a method of treating cancer (e.g., prostate cancer) in an individual wherein XMRV is present in the individual, comprising administering to the individual an effective amount of an agent that inhibits XMRV. In another embodiment, the invention is directed to a method of detecting asymptomatic (early stage) cancer in an individual wherein XMRV is present in the individual, comprising detecting the presence of an XMRV in the individual, wherein the presence of XMRV in the individual is indicative of early stage cancer in the individual. In yet another embodiment, the invention is directed to a method of identifying an individual at risk for developing cancer, comprising determining whether an XMRV is present in the individual, wherein if XMRV is present in the individual then the individual is at risk for developing cancer.

The XMRV therapeutic compound(s) are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The invention will be further described by the following non-limiting examples.

EXEMPLIFICATION

Example 1

General Overview of Methods Used to Identify Gammaretrovirus in Prostate Tissue

Methods and Results
1. Genotyping, Processing of Prostate Tissues, and Isolation of RNA.

Men scheduled to undergo prostatectomies at the Cleveland Clinic Foundation were genotyped for the R462Q (1385G->A) mutation in RNASEL using an Amplification Refractory Mutation System (ARMS) assay on DNA isolated from PBMC. The analysis employs a PCR-based assay that uses allele-specific forward primer sequences, capable of detecting homozygous wild-type (GG), heterozygous (GA), or homozygous mutant (AA) mutations in RNASEL (Casey G., et al., *Nat. Genet.* 32(4):581-3, 2002). Immediately after prostatectomies, tissue cores were taken from both the transitional zone (the site of benign prostatic hyperplasia, BPH) and the peripheral zone (where cancer generally occurs) and frozen on dry ice and stored in liquid nitrogen or at −70° C. (by the Department of Laboratory Medicine, Cleveland Clinic). Immediately after cores were removed from the freshly removed prostates, the remaining prostate tissue was placed in 10% neutral buffered formalin for fixation. The fixed tissue was processed and embedded in paraffin for later histological use. Thus far, 150 patients that underwent prostatectomy have been genotyped, consisting of 73 (48.7%) with 1385GG (homozygous wild type); 62 (41.3%) with 1385GA (heterozygous); and 15 (10%) with 1385AA (homozygous mutant). A blood specimen was also collected from these men and processed into plasma and frozen at −70° C.

Transitional and peripheral cores were received on dry ice directly from the CCF anatomic pathology laboratory where they were being stored in liquid nitrogen. Once obtained, the tissue was transferred from dry ice immediately to TRIzol reagent, homogenized to completion using a power homogenizer, and processed for RNA isolation according to the manufacturer's instructions (Invitrogen). The prostate tissue RNA was then subjected to DNase I digestion. To recover the maximum amount of RNA after DNase digestion, the extracted phenol was back-extracted twice with RNase-free TE buffer. The extracted RNA was precipitated overnight at −20° C. Poly A+ RNA was isolated from the DNase digested total RNA using the Oligotex® mRNA Midi Kit (Qiagen) as instructed by the manufacturer. The poly A+ RNA was then measured using the RIBOgreen quantitation kit (Molecular Probes). The samples were kept frozen at −70° C., until they were shipped on dry ice for Virochip microarray analysis.

2. Probing Virochips with cDNAs Derived from Prostate RNA.

Briefly, the prostate tissue total RNA and polyA+ RNA were reverse transcribed into cDNA using an oligo-dT primer for first-strand synthesis. Cy5 fluorophores were incorporated into the reaction mix in the presence of unlabeled nucleotides. The resulting labeled cDNA was purified by centrifuging the sample through a Centricon-30 microconcentrator (Amicon). The purified probe was added to the Virochip microarray and allowed to hybridize for at least 12 hours. The hybridized microarray was then washed using a stringent salt solution to remove any unbound or non-specific probe from the array. The slides were then analyzed within 2-3 hours using a scanner to visualize the fluorescent signals of probe hybridization to the array. The array hybridizations used Cy5-labeled amplified probes from either prostate tissue total RNA, polyA+ RNA, or water (control). A reference signal was generated by using a Cy3-labeled reverse complement version of a single defined 70-mer present in each spot on the microarray. Positive signals were assessed by Cy5 intensity relative to that of the controls.

Results obtained after hybridization, when using total RNA isolated from the prostate cancer tissue, was a positive signal in 9 of 14 patients genotyped as homozygous mutant for RNase L (1385AA). The virus signal was detected in 0 of 10 heterozygous (13 85GA) tissues examined and in 2 of 13 homozygous wild-type RNase L (1385GG) prostates examined, thus indicating that RNase L suppresses the virus from replicating (Table 1). The Cy5-labeled probe bound to Murine Leukemia Virus (MLV) DNA.

3. Isolation and Sequence Analysis of Full-Length the Viral cDNA.

Figure 3:
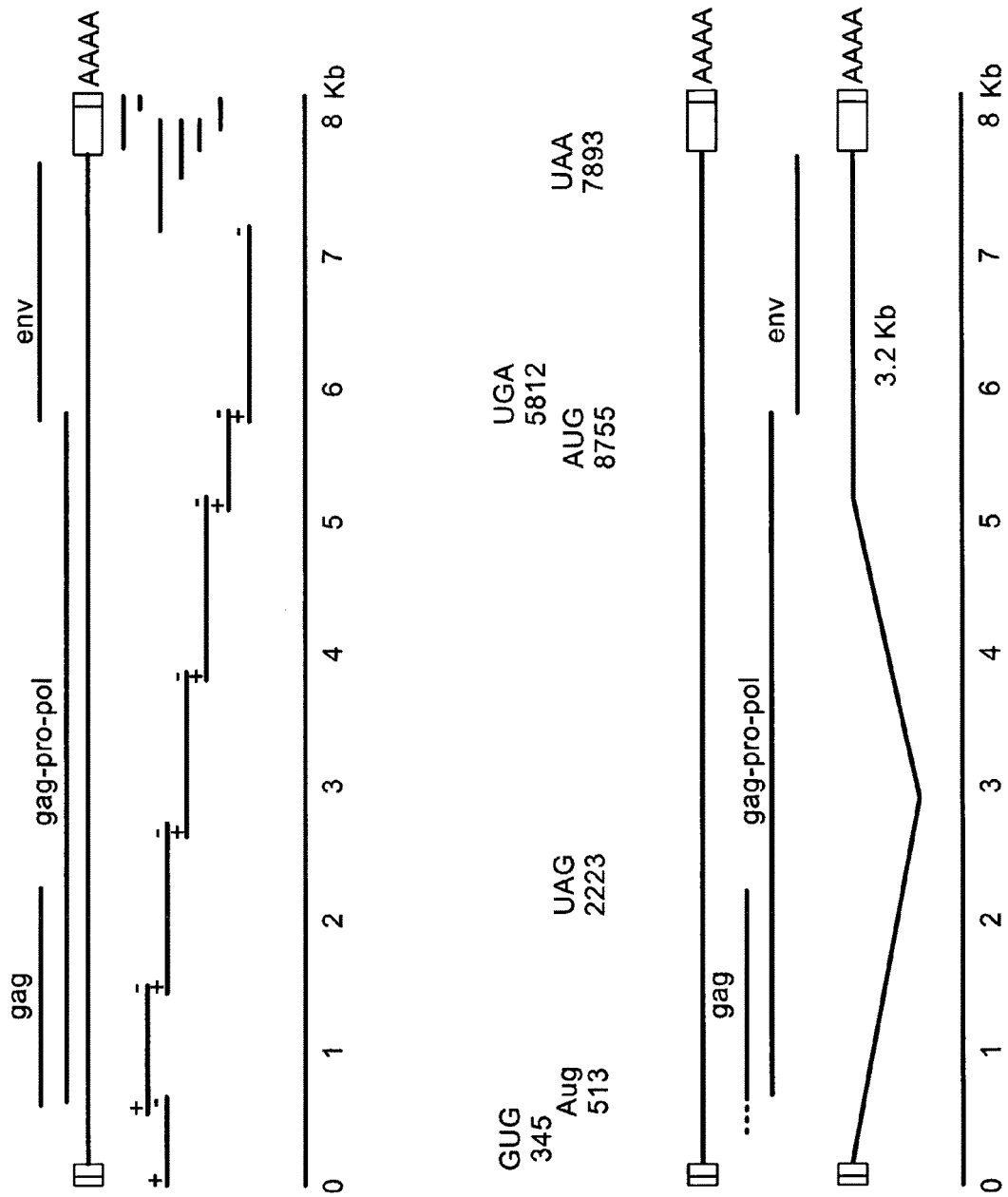
FIG. 3 is a schematic illustrating the genomic structure of HXV aligned to viral transcripts.
Figure 4:
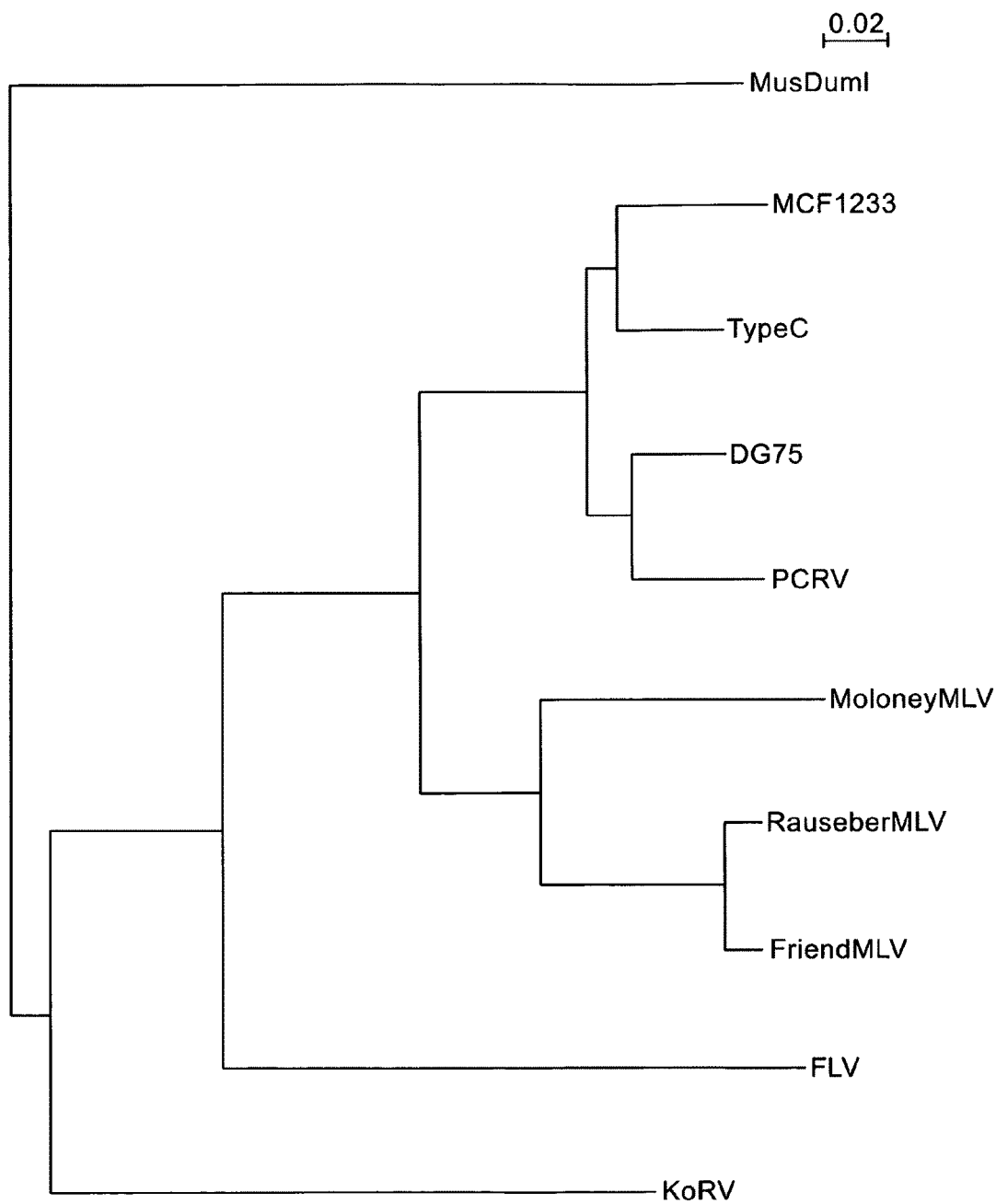
FIG. 4 is a dendrogram of the relationship between $HXV_{35}$ (indicated in diagram as "PCRV") and other gammaretroviruses.

To establish the full identity of the candidate virus, viral RNA was recovered from a prostate sample by hybridization/selection. This material was subsequently amplified, cloned and sequenced. Initially, the largest clone spanned approximately 1.0 kb; this fragment encompassed the 3' UTR conserved motif and extended into the most 3' coding region of the viral genome. The complete cloning of the entire 8,188 nt viral genomic RNA (SEQ ID NO: 1) from patient 35 was subsequently determined (Table 2). The viral genome is that of a canonical gammaretrovirus with gag, pro-pol and env genes (FIG. 3). All three open reading frames (ORF) are intact, therefore, it has the potential to generate infectious virus. Gammaretroviruses have C-type morphology, assemble at the plasma membrane with a central, symmetrical, spherical core, and contain the largest number of known members of the retroviridae, including murine leukemia virus (MLV), feline leukemia virus (FeLV) and gibbon ape leukemia virus (GALV) (Goff, S., et al., *Field's Virology*, fourth edition, (Knipe, D. M. and Howley, P. M., eds.). Lippincott Williams & Wilkins. New York. 2001, pp. 1871-1939). The most significant match in the full length viral genome database is to a xenotropic murine type C retrovirus known as DG-75 (GI 9628654) (93% identity at the nucleotide level) (FIG. 4). DG-75 retrovirus was described as an exogenous contaminant of an EBV-negative, B-lymphoblastoid cell line of the same name (Raisch K P., et al., *Virology* 250(1):135-9, 1998; Raisch K P., et al., *Virology* 308(1):83-91, 2003). An early passage of the DG-75 cell line (HAD subline), was found to be free from retroviruses, and the origin of the DG-75 virus is unknown. The divergence of the newly isolated virus (referred to herein as HXV for human xenotropic virus, or in the alternative, XMRV for xenotropic murine leukemia virus (MLV) related virus) from DG-75 virus indicates that two viruses are distinct, but related. The similarity index between the HXV$_{35}$ and DG-75 coding sequences of gag, pro-pol, and env are 96.3%, 96.3%, and 93.8%, respectively (Lipman-Pearson Alignment) (Tables 3, 4 and 5). The HXV and DG-75 branch is most closely related to MCF1233, a C57BL-derived MLV that causes T and B lymphomas in an MHC-associated manner (Sijts E J, et al., *Virus Res* 34(3):339-49, 1994). MCF1233 has an ecotropic backbone with polytropic sequences in the 5'-region. The next most closely related branch contains the classical ecotropic MLV strains, Moloney, Rauscher and Friend. Separate sub-branches of related viruses include KoRv, a virus isolated from koalas that clusters with gibbon ape leukemia virus (GALV) (Hanger J J, et al., *J Virol* 74(9):4264-72, 2000). All of these MLV family members are related to endogenous MLV of *Mus Dunni*.

The HXV$_{35}$ genome has at its 5' (nt 1 to 69) and 3' (nt 8116 to nt 8184) termini a 69-nt repeat (R) region. Downstream of the 5' R region is the 76-nt U5 region followed by the primer binding site (PBS) (Table 6). The HXV$_{35}$ PBS is complementary to the last 18-nt of proline tRNA (Itin and Keshet, *J. Virol.* 54(1):236-239 (1985)), and is thus different from the DG-75 PBS complementary to glutamine or theonine tRNAs (Raisch K P., et al., *Virology* 308(1):83-91, 2003). The gag pro-pol region is interrupted by a single UAG stop codon (at nucleotide 2223) that separates gag from pro pol, a conserved feature in both gamma- and epsilonretroviruses (Goff, S., et al., *Field's Virology*, fourth edition, (Knipe, D. M. and Howley, P. M., eds.). Lippincott Williams & Wilkins. New York. 2001. pp. 1871-1939, 2001). There is readthrough of the stop codon 5% to 10% of the time providing for the synthesis of the pro-pol polypeptide that is processed into protease (PR), reverse transcriptase (RT) and integrase (IN). The gag gene encodes a 536 amino acid polypeptide that is processed into the Matrix (M), p12 protein, Capsid (CA) and Nucleocapsid (NC) proteins (Table 3). The env open reading frame, transcribed as a spliced mRNA, encodes a 645 aa precursor of the envelope glycoproteins, Surface Subunit (SU) and the Transmembrane Subunit (TM) (Table 5). TM contains the transmembrane and the hydrophobic fusion segments that functions in the fusion of viral and cellular membranes. SU is the major determinant of host range and the receptor-binding site. There are hypervariable sequences in the SU protein responsible for selectively binding to the host cell surface receptor. In the SU protein, the variable region A functions in receptor recognition and variable region B stabilizes the virus with its specific receptor (Battini J L, et al., *Proc Natl Acad Sci USA.* 96(4):1385-90, 1992; Fass D., et al., *Science* 277(5332):1662-6, 1997). These variable regions in HXV$_{35}$ are nearly identical in the xenotropic strain DG-75 and are distinct from those in amphotropic and ecotropic MLV s (Table 7). The human cell-surface receptor for xenotropic MLV strains is XPR-1 (xenotropic and polytropic receptor 1), containing multiple transmembrane spanning domains (Battini J L, et al., *Proc Natl Acad Sci USA*. 96(4):1385-90, 1992). XPR-1 is thus the putative cell-surface receptor for HXV.

Figure 5:
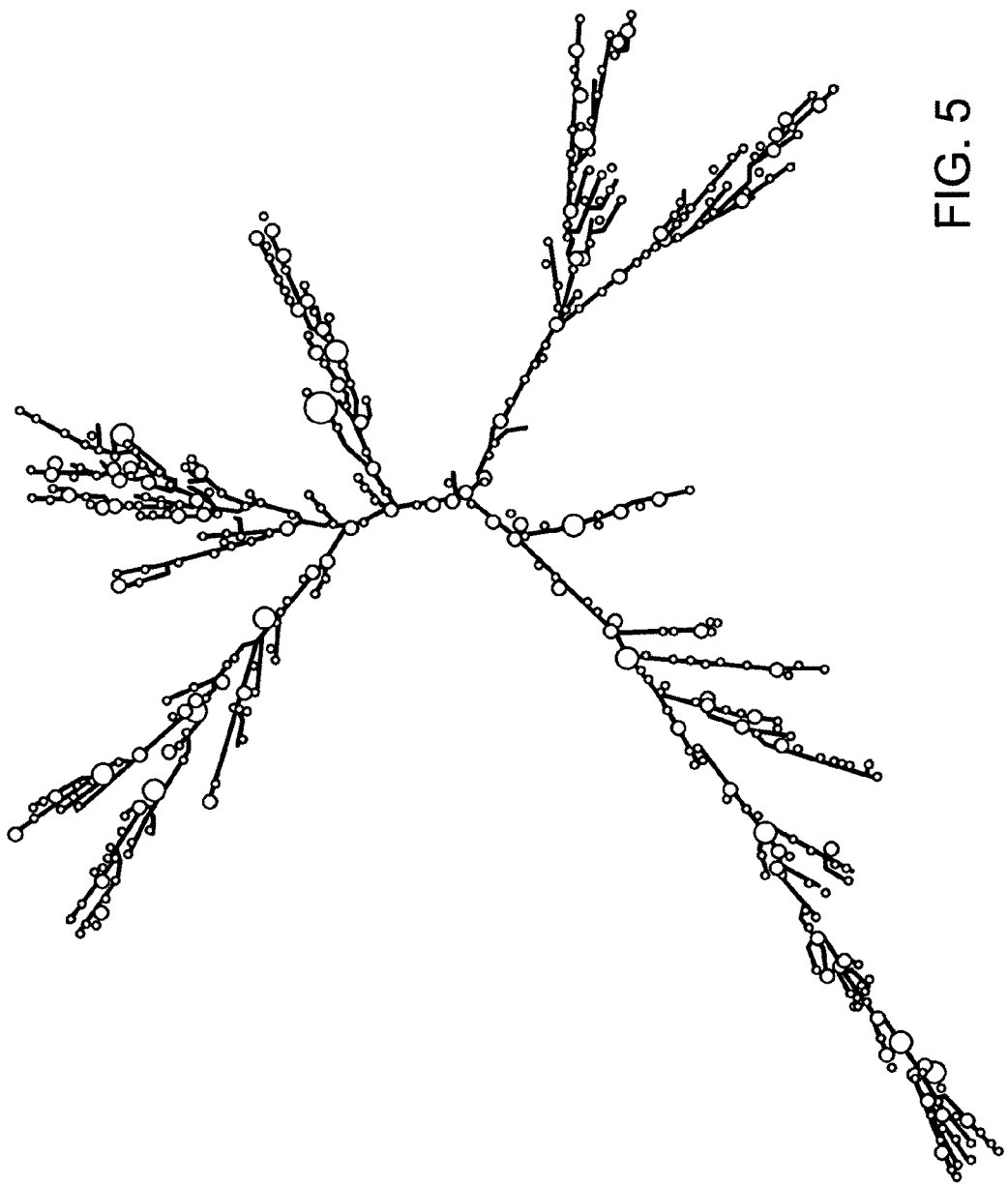
FIG. 5 illustrates the predicted secondary structure of $HXV_{35}$ genomic RNA performed using MFOLD (Zuker M, et al., RNA, 1998, 4(6):669-79, 1998).
Figure 9:
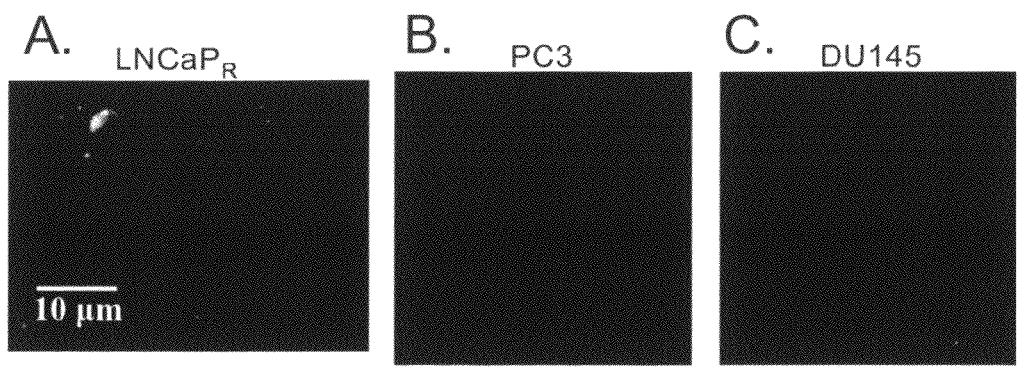
FIG. 9 shows the presence of virus in LNCaP cell line as determined by fluorescence in situ hybridization. FISH analysis on cytoblocks prepared from $LNCaP_R$ (A), PC3 (B) and DU145 (C) cells. The virus FISH probe was generated using a 2.14 kb segment of the viral env genome. (A) Positive fluorescent green signals were seen in both the cytoplasm and nucleus of the $LNCaP_R$ cells indicating labeling of both viral RNA and DNA. (B) Absence of fluorescent signal in PC3 cells and (C) DU145 cells. Method: The deparaffinized slides were rehydrated through a series of decreasing ethanol concentrations. The rehydrated tissue was subjected to target retrieval for 40 min at ~95° C., then allowed to cool to room temperature for 20 min. The tissue was rinsed in $H_2O$, and then 300 μl proteinase K was applied directly to slides for 10 min at room temperature. The tissue was rinsed again in $H_2O$ and dehydrated through increasing EtOH concentrations, then allowed to air dry. Ten ul of probe mix was applied and the slides were coverslipped, debubbled and sealed with rubber cement. The probe and target DNA were codenatured at 73° C. Hybridization occurred at 37° C. overnight. The slides were stringently washed for 3 sec, and incubated for 1 min in a 2×SSC wash at 57° C. The slides were then rinsed with 2×SSC. Vectashield Mounting Medium with DAPI (Vectashield Inc.) counterstain was applied and the slides were left to incubate in the dark at room temperature for at least 30 min to allow the DAPI to fully bind the nucleic acids for clearer nuclear visualization. BLUE: DAPI, GREEN: Virus
Figure 10:
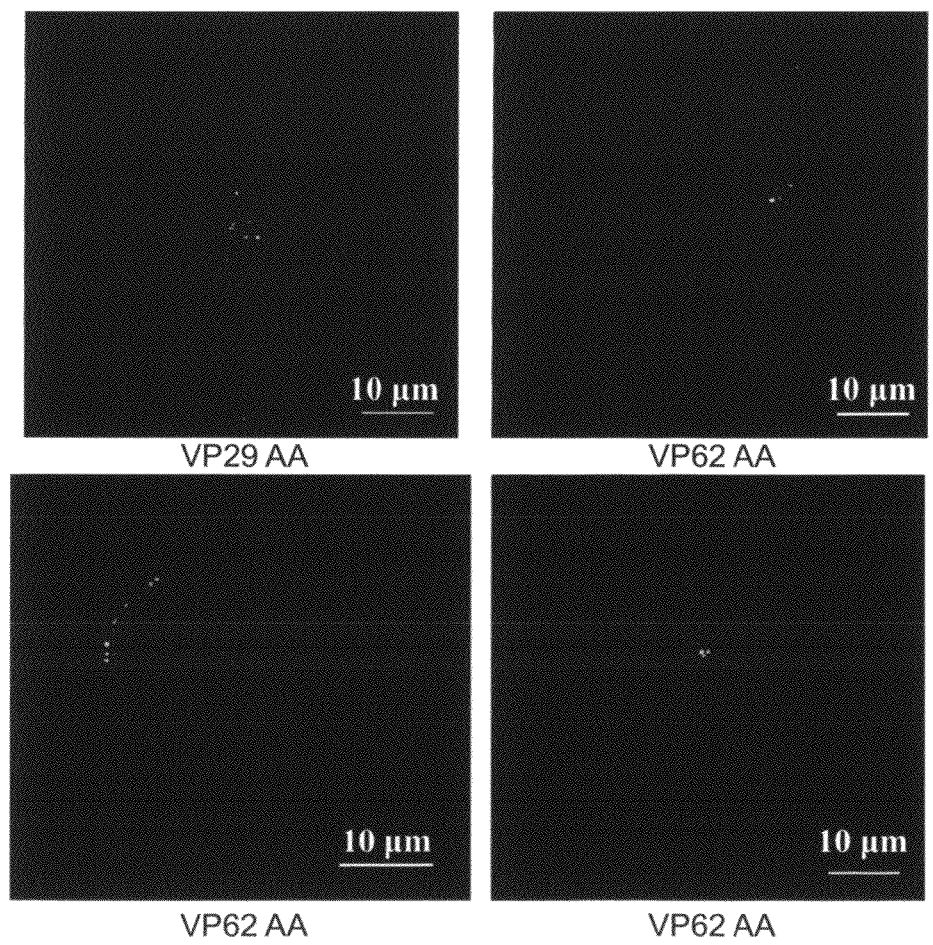
FIG. 10 shows the presence of viral RNA in human prostate cancer tissue. Confocal fluorescent microscopy of FISH on human prostate cancer TMA from two different homozygous mutant RNase L patients (A) Patient VP29, (B, C, D,) Patient VP62. Method: The deparaffinized human prostate cancer TMA slides were rehydrated through a series of decreasing EtOH concentrations. The rehydrated tissue was subjected to target retrieval for 40 min at ~95° C., then allowed cool down to room temperature for 20 min. The tissue was rinsed in $H_2O$, and then ~300 μl proteinase K was applied directly to slides for 10 min at room temperature. The tissue was rinsed again in $H_2O$ and dehydrated through increasing ethanol concentrations, then allowed to air dry. Ten ul's of probe mix was applied and the slides were coverslipped, debubbled and sealed with rubber cement. The probe and target DNA were co-denatured at 73° C. Hybridization occurred at 37° C. overnight. The slides were stringently washed for 3 sec, and incubated for 1 min in a 2×SSC wash at 57° C. The slides were then rinsed with 2×SSC. Vectashield Mounting Medium with DAPI (Vectashield Inc.) counterstain was applied and the slides were left to incubate in the dark at room temperature for at least 30 min to allow the DAPI to fully bind the nucleic acids for clearer nuclear visualization. BLUE: DAPI, GREEN: Virus

2-5A synthetase is activated by viral dsRNA or by stem structures in otherwise single-stranded RNA. For example, the HIV-1 TAR RNA, is capable of activating 2-5A synthetase in vitro (Maitra, R K, et al., *Virology,* 1994, 204(2):823-7). In addition, RNase L is able to potently suppress replication of HIV-1 (Maitra, R K, et al., *J. Virol.,* 1998, 72(2):1 146-52). The MFOLD predicted secondary structure of genomic HXV$_{35}$ RNA is shown (FIG. 5) (Zuker M, et al., *RNA,* 1998, 4(6):669-79). There are extensive regions of internal base-pairing folding into regions of double-stranded stem structures. HXV$_{35}$ RNA will be analyzed to determine if there is sufficient double-stranded character to activate 2-5A synthetase.

To verify the presence of HXV in patient tissue, a frozen prostate core (from patient VP35 previously shown to be positive for the virus by both Virochip analysis and RT-PCR, Table 1) was obtained from the CCF surgical pathology lab in a biohazard plastic container and sent directly to the UCSF group for analysis. PCR was performed on genomic DNA isolated from the prostate tissue (case VP35) and confirmed the presence of HXV DNA by agarose gel electrophoresis and sequencing. These results confirmed that the HXV was present in the human prostate cancer tissue. In addition, nested RT-PCR parameters were developed and used to both confirm initial retrovirus positive tissues and to screen for the presence of the retrovirus in the remaining human prostate cancer tissue. Two nested PCR conditions were designed. The first reaction uses primers that are specific for a region (400 bp) in the gag portion of the virus

```
                                            (SEQ ID NO: 34)
PCRV-GAG-Outside Forward, 5' CGCGTCTGATTTGTTTTGTT
3';

(SEQ ID NO: 35)
PCRV-GAG-Outside Reverse, 5' CCGCCTCTTCTTCATTGTTC
3';

(SEQ ID NO: 36)
PCRV-GAG-Inside Forward, 5' TCTCGAGATCATGGGACAGA
3';

(SEQ ID NO: 37)
PCRV-GAG-Inside Reverse, 5' AGAGGGTAAGGGCAGGGTAA
3',
``` while the second uses primers that amplify 7200 bp of the entire viral genome

```
(HEMI-nested)
                                            (SEQ ID NO: 38)
Env 7600 Outside Forward, 5'CGCTTGGTCCAGTTTGTAAAA
3';

(SEQ ID NO: 39)
Env 227 Reverse, 5' TGGGGAACTTGAAACTGAGG 3';

(SEQ ID NO: 40)
Env 7200 Inside Forward, 5' CTAGTGGCCACCAAACAATTC
3'.
```

7600 Outside Forward and 227 Reverse are the outside oligonucleotide primers for the hemi-nested PCR in the env-LTR region. 7200 Outside Forward is the nested primer. Gel electrophoresis of 3 nested RT-PCRs from different VP patients found to be homozygous mutant (1385AA, R462Q) for RNASEL demonstrate that the nested RT-PCR using the gag region was able to detect the virus in 1 (VP10) of the 3 patients, while the HEMI-nested primers amplified non-specific products (FIG. 6). Sequencing analysis of the PCR product verified the viral RNA to be from HXV.

4. Identification of an HXV-Related Virus in the Human Prostate Cancer Cell Line, LNCaP.

To determine if the common human prostate cancer cell lines (PC3, LNCaP and DU 145) or normal prostate epithelial cells (PrEC, Clonetics Co.) contained HXV or a closely-related virus, RT-PCR was performed on RNA from these cells using primers specific for a conserved 700 bp region within the env protein encoding region of HXV (FIG. 7). RT was performed using random hexamer primers (Applied Biosystems). PCR was subsequently performed on the cDNA produced using primers specific for the conserved 700 bp region of HXV (Virus forward, 5' GTT TAT GGC CAG TTT GGA AA 3' (SEQ ID NO:41); Virus reverse, 5' GCC TTA TGG TGG GGT CTT TC 3' (SEQ ID NO:42)). As a positive control, GAPDH exon 8 specific primers were used. Results showed a band of the correct size for an HXV-related env product from only LNCaP cells (Virus 700 bp) when analyzed by agarose gel electrophoresis. The GAPDH DNA product (391 bp) was present in the RT-PCR reactions from all cell lines (FIG. 6). Interestingly, the LNCaP cell line is heterozygous for an inactivating deletion mutation in RNase L (4710AAAG) and is heterozygous for R462Q. In contrast, PC3, DU 145 and PrEC have wild type RNase L (Xiang Y., et al., Cancer Res. 2003, 63(20):6795-801; Malathi K., et al., Cancer Res. 64(24):9144-51, 2004 et al., 2004). The results described herein thus indicate that RNase L suppresses HXV infections or replication. The env PCR fragment from the LNCaP was cloned into the pGEM®-T Easy Vector (Promega) and sequenced to determine sequence similarity to the virus sequence found in the human prostate tissue samples. After sequence alignment of a 675 nt segment of the LNCaP virus env gene, using BLAST, the LNCaP virus was found to be 97% homologous at both the nucleotide and amino acid levels to the prototype virus, HXV$_{35}$ (Table 8). The same plasmid containing the purified PCR fragment was sequenced another three times to determine if there were errors in the DNA sequencing analysis. It was thus confirmed that the virus from LNCaP cells differs approximately 3-4% through this particular stretch of 700 bp. It is likely that the inactivation of the RNase L, as a result of this mutation, allows the HXV-related virus to infect and replicate in LNCaP cells.

To determine if retrovirus particles with reverse transcriptase activity were being released into the media of these virus infected LNCaP cells, the tissue culture media of the infected LNCaP cells were assayed at 2, 4 and 8 days incubation for reverse transcriptase activity. This assay uses a synthetic homopolymeric polyriboadenylic acid [poly(rA)] as a template, and oligodeoxythymidylic acid [oligo(dT)] as primer. The tissue culture media was incubated with this primer-template and $\forall$-$^{32}$P-dTTP; the resulting dTMP incorporation was monitored by spotting reaction aliquots onto DEAE paper and washing away unincorporated dTTP. Aliquots of undiluted or diluted LNCaP media were spotted onto dry DEAE paper and dried for 30 min under a heat lamp. Mock reactions containing no media were used as negative controls. The paper was washed three times in 2×SSC, rinsed briefly with 95% EtOH twice and dried under a heat lamp. The paper was wrapped in plastic and left to expose x-ray film (Kodak) at −70° C. for 12 hr. Results demonstrate that the LNCaP tissue culture media contains active reverse transcriptase while the mock controls showed only unincorporated a $\forall^{32}$P-dTTP as background (FIG. 8). It has also demonstrated that media from the infected LNCaP cells are capable of infecting both uninfected LNCaP and DU145 cells, though the amount of virus present in the DU145 cells was lower than that in LNCaP after infection as indicated by RT-PCR analysis using primers specific for the retrovirus. DU145 is homozygous wild type for RNase L (Xiang Y., et al., *Cancer Res.*, 2003, 63(20):6795-801). The difference in the amount of virus present in these cells after infection may be due to the mutations in RNase L found in the LNCaP cell line not present in the DU145 cells. The RNase L enzymatic deficiency in the LNCaP may allow the virus to escape the anti-viral affect of RNase L, while virus load in the DU145 cells is decreased owing to these cells having fully functional RNase L.

5. Identification of HXV Nucleic Acid in Prostate Cancer Tissue by Fluorescence in Situ Hybridization (FISH) Methods.

To directly demonstrate the presence of HXV DNA in prostates, FISH was performed on human prostate tissues collected by prostatectomy, and subsequently fixed in formalin and embedded in paraffin. The LNCaP cell line, confirmed to have a quasispecies of the virus by RT-PCR and sequencing analyses, were used as a positive control, while the PC3 and DU145, which were found negative for the virus, were used as negative controls. Cytoblocks were prepared from the three cell lines. Approximately $10^9$ cells were washed with Hanks balanced salt solution (HBSS) without phenol red, or $Ca^{++}$ & $Mg^{++}$ (GIBCO) and resuspended gently, but completely, with 10% neutral buffered formalin. The cell suspension was then fixed overnight at 4° C. The cells were then centrifuged and washed twice with HBSS. The supernatant was aspirated and the cells were resuspended with one drop of HBSS. The cell suspension was then pipetted into the well of a cytoblock cassette. The fixed cell culture cytoblocks were sent to the histology lab to be processed within 24 hr. The processed cytoblocks were then embedded into paraffin blocks, cut at 4-6 μm thick sections onto super-frost slides and baked for at least 4 hr at 60-65° C. to ensure the cells adhered to the slides.

The $HXV_{VP35}$ FISH probe was generated using a 2.15 kb segment of the viral genome Virus 2345 forward, 5' ACC CCT AAG TGA CAA GTC TG 3' (SEQ ID NO:43); Virus 4495 reverse, 5' CTG GAC AGT GAA TTA TAC TA 3' (SEQ ID NO:44) that was cloned into the pGEM®-T Easy Vector. The recombinant vector was restricted using EcoRI to release the 2.15 kb viral cDNA fragment and purified (Qiagen) for FISH probe generation. The purified 2.15 kb viral cDNA insert was used in a nick translation reaction (Vysis Inc.) as described in the manufacturer's instructions to a produce fluorescently labeled probe. The probe size, approximately 250 bp, was determined on an agarose gel. To the sample, Human COT1-DNA (Vysis Inc.) and human placental DNA (Sigma) was added as blocking agents. The probe was then precipitated and resuspended in nuclease-free water. To determine incorporation, the fluorescent emission of the supernatant from the precipitation step was compared to that of the resuspended probe. The average SpectrumGreen-dUTP incorporation was determined to be 19%.

Freshly baked LNCaP, DU145 and PC3 slides cut at ~4 μm sections were first deparaffinized through a series of xylene washes. The deparaffinized slides were then rehydrated through a series of decreasing ethanol concentrations. The rehydrated tissue was subjected to target retrieval and rinsed in $H_2O$. Proteinase K (Dako) was applied directly to slides for 10 min at room temperature. The tissue was rinsed again in $H_2O$ and dehydrated through solutions with increasing ethanol concentrations. The remaining steps were performed in reduced light to minimize probe photobleaching. Onto freshly dried slides, probe mix [3:1 probe+7:1 Hybridization buffer (Vysis Inc.)] was applied. Coverslips were placed on the slides which were debubbled and sealed with rubber cement. The probe and target DNA were codenatured using a Vysis Hybrite (Vysis). Hybridization occurred at 37° C. overnight in a humidified, light tight chamber. The next day, coverslips were removed by soaking the slides in 2×SSC. The slides were then agitated for 3 sec, and incubated for 1 min in a 2×SSC wash at 57° C. The slideswere then rinsed with 2×SSC at room temperature gently, followed by distilled water, and allowed to air dry. Vectashield Mounting Medium with DAPI (Vectashield Inc.) counterstain was applied to the dried tissue and coverslips were added.

Results show positive fluorescent green signals were seen in both the cytoplasm and nucleus of the LNCaP cells, while no signal was observed in the DU145 or PC3 cells (FIG. 9). These results correlate with the RT-PCR data which showed that the virus was present in the LNCaP cells, and not the DU145 or PC3 cell line. Intense staining observed within the cytoplasm indicated that some probe may be binding viral RNA as well as DNA. After performing an RNase pretreatment of the tissue, a significant amount of the labeling was diminished in the cytoplasm, confirming RNA hybridization, and indicating that the labeling in the cytoplasm may be probe binding to RNA and unintegrated viral DNA. A DNase digestion following the RNase digestion completely obliterated the fluorescent signals both in the cytoplasm and nucleus, specifying probe hybridization to viral DNA (not shown). DNase or RNase pretreatment of the human prostate tissue was not preformed in the subsequent experiments. As a result, the possibility of the probe hybridizing to any viral sequence (RNA or DNA) in the patient tissues was maintained.

Results of initial experiments using the human prostate cancer tissue microarray (TMA) slides (FIG. 10) demonstrate approximately 1% of cells having specific hybridization for the HXV DNA probe, and those positives are present in patients found to be positive for the virus by RT-PCR by the UCSF group (Table 9). The slides were examined in a blinded study, allowing unbiased investigation of the FISH experiments. An arbitrary cutoff value was assigned for quantitating the FISH results. The guidelines for monitoring positive FISH results were as follows: <1 positive cell/500 cells counted=−; 1-2 positive cells/500 cells counted=+/−; 3-4 positive cells/500 cells counted=+; and 5-6 positive cells/500 cells counted=++. The positive FISH results correlated with RT-PCR results by the UCSF group. Although positive hybridizations were seen in 5 out of 8 tissues from patients found to be HXV positive by RT-PCR, one tissue (VP3 1) was determined to be "++" for FISH, without being positive for the virus by RT-PCR. Likely explanations of obtaining only 5 out of 8 positives using FISH could be differences in the frequency of the virus within the specific tissue specimen being analyzed compared to that of the tissue used for RT-PCR analysis, resulting in a viral number below the detectable limit of the FISH method. Alternately, a technical problem may have also been encountered during tissue harvesting and processing, which caused RNA or DNA degradation.

6. Detection of HXV with Novel Affinity-Purified, Anti-HXV Peptide Antibodies.

To detect HXV gag protein in infected cells and tissues, novel antibodies were generated (Open Biosystems, Inc.). A hydropathy plot was generated from HXV35 gag protein, from which the following peptides were chosen as immunogen (FIG. 11):

```
MA: DVKKRRWVTFCSAE          (SEQ ID NO: 7)
(antibody 401)
```

-continued

CA: EAGKAVRGNDGRPTQL (SEQ ID NO: 8)
(antibody 402)

NC: KDCPKKPRGPRGPR (SEQ ID NO: 9)
(antibody 403)

Figure 12:
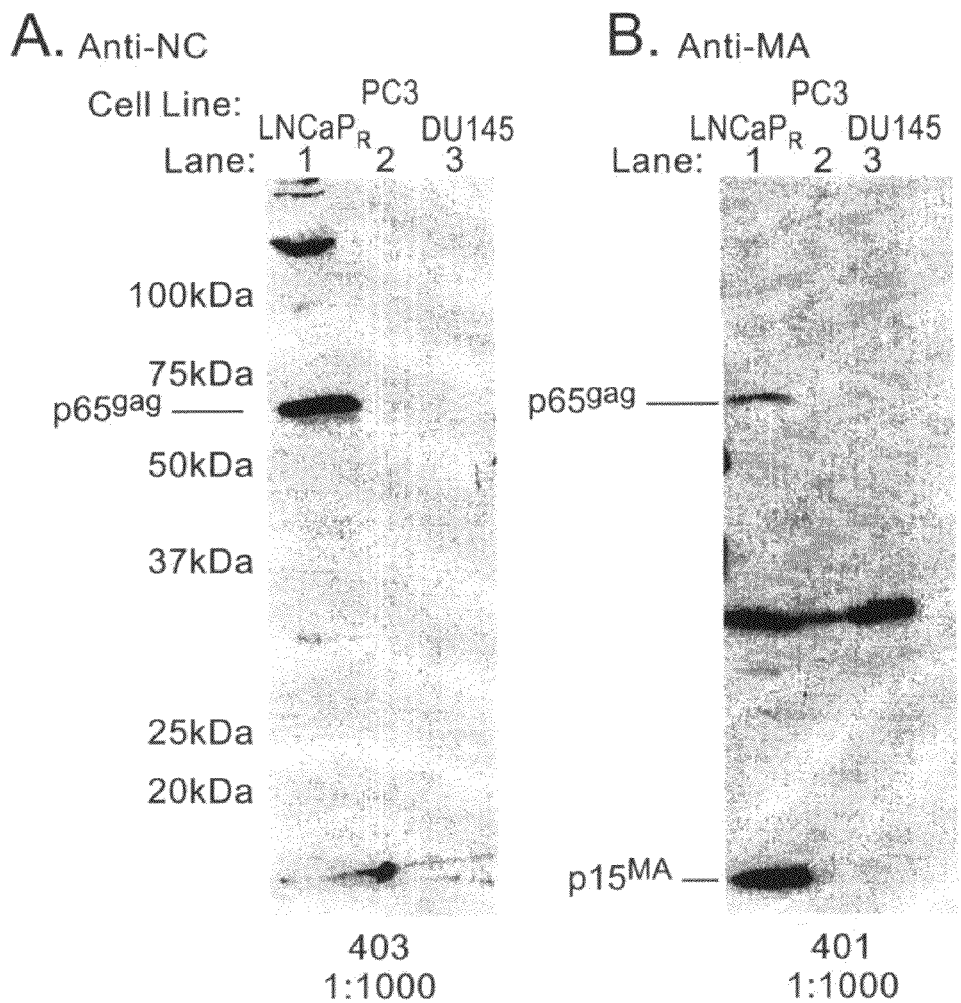
FIG. 12 shows western blots using (A) anti-NC, and (B) anti-MA antibodies on separate proteins from (lane 1) $LNCaP_R$, (lane 2) PC3, and (lane 3) DU145 cells.
Figure 18C:
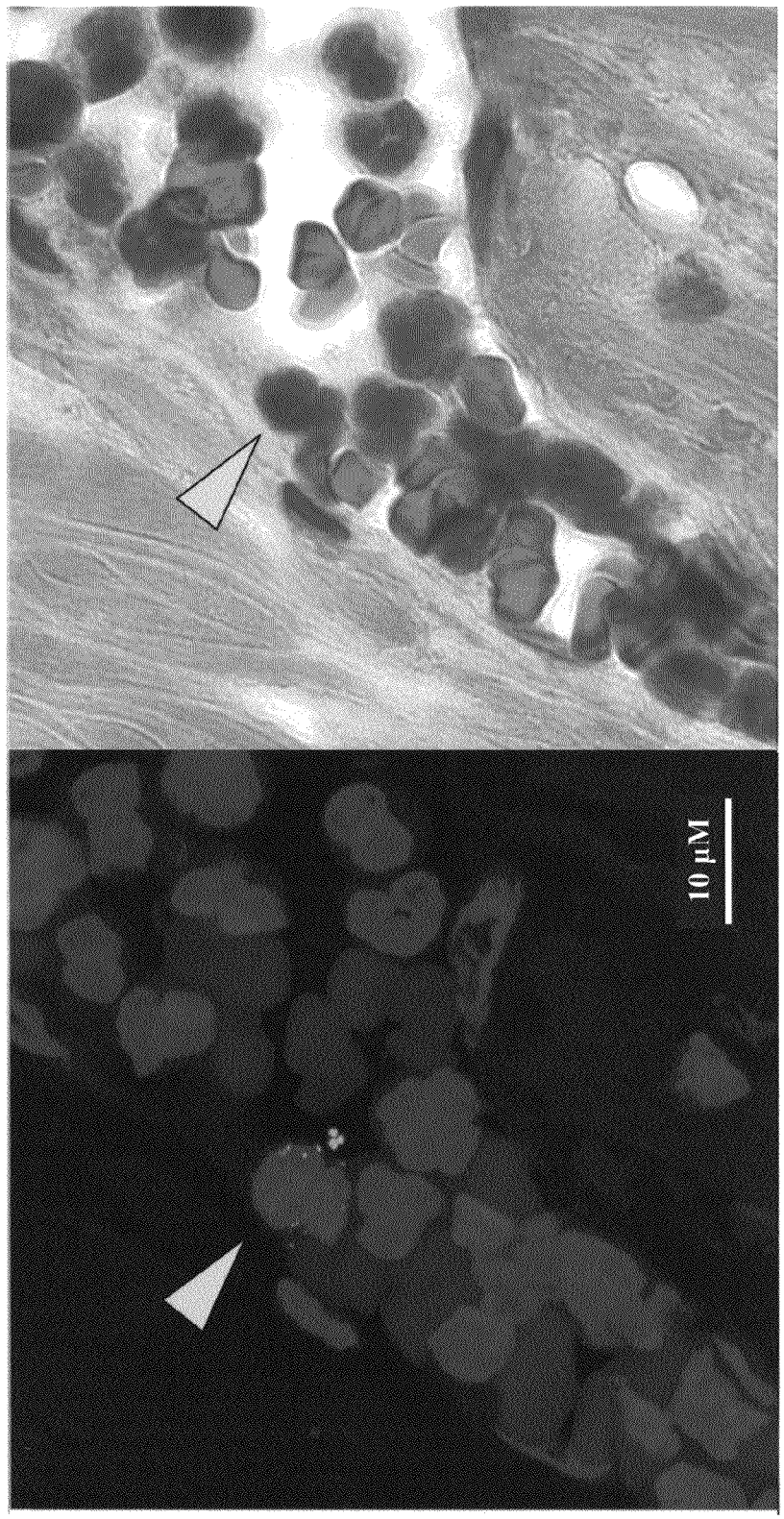
Figure 18D:
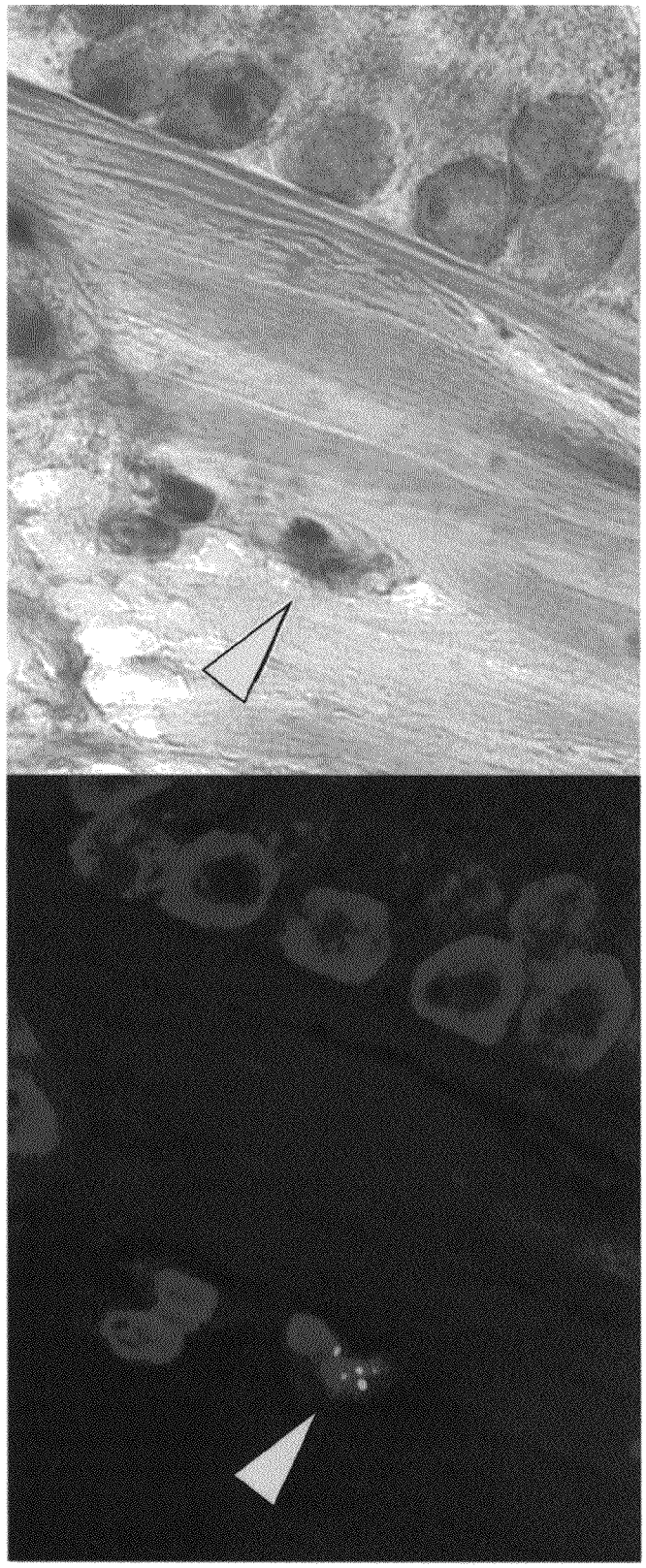
Figure 19:
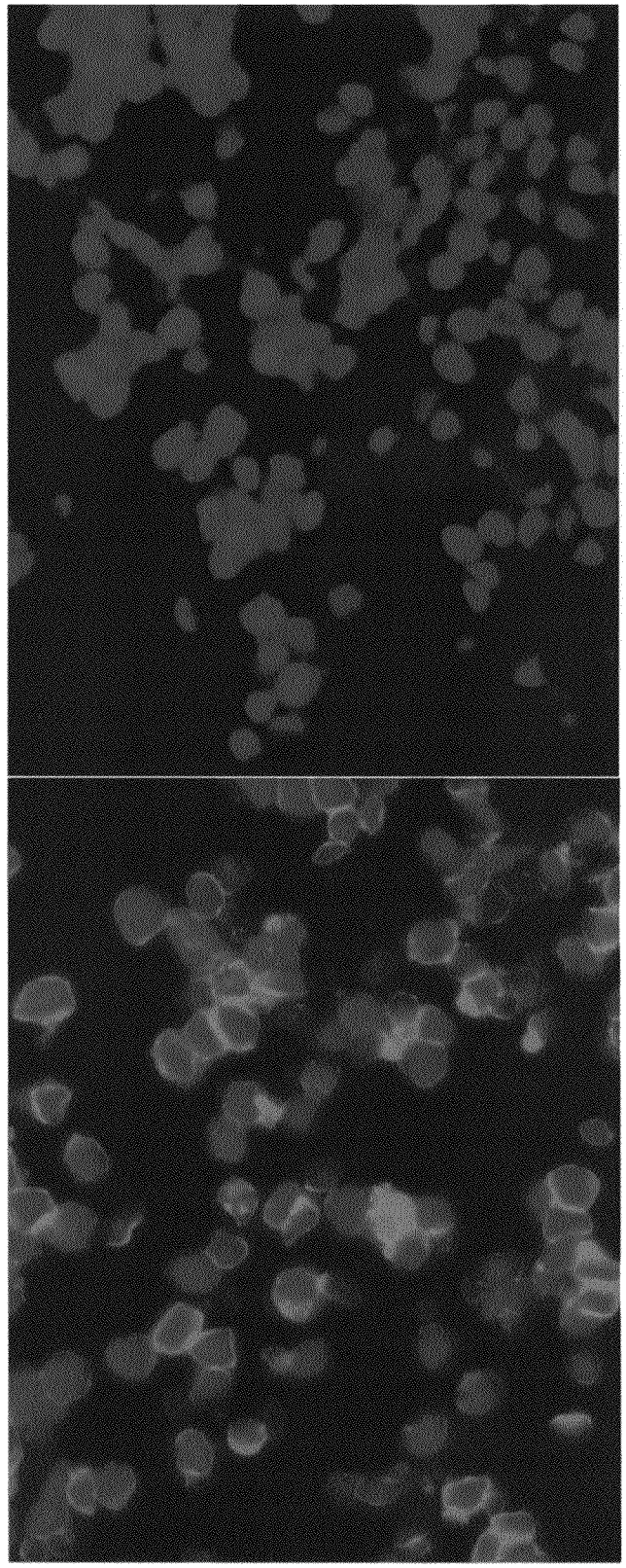
FIG. 19 immunohistochemical analysis of LNCaP, clone R, which shows that LNCaP clone R is XMRV positive by IHC with antibody to p30 capsid.
Figure 20:
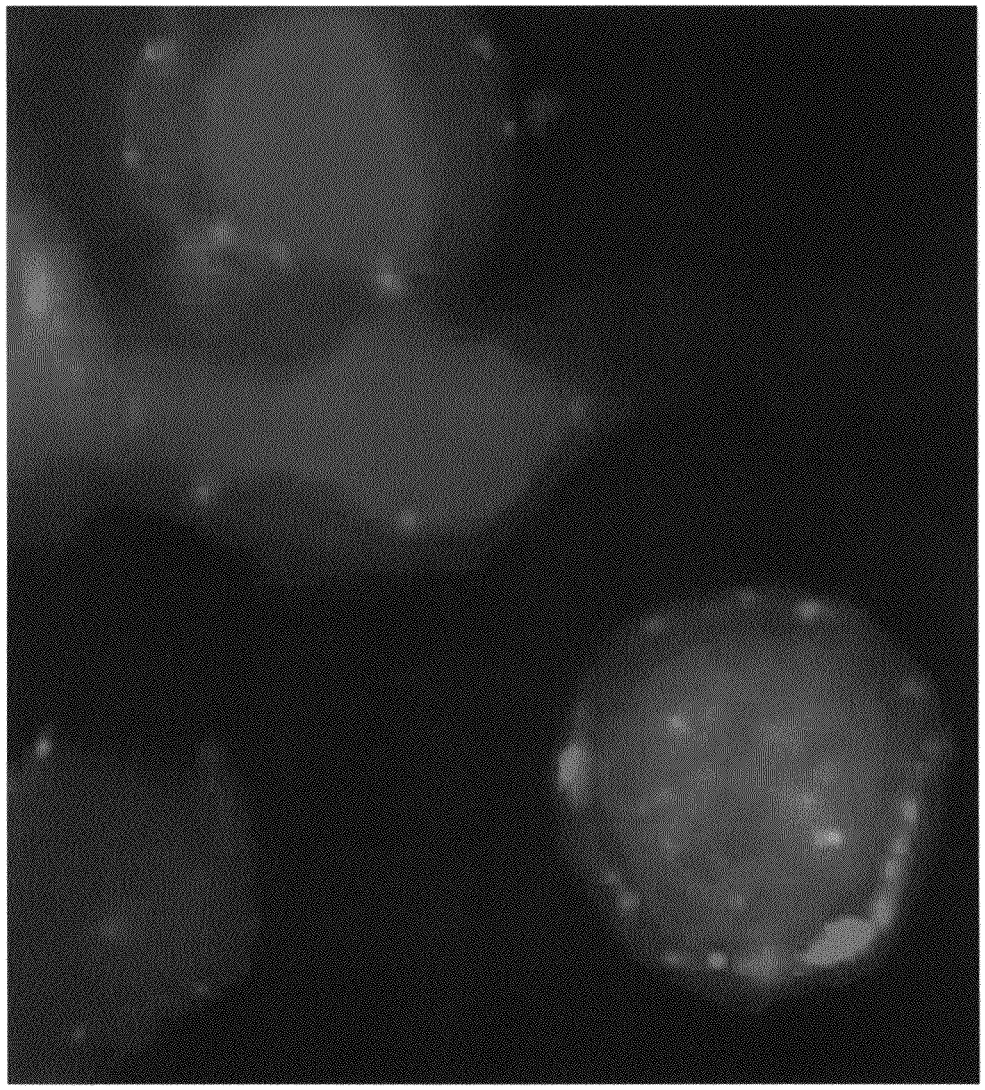
FIG. 20 shows doubling labeling by IHC and FISH of HXV in LNCaP infected cells which shows that LNCaP clone R is XMRV positive by FISH and IHC. Immunohistochemistry with specific antiserum prepared in goats to Rauscher mouse leukemia virus p30 protein (ATCC, catalog no. VR-1564AS-Gt) showing labeling of HXV gag protein plus DAPI (blue) staining of nuclei plus FISH labeling (green) of virus nucleic acid as described in FIGS. 18A-18D.
Figure 21:
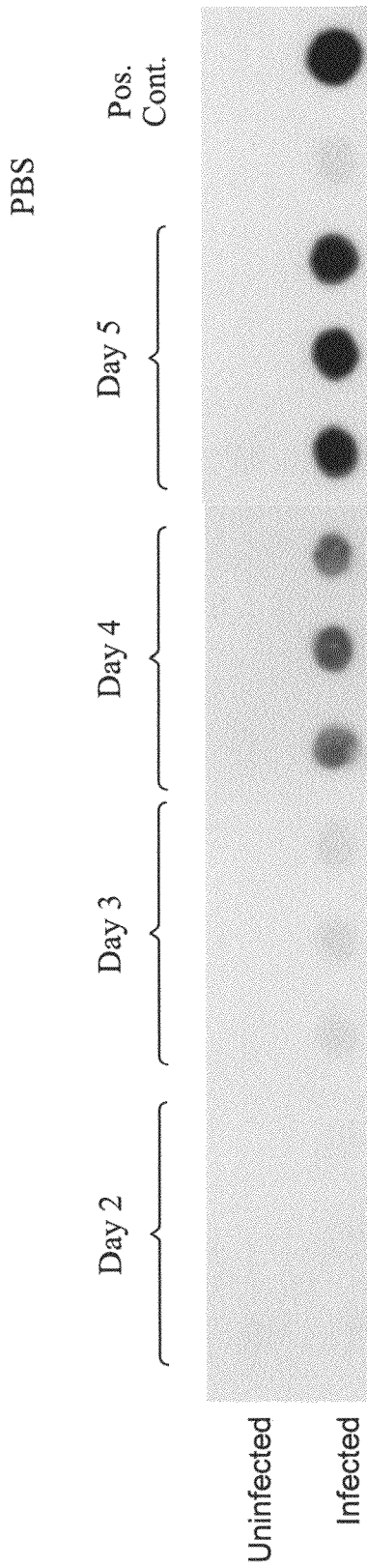
FIG. 21 shows the results of a reverse transcriptase assay which shows that the virus (XMRV-LN) produced by LNCaP cells is infectious when used to infect DU145 human prostate cancer cells. DU145 cells were infected with 500 uls of LNCaP infected supernatant for 3 hours in the presence of 8 ug/ml polybrene, –FBS. Virus was monitored by reverse transcriptase assay.

Antibodies were generated in rabbits and subsequently affinity purified by binding to and elution from the immobilized proteins (according to protocols developed at Open Biosystems, Inc.). The antibodies to MA (401) and NC (403) were successful in detecting gag from the HXV-related infected LNCaP$_R$ cells (FIG. 12).

Conclusions

Described herein is the discovery of the novel gammaretrovirus, HXV, present in tumor-bearing prostates. The percentage of prostate containing HXV is significantly higher in patients with a homozygous R462Q variant of RNase L (HPC1) (60%) than in patients that are wild type or heterozygous (<10%). The potential involvement of HXV in this disease is thus based primarily on a higher rate of occurrence of HXV in prostates of patients with homozygous germline mutations in the gene for RNase L, a candidate prostate cancer susceptibility gene (HPC1). Beyond this correlation, the evidence that HXV infections contribute to prostatic carcinogenesis is as follows. As a group, retroviruses are responsible for a wide-range of different diseases including immunodeficiency, leukemia and neurological disease (Goff, S., Retroviridae: The Retroviruses and Their Replication, Chapter 57 in "Field's Virology", fourth edition. (Knipe, D. M. and Howley, P. M., eds.). Lippincott Williams & Wilkins. New York, pp. 1871-1939, 2001). Nevertheless, many of the simple retroviruses are relatively benign and are even widely used as backbones of gene therapy vectors. A relatively small number of retroviruses such as the lentivirus, HIV-1, and some avian retroviruses are cytopathic. Others, namely the acute transforming retroviruses, contain host genes that cause aggressive tumors in the absence of latency. But most retroviruses are not cytopathic and have minimal effects on cellular replication or physiology. These retroviruses, unlike many other viruses, use only a small proportion of the cell's capacity to replicate. In vivo low level viremia is often obtained and is persistent for the life of the animal. However, even when they are not cytopathic, retroviruses cause disease by insertional mutagenesis that alters control of cell division or survival. These DNA insertion events can activate endogenous proto-oncogenes and lead to tumorigenesis. The disease process can be very slow, as in the case of mouse mammary tumor virus (MMTV). HXV may be a member of the latter category of simple, replication-competent retroviruses characterized by slow growth and a long latency period. Simple retroviruses are linked primarily to leukemia or lymphoma, diseases not presently implicated in HXV infections. The number of HXV-infected prostate cells, even in homozygous RNase L (R462Q) cases, is low (on the order of 1%) (Table 9). The potential contribution of HXV to cancer could be owing to a slow infection resulting in proliferative inflammatory atrophy, a suspected precursor to prostatic intraepithelial neoplasia and carcinoma (Nelson W G., et al., *N Engl J Med*, 349(4):366-81, 2003). The infected cells, while few in number, could be producing growth factors, cytokines or other factors that are indirectly contributing to cell proliferation (Brightman B K, et al., J. Virol., 1990 September; 64(9): 4582-4). Regardless of the mechanism, it is likely that any carcinogenesis caused by HXV would occur as a multistep process that occurs over the course of many years. The fact that prostate cancer is a disease of aging that is usually not apparent until after age 65 is consistent with a slow-virus causing chronic or recurrent inflammation.

The general overview described in Example 1 is even more fully detailed in Examples 2 and 3 as follows.

Example 2

Identification of a Distinctive Gammaretrovirus Genome in Prostate Tumors of Patients Homozygous for R462Q RNASEL Variant RNase L is an important effector of the innate antiviral response. Mutations or variants that impair function of RNase L, particularly R462Q, have been proposed as susceptibility factors for prostate cancer. As shown herein, a viral infection likely contributes to prostate cancer in individuals harboring the R462Q variant. Randomly amplified cDNA from prostate tumors was assayed for the presence of viral sequences by hybridization to a DNA microarray composed of oligonucleotides corresponding to the most conserved sequences of all known viruses. The presence of retroviral sequences was revealed by microarray in 7 of 11 R462Q-homozygous (QQ) cases, and in one among 8 heterozygous (RQ) and homozygous wild-type (RR) cases. Full-length viral genomes were cloned and sequenced from the tumor tissue of two QQ cases. The virus is closely related to xenotropic murine leukemia viruses (MuLVs), but its sequence is clearly distinct from all known members of this group. Based on recovered sequence, a specific RT-PCR assay was developed and testing of tumor tissue was expanded to a total of 86 cases. Eight of 20 QQ cases (40%) were found to be positive, compared to only one sample (1.5%) among 66 RQ and RR cases. Comparison of gag and pol sequences from different tumor isolates indicated infection with the same virus in all cases, yet sequence variation was consistent with the infections being independently acquired. These data provide the first demonstration that xenotropic MuLV-related viruses can produce an authentic human infection, and strongly implicate RNase L activity in the prevention or clearance of infection in vivo. These findings also demonstrate a relationship between exogenous infection and cancer development in genetically susceptible individuals.

Materials and Methods

Genotyping of Patients and Prostate Tissue Processing

All human samples used in this study were obtained according to protocols approved by the Cleveland Clinic's Institutional Review Board. Men scheduled to undergo prostatectomies at the Cleveland Clinic were genotyped for the R462Q (1385G->A) RNASEL variant using a premade TAQ-MAN genotyping assay (Applied Biosystems, Foster City, Calif., USA; Assay c_935391_1) on DNA isolated from peripheral blood mononuclear cells (PBMC). Five nanograms of genomic DNA were assayed according to the manufacturer's instructions, and analyzed on an Applied Biosystems 7900HT Sequence Detection System instrument. Immediately after prostatectomies, tissue cores were taken from both the transitional zone (the site of benign prostatic hyperplasia, BPH) and the peripheral zone (where cancer generally occurs), snap-frozen in liquid nitrogen and then stored at −80° C. Remaining prostate tissue was fixed in 10% neutral buffered formalin, processed and embedded in paraffin for later histological analyses. Frozen tissue cores were transferred from dry ice immediately to TRIZOL reagent (Invitrogen, Carlsbad, Calif., USA), homogenized with a power homogenizer or manually using a scalpel followed by a syringe, and total RNA was isolated according to the manufacturer's instructions. The prostate tissue RNA was then subjected to RNase-free DNase I (Ambion, Austin, Tex., USA) digestion for 30 minutes at 37° C. The sample was then extracted with phenol and the RNA was precipitated with isopropanol overnight at −20° C. followed by centrifugation at 12,000 g for 30 minutes at 4° C. Poly-A RNA was isolated from the DNase digested total RNA using the Oligotex mRNA Midi Kit (Qiagen USA, Valencia, Calif., USA) as instructed by the manufacturer. The poly-A RNA concentration was measured using the RIBOgreen quantitation kit (Molecular Probes, Invitrogen, Carlsbad, Calif., USA), and the samples were stored at −80° C.

Microarray Screening

Virochip microarrays used in this study were identical to those previously described (Wang D, et al., 2002, Proc Natl Acad Sc. USA 99: 15687-15692; Wang D, et al., 2003, PLoS Biol 1: E2; Urisman A, et al., 2005, Genome Biol 6: R78) Prostate tumor RNA samples were amplified and labeled using a modified Round A/B random PCR method and hybridized to the Virochip microarrays as reported previously (Wang D, et al., 2003, PLoS Biol 1: E2). Microarrays were scanned with an Axon 4000B scanner (Axon Instruments, Union City, Calif., USA) and gridded using the bundled GenePix 3.0 software. Microarray data have been submitted to the NCBI GEO database (GSE3607). Hybridization patterns were interpreted using E-Predict as previously described (Urisman A, et al., 2005, Genome Biol 6: R78) (Table 12). To make FIGS. 22A-22B, background-subtracted hybridization intensities of all retroviral oligonucleotides (205) were used to cluster samples and the oligonucleotides. Average linkage hierarchical clustering with Pearson correlation as the similarity metric was carried out using Cluster (v. 2.0) (Eisen, M B., PNAS 95:14863-14868 (1998)).Cluster images were generated using Java TreeView (version 1.0.8) (Saldanha, A J., 2004, Bioinformatics 20: 3246-3248).

Genome Cloning and Sequencing

Amplified and labeled cDNA from the VP35 tumor sample was hybridized to a hand-spotted microarray containing several retroviral oligonucleotides, which had high hybridization intensity on the Virochip during the initial microarray screening. Nucleic acid hybridizing to two of the oligonucleotides (9628654_317 rc derived from MTCR: TTC GCT TTA TCT GAG TAC CAT CTG TTC TTG GCC CTG AGC CGG GGC CCA GGT GCT CGA CCA CAG ATA TCC T (SEQ ID NO:45); and 9626955_16 rc derived from Spleen focus-forming virus: TCG GAT GCA ATC AGC AAG AGG CTT TAT TGG GAA CAC GGG TAC CCG GGC GAC TCA GTC TGT CGG AGG ACT G (SEQ ID NO:46)) was then individually eluted off the surface of the spots and amplified by PCR with Round B primers. Preparation of the hand-spotted array, hybridization, probe recovery, and PCR amplification of the recovered material were carried out. The recovered amplified DNA samples were then cloned into pCR2.1-TOPO TA vector (Invitrogen), and the resulting libraries were screened by colony hybridization with the corresponding above oligonucleotides as probes. Hybridizations were carried out using Rapid-Hyb buffer (Amersham, Piscataway, N.J., USA) according to the manufacturer's protocol at 50° C. for 4 hours. Eight positive clones were sequenced, of which two (one from each library; clones K1 and K2R1 in FIG. 23A) were viral and had 94-95% nucleotide identity to MTCR.

To sequence the remainder of the VP35 genome as well as the entire genome from the VP42 tumor, fragments of the genome were amplified by PCR using either amplified (Round B) or unamplified (Round A) cDNA prepared for original Virochip screening. This was accomplished first using a combination of primers derived from the sequence of MTCR (GenBank: NC 001702) and earlier recovered clones of XMRV; all primers are listed in Table 11. The amplified fragments were cloned into pCR2.1-TOPO TA vector (Invitrogen) and sequenced using M13 sequencing primers. Genome assembly was carried out using CONSED version 13.84 for Linux (Gordon, D., et al., 1998, Genome Res 8: 195-202). Assembled genome sequences of XMRV VP35 and VP42 have been submitted to GenBank (accessions DQ241301 and DQ241302).

PCR

Screening of tumor samples by gag nested RT-PCR was carried out according to Protocol S3. PCR fragments in all positive cases were gel purified using QIAEX II gel extraction kit (Qiagen), cloned into pCR2.1-TOPO TA vector (Invitrogen), and sequenced using M13 sequencing primers. Pol PCR was carried out using amplified cDNA (Round B material) as the template. Sequence of the primers used for amplification (2670F, 3870R, 3810F, and 5190R) are listed in Table 11. Amplified products were gel purified using QIAEX II gel extraction kit (Qiagen), and purified products were directly used for sequencing.

Phylogenetic Analysis

Figure 24:
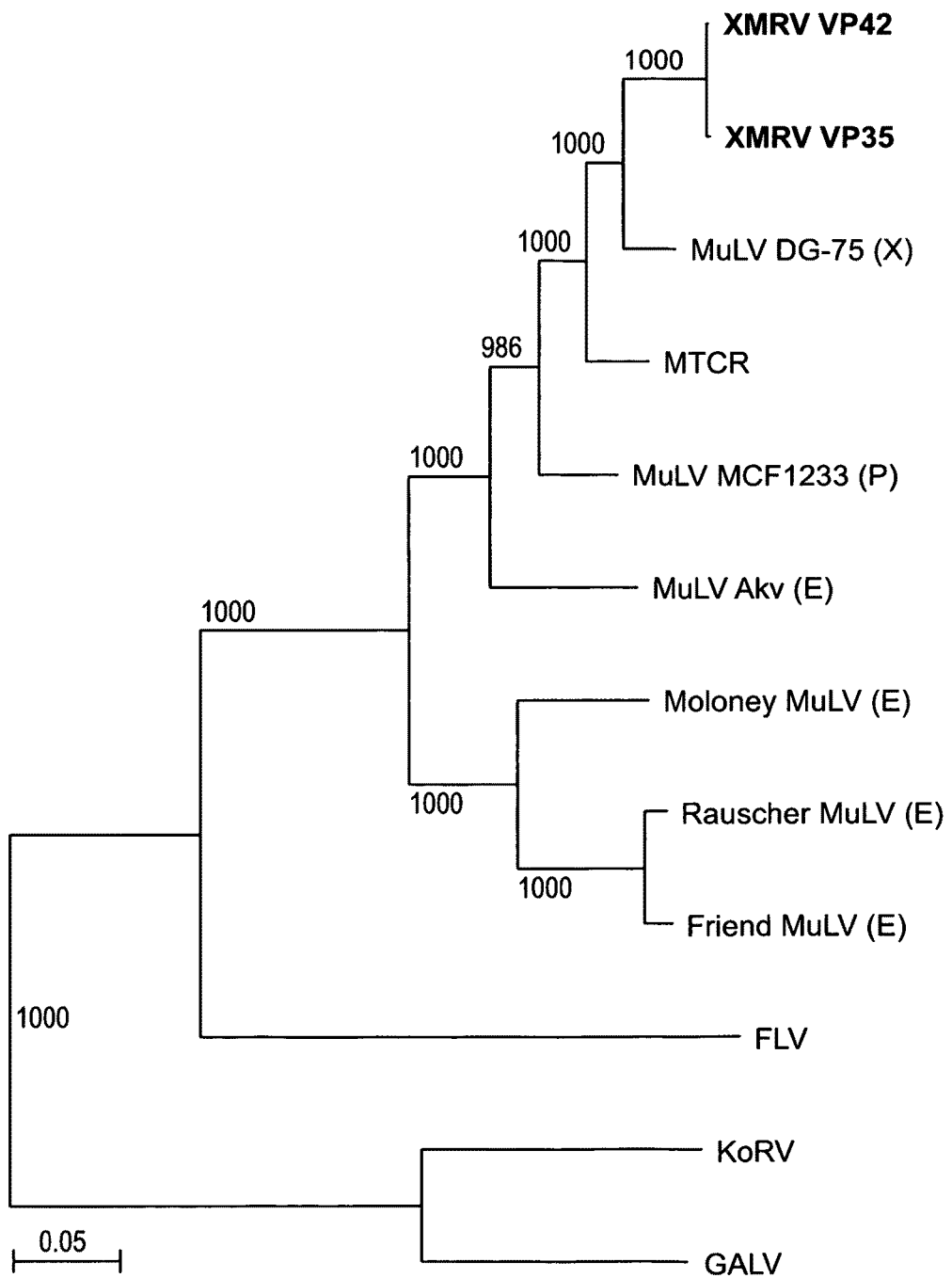
FIG. 24 shows the phylogenetic analysis of XMRV based on complete genome sequences. Complete genomes of XMRV VP35 and VP42; MTCR; MuLVs DG-75, MCF1233, Akv, Moloney, Friend, and Rauscher; Feline leukemia virus (FLV); Koala retrovirus (KoRV); and Gibbon ape leukemia virus (GALV) were aligned using ClustalX (see Materials and Methods). An unrooted neighbor joining tree was generated based on this alignment, excluding gaps and using Kimura's correction for multiple base substitutions. Bootstrap values (N=1000 trials) are indicated. MuLV genomes are labeled as xenotropic (X), polytropic (P), or ecotropic (E) based on published experimental evidence (Raisch K P, et al., *Virology* 308: 83-91; O'Neill R R., et al., *J Virol* 53: 100-106; Perryman S., et al., *Nucleic Acids Res* 19: 6950; Shinnick T M., et al., *Nature* 293: 543-548; Sijts E J., et al., *Virus Res* 34: 339-349; Khimani A H., et al., *Virology* 238: 64-67; Lenz J., et al., *J Virol* 42: 519-529).

The neighbor joining tree of full-length genomes (FIG. 24) was generated as follows. Genomes of XMRV VP35 (GenBank: DQ241301) and VP42 (GenBank: DQ241302), MTCR (GenBank: NC 001702), MuLV DG-75 (GenBank: AF221065), MuLV MCF1233 (GenBank: U13766), AKV MuLV (GenBank: J01998), Friend MuLV (GenBank: NC 001362), Rauscher MuLV (GenBank: NC 001819), Moloney MuLV (GenBank: NC 001501), Feline leukemia virus (GenBank: NC 001940), Gibbon ape leukemia virus (GenBank: NC 001885), and Koala retrovirus (GenBank: AF151794) were first manually edited to make all genomes the same length, i.e. R to R. The edited sequences were then aligned with ClustalX version 1.82 for Linux (Thompson, J D., et al., 1997, Nucleic Acids Res 25: 4876-4882; Jeanmougin, F., et al., 1998, Trends Biochem Sci 23: 403-405) using default settings. The tree was generated based on positions without gaps only; Kimura correction for multiple base substitutions (Kimura, M., 1980, J Mol Evol 16: 111-120) and bootstrapping with N=1000 were also used.

Figure 27A:
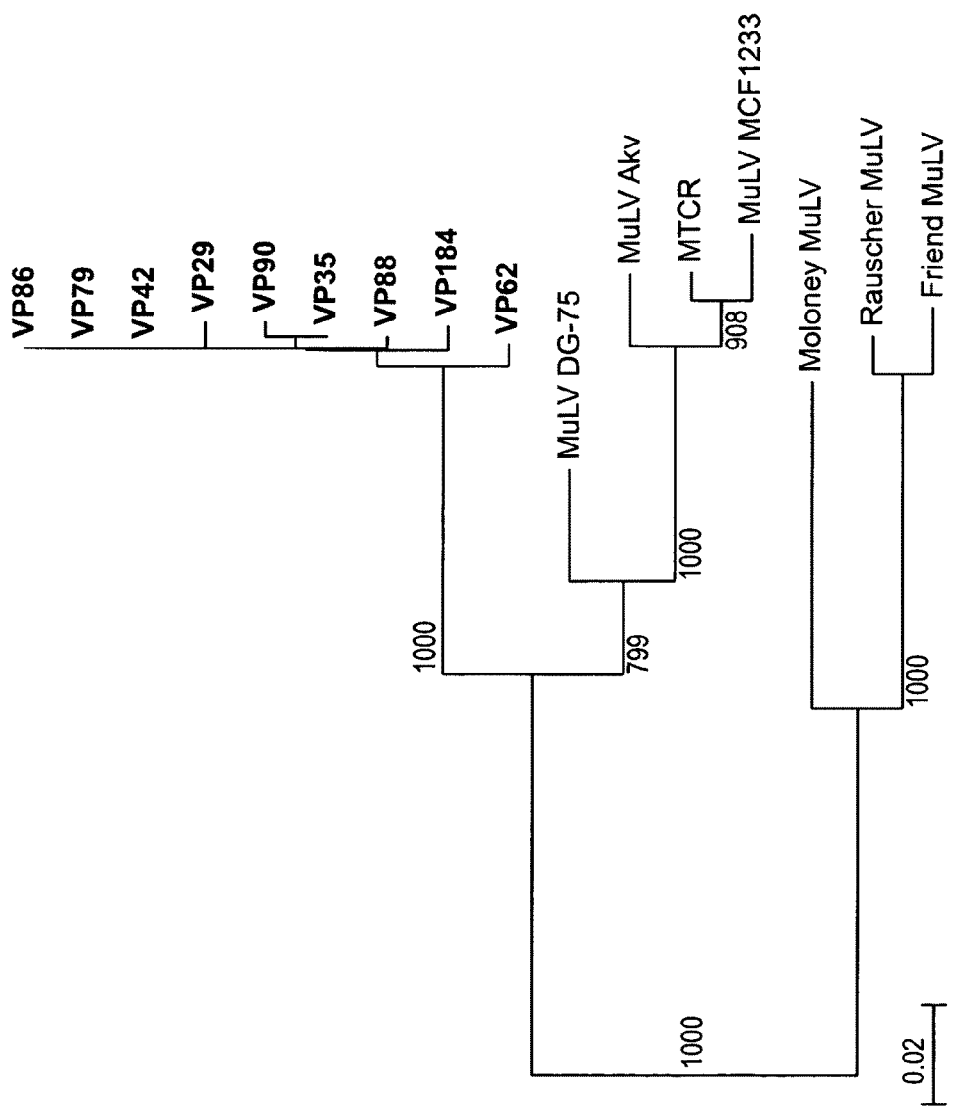
FIGS. 27A-27B shows a comparison of XMRV sequences derived from tumor samples of different patients.
Figure 27B:
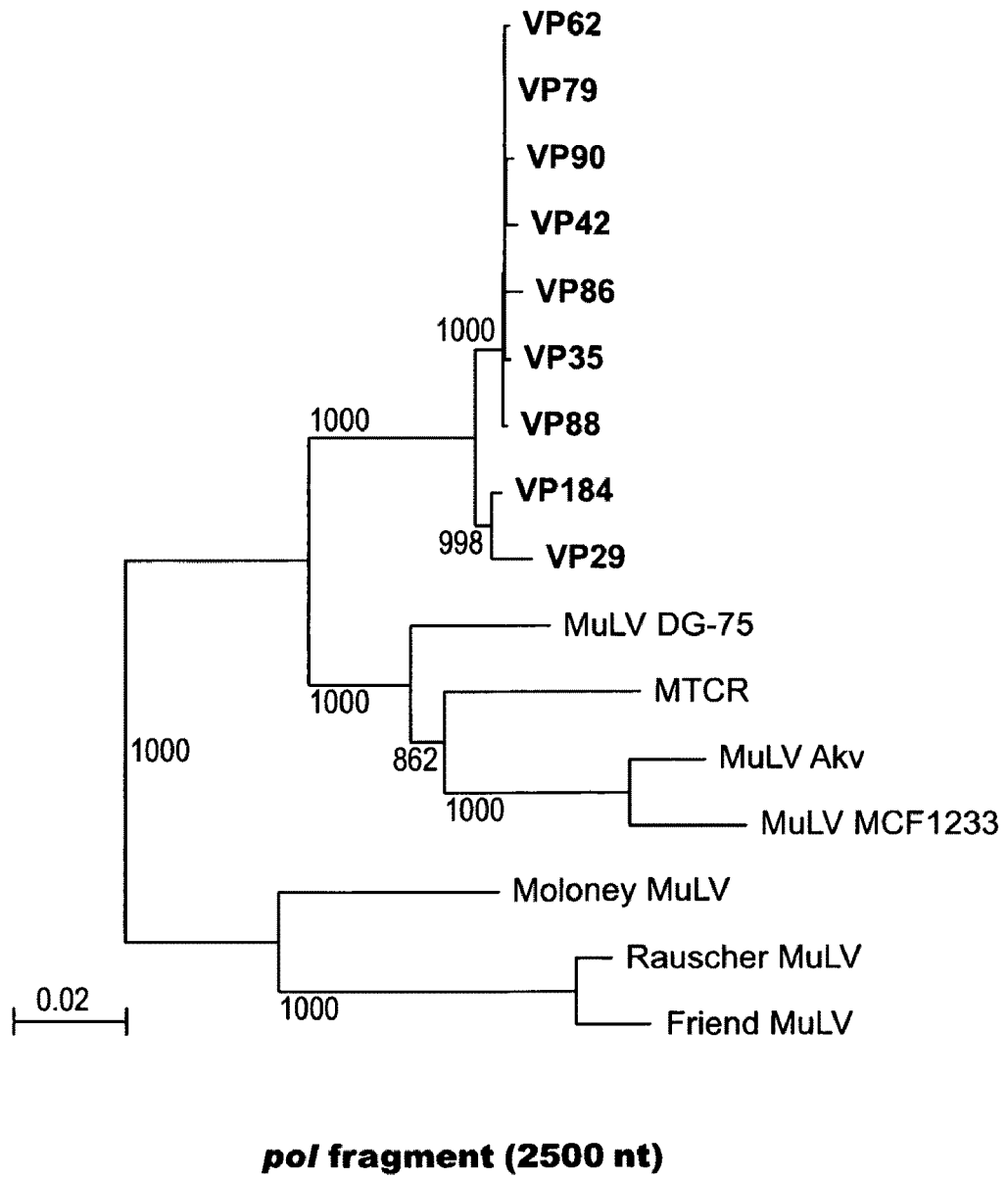

The neighbor-joining trees of gag and pol fragments from different patients (FIGS. 27A-27B) were generated as above, except only MuLV genomes were included.

The neighbor-joining trees of Gag-Pro-Pol (FIG. 29A) and Env (FIG. 29B) polyproteins were based on alignments of protein sequences extracted from the GenBank records of the above 12 genomes and were generated as above, except gaps were included, and Kimura correction was not used.

Abbreviations 2-5A—5'-phosphorylated 2'-5' oligoadenylate; CAT-I—Cationic amino acid transporter; FLV—Feline leukemia virus; GALV—Gibbon ape leukemia virus; GRE—Glucocorticoid response element; HPC—Hereditary prostate cancer; IFN—Interferon; KoRV—Koala retrovirus; MCF1233—Mink cell focus-inducing 1233 murine leukemia virus; MuLV—Murine leukemia virus; MTCR—Murine type C retrovirus; NZB-9-1—New Zealand Black 9-1 xenotropic retrovirus; OAS—2'-5' oligoadenylate synthetases; QQ—RNASEL homozygous R462Q; QR—RNASEL heterozygous R462Q; RNase L—Ribonuclease L; RR—RNASEL homozygous wild-type; SCLC—Human small cell lung cancer; SYG 1—Suppressor of yeast gpal; VRA—Variable region A; VRB—Variable region B; XMRV—Xenotropic MuLV-related virus; XPR1—Xenotropic and polytropic retrovirus receptor Results
Detection of XMRV by Microarray-Based Screening To search for potential viruses in prostate cancer tumors, a DNA microarray-based strategy designed was employed to screen for viruses from all known viral families (Wang D, et al., 2002, *Proc Natl Acad Sc. USA* 99: 15687-15692; Wang D, et al., 2003, *PLoS Biol* 1: E2). Total or polyadenylated RNA extracted from tumor tissue was first amplified and fluorescently labeled in a sequence-nonspecific fashion. The amplified and labeled fragments, which contained host as well as potential viral sequences, were then hybridized to a DNA microarray (Virochip) bearing the most conserved sequences of ~950 fully-sequenced NCBI reference viral genomes (~11,000 70-mer oligonucleotides).

The Virochip was used to screen RNA samples isolated from prostate tumors of 19 individuals (FIG. 22A). A positive hybridization signal suggestive of a gammaretrovirus was detected in 7 of 11 tumors from patients homozygous for the R462Q RNASEL variant (QQ). In contrast, no virus was detected in 3 tumors from RQ heterozygotes, and only 1 of 5 tumors from RR individuals was positive. Clustering of the microarray oligonucleotide intensities (FIG. 22A) revealed a similar hybridization pattern in all positive cases. Furthermore, a computational analysis using E-Predict, a recently described algorithm for viral species identification (Urisman, A., et al., 2005, *Genome Biol* 6: R78), assigned highest probabilities to several closely related mammalian gammaretroviruses, suggesting that the same or similar virus was present in all positive tumors (Table 12). Thus, Virochip detected the presence of a probable gammaretrovirus in nearly half of the QQ tumor samples and only one non-QQ sample.

Characterization of XMRV Genome

Figure 23A:
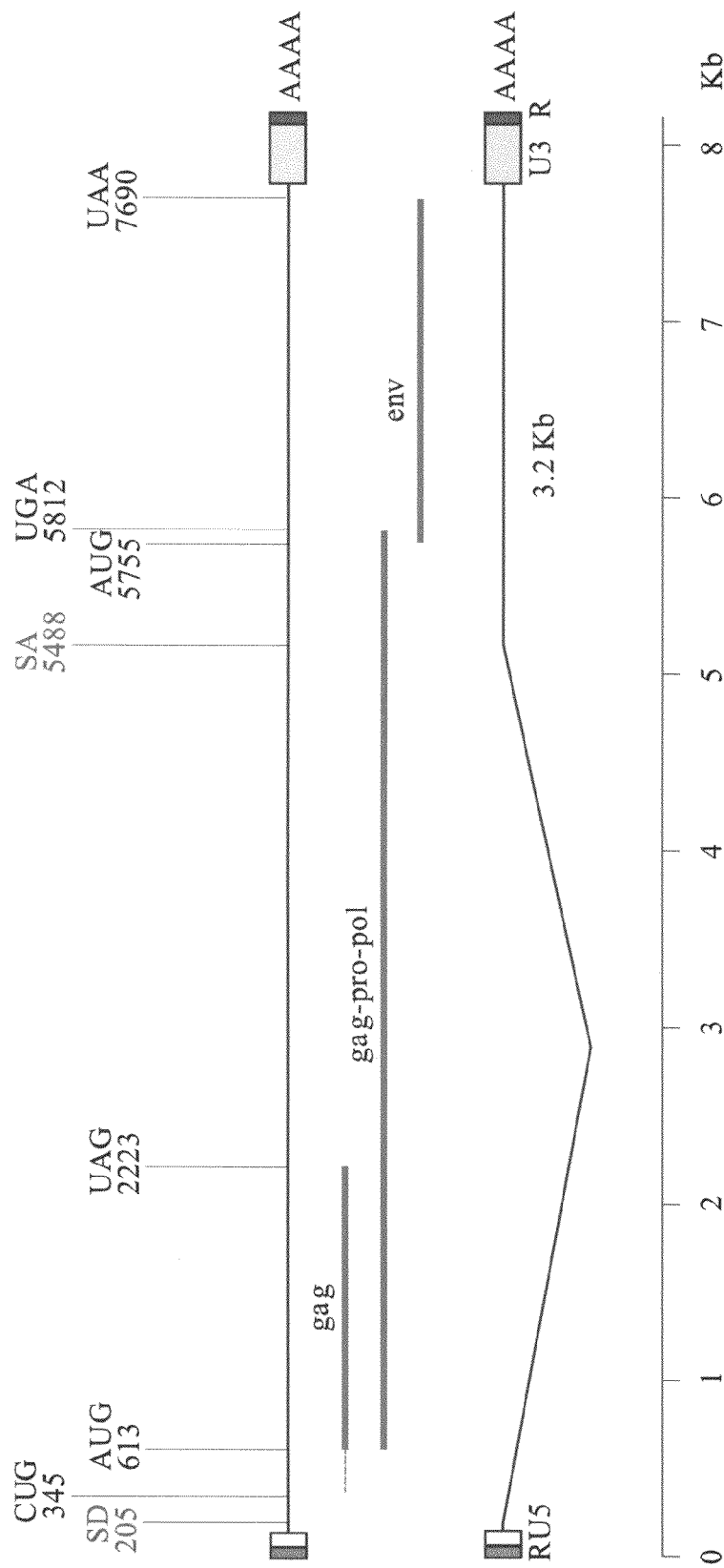
FIGS. 23A-23C show the complete genome of XMRV.
Figure 23B:
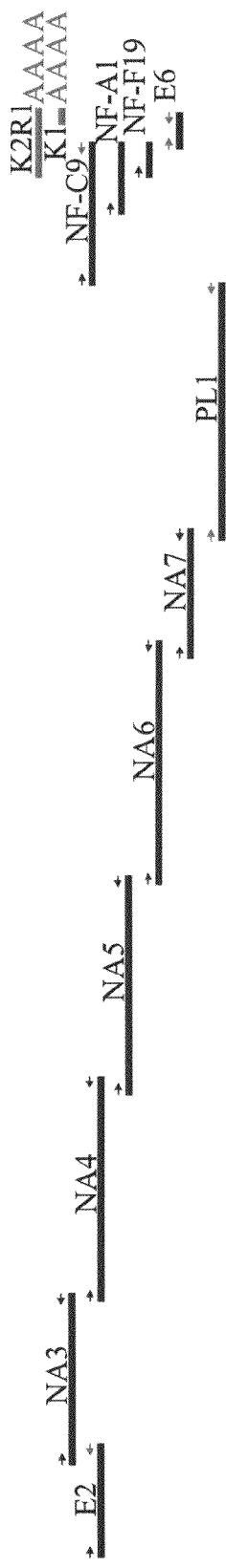
Figure 23C:
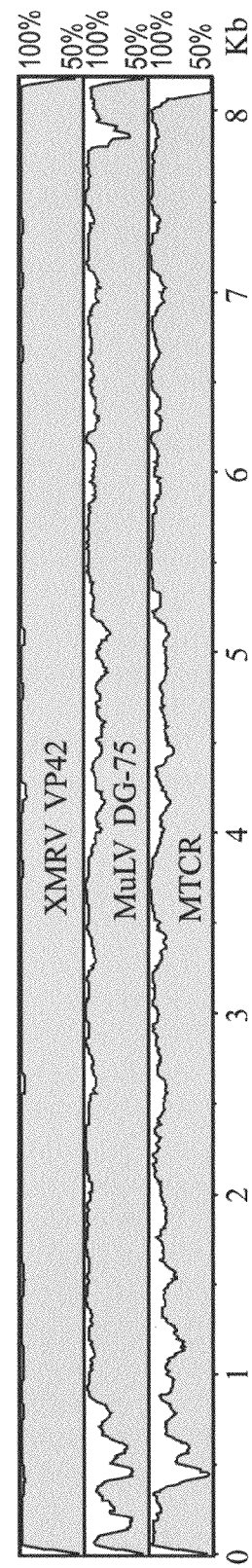

To further characterize the virus its entire genome was recovered from one of the tumors (VP35) (FIG. 23A-23C). To obtain viral clones, a direct microarray recovery technique described previously was first employed (Wang, D., et al., 2003, *PLoS Biol* 1: E2). Briefly, amplified nucleic acid from the tumor tissue, which hybridized to viral microarray oligonucleotides, was eluted from two specific spots. The eluted DNA was re-amplified, and plasmid libraries constructed from this material were screened by colony hybridization using the spots' oligonucleotides as probes. The array oligonucleotides used in this case derived from the LTR region of Murine Type-C Retrovirus (MTCR; GenBank: NC_001702) and Spleen focus-forming virus (GenBank: NC 001500; (Clark, S P., et al., 1983, *Proc Natl Acad Sci USA* 80: 5037-5041). The largest recovered fragment was 415 nucleotides in length, and had 96% nucleotide identity to the LTR region of MTCR, a MuLV identified in the genome of a mouse myeloma cell line (Heinemeyer T; unpublished). These findings established that the virus in question was indeed a gammaretrovirus, and likely a relative of murine leukemia viruses. To clone and sequence the rest of the viral genome, tumor cDNA was used to PCR-amplify overlapping segments using primers derived from MTCR; gaps were closed using primers from earlier recovered clones (FIGS. 23A-23C). Using a similar strategy, the full sequence of the virus from a second tumor, VP42, was also determined. The two genomes share >98% nucleotide identity overall and >99% amino acid (aa) identity for predicted open reading frames (ORFS), and thus represent the same virus.

The full genome of the virus (FIGS. 23A-23C and 28) is 8185 nucleotides long and is distinct from all known isolates of MuLV. The genome is most similar to the genomes of MuLV DG-75 cloned from a human B-lymphoblastoid cell line (GenBank: AF221065, (Raisch, K P., et al., 2003, *Virology* 308: 83-91) and of MTCR, with which it shares 94 and 93% overall nucleotide sequence identity, respectively. Phylogenetic trees constructed using available mammalian type C retroviral genomes (FIGS. 24 and 29A-29B) showed that the newly identified virus is more similar to xenotropic and polytropic than to ecotropic genomes. Based on these findings the provisional name "Xenotropic MuLV-related virus" (or XMRV) for this agent was proposed.

Figure 29A:
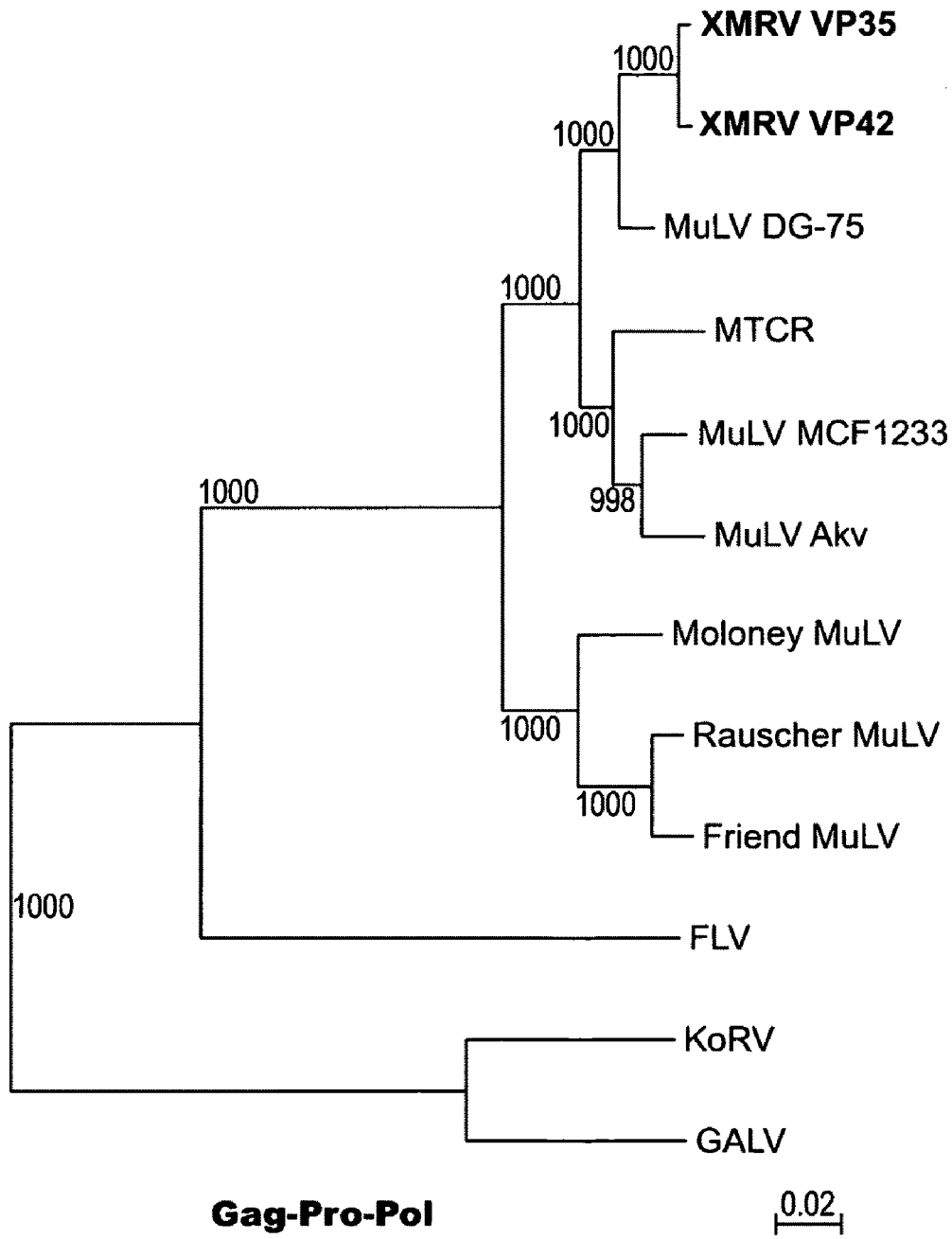
FIGS. 29A-29B show phylogenetic analysis of XMRV based on predicted Gag-Pro-Pol (FIG. 29A) and Env (FIG. 29B) polyproteins. Predicted Gag-Pro-Pol and Env sequences of XMRV VP35 and VP42 as well as the corresponding sequences from MTCR; MuLVs DG-75, MCF1233, Akv, Moloney, Friend, and Rauscher; Feline leukemia virus (FLV); Koala retrovirus (KoRV); and Gibbon ape leukemia virus (GALV) were aligned using ClustalX. Resulting alignments were used to generate unrooted neighbor joining trees (see Example 2, Materials and Methods). Bootstrap values (N=1000 trials) are indicated.
Figure 29B:
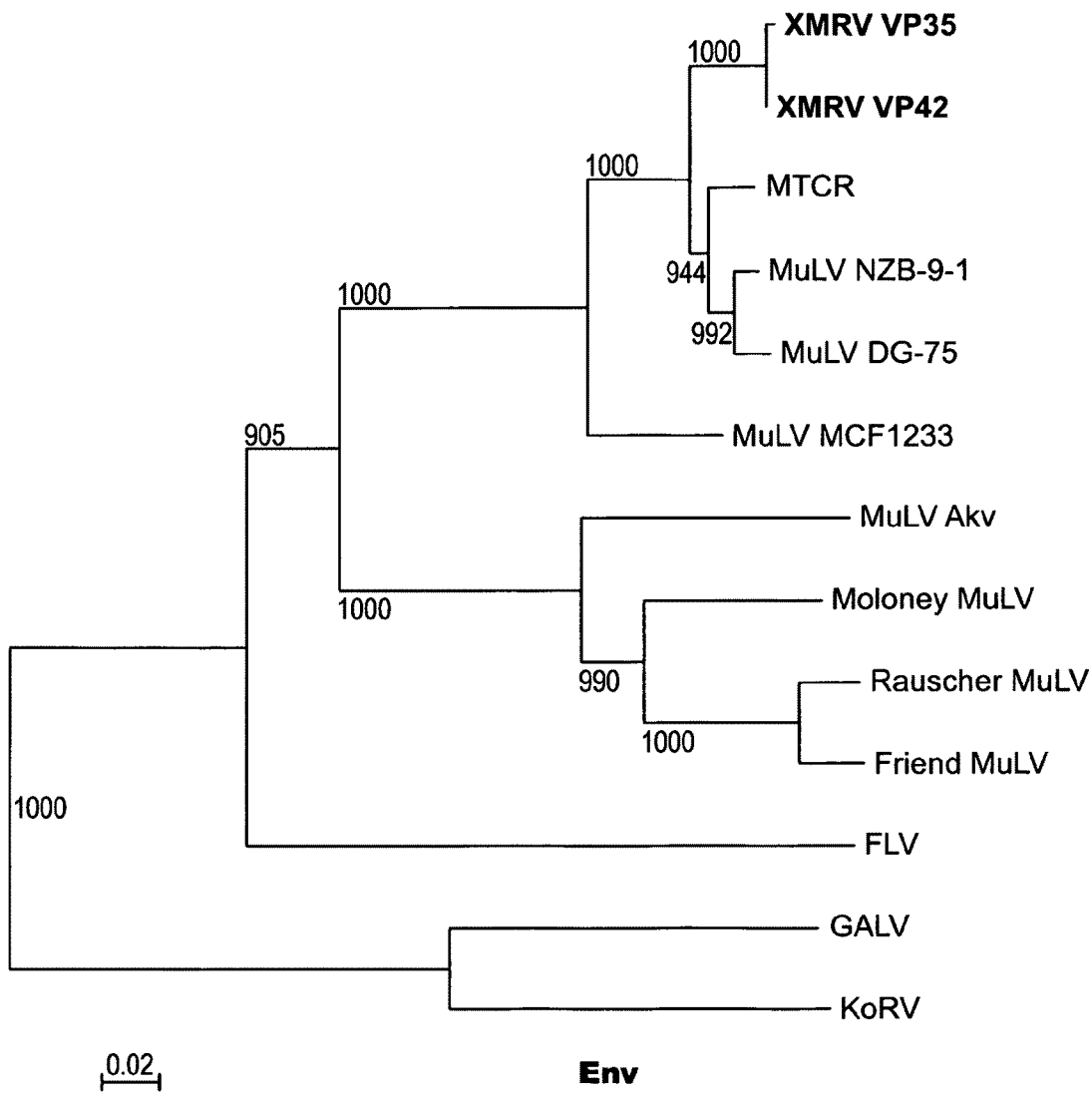

Translation of the XMRV genomic sequence using ORF Finder (Wheeler, D L., et al., 2003, *Nucleic Acids Res* 31: 28-33) identified two overlapping ORFs coding for the full-length Gag-Pro-Pol and Env polyproteins. No exogenous coding sequences, such as viral oncogenes, could be detected in the XMRV genome. The predicted Gag-Pro-Pol polyprotein is 1733 aa long and has the highest aa identity with MuLV DG-75 (95%) (FIG. 29A). An amber (UAG) stop codon separates the 536 aa Gag and 1197 aa Pro-Pol ORFs, analogous to other MuLVs in which a translational read-through is required to generate the full-length Gag-Pro-Pol polyprotein (reviewed in Wills, N M., et al., 1991, *Proc Natl Acad Sci USA* 88: 6991-6995).

Figure 25:
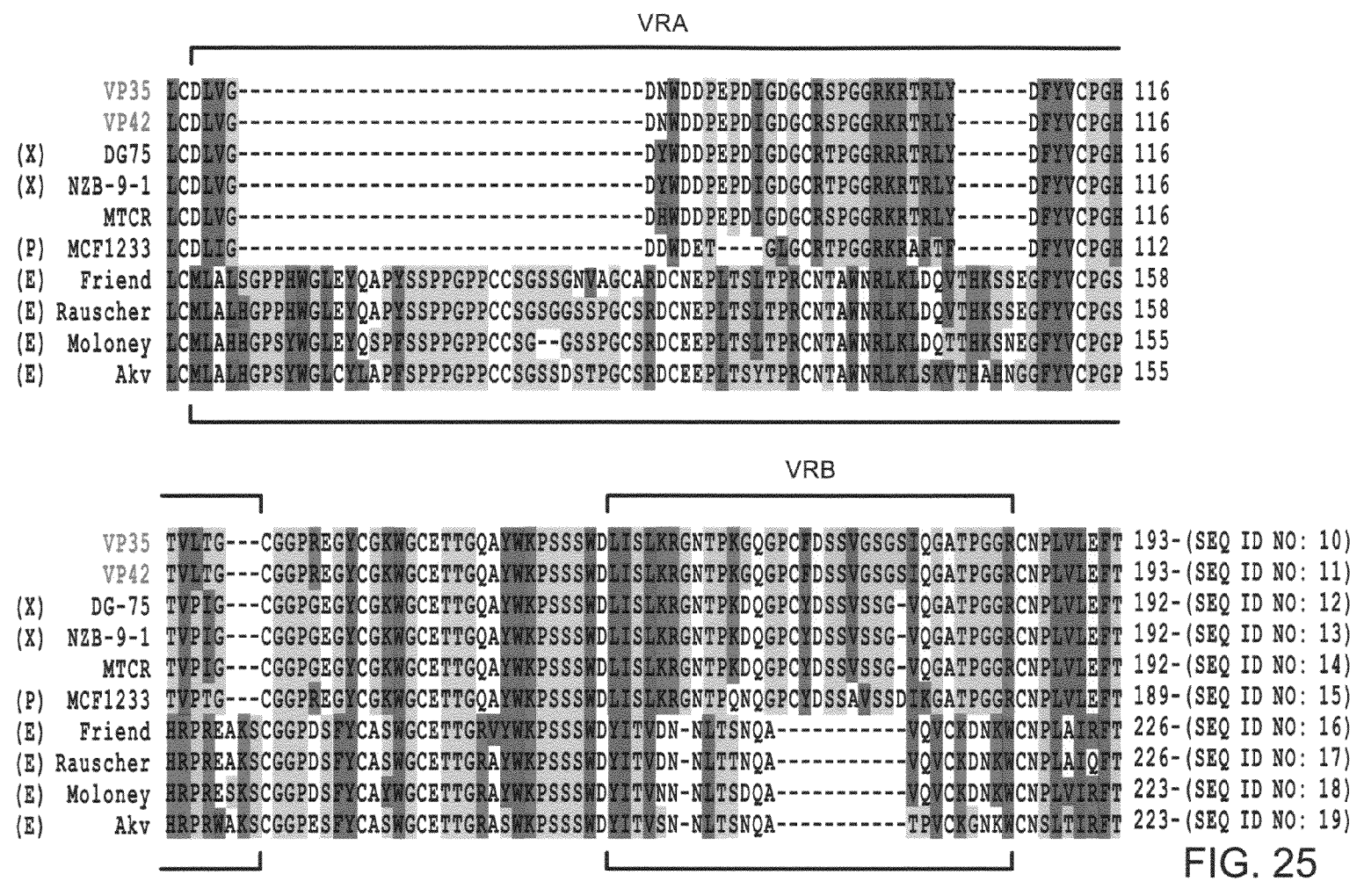

Similar to other MuLVs (Clark, S P., et al., (1983), *Proc Natl Acad Sci USA* 80: 5037-5041; Raisch, K P., et al., (2003), *Virology* 308: 83-91; Herr, W., 1984, *J Virol* 49: 471-478; O'Neill, R R., et al., (1985), *J Virol* 53: 100-106; Perryman, S., 1991, *Nucleic Acids Res* 19: 6950; Shinnick, T M., et al., (1981), *Nature* 293: 543-548; Sijts, E J., et al., (1994), *Virus Res* 34: 339-349), the Env polyprotein of XMRV is in a different reading frame compared to Gag-Pro-Pol. The Env protein sequence is 645 aa long, and has the highest amino acid identity with the Env protein of an infectious MuLV isolated from a human small cell lung cancer (SCLC) line NCl-417 (GenBank: AAC97875; (Antoine, M., et al., (1998), *Virus Genes* 17: 157-168)) and MuLV NZB-9-1 (GenBank: K02730; (O'Neill, R R., Buckler et al., (1985), *J Virol* 53: 100-106)), 95% and 94%, respectively. Conserved splice donor (AGGTAAG (SEQ ID NO:47), position 204) and acceptor (CACTTACAG (SEQ ID NO:48), position 5479) sites involved in the generation of env subgenomic RNAs (Coffin, J M., et al., (1997), Retroviruses. Cold Spring Harbor, N.Y.: Cold Spring Harbor Laboratory Press) were found in the same relative locations as in other MuLV genomes. A multiple sequence alignment of XMRV Env and corresponding protein sequences of other gammaretroviruses (FIG. 25) showed that within two highly variable regions (VRA and VRB) known to be important for cellular tropism (Battini, J L., et al., (1992), *J Virol* 66: 1468-1475; Tailor, C S., et al., (2003), *Curr Top Microbiol Immunol* 281: 29-106), XMRV shares high aa identity with MuLV DG-75 and MuLV NZB-9-1 xenotropic envelopes (87% for VRA and 78% for VRB). Based on this finding, it was predicted that the cellular receptor for XMRV is XPR1 (SYG1), the recently identified receptor for xenotropic and polytropic MuLVs (Battini, J L., et al., (1999), Proc Natl Acad Sci USA 96: 1385-1390; Tailor C S, et al., (1999), Proc Natl Acad Sci USA 96: 927-932; Yang, Y L., et al., (1999), Nat Genet. 21: 216-219).

The long terminal repeat (LTR) of XMRV is 535 nucleotides long and has highest nucleotide identity with the LTRs of MTCR (96%) and MuLV NZB-9-1 (94%). The XMRV LTRs contain known structural and regulatory elements typical of other MuLV LTRs (Coffin, J M., et al., (1997), Retroviruses. Cold Spring Harbor, N.Y.: Cold Spring Harbor Laboratory Press; Temin, H M., (1981), Cell 27: 1-3) (FIG. 28). In particular, the CCAAT (SEQ ID NO:49) box, TATAAAA (SEQ ID NO:50) box, and AATAAA (SEQ ID NO:51) polyadenylation signal sequences were found in U3 at their expected locations. U3 also contains a glucocorticoid response element (GRE) sequence AGA ACA GAT GGT CCT (SEQ ID NO:52). Essentially identical sequences are present in genomes of other MuLVs. These elements have been shown to activate LTR-directed transcription and viral replication in vitro in response to various steroids including androgens (Celander, D., et al., (1988), *J Virol* 62: 1314-1322; Speck, N A., et al., (1987), *Mol Cell Biol* 7: 1101-1110; DeFranco, D., et al., (1986), *Mol Cell Biol* 6: 993-1001; Miksicek, R., et al., (1986), *Cell* 46: 283-290). In addition, presence of an intact GRE is thought to be the determinant of higher susceptibility to FIS-2 MuLV infection in male compared to female NMRI mice (Bruland, T., et al., (2003), *J Gen Virol* 84: 907-916; Bruland, T., et al., (2001), *J Gen Virol* 82: 1821-1827).

Figure 26:
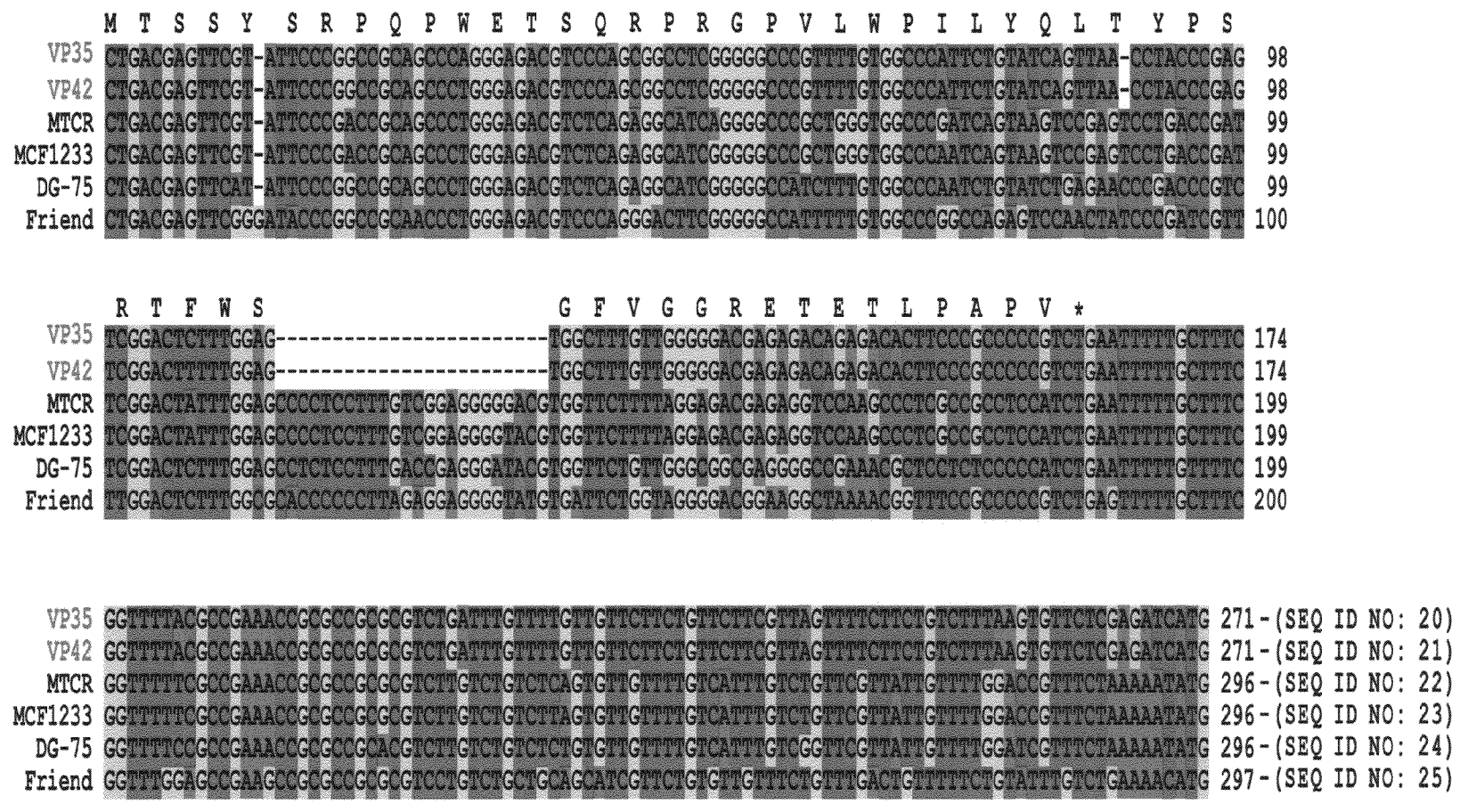

The 5' gag leader of XMRV, defined as the sequence extending from the end of U5 to the ATG start codon of gag, consists of a conserved non-coding region of ~200 nucleotides, containing a proline tRNA primer binding site as well as sequences required for viral packaging (Adam, M A., et al., (1988), *J Virol* 62: 3802-3806; Fisher, J., et al., (1998), *Virology* 244: 133-145) and the initiation of translation (Berlioz, C., et al., (1995), *J Virol* 69: 2214-2222; Vagner, S., et al., (1995), *J Biol Chem* 270: 20376-20383). The non-coding region is followed by a ~270 nucleotide region extending from the conserved CTG alternative start codon of gag. This region represents the most divergent segment of the genome compared to other MuLVs (FIGS. 26 and 23B). Unlike ecotropic MuLVs, where translation from this codon adds a ~90 aa N-terminal leader peptide in frame with the rest of the Gag protein, thus generating a glycosylated form of Gag (Prats, A C., et al., (1989), *J Mol Biol* 205: 363-372), XMRV has a stop codon 53 aa residues downstream from the alternative start. Interestingly, both MuLV DG-75 and MTCR gag leader sequences are also interrupted by stop codons, and therefore are not expected to produce full-length glyco-Gag. Furthermore, a characteristic 24-nucleotide deletion was present in this region of the XMRV genome, which is not found in any known exogenous MuLV isolate or endogenous retroviral element in the sequenced mouse genome. In cell culture, expression of intact glyco-Gag is not essential for viral replication (Fan, H., et al., (1983), *Proc Natl Acad Sci USA* 80: 5965-5969; Schwartzberg, P., et al., (1983), *J Virol* 46: 538-546). However, lesions in this region have been associated with interesting variations in pathogenetic properties in vivo (Chun, R., et al., (1994), *J Biomed Sci* 1: 218-223; Corbin, A., et al., (1994), *J Virol* 68: 3857-3867; Fujisawa, R., et al., (1997), *J Virol* 71: 5355-5360; Munk, C., et al., (2003), *Virology* 313: 44-55; Portis, J L., et al., (1996), *Virology* 226: 384-392). For example, an alteration in 10 nucleotides affecting 5 residues in the N-terminal peptide of glyco-Gag was found to be responsible for a 100-fold difference in the frequency of neuroinvasion observed between CasFrKP and CasFrKP41 MuLV strains (Fujisawa, R., et al., (1998), *J Virol* 72: 5619-5625). In addition, insertion of an octanucleotide resulting in a stop codon downstream of the CUG start codon prevented severe early hemolytic anemia and prolonged latency of erythroleukemia in mice infected with Friend MuLV (Corbin, A., et al., (1994), *J Virol* 68: 3857-3867). While the pathogenetic significance of the lesions in XMRV glyco-Gag is not known, the high degree of sequence divergence indicates that this region is under positive selective pressure, and therefore, likely relevant to the establishment of infection within the human host.

Association of XMRV Infection and R462Q RNASEL Genotype

To further examine the association between presence of the virus and the R462Q (1385G->A) RNASEL genotype, a specific nested RT-PCR assay based on the virus sequence recovered from one of the tumor samples (VP35, see above) was developed. The primers in this assay (FIGS. 28A-28B) amplify a 380-nucleotide fragment from the divergent 5' leader and the N-terminal end of gag. The RT-PCR was positive in 8 (40%) of 20 examined tumors from homozygous (QQ) individuals. In addition, one tumor from a homozygous wild-type (RR) patient was positive among 52 RR and 14 RQ tumors examined (FIG. 22B and Table 10). Interestingly, this case was associated with the highest tumor grade among all XMRV-positive cases (Table 11 in Molinaro et al, 2005). PCR specific for the mouse GAPDH gene was negative in all samples, arguing strongly against the possibility that the tumor samples were contaminated with mouse nucleic acid. Collectively, these data demonstrate a strong association between the homozygous (QQ) R462Q RNASEL genotype and presence of the virus in the tumor tissue (p<0.00002 by two-tail Fisher's exact test).

XMRV Sequence Diversity in Samples from Different Patients

To examine the degree of XMRV sequence diversity in different patients, the amplified fragments from all 9 samples, which were positive by the nested gag RT-PCR, were sequenced. The amplified gag fragments were highly similar (FIG. 27A) with >98% nucleotide and >98% aa identity to each other. In contrast, the fragments had <89% nucleotide and <95% aa identity with the most related sequence of MuLV DG-75. In addition to the gag gene, the same patient samples were also examined for sequence variation in the pol gene. PCR fragments obtained with a set of primers targeting a 2500-nucleotide stretch in the pol gene were sequences (FIGS. 28A-28B). Similar to the gag fragments, the amplified pol fragments were highly similar (FIG. 27B) and had >97% nucleotide and >97% aa identity to each other. In contrast, the fragments had <94% nucleotide and <95% aa identity with the most related sequence, that of MuLV DG-75.

Close clustering of the sequenced gag and pol fragments (FIGS. 27A-27B) indicates that all microarray and RT-PCR positive cases represent infection with the same virus. On the other hand, the degree of sequence variation in the examined fragments is higher than that expected from errors introduced during PCR amplification and sequencing. The frequency of nucleotide misincorporation by Taq polymerase has been estimated as $10^{-6}$-$10^{-4}$ ((Bracho, M A., et al., (1998), *J Gen Virol* 79 (Pt 12): 2921-2928) and references therein), compared to the observed rate of up to 2% in the gag and pol fragments. These findings indicate that the observed XMRV sequence variation is a result of natural sequence diversity, consistent with the virus being independently acquired by the affected patients, and argue against laboratory contamination as a possible source of XMRV.

Discussion

The results presented here identify XMRV infection in prostate tissue from approximately half of patients with prostate cancer who are homozygous for the R462Q variant (QQ) of RNase L, as judged by both hybridization to the Virochip microarray and by RT-PCR with XMRV-specific primers. Parallel RT-PCR studies of prostate tumors from wild-type (RR) and heterozygous (RQ) patients revealed evidence of XMRV in only 1 of 66 samples, clearly demonstrating that human XMRV infection is strongly linked to decrements in RNase L activity. This result supports the view that the R462Q RNase L variant leads to a subtle defect in innate (IFN-dependent) antiviral immunity.

As its name indicates, XMRV is closely related to xenotropic murine leukemia viruses (MuLVs). Unlike ecotropic MuLVs, such as the canonical Moloney MuLV, which grow only in rodent cells in culture, xenotropic MuLVs can grow in non-rodent cells in culture but not in rodent cell lines. Xenotropic MuLVs are thought to result from in vivo recombination events between an exogenous ecotropic virus infecting a susceptible mouse strains and numerous endogenous MuLV-like sequences present in the mouse genome. These endogenous elements are relics of ancestral retroviral integration events into the mouse germline, and most have suffered inactivating deletions and other rearrangements over evolutionary time. Some, though, are full-length and are expressed in certain mouse backgrounds (Levy, J A, (1973), *Science* 182: 1151-1153; Levy, J A, (1978), *Curr Top Microbiol Immunol* 79: 111-213). The recombination invariably involves substitution of the 5' end of the env gene encoding the N-terminal region of the mature SU glycoprotein ((Evan, L H., et al., (2003), *J Virol* 77: 10327-10338) and references therein). This region specifies receptor preference of the SU glycoprotein, and thus determines the host range of the recombinant virus (Battini, J L., et al., (1992), *J Virol* 66: 1468-1475; Ott, D., et al., (1992), *J Virol* 66: 4632-4638). Unlike ecotropic MuLVs, which can only recognize a receptor (CAT-1) specific to mouse and rat species (Albritton, L M., et al., (1989), *Cell* 57: 659-666; Kim, J W., et al., (1991), *Nature* 352: 725-728; Wang, H., et al., (1991), *Nature* 352: 729-731), xenotropic strains recognize a protein known as XP RI or SYGI. XPR1 is expressed in all higher vertebrates, including mice, but polymorphisms in the murine gene render it unable to mediate xenotropic MuLV entry (Battini, J L., et al., (1999), *Proc Natl Acad Sci USA* 96: 1385-1390; Tailor C S, et al., (1999), *Proc Natl Acad Sci USA* 96: 927-932; Yang, Y L., et al., (1999), *Nat Genet.* 21: 216-219). Thus, xenotropic MuLVs have a potential to infect a wide variety of mammalian species, including humans.

Xenotropic MuLVs have occasionally been detected in cultured human cell lines. For example, MuLV DG-75 was cloned from a human B-lymphoblastoid cell line (Raisch, K P., et al., (2003), *Virology* 308: 83-91), and an infectious xenotropic MuLV was detected in a human small cell lung cancer (SCLC) line NCI-417 (Antoine, M., et al., (1998), *Virus Genes* 17: 157-168). Although laboratory contamination, either in culture or during passage of cell lines in nude mice, cannot be ruled out as a possible source in these cases, such contamination cannot explain our results. The evidence for this is as follows: (i) XMRV was detected in primary human tissues; (ii) no murine sequences (e.g. GAPDH) could be detected in our materials by PCR; and (iii) infection was predominantly restricted to human samples with the QQ RNASEL genotype; (iv) polymorphisms were found in the XMRV clones recovered from different patients consistent with independent acquisition of the virus by these individuals. Finally, it is shown in Example 3 (Molinaro et al, 2005) that viral transcripts and antigens can be detected in infected QQ prostate tissue by fluorescence in situ hybridization and immunohistochemistry, respectively, providing additional evidence for infection in vivo. Taken together, the above evidence argues strongly against laboratory contamination with virus or cloned DNA material as the source of XMRV infection in the analyzed samples. The findings described herein are examples of authentic infection of humans with a xenotropic MuLV-like agent.

The XMRV sequence is not found in human genomic DNA (as represented in sequence databanks), indicating that it must have been acquired exogenously by infection in positive subjects. From what reservoir, and by what route such infections were acquired is unknown. It seems unlikely that direct contact with feral mice could explain the observed distribution of infection in our cohort, since there is no reason to believe that rodent exposure would vary according to RNASEL genotype. It is possible that infection is more widespread than indicated by the present studies, especially if, as seems likely, individuals with the wild-type RNase L clear infection more promptly than those with the QQ genotype. But if so, a cross-species transfer model of XMRV infection would require improbably high levels of rodent exposure for a developed society like our own. Thus, although the viral sequence suggests that the ultimate reservoir of XMRV is probably the rodent, the proximate source of the infection seems unlikely to be mice or rats.

The data described herein do indicate that XMRV is not functioning by encoding a dominantly-acting oncogene, as XMRV is a simple retrovirus composed solely of gag, pol and env sequences, and has no acquired host-derived sequences in its genome. Moreover, the single cell analyses of Example 3 show that the viral genome is not present in the cancer cells themselves, but appears to target stromal cells whose identities are still under examination. This renders unlikely another model of retroviral oncogenesis—namely, host oncogene activation by insertion into the cellular genome of prostatic epithelial cells as the proximal cause of clonal expansion of these cells.

Example 3

XMRV Infection in Tissues and Cell Lines from Prostate Cancers with RNASEL/HPC1 Mutations RNase L is a unique antiviral protein activated by 5'-phosphorylated, 2'-5'-oligoadenylates. Example 2 describes the identification of the genome of a novel gammaretrovirus, named xenotropic MuLV related virus (XMRV), in prostate cancer cases homozygous for a reduced activity variant of RNase L (R462Q). Shown herein by fluorescence in situ hybridization, and immunohistochemistry that XMRV nucleic acid and protein can be detected in about 1% of cells in prostate tissues from cases infected with XMRV and homozygous for the RNase L variant. The infected cells are prostatic stromal cells, predominantly fibroblasts and hematopoietic elements, in regions adjacent to the carcinoma. Screening of cell lines derived from prostate cancer revealed that a single clone of LNCaP cells, which also bears mutations in RNase L, harbors an XMRV-like genome closely related to those found in tumors in vivo. This clone expresses genomic and subgenomic viral transcripts, and releases infectious particles into the medium; these particles can be serially propagated in several cell lines of human but not murine origin. The availability of replication-competent XMRV should facilitate the study of viral replication, its link to RNase L variants and its relationship to prostatic and other diseases.

Materials and Methods

Genotyping of Patients and Prostate Tissue Processing

Men scheduled to undergo prostatectomy with curative intent at the Cleveland Clinic were genotyped for the R462Q (1385G->A) RNASEL variant using a premade TAQMAN genotyping assay (Applied Biosystems, assay c_935391_1) on DNA isolated from perpheral blood mononuclear cells. Immediately after radical prostatectomy, tissue cores were taken from the peripheral zone (where most cancer occurs) and frozen in liquid nitrogen for subsequent RNA isolation (Urisman, A., et al., (2005), *PLOS Pathogens*). For histologic analysis, freshly excised prostate tissue was fixed in 10% neutral buffered formalin, processed and embedded in paraffin. Tissue microarrays were used for some experiments (see legend to FIG. 31). All of these studies were performed under a Cleveland Clinic institutional review board approved protocol.

Antibodies

Monoclonal antibody to SFFV Gag protein was produced from R187 cells (ATCC; CRL-1912) grown in DMEM (Media Core, Cleveland Clinic Foundation, Cleveland, Ohio) with 10% ultra-low IgG FBS (Invitrogen) until confluent. Conditioned media was collected every three days from confluent cultures. Five ml of conditioned media per preparation was centrifuged at 168×g for 5 min at 4° C. Supernatant was filtered through a 0.22 µm syringe filter unit (Millipore Corp.) and concentrated 16-fold in an Amicon ultrafiltration unit with a 100 kDa molecular weight cutoff membrane (Millipore Corp.). Sodium azide was added to a final concentration of 0.02%. Rabbit polyclonal antibody to the conserved MuLV NC peptide sequence: KDCPKKPRGPRGPR (SEQ ID NO:53) conjugated to keyhole limpet hemocyanin was prepared by Open Biosystems, Inc., Huntsville, Ala. The antibody was affinity purified by a protocol including linking the peptide to sepharose, binding then eluting the antibody from the column. Concomitant XMRV FISH/cytokeratin immunofluorescence was performed using a mouse anti-cytokeratin AE1/AE3 (20:1 mixture) monoclonal antibody (Chemicon) capable of recognizing normal and neoplastic cells of epithelial origin.

Cell Culture

Cell lines, LNCaP-R (W. Heston, Cleveland), LNCaP-FGC (ATCC Cat# CRL-1740), DU145 (ATCC Cat# HTB-81) and PC3 (ATCC Cat# CRL-1435) were grown in RPMI 1640 medium with 2 mM L-glutamine, fetal bovine serum, 10%; 200 units penicillin G and 200 µg/ml streptomycin. Normal prostate epithelial cells (PrEC) were obtained from Clonetics Corporation (San Diego, Calif.) and were maintained in PrEGM supplemented with a mixture of various growth factors (SingleQuots) (Clonetics); fetal bovine serum, 10%.

Cytoblock Preparation

Approximately $10^9$ cells (LNCaP-R, LNCaP-FGC, DU145 and PC3) were washed with Hanks balanced salt solution (HBSS) without phenol red, Ca++ or Mg++ (Invitrogen) and resuspended gently, but completely, with 10% neutral buffered formalin. The cell suspensions were fixed overnight at 4° C., centrifuged and washed twice with HBSS. The supernatant was aspirated and the cells were resuspended in one drop of HBSS. Cell suspensions were pipetted into a cytoblock cassette (Thermo Electron Corp.). The fixed cell culture cytoblocks were processed and embedded into paraffin blocks within 24 hr. The embedded cytoblocks were cut into ~4 µm thick sections placed onto charged slides and baked for at least 4 hr at 60-65° C. for immunofluorescence.

RNA Isolation and RT-PCR

Total RNA was isolated from cells using TRIzol reagent (Invitrogen). The RNA was treated with DNase I (RNase-free) (Ambion), acid phenol:chloroform extracted and precipitated for RT-PCR analysis. First strand cDNA synthesis was performed using 1 µg RNA and random hexamer primers with the TaqMan® Reverse Transcription Reagents kit (Applied Biosystems). PCR was performed on the first strand cDNA using primers specific for a 700 by env region of XMRV-35; forward primer-7050, 5' GTT TAT GGC CAG TTT GGA AA 3' (SEQ ID NO:41), and reverse primer-7750, 5' GCC TTA TGG TGG GGT CTT TC 3' (SEQ ID NO:42). GAPDH exon 8 specific primers were used as a positive control; forward primer, 5' TGC CAT CAC TGC CAC CCA GA 3' (SEQ ID NO:54), and reverse primer, 5' CTT GAC AAA GTG GTC GTT GA 3' (SEQ ID NO:55).

FISH

The XMRV-35 FISH probe cocktail was generated using both 2.15 kb and 1.84 kb segments of the viral genome obtained by PCR with forward primer-2345, 5' ACC CCT AAG TGA CAA GTC TG 3' (SEQ ID NO:43) with reverse primer-4495, 5' CTG GAC AGT GAA TTA TAC TA 3' (SEQ ID NO:44) and forward primer-4915, 5' AAA TTG GGG CAG GGG TGC GA 3' (SEQ ID NO:56) with reverse primer-6755, 5' TTG GAG TAA GTA CCT AGG AC 3' (SEQ ID NO:57), both cloned into pGEM®-T (Promega). The recombinant vectors were digested with EcoRI to release the viral cDNA fragments, which were purified after gel electrophoresis (Qiagen). The purified viral cDNA inserts were used in nick translation reactions to produce SpectrumGreen™ dUTP fluorescently labeled probe according to manufacturer's instructions (Vysis Inc.). Freshly baked slides of prostatic tissues or tissue microarray arrays with ~4 µm thick tissue sections were deparaffinized, rehydrated, and subjected to Target Retrieval (Dako) for 40 min at 95° C. Slides were cooled to room temperature and rinsed in H2O. Proteinase K (Dako) at 1:5000 in Tris-HCl pH 7.4 was applied directly to slides for 10 min at room temperature. Adjacent tissue sections were also probed with SpectrumGreen™ dUTP fluorescently labeled KSHV-8 DNA (nts 85820-92789) as a negative control or, as a positive control with SpectrumGreen™ and SpectrumOrange™ labeled TelVysion™ DNA Probe cocktail (Vysis Inc.), specific for different arms of human chromosome 1 as a positive control to ensure the tissue was completely accessible to FISH. FISH slides were examined using a Leica DMR microscope (Leica Micro-Systems, Heidelberg, Germany), equipped with a Retiga EX CCD camera (Q-Imaging, Vancouver, British Columbia, Canada). FISH images were captured using a Leica TCS SP2 laser scanning confocal with a 63× oil objective numerical aperature (N.A.) 1.4 (Leica Micro-Systems, Heidelberg, Germany) microscope. XMRV nucleic acids were visualized using maximum intensity projections of optical slices acquired using a 488 nm argon-laser (emission at 500 to 550 nm). TelVysion™ DNA Probes were visualized using maximum intensity projections of optical slices acquired using a 488 nm argonlaser (emission at 500 to 550 nm) and 568 nm krypton-argon-laser (emission at 575 to 680 nm). DAPI was visualized using maximum intensity projections of optical slices acquired using a 364 nm UV-laser (emission at 400 to 500 nm). Slides were subsequently washed in 2×SSC [0.3 M sodium chloride and 0.03 M sodium citrate (pH 7.0)] to remove coverslips, and H&E stained for morphological evaluation.

IHC

IHC on human tissues was performed on a Benchmark Ventana Autostainer (Ventana Inc.). Unstained, formalin fixed, paraffin embedded prostate sections were placed on electrostatically charged slides and deparaffinized followed by a mild cell conditioning achieved through the use of Cell Conditioner #2 (Ventana Inc.). The concentrated R187 monoclonal antibody against SFFV p30 Gag was dispensed manually onto the sections at 10 µg per ml (Ventana Inc.) and allowed to incubate for 32 min at 37° C. Endogenous biotin was blocked in sections using the Endogenous Biotin Blocking Kit (Ventana Inc.). Sections were washed, and biotinylated ImmunoPure Goat Anti-Rat IgG (Pierce) was applied at a concentration of 4.8 µg/ml for 8 min. To obtain Gag protein localization, the Ventana Enhanced Alkaline Phosphatase Red Detection Kit (Ventana Inc.) was used. Sections were briefly washed in distilled water and counterstained with Hematoxylin II (Ventana Inc.) for approximately 6 min. Sections were washed, dehydrated in graded alcohols, incubated in xylene for 5 min and coverslips were added with Cytoseal (Microm Int.). Negative controls were performed as above except without the addition of the R187 monoclonal antibody.

Concomitant XMRV FISH/cytokeratin IHC was performed on slides of prostate tissue from patient VP62. First, sections were immunostained for cytokeratin AE1/AE3 using the Alexa Fluor 594 Tyramide Signal Amplification Kit (Molecular Probes) exactly as described below except Protease II (Ventana Inc.) was used for 3 min at room temperature and goat anti-mouse IgG-horseradish peroxidase (Molecular Probes) was added. Slides were placed in Target Retrieval solution (Dako) for 40 min at 95° C. FISH for XMRV was performed as described above except in the absence of proteinase K treatment. After FISH, the slides were mounted with Mounting Medium plus DAPI (Vectashield Inc.) and examined using fluorescence microscopy. Immunofluorescence images were captured using a Texas red filter with a Leica DMR microscope (Leica Micro-Systems, Heidelberg, Germany), equipped with a Retiga EX CCD camera (QImaging, Vancouver, British Columbia, Canada).

Immunofluoresence of the LNCaP-R, LNCaP-FGC, DU145 and PC3 cytoblock sections was performed manually using the Alexa Fluor 594 Tyramide Signal Amplification Kit (Molecular Probes). Briefly, unstained, formalin fixed, paraffin embedded cytoblock sections cut at ~4 µm were placed on electrostatically charged slides, baked at 65° C. for at least 4 hr, deparaffinized in xylene and rehydrated through decreasing alcohol concentrations. Slides were incubated in Protease III (Ventana Inc.) for 3 min at room temperature and washed in phosphate buffered saline (PBS) in peroxidase quenching buffer (PBS+3% $H_2O_2$) for 60 min at room temperature, incubated with 1% blocking reagent (10 mg/ml BSA in PBS) for 60 min at room temperature. The slides were incubated with the antibody against XMRV-35 NC (Gag) peptide (Open Biosystems) at a concentration of 0.25 µg/ml diluted in 1% blocking reagent for 60 min at room temperature and rinsed three times in PBS. Goat anti-rabbit IgG-horseradish peroxidase (Molecular Probes) was added and incubated for 60 min at room temperature. The slides were rinsed three times in PBS. The tyramide solution was added to the slides for 10 min at room temperature and the slides were rinsed 3× in PBS. The slides were mounted with Mounting Medium plus DAPI (Vectashield Inc.) and examined using fluorescence microscopy.

Virus Infections and RT Assays

LNCaP-FGC cells were plated at 20% confluency and washed with PBS. Five hundred µl LNCaP-R supernatant, centrifuged at 3000 g for 15 min and filtered twice through a 0.22 µm filter, was added to the cells diluted 1:2 in RPMI with 8 µg/ml polybrene (Sigma) without FBS or antibiotics for 3 hr. Virus was removed, and cells were replenished with RPMI, 90%; fetal bovine serum, 10%; 200 Units Penicillin/Streptomycin. RT activity was measured after incubating at 37° C. for 1 hr as described (Telesnitsky, A., et al., (1995), *Methods Enzymol* 262: 347-362). All reactions were performed with $\alpha$-$^{32}$P-dTTP, and aliquots of tissue culture media were collected each day post-infection and tested for RT activity. Quantitation was by phosphorimage analysis using a Storm Scanner 840 (GE Healthcare), and software ImageQuant V5.2 (Molecular Dynamics). PBS was used as a negative control, and 0.4 units of MLV-RT (Invitrogen) were used as a positive control in the RT assays.

Northern Blots

RNA was separated on a 1% agarose formaldehyde gel and then transferred to nylon membranes using Turbo Blot kits (Schleicher and Schuell) according to the manufacturer's instructions. The transferred membranes were rinsed in 2×SSC and autocrosslinked (UV Stratalinker 2400; Stratagene). The blots were prehybridized in Ultrahyb (Ambion) and then hybridized with $^{32}$P-labeled probes. DNA probes were generated using RediPrimeII (Amersham Biosciences) according to the manufacturers' instructions.

Southern Hybridization

Cells growing in 75-cm² flasks were trypsinized and lysed in sodium dodecyl sulfate buffer (100 mM Tris, 150 mM NaCl, 10 mM EDTA, 0.1% sodium dodecyl sulfate) containing 100 µg of proteinase K per ml for 1 hr at 55° C. followed by RNaseA treatment, 30 min at 37° C. DNA was extracted with phenol-chloroform, ethanol precipitated, and digested with PstI. 20 αg of DNA for each sample was separated by agarose gel electrophoresis, transferred to a nylon membrane (alkalic transfer), neutralized with 2×SSC, crosslinked and hybridized to a radiolabeled XMRV VP35 U3 LTR probe corresponding to position 7780-7991. The membrane was washed and exposed to Kodak XAR5 film for 1-12 hr.

Genome Cloning and Sequencing

Genome cloning and sequencing of XMRV-LNCaP RV were performed as described in (Urisman, A., et al., (2005), *PLOS Pathogens*).

Phylogenetic Analysis

The neighbor-joining tree of full-length genomes was generated as follows. Genomes of XMRV LNCaP-R (Genebank: DQ272467), VP35 (GenBank: DQ241301) and VP42 (GenBank: DQ241302), MTCR (GenBank: NC_001702), MuLV DG-75 (GenBank: AF221065), MuLV MCF1233 (GenBank: U13766), AKV MuLV (GenBank: J01998), Friend MuLV (GenBank: NC_001362), Rauscher MuLV (GenBank: NC_001819), Moloney MuLV (GenBank: NC_001501), Feline leukemia virus (GenBank: NC_001940), Gibbon ape leukemia virus (GenBank: NC_001885), and Koala retrovirus (GenBank: AF 151794) were aligned with ClustalX version 1.83 using default settings. The tree was generated as described by Urisman, A., et al., (2005), *PLOS Pathogens*. The neighbor-joining trees of Gag-Pro-Pol and Env polyproteins were based on alignments of protein sequences extracted from the GenBank records of the above 12 genomes and were generated as described in Urisman, A., et al., (2005), *PLOS Pathogens*.

Cloning and Mapping of Integration Sites

Twenty micrograms of genomic DNA was digested with Pst I and extracted with phenol:chloroform (1:1, v/v), followed by ethanol precipitation. Pst I cleaves once in the viral genome at nucleotide position 7,150 and was used to produce DNA fragments containing the right LTR and the neighboring cellular DNA. The digested DNA was annealed with 0.1 µM of a biotinylated primer B-7151F (5' Bio-TEGGGAGTTG-GAACAGGGACTACA (SEQ ID NO:58); Operon), which is complementary to nucleotide positions 7,151-7,171, about 600 by upstream of the right LTR. The annealed primer was then extended in a final volume of 300 µl using 10 units pfuUltra DNA polymerase and 0.2 mM dNTPs in 1×PfuUltra buffer (Stratagene). The reaction mixture was heated to 94° C. for 5 min, cooled down to 56° C. for 5 min, and then kept at 72° C. for 20 min. After chain elongation, the free biotinylated primer was removed by *E. coli* exonuclease I digestion, and the sample was treated with phenol:chloroform extraction and ethanol precipitation. The biotinylated DNA was isolated using the Dynabeads kilobase BINDER kit (DYNAL Biotech) as described by the manufacturer. The isolated DNA was digested with NspI and washed with 2×800 µl buffer A (10 mM Tris-HCl, pH7.5, 1 M NaCl, 1 mM EDTA, 200 µg/ml bovine serum albumin) and 2×800 µl 1×T4 DNA ligation buffer. The DNA was then ligated to the Nsp-linker using T4 DNA Ligase (Invitrogen) for 3 hr at 16° C. with occasional tapping. The Nsp-Linker was prepared by annealing 20 µM Link-A (5' CGGATCCCGCATCATATCTCCAGGTGTGACAGTTT (SEQ ID NO:59)) with 20 μM Link-Nsp-S (5'AACCTG-GAGATATGATGCGGGATCCGCATG (SEQ ID NO:60)). The excess Nsp-linkers were removed by washing the Dynabeads with 2×800 μl buffer A, followed with 2×800 μl buffer B (5 mM Tris-HCl, pH7.5, 0.1 mM EDTA). The proviral DNA junctions were amplified by PCR using 0.5 μM of U38F (5'-CGTGTTCCCAATAAAGCCTT (SEQ ID NO:61)) and NspL-R (5'-TAACCTGGAGATATGATGCGGGA (SEQ ID NO:62)) as the forward and reverse primers, respectively. The reaction mixture, which contained PfuUltra DNA polymerase, 0.2 mM of dNTPs, and 1×PfuUltra buffer, was heated to 94° C. for 2 min, then cycled 27 times at 94° C. for 30 s, 56° C. for 40 s, and 72° C. for 8 min, and followed with a final extension at 72° C. for 15 min. The amplified DNA was cloned using the Zero Blunt PCR Cloning Kit (Invitrogen) and sequenced. The chromosomal sequences adjacent to the viral LTR were mapped onto the human genome using UCSC Genome Browser on Human May 2004 Assembly.

Abbreviations

Figure 30:
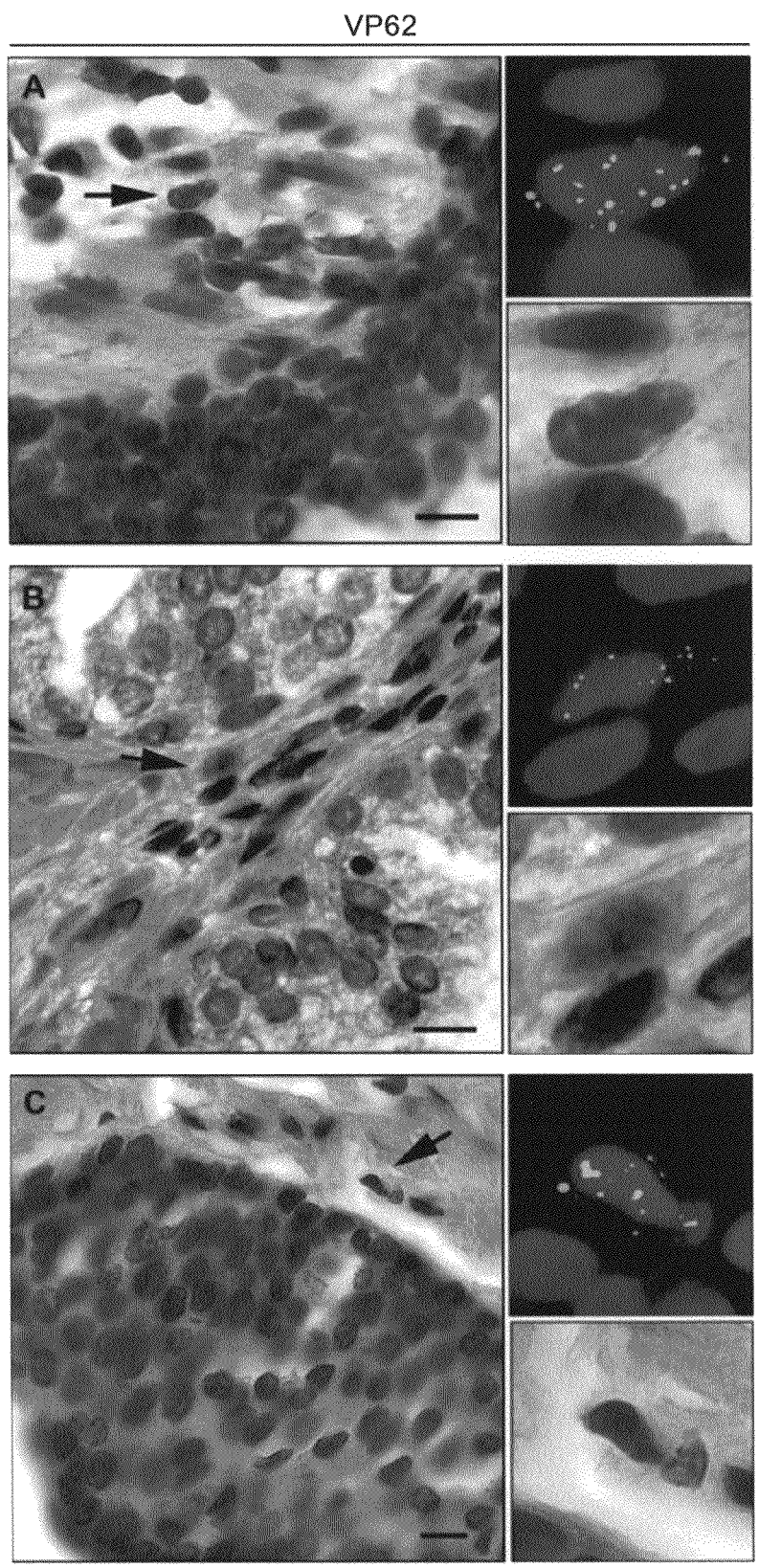
FIG. 30 shows the presence of XMRV nucleic acid in prostatic tissues determined by FISH. Prostatic tissue from prostate cancer cases VP62 (panels A to C) and VP88 (panels D to F) were visualized by H&E staining (left) after being probed with SpectrumGreen™ labeled XMRV-35 DNA probes (enlargements on right). Nuclei were counterstained with DAPI in FISH panels. Arrows in H&E photographs indicate FISH positive cells. Bars shown in panels are 10 μm. Enlargements are images capture with a 63×1.4 N.A. objective zoom 2.
Figure 30:
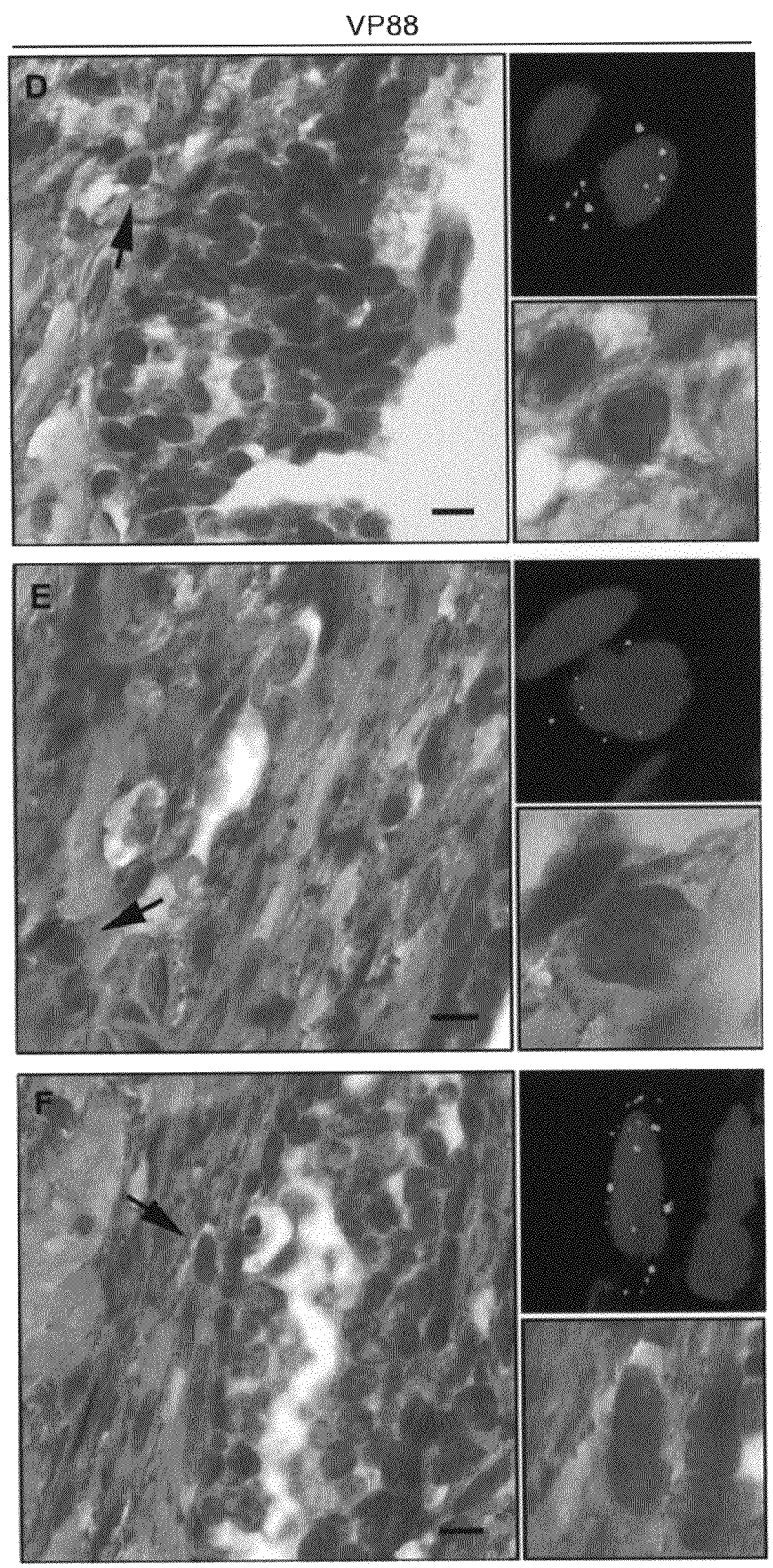
Figure 31:
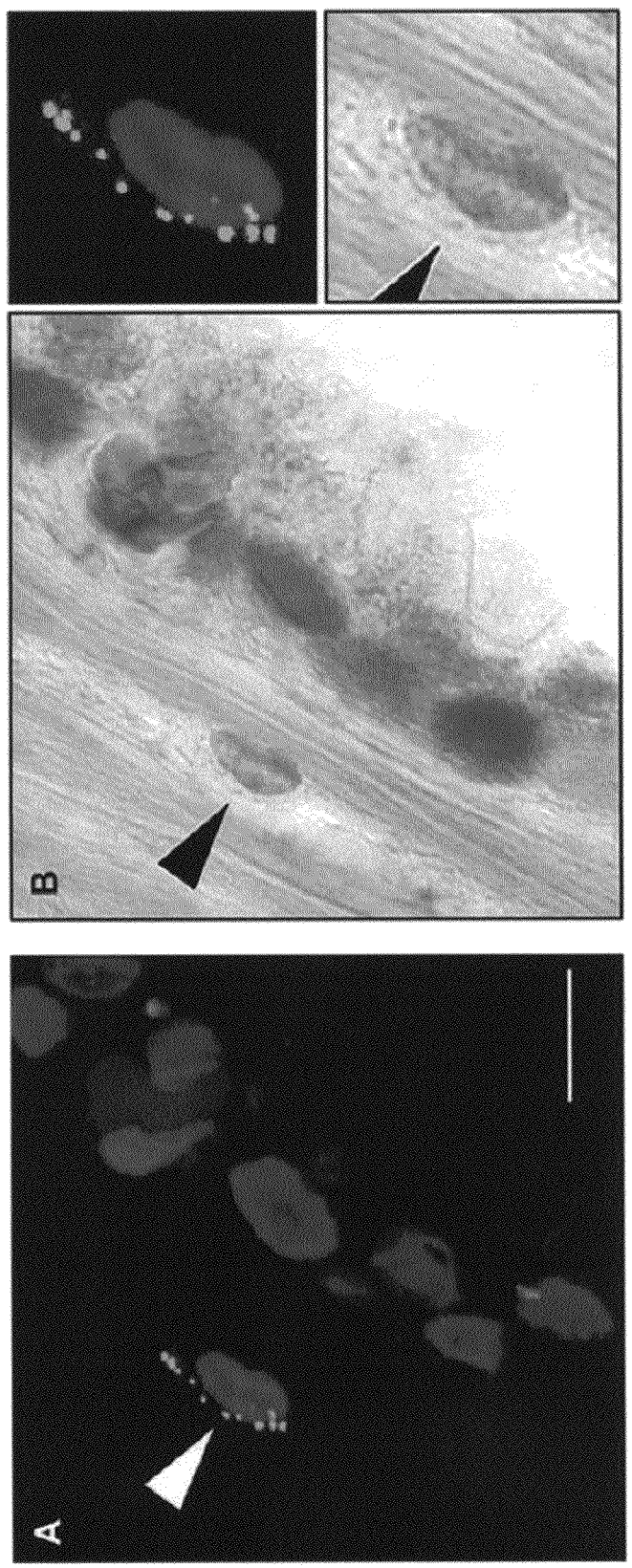
FIG. 31 shows the characterization of XMRV-infected prostatic stromal cells by FISH and concomitant FISH/immunofluorescence. Using a tissue microarray, prostatic tissue from prostate cancer case VP62 analyzed by FISH with XMRV-35 probes (green) (panels A&C) and corresponding H&E staining (panels B&D), respectively. Arrowheads indicate FISH positive cells. The enlargement images (on right) are FISH positive cells (arrows) captured as described in the legend to FIG. 30. The FISH positive cell in panels A and B is a stromal fibroblast; in panels C and D a mitotic figure in a stromal cell, and in E and F a stromal hematopoietic element. (Panel E) Concomitant staining for XMRV by FISH (green) and cytokeratin AE1/AE3 by immunofluorescence (red). Bars shown in panels are 10 μm.
Figure 31:
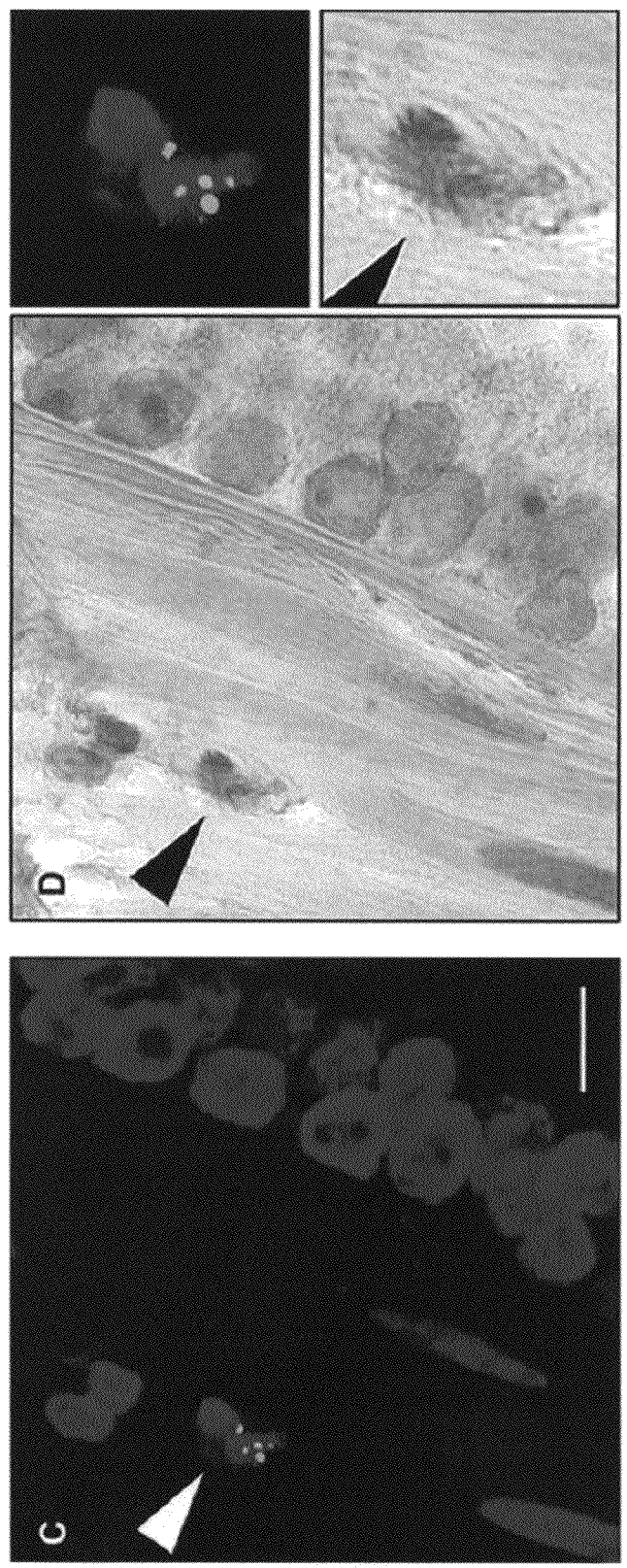
Figure 31:
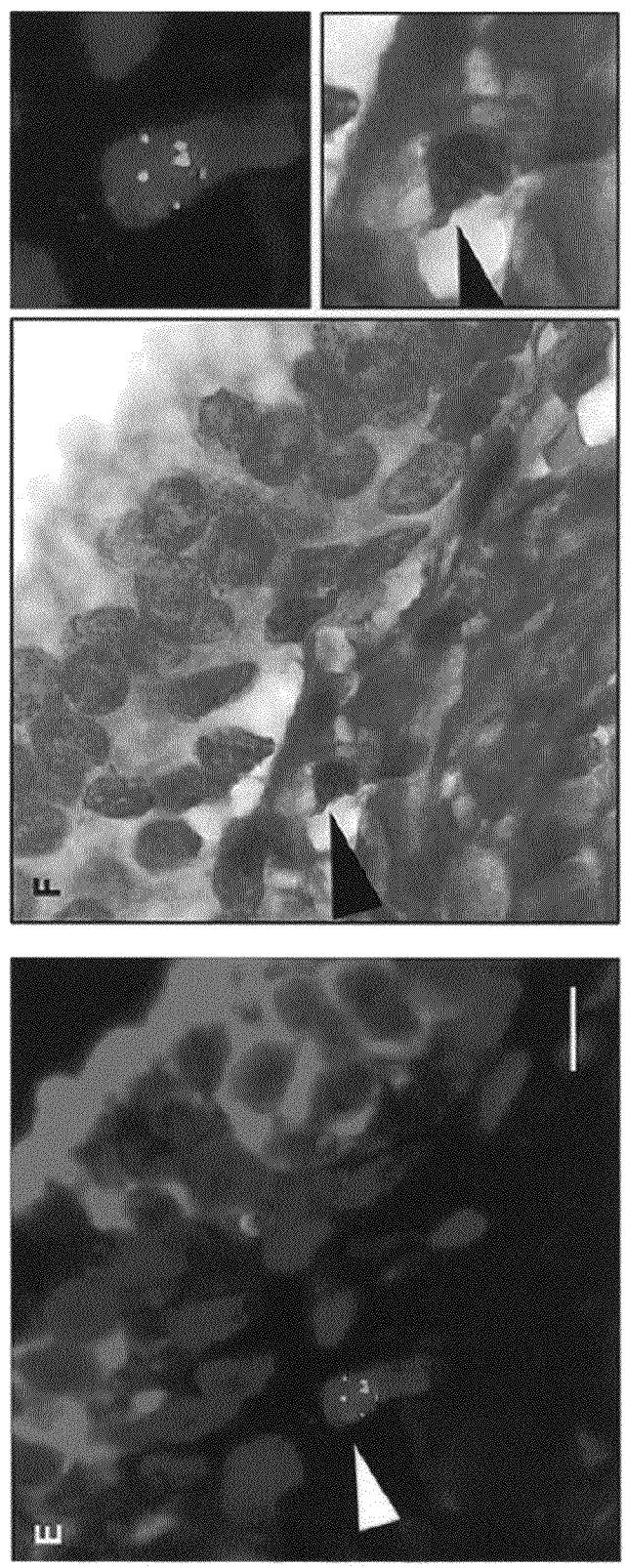

FISH—Fluorescence in situ hybridization; H&E—Hematoxylin and eosin; HPC—Hereditary prostate cancer; IFN—Interferon; IHC—Immunohistochemistry; FLV—Feline leukemia virus; GALV—Gibbon ape leukemia virus; KoRV—Koala retrovirus; MCF1233—Mink cell focus-inducing 1233 murine leukemia virus; MuLV—Murine leukemia virus; MTCR—Murine type C retrovirus; N.A.—numerical aperature; OAS—2'-5' oligoadenylate synthetases; PBS—Phosphate buffered saline; PCR—Polymerase chain reaction; PIA—Proliferative inflammatory atrophy; PIN—Prostatic intraepithelial neoplasia; 2-5A—5'-phosphorylated 2'-5' oligoadenylate; QQ—RNASEL homozygous R462Q; QR—RNASEL heterozygous R462Q; RNase L Ribonuclease L; RT—Reverse transcriptase; RR—RNASEL homozygous wild-type 462R; SNP—Single nucleotide polymorphism; VRA—Variable region A; VRB—Variable region B; XMRV—Xenotropic MuLV-related virus Results XMRV Nucleic Acid is Present in Tumor-Bearing Prostate Tissue To localize XMRV within human prostatic tissues, and to measure the frequency of the infected cells, in situ molecular techniques were used. XMRV nucleic acid was visualized using fluorescence in situ hybridization (FISH) on formalin-fixed prostate tissues. A SpectrumGreen fluorsescently labeled FISH probe cocktail spanning all viral genes was prepared using cDNA derived from the XMRV isolate cloned from patient VP35 (Materials and Methods). Distinct FISH-positive cells were observed in the tumors positive for XMRV by RT-PCR (e.g. VP62 and VP88) (FIG. 30). To identify cell types associated with the positive FISH signal, the same sections were subsequently stained with hematoxylin and eosin (H&E). Most FISH-positive cells were stromal fibroblasts, although occasional infected hematopoietic cells were also seen. While the XMRV nucleic acid was usually present within nuclei, indicating integrated proviral DNA, some cells showed cytoplasmic staining adjacent to the nucleus, suggestive of pre-integration complexes in non-dividing cells (FIG. 31, panel A). An example of an XMRV-infected leukocyte is shown adjacent to a prostatic gland stained (red) with cytokeratin AE 1/AE3 murine monoclonal antibody cocktail specific for epithelial cells (Wernert, N., et al., (1987), *Pathol Res Pract* 182: 617-626)(FIG. 31, panels E&F). The infected cell in the stroma is negative for cytokeratins AE1/AE3, confirming its non-epithelial origin. The indented nucleus and the dark and condensed chromatin are consistent with a stromal hematopoietic cell.

Frequency of XMRV-Infected Prostatic Cells

Figure 32:
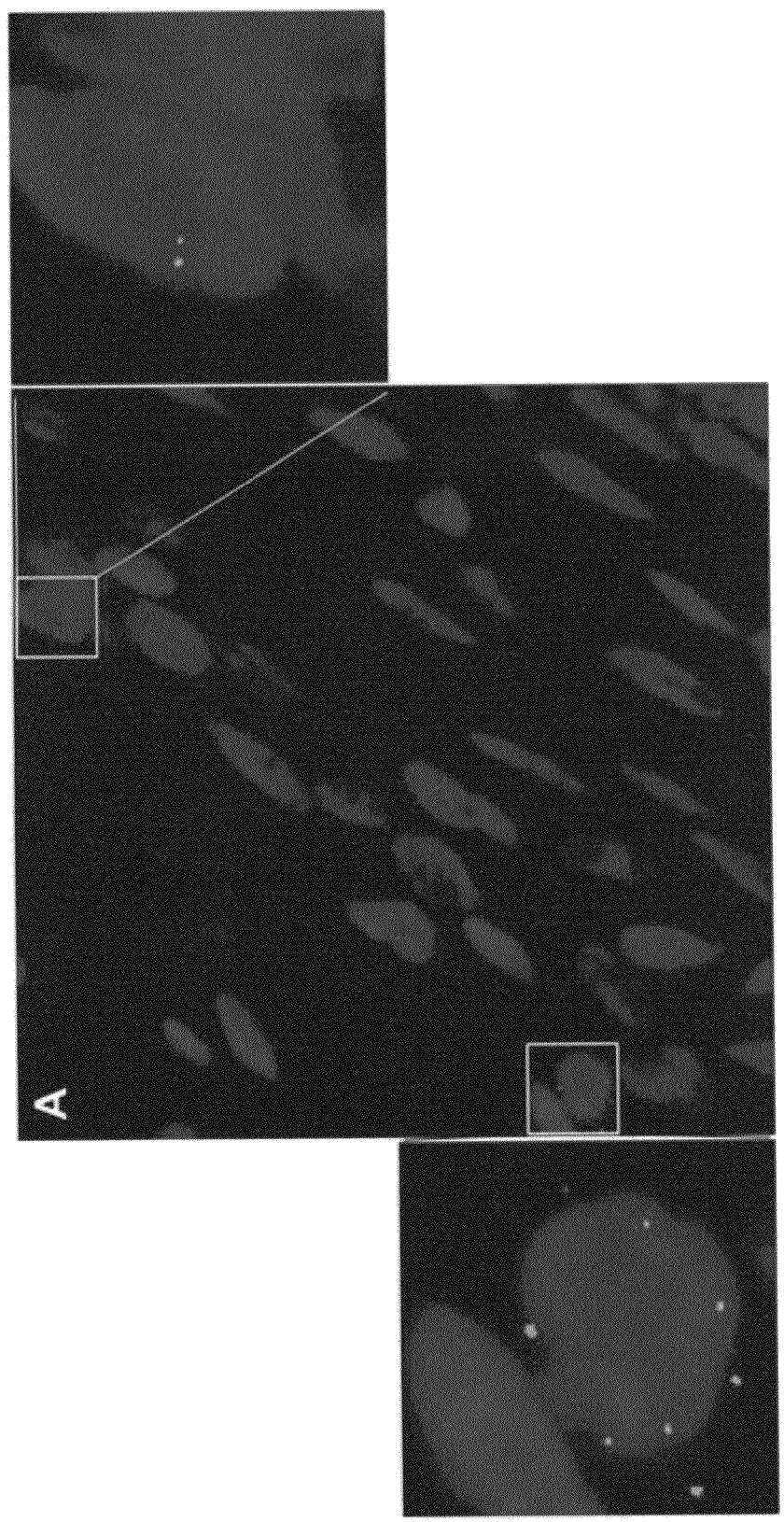
FIG. 32 shows FISH on prostatic tissues of case VP88 with XMRV-35 probes (green) (panel A) and control probes (red and green) specific for two arms of chromosome 1 (panel B) (Example 3, Materials and Methods). Bars shown in panels are 10 μm. Enlargements were performed as described in the legend to FIG. 31.
Figure 32:
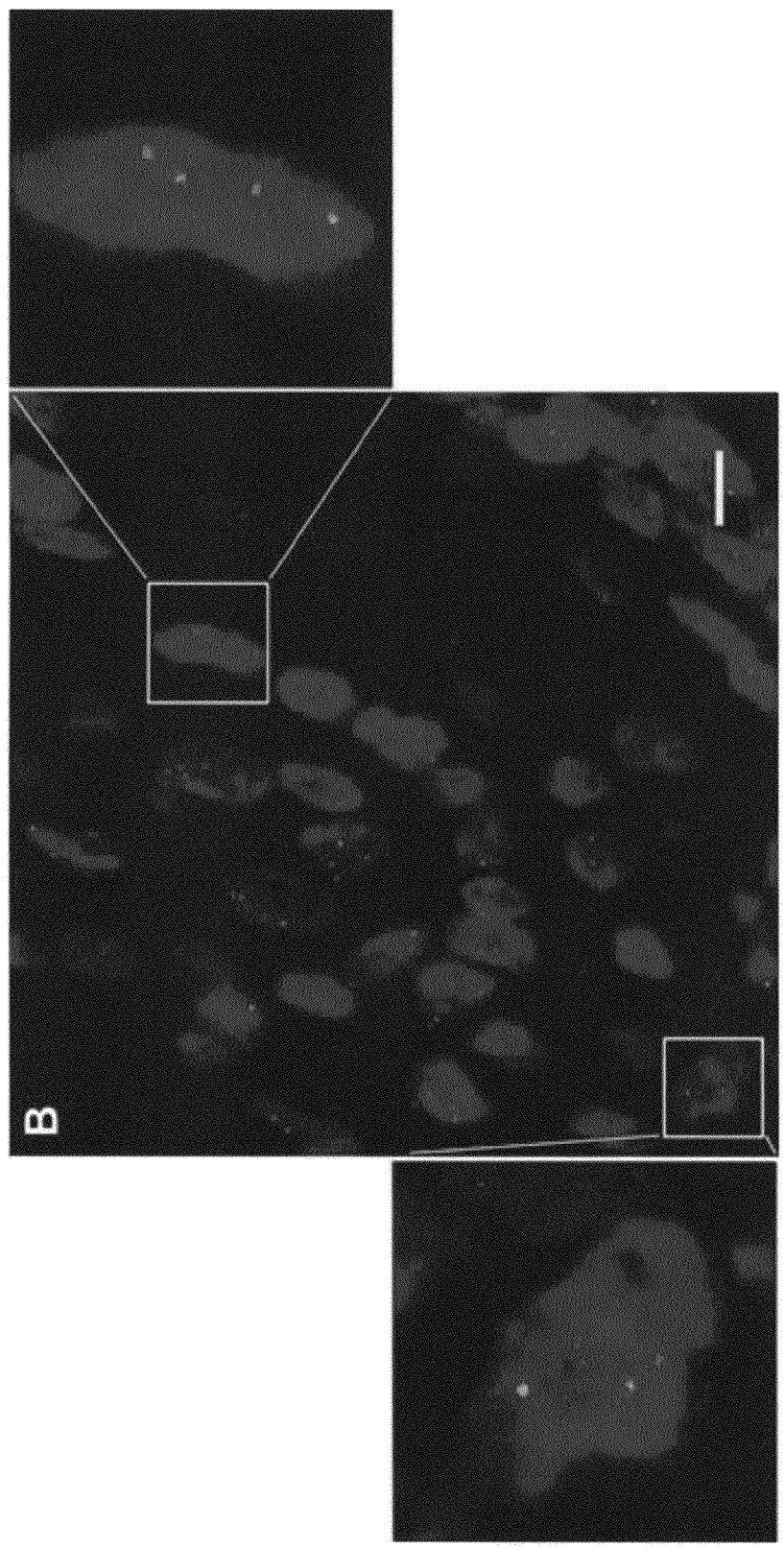

FISH was used to obtain a minimal estimate of the frequency of XMRV-infected prostatic cells. The XMRV FISH probes were compared with two FISH probes specific for subtelomeric regions of the p and q arms of chromosome 1 (labeled with SpectrumGreen and SpectrumOrange, respectively) (FIG. 32). Whereas two XMRV/FISH positive cells were observed in a field of VP88 prostatic tissue (green signals in FIG. 32, panel A), essentially every cell in an adjacent section was labeled with the chromosome 1-specific probes (red and green signals in FIG. 32, panel B). Because of the low frequency of XMRV positive cells, negative controls were performed using a probe targeting Kaposi's sarcoma-associated herpesvirus (KSHV) DNA (nts 85820-92789) which did not label any cells in prostate specimens VP88 and VP51, but this probe did efficiently label 293T cells transfected with KSHV DNA. Additional XMRV FISH experiments were performed on a tissue microarray containing duplicates of fourteen different prostate cancer tissue specimens (Table 13). Five homozygous RNase L 462Q (QQ) cases (VP29, 31, 42, 62, and 88) showed 5 to 10 XMRV/FISH positive cells each (about 1% of prostate cells observed). Patient sample VP79, also a QQ case, contained 2 positive cells (0.4% of total cells examined). All of the XMRV FISH positive cells observed were stromal cells. In contrast, three RR tissue samples and two RQ tissue samples showed one or no (<0.15%) FISH positive cells. Two of the QQ cases, VP35 and VP90, positive by gag RT-PCR (Urisman, A., et al., (2005), *PLOS Pathogens*) showed only one FISH positive cell each (Table 13). Conversely, one case, VP31, was FISH positive, but gag RT-PCR negative. These results could be due to heterogeneity in virus copy numbers between specific regions of the prostate sampled.

Presence of XMRV in Prostatic Tissues as Determined by Immunohistochemistry

Figure 33:
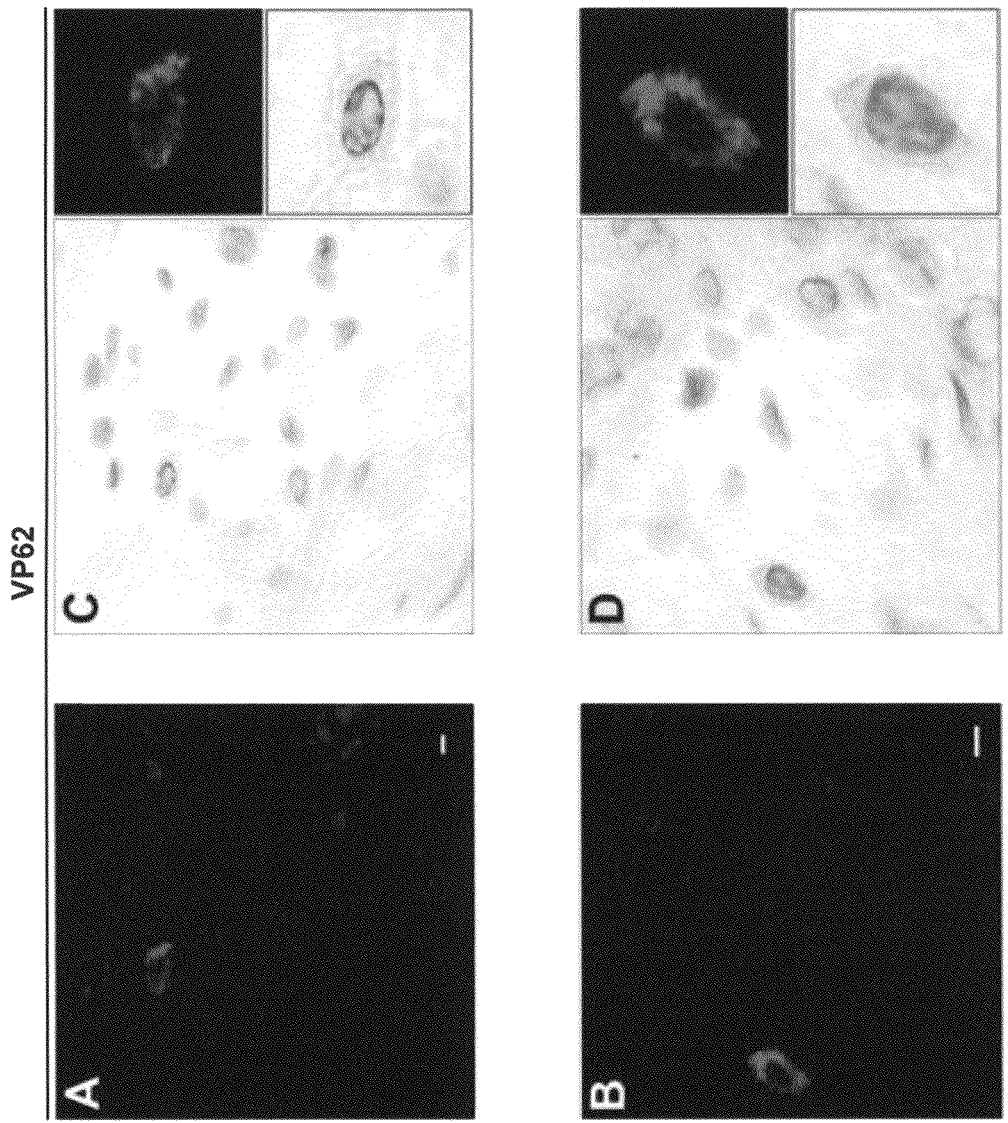
FIG. 33 shows the presence of Gag protein in prostate tissues. IHC with monoclonal antibody to SFFV Gag p30 was performed on prostatic tissue of cases VP62 (panels A to D), VP88 (panels E to H), and VP51 (panels I, J). Visualization of bi-functional chromagen indicating Gag protein shown by immunofluorescence (panels A, B, E, F and enlargements [right]) and bright field (panels C, D, G, H and enlargements [right]) is detected by granular cytoplasmic staining (red) in stromal cells of the homozygous RNase L 462Q cases VP62 and VP88, but not in the homozygous RNase L 462R case VP51 (panels I&J). The positive cells in G and H are stromal lymphocytes. Bars in panels A, B and I were 5 μm and in panels E and F were 10 μm. Enlargements were performed as described in the legend to FIG. 31.
Figure 33:
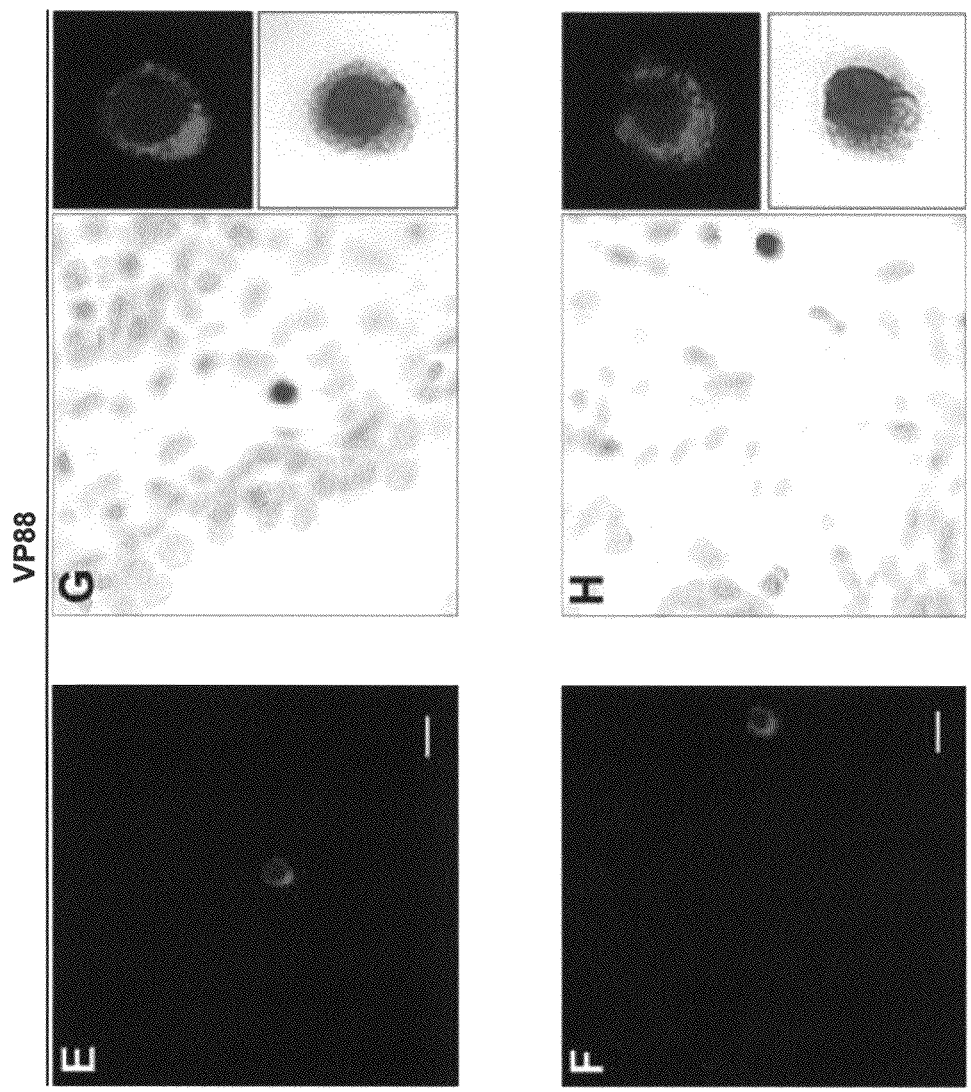

To identify cells expressing XMRV proteins, the presence of Gag protein was investigated using a monoclonal antibody against spleen focusing forming virus (SFFV); this antibody is reactive against Gag proteins from a wide range of different ecotropic, amphotropic and xenotropic MuLV strains (Chesebro, B., et al., (1983), *Virology* 127:134-148). Using this antibody, positive signal by IHC was observed in prostatic tissues of XMRV-positive cases VP62 and VP88, both QQ (FIG. 33). An enhanced alkaline phosphatase red detection method allowed Gag detection in the same cells with both fluorescence (FIG. 33, panels A, B, E&F) and bright field (FIG. 33 panels C, D, G&H) microscopy. The Gag expressing cells were observed in prostatic stromal cells with a distribution and frequency similar to that detected by FISH (FIG. 33). In contrast, no Gag positive cells were observed in VP51 prostatic tissue, which is of RR genotype (FIG. 33, panels I&J).

A Related Gammaretrovirus in a Prostate Cancer Cell Line

Figure 34A:
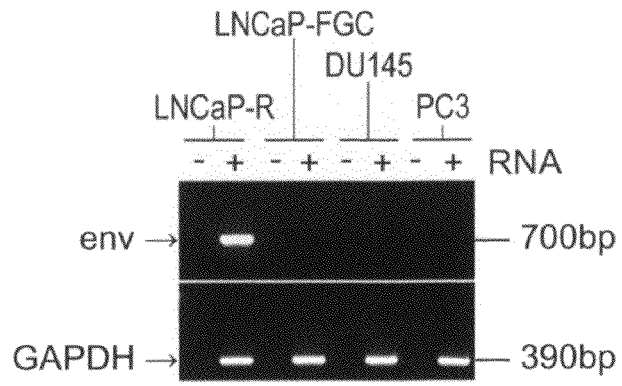
FIGS. 34A-34D show the following.
Figure 34B:
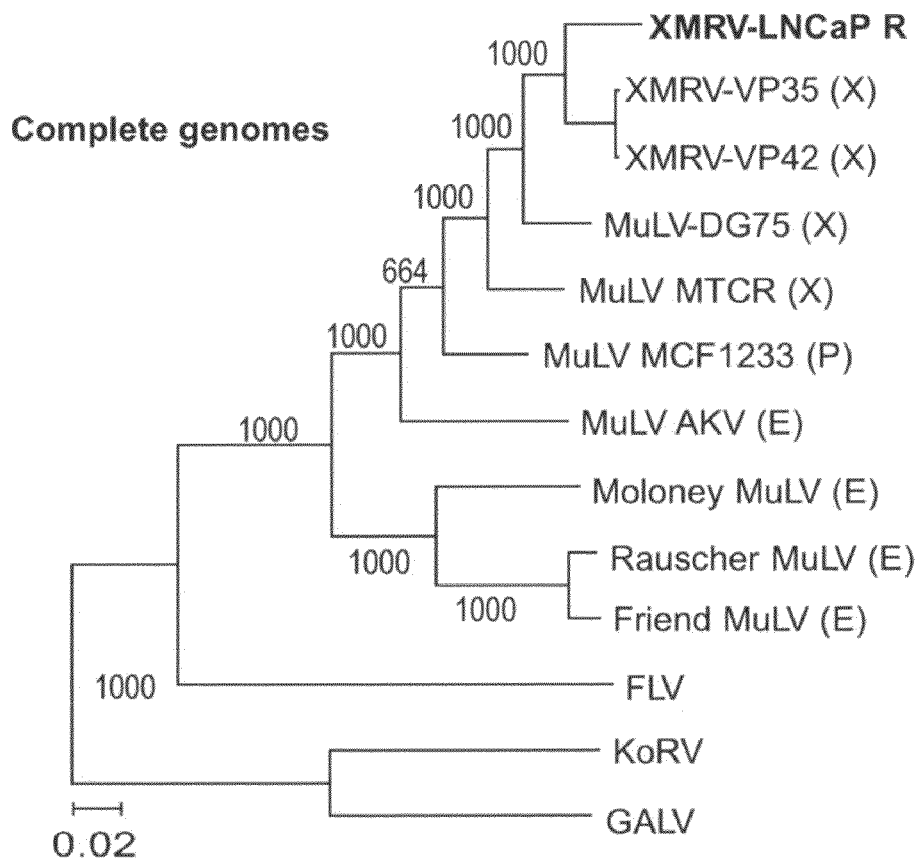
Figures 34C, 34D:
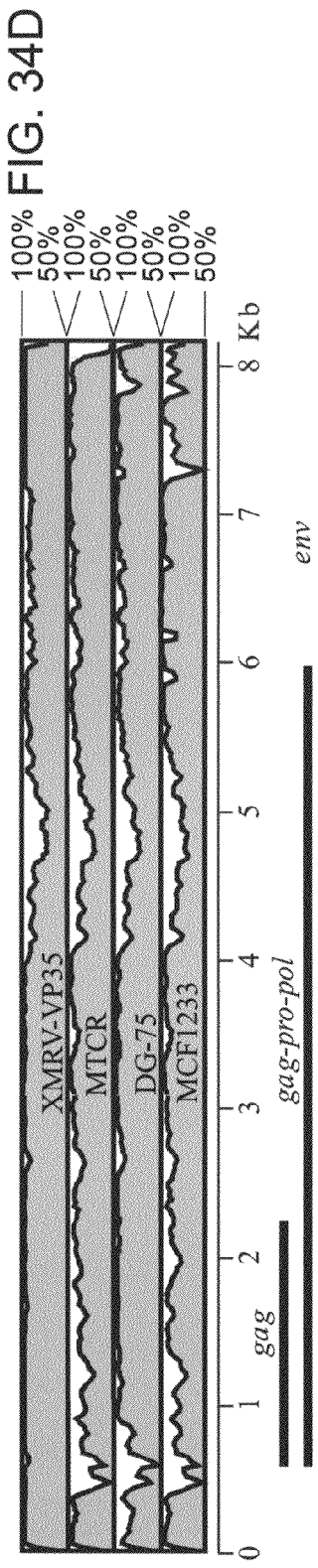

Over the years, several cell lines have been derived from human prostate cancers. Two of these, PC3 and DU145, are wild-type with respect to RNASEL, while the widely-studied LNCaP line is heterozygous both for an inactivating deletion mutation in RNASEL (471ΔAAAG) and for the R462Q variant (Rennert, H., et al., (2002), *Am J Hum Genet* 71: 981-984; Xiang, Y., et al., (2003), *Cancer Res* 63: 6795-6801). Once the relation between XMRV infection and RNASEL mutations was established (Urisman, A., et al., (2005), *PLOS Pathogens*), evidence of infection with XMRV-like agents was investigated in these cell lines; additionally, a line of normal prostatic epithelial cells (PrEC) were investigated. Two clones of LNCaP were studied, one of which, LNCaP-FGC, was freshly obtained for this purpose from the ATCC repository; the other (LNCaP-R) had been serially passaged in the laboratory. [LNCaP-R is the name for an isolate originally obtained from ATCC (as LNCaP-FGC) and maintained at the Cleveland Clinic, Department of Cancer Biology (laboratory of W. Heston)]. RT-PCR was performed on RNA from these cell lines using primers specific for a conserved 700 by region within the env protein encoding region of XMRV VP35 (FIG. 34, panel A). No PCR products were detected in most cell lines, including all those with wild-type RNASEL. Notably, however, one of the two tested clones of LNCaP (LNCaP-R) was positive for a band of the expected size, while the other (LNCaP-FGC) was negative. The positive control GAPDH amplimer (391 bp) was present at similar levels after RT-PCR reactions from each of the cell lines.

The Genome of the LNCaP-R Retrovirus

The entire retroviral genome from LNCaP-R cells was recovered as overlapping cDNA fragments applying the same RT-PCR strategy used to recover XMRV genome from prostate tumor samples (FIG. 31, panel A and Urisman, A., et al., (2005), *PLOS Pathogens*). Briefly, total RNA from the LNCaP-R clone was reverse transcribed using random hexamer oligonucleotides, followed by PCR with XMRV-specific PCR primers (Urisman, A., et al., (2005), *PLOS Pathogens*). The amplified PCR fragments were then cloned and sequenced.

The deduced LNCaP-R retrovirus genome (GenBank: DQ272467) is 8185 nt long and is most similar to the two XMRV genomes (XMRV VP35 and XMRV VP42) derived from prostate tumors (Urisman, A., et al., (2005), *PLOS Pathogens*), with which it shares 94% nucleotide identity (FIG. 34, panel B [tree and similarity plots]). The recovered genome also shares high nucleotide identity (92%) with two other xenotropic MuLV genomes: Murine type C retrovirus (GenBank: NC_001702, Heinemeyer T., unpublished) and MuLV DG-75 (GenBank: AF221065, (Raisch, K P., et al., (2003), *Virology* 308: 83-91)). Based on these findings, we assigned the virus a provisional name of XMRV LNCaP-R.

Figure 35A:
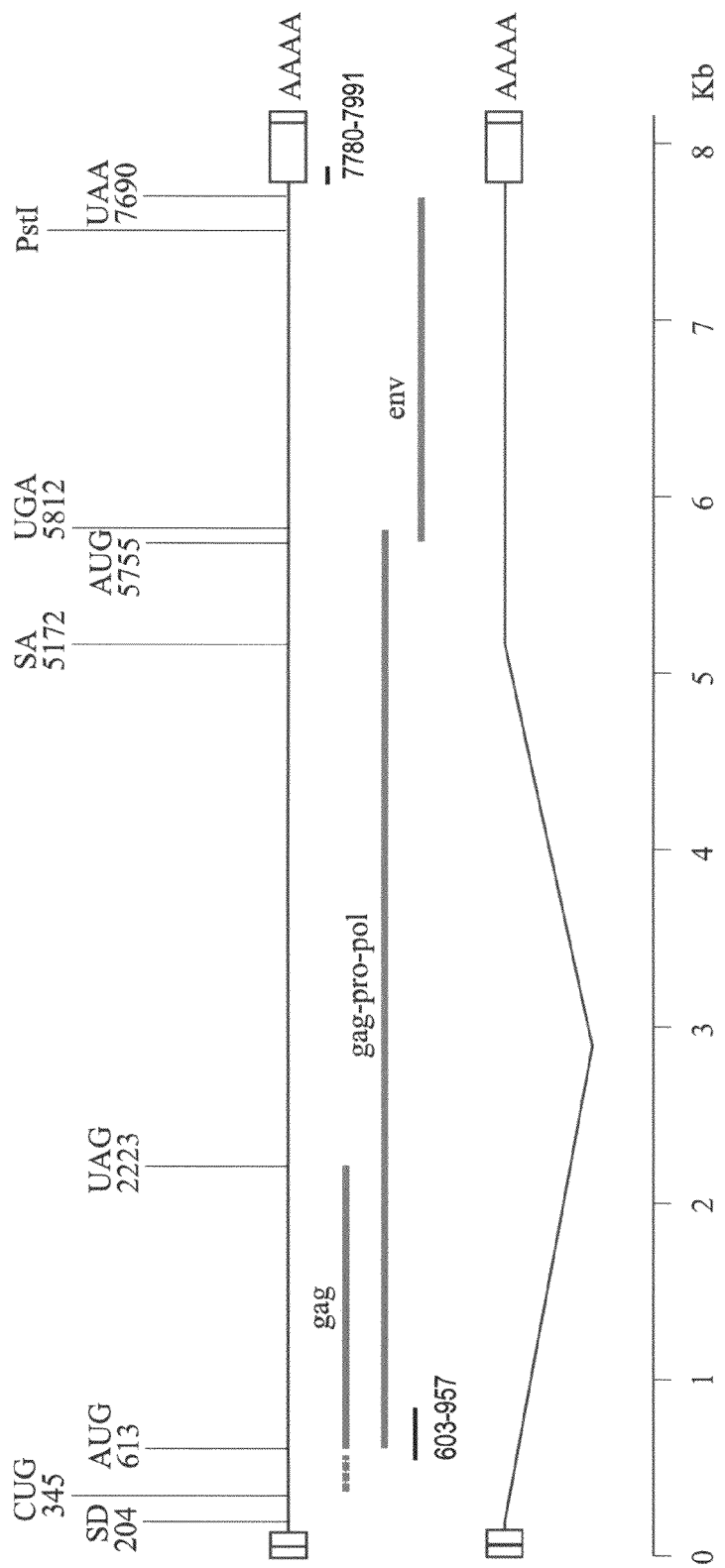
FIGS. 35A-35C show the following.

The genome of XMRV LNCaP-R contains two overlapping ORFs, encoding the full-length Gag-Pro-Pol and the Env polyproteins (FIG. 35A). Similar to the tumor-derived relatives, XMRV LNCaP-R is a canonical simple retrovirus lacking accessory viral regulatory genes or host-derived oncogene sequences. The Gag protein is 536 aa long and shares its highest aa identity with XMRV VP35 (98%) (FIG. 34, panel D). Upstream of gag AUG is a ca. 300 nt region known as the 5' gag leader, which in most ecotropic MuLVs encodes a minor glycosylated form of Gag (glyco-Gag) expressed from an alternative CUG start codon (Prats, A C., et al., (1989), *J Mol Biol* 205: 363-372). The 5' gag leader was found to be the most divergent region in the tumor-derived XMRV genomes as compared to other MuLVs (Urisman, A., et al., (2005), *PLOS Pathogens*). Just as in XMRV VP35 and VP42, this region is interrupted by a stop codon 53 aa downstream from the CUG initiation codon of glyco-Gag and bears a signature 24-nt deletion characteristic of XMRV (FIG. 34, panel C) and not found in any other known gammaretroviral genome. (Note: since the glyco-gag protein is dispensable for retroviral replication (Fan, H., et al., (1983), *Proc Natl Acad Sci USA* 80: 5965-5969; Schwartzberg P, et al., (1983), *J Virol* 46: 538-546), these lesions are not expected to disrupt XMRV infectivity; see below). Similarly, all regulatory sequences present in the tumor-derived XMRV genomes were also found in the same positions in the genome of XMRV LNCaP-R. These include a binding site for a prolyl-tRNA, which functions as the primer for reverse transcription during viral replication (Adam, M A., et al., (1988), *J Virol* 62: 3802-3806; Fisher, J., et al., (1998), *Virology* 244: 133-145; Berlioz, C., et al., (1995), *J Virol* 69: 2214-2222; Vagner, S., et al., (1995), *J Biol Chem* 270:20376-20383); splice donor and acceptor sites involved in the generation of env subgenomic RNAs (see below); TATAAA (SEQ ID NO:50) and CCAAT (SEQ ID NO:49) boxes involved in transcription initiation (Temin, H M, (1981), *Cell* 27: 1-3; Coffin, J M., et al., (eds.) (1997) Retroviruses. Cold Spring Harbor, N.Y.: Cold Spring Harbor Laboratory Press); a glucocorticoid response element (GRE); and AATAAA (SEQ ID NO:51) polyadenylation signal.

However, despite its overall similarity to the characterized XMRVs, the LNCaP-R isolate is nonetheless distinct from these tumor-derived isolates. At the level of the whole genome, the isolate is not as closely related to the XMRV VP35 and VP42 sequences as the latter two are to each other. For the predicted pro-pol region (1084 aa encoding the protease, reverse transcriptase and integrase activities), aa identity with the tumor-derived XMRVs is lower than in other regions (92%), and is similar to that seen with MuLV DG-75 or MTCR. In addition, portions of the env region show significant divergence from the characterized XMRVs (see FIG. 34, panel D for a similarity plot comparing XMRV35 with XMRV LNCaP R). The env region nonetheless is most similar to the xenotropic/polytropic gammaretroviruses indicating that the virus should display a host range that includes human cells (see below).

Viral Gene Expression in XMRV LNCaP-R

Figure 35B:
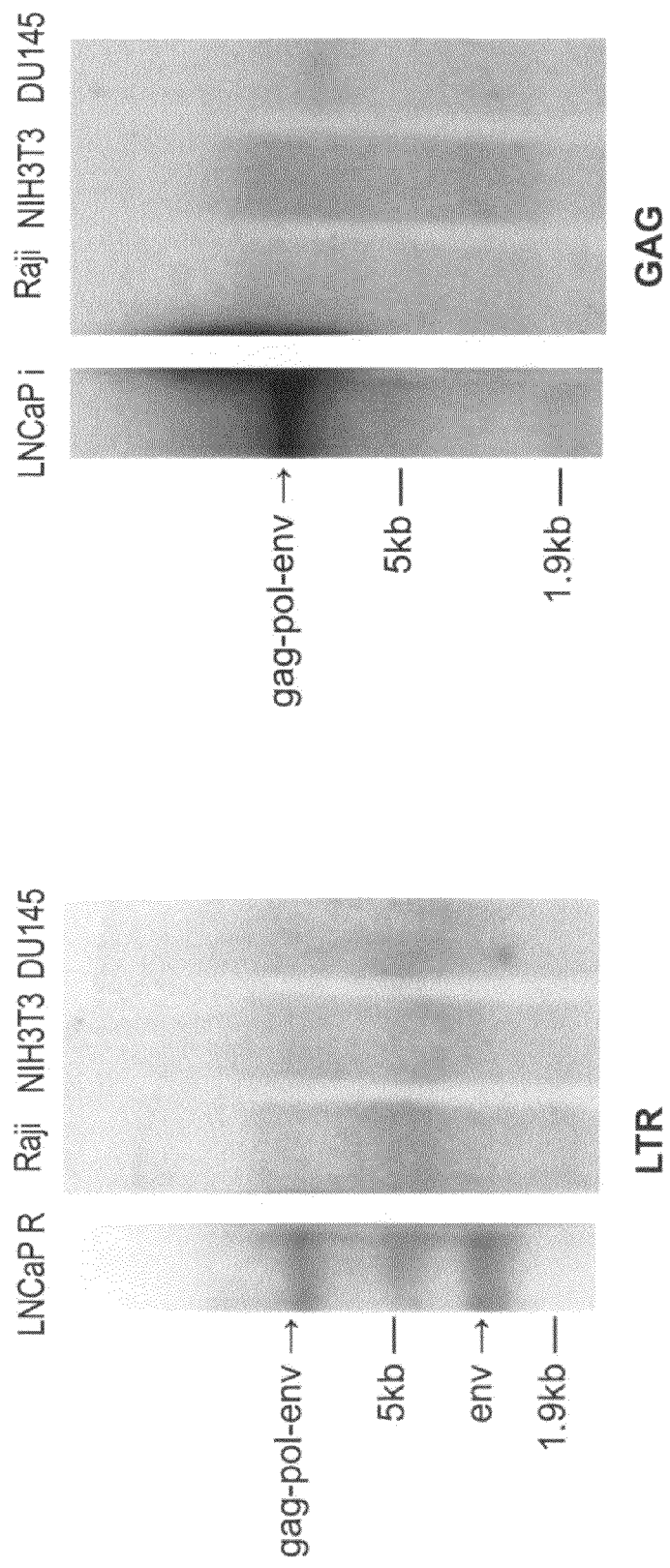
Figure 35C:
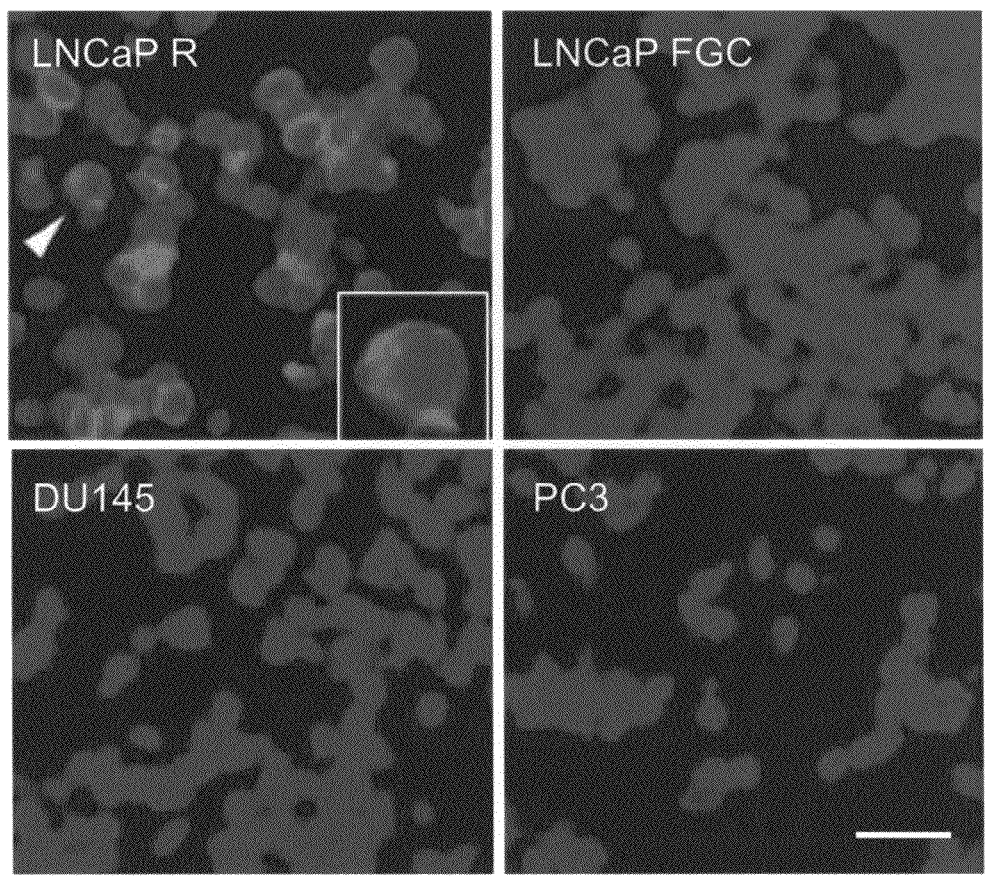

As noted above, conserved splice donor (AGGTAAG (SEQ ID NO:47), position 204) and acceptor (CACTTACAG (SEQ ID NO:48), position 5479) sites involved in the generation of env subgenomic RNAs were found in the same position as in XMRV (Urisman, A., et al., (2005), *PLOS Pathogens*). Transcripts for both the complete, unspliced 8.2 kb transcript encoding gag and pro-pol, and the spliced env transcript (3.2 kb) were confirmed in LNCaP-R cells by Northern analysis using an LTR probe (nucleotide positions 7780 to 7991), which detects both messages (FIG. 35B). As predicted, a gag-specific probe (nucleotide positions 603 to 957) detects only the full length genomic RNA (FIG. 35B); env mRNA is not detectable with this probe because gag sequences have been removed by splicing. Consistent with the expression of these transcripts, a large proportion of LNCaP-R cells stained positively with anti-Gag antibody, while LNCaP-FGC cells did not (FIG. 35C).

LNCaP-R Cells Produce Infectious XMRV

Figure 36A:
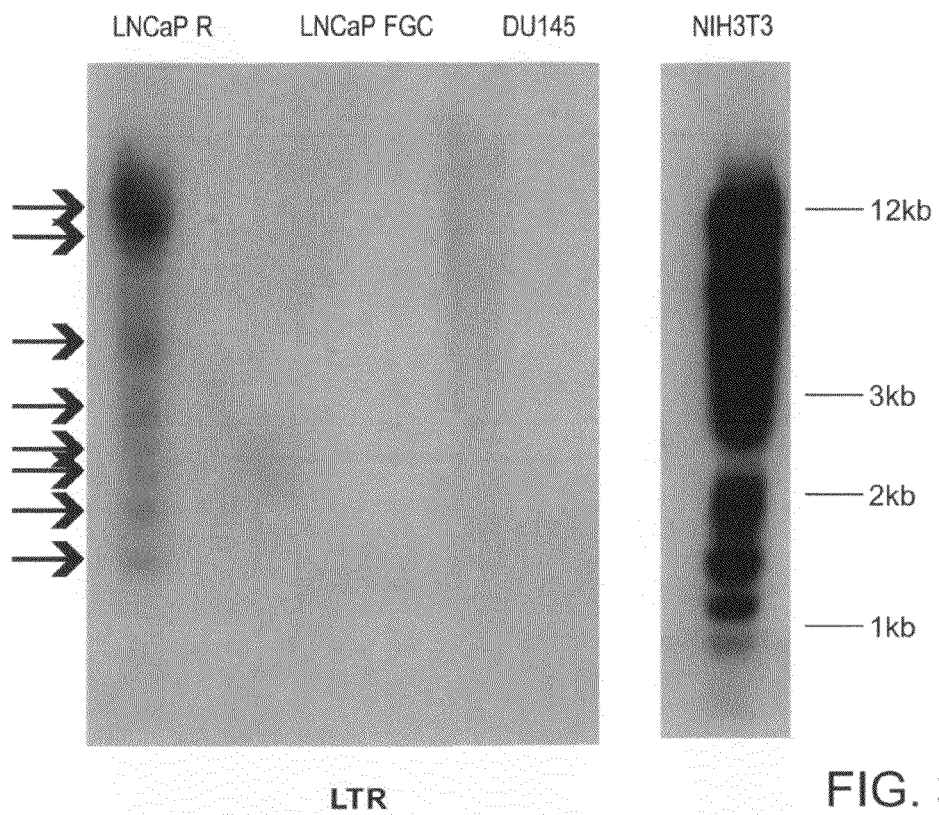
Figure 36B:
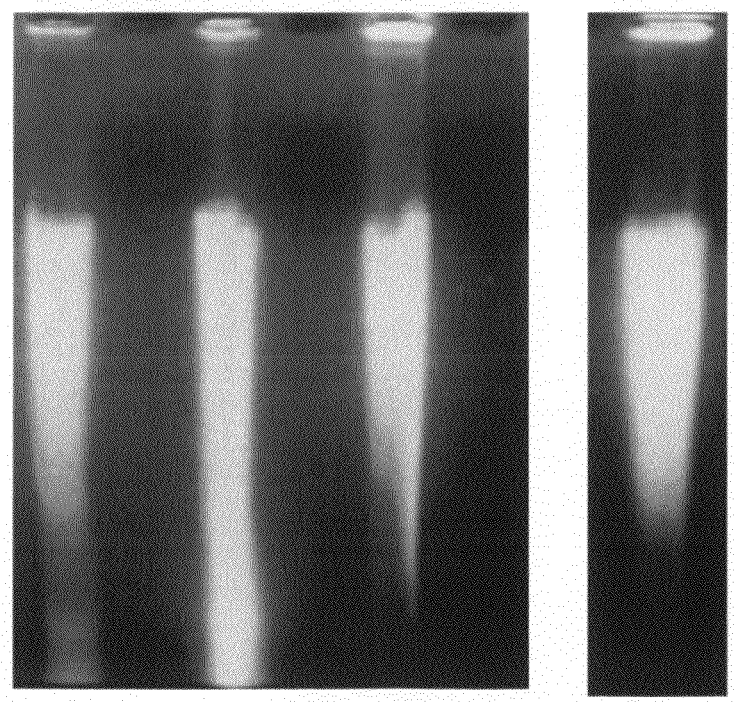

The presence of genomic and subgenomic mRNAs strongly implied the existence of integrated proviral DNA in LNCaP-R cells. To search for this directly, genomic DNA, cleaved with the restriction enzyme PstI (which cleaves once, within the env region) was extracted and examined. The resulting fragments were examined by Southern blotting with a probe corresponding to the U3 region (positions 7780-7991). As shown in FIG. 36A, a complex array of bands, suggestive of multiple insertion sites, were observed in LNCaP-R but not in the virus-negative lines. PCR-based cloning of several host-viral junctions affirmed that multiple distinct integration sites on different human chromosomes are present in LNCaP-R DNA (FIG. 36C).

Figure 37A:
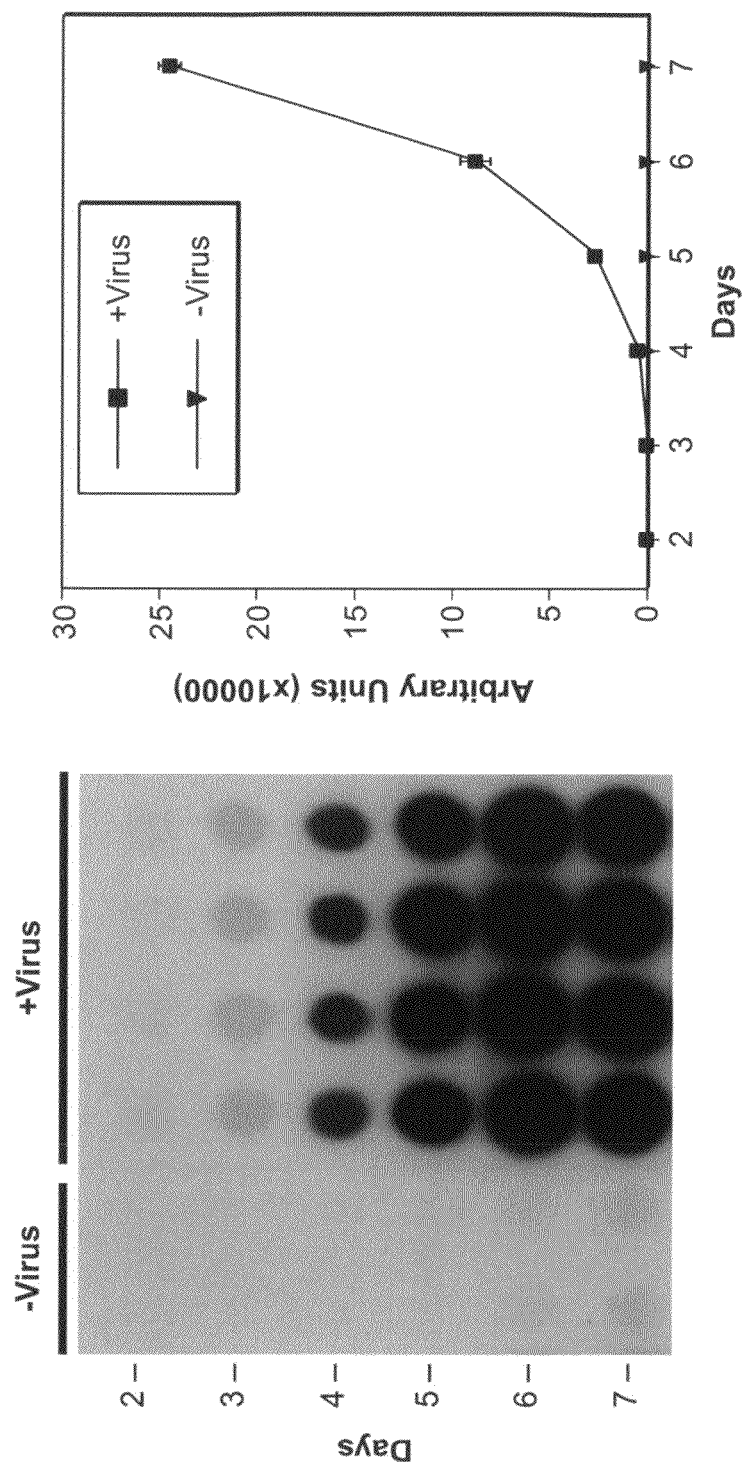
FIGS. 37A-37C show XMRV LNCaP-R is an infectious virus. LNCaP-FGC cells were either mock infected (−Virus) or infected with LNCaP-RV (+Virus) (Example 3, Material and Methods).

The pattern of viral integrants in LNCaP-R implied that multiple de novo infections had occurred within this subline, indicating the production of infectious virus. To directly demonstrate this, whether supernatants from LNCaP-R could transmit infection to other lines was determined. Supernatant from LNCaP-R cells was transferred to LNCaP-FGC cells and incubated for 2 hr; following this, the cells were washed, fresh medium added and supernatant sampled daily for the ensuing week. FIG. 37A shows a progressive rise in reverse transcriptase activity in the recipient culture medium during this time period, indicative of virus replication and spread.

Figure 37B:
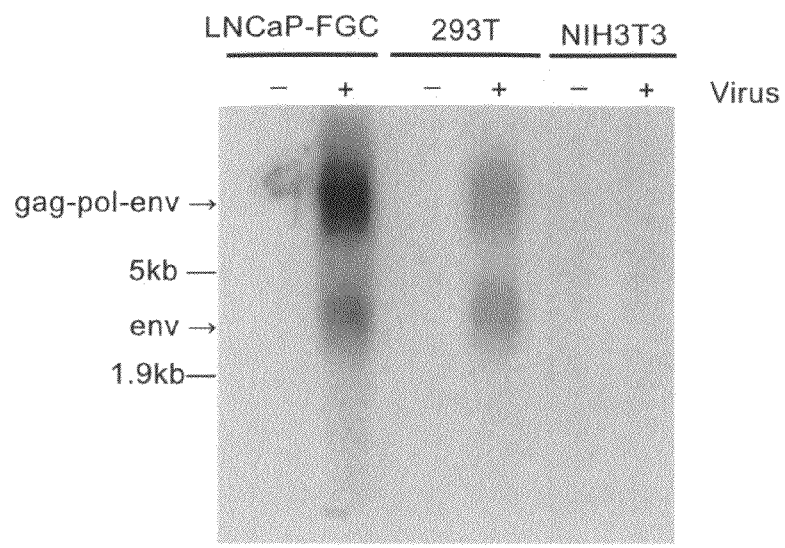

To examine the host range of XMRV-LNCaP R, human (DU145, LNCaP-FGC and 293T) or murine (3T3) cells were inoculated with LNCaP-R supernatants; 24 or 36 hr later, RNA and DNA were prepared and examined by blot-hybridization. A Northern blot of infected human (LNCaP-FGC and 293T cells) and murine 3T3 cells showed genomic and subgenomic transcripts in the human lines, but no XMRV mRNA is seen in the 3T3 cells (FIG. 37B). Southern blot analyses of viral DNA in the recipient human cells (LNCaP-FGC and DU145) (FIG. 37C) showed a diffuse smear of bands, indicative of multiple independent integrations, in inoculated, but not uninoculated, human lines. (Mouse 3T3 cells were used here only as a positive hybridization control, and revealed multiple integration sites derived from endogenous mouse retroviruses; this high background prevents effective use of Southern blotting for XMRV proviruses in this line). The finding that human but not mouse cells are vulnerable to infection is consistent with the xenotropism predicted from the sequence of the viral envelope protein.

Discussion

XMRV is a novel gammaretrovirus originally detected in prostate tissue of patients with prostate cancer and genomic mutations in RNASEL (Urisman, A., et al., (2005), *PLOS Pathogens*). XMRV is the first example of a xenotropic retrovirus infection of human tissue, and the epidemiologic link to RNASEL lesions strongly implies an important role for RNase L in the control of infection. These findings are supported by the in situ analyses of prostate tissue described herein, which reinforce that infection is found primarily in subjects homozygous for the R462Q RNase L variant. Importantly, we now show that the infection is not present in the carcinoma cells themselves, but rather in a subset of stromal cells, chiefly fibroblasts and blood elements. These findings provide the boundary conditions within which we can frame the two major questions posed by XMRV: (i) how does RNase L activity influence XMRV infection? And (ii) what, if any, is the relationship between XMRV infection and prostatic cancer?

RNase L Action and XMRV Infection

Figure 37C:
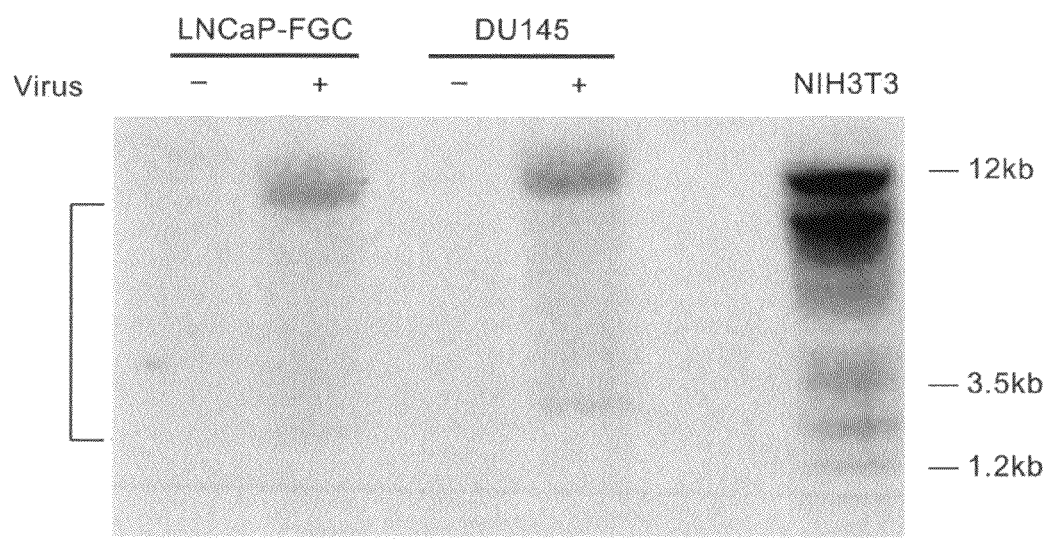

The data provided herein and that of Urisman and coworkers (Urisman, A., et al., (2005), *PLOS Pathogens*) provide strong empiric evidence that down-mutations in RNASEL are important in the acquisition or persistence of XMRV infection in vivo (Urisman, A., et al., (2005), *PLOS Pathogens*). Although there is considerable evidence from animal studies and cell culture that RNase L is an important antiviral protein, most studies have focused on viruses with RNA-based replication cycles, including picornaviruses (Zhou, A., et al., (1997), *Embo J* 16: 6355-6363; Flodstrom-Tullberg, M., et al., (2005), *J Immunol* 174: 1171-1177), paramyxoviruses (Behera, A K., et al., (2002), *J Biol Chem* 277: 25601-25608), alphaviruses (Ryman, K D., et al., (2002), *Viral Immunol* 15: 53-76) or retroviruses (Smith, J A., et al., (2005), *J Virol* 79: 2240-2250). Relatively few studies have focused on the role of the 2-5A/RNase L system in retrovirus infections. Type I interferons clearly inhibit retroviral replication, but these cytokines activate many downstream effectors in addition to RNase L, and can create blocks at many stages of retroviral replication, including reverse transcription, translation, viral assembly and release (Pitha, P M., (1994) *Antiviral Res* 24: 205-219; Poli, G., et al., (1994), *Antiviral Res* 24: 221-233; Friedman, R M., et al., (1974) *Proc Natl Acad Sci USA* 71: 3542-3544). Nonetheless, experimental overexpression of OAS (Schroder, H C., et al., (1992), *Int J Biochem* 24: 55-63) or RNase L (Maitra, R K, et al., (1998), *J Virol* 72: 1146-1152) in cultured cells impairs HIV replication, and suppression of RNase L activity by overexpression of an RNase L inhibitor also modestly enhances HIV growth in culture (Martinand, C., et al., (1999), *J Virol* 73: 290-296). In HIV infection, OAS can be activated by structured RNA regions within the 5' UTR and TAR; OAS can thus be thought of as one cellular "sensor" for HIV (Maitra, R K., et al., (1994), *Virology* 204: 823-827). Regions of XMRV RNA detected by OAS, or how RNase L activation affects XMRV replication is unclear, but recovery of an infectious XMRV family member from LNCaP-R cells opens both questions to experimental study. The barrier to XMRV infection posed by RNase L is relative, not absolute: DU145, which have no lesions in RNASEL, can be infected by XMRV under conditions of high multiplicity of infection (MOI) in vitro (FIGS. 37A-37C). This should not be entirely surprising, as it is in keeping with other known restriction factors for retroviral replication, like Fv-1 restriction of MuLV and more recently identified restrictors of HIV and SIV, all of which can be overcome by high MOI (Goff, S P., (2004), *Mol Cell* 16: 849-859; Bieniasz, P D., (2003), *Trends Microbiol* 11: 286-291). Since most in vivo infections are established initially under low MOI conditions, it is restriction at this MOI level that is presumably selected for during viral evolution.

From the results examining human prostate cancer cell lines described herein, several conclusions can be drawn. First, the absence of viral DNA in the genomic DNA of most human cells indicates that XMRV is not an endogenous retrovirus, but an exogenously acquired agent. Second, although LNCaP cells were reportedly established from a clonal tumor, the integration sites do not appear to be clonal. This indicates that the infection of the cell line postdated the establishment of the clonal line; the multiplicity of integrants presumably reflects horizontal spread of infection within the line. This interpretation is also consistent with the fact that the LNCaP-FGC clone is negative for infection. Since the in situ analyses of prostate tumors (FIGS. 30-33) indicate that carcinoma cells are not infected in vivo, this infection must have occurred in vitro. Therefore, two possible scenarios for such infection: (i) during explantation of the original tumor, a small number of tumor cells might have acquired infection by spread from stromal cells; or (ii) infection may have occurred in the laboratory during serial passage of the line. If LNCaP-FGC cells were clonally purified prior to deposition at ATCC, then possibility (ii) is more likely.

XMRV Infection and Prostate Cancer

The findings described herein that XMRV infection is targeted to stromal cells and not to carcinoma cells has major implications for considering the relation of XMRV infection to prostate cancer. This finding, and the fact that the XMRV genome harbors no host-derived oncogenes, rules out two classical models for retroviral oncogenesis: direct introduction of a dominantly acting oncogene and insertional activation of such a gene. It is emphasized that the epidemiologic described herein links XMRV infection to the RNASEL genotype but does not mandate any etiological link to prostate cancer. While its exclusion from the carcinoma cells makes direct oncogenesis by XMRV improbable, more indirect contributions of the virus to the tumor can certainly be envisioned. Prostate cancer is a disease with a long natural history, and many histologic changes occur in the gland prior to the supervention of overt malignancy. Recent work emphasizes that prostate cancers are very commonly accompanied by evidence of chronic prostatic inflammation, and a lesion called proliferative inflammatory atrophy (PIA) is often found in premalignant stages of the disease (Nelson, W G., et al., (2003), *N Engl J Med* 349:366-381). It is speculated that byproducts of this inflammation (e.g. free radicals and oxidative damage) can trigger injury and regeneration in the prostatic epithelium. This enhanced proliferation allows opportunities for replicative errors to engender mutations; those that deregulate growth then have a selective advantage. PIA is often found adjacent to high grade prostatic intraepithelial neoplasia (HGPIN) or early cancer, and accumulating evidence suggests an identifiable genetic pathway between PIA, HGPIN, and cancer (Nelson, W G., et al., (2003), *N Engl J Med* 349:366-381). In support of the infection/inflammation hypothesis are observations that variants or epigenetic events in other genes involved in innate immunity (the TLR family), control of the inflammatory response (MSR1 and MIC-1), antioxidant activity (PON1 and GSTP1), or DNA repair in response to oxidative stress (OGG1, CHEK2, and BRCA2) have also been reported to predispose men to prostate cancer (Zheng, S L., et al., (2004), *Cancer Res* 64: 2918-2922; Xu, J., et al., (2002), *Nat Genet.* 32: 321-325; Lindmark, F., et al., (2004), *J Natl Cancer Inst* 96: 1248-1254; Marchesani, M., et al., (2003), *J Natl Cancer Inst* 95: 812-818; Xu. J et al., (2002), *Cancer Res* 62:2253-2257; Dong, X., et al., (2003), *Am J Hum Genet.* 72: 270-280; Edwards, S M., et al., (2003), *Am J Hum Genet.* 72: 1-12). While the cause of the inflammation in PIA is unknown, infection is an obvious potential trigger, and a persistent viral infection restricted to the stroma would be well-positioned to contribute to such a process. In this view, one reason for the link between RNASEL mutations and prostate cancer would be the inability of an RNase L-deficient innate immune system to terminate a stromal XMRV infection; the resulting persistent infection would then contribute to a chronic inflammatory state whose end result can be PIA. (We note that XMRV need not be the sole infectious precipitant in such a scenario).

The finding that XMRV primarily affects stromal cells raises still another potential mechanism for contributing to prostatic neoplasia. Recent work has shown that stromal cells have an active role in promoting tumorigenesis of adjacent epithelial cells by producing various cytokines and growth factors that serve as proliferative signals (Tlsty, T D., et al., (2001), *Curr Opin Genet Dev* 11: 54-59). In particular, cancer associated fibroblasts stimulate growth of human prostatic epithelial cells and alter their histology in vivo (Olumi, A F., et al., (1999), *Cancer Res* 59: 5002-5011). It is conceivable that XMRV-infected prostatic stromal cells could produce and secrete growth factors, cytokines or other factors that stimulate cell proliferation in surrounding epithelia. Such a paracrine mechanism could still function quite efficiently even with the relatively small number of XMRV-infected cells that characterize the lesion.

Finally, it is noted that the identification of an exogenous infection like XMRV could help explain why not all genetic studies have consistently identified RNase L as a prostate cancer susceptibility factor. If such an infection were linked, however indirectly, to prostate cancer risk, and if the prevalence of infection is not uniform in different populations, populations with low XMRV prevalence might be expected to show no association of RNASEL lesions to prostate cancer.

TABLE 1

Detection of HXV in Prostates (Masterlist)

| Lab ID | J-Number | Study number | 1385 SNP | Received? | ArrayID (Total) | Array (Total) | ArrayID (Poly A) | Array (Poly A) |
|---|---|---|---|---|---|---|---|---|
| VP10 | | 3-03-0291A/D | AA | X | 7-247 | MR | 7-244 | neg |
| VP10 | J8 | 3-03-0291A/D | AA | X | 6-151 | neg | 6-108 | neg |
| VP107 | | 3-04-0661A/B | AA | | 7-249 | neg | 7-246 | neg |
| VP24 | | 3-03-0434A/D | AA | | | | | |
| VP27 | | 3-03-0452A/D | AA | X | 7-248 | neg | 7-245 | neg |
| VP27 | J9 | 3-03-0452A/D | AA | X | 6-152 | neg | 6-108 | neg |
| VP29 | | 3-03-0473B/D | AA | X | 5-169 | neg | 5-174 | MR |
| VP31 | | 3-03-0481A/D | AA | X | 5-171 | neg | 5-176 | neg |
| VP35 | | 3-03-0530A | AA | X | 5-172 | MR | 5-177 | MR |
| VP42 | | 3-03-0647A/B | AA | X | 5-173 | | 5-178 | MR |
| VP62 | | 3-03-1040A/B | AA | X | | neg | | |
| VP79 | | 3-04-0116A1 | AA | X | | | | |
| VP88 | | 3-04-0381A/B | AA | X | | | | |
| VP90 | | 3-04-0430A/B | AA | X | | | | |
| VP94 | | 3-04-0286A/B | AA | | | | | |
| VP104 | | no label | AG | | | | | |
| VP33 | | 3-03-0518A | AG | | | | | |
| VP37 | | 3-03-0556A | AG | | | | | |
| VP40 | | 3-03-0629A/D | AG | | | | | |

TABLE 1-continued

Detection of HXV in Prostates (Masterlist)

| VP41 | | 3-03-0631A | AG | | | | | |
|---|---|---|---|---|---|---|---|---|
| VP44 | | 3-03-03702B/D | AG | | | | | |
| VP45 | | 3-03-0707 | AG | X | 5-190 | neg | | 5-195 |
| VP46 | | 3-03-0742A/B | AG | X | 5-191 | neg | | 5-196 |
| VP49 | | 3-03-0791A1 | AG | X | 5-192 | neg | | 5-197 |
| VP55 | | 3-03-0898C/D | AG | | | | | |
| VP81 | | 3-04-0149A1 | AG | | | | | |
| VP82 | | 3-04-0210A/B | AG | | | | | |
| VP83 | | 3-04-0237A/B | AG | | | | | |
| VP89 | | 3-04-0428A/B | AG | | | | | |
| VP92 | | ? | AG | | | | | |
| VP04 | J3 | 3-03-0237 | GA | X | 6-112 | neg | 6-103 | neg |
| VP05 | J4 | 3-03-0244A/D | GA | X | 6-113 | neg | 6-104 | neg |
| VP07 | J6 | 3-03-00252A/D | GA | X | 6-115 | neg | 6-106 | neg |
| VP08 | J7 | 3-03-0262A/D | GA | X | 6-150 | neg | 6-107 | neg |
| VP09 | | 3-03-0271A/D | GA | | | | | |
| VP100 | | 3-04-0496A/B | GA | | | | | |
| VP108 | | 3-04-0704A/B | GA | | | | | |
| VP11 | | 3-03-0307A/D | GA | | | | | |
| VP111 | | 3-04-0755A/B | GA | | | | | |
| VP112 | | 3-04-0759A/B | GA | | | | | |
| VP115 | | 3-04-0780A/B | GA | | | | | |
| VP14 | | 3-03-0329A | GA | | | | | |
| VP15 | | 3-03-0330A1 | GA | | | | | |
| VP18 | | 3-03-0367C/D | GA | | | | | |
| VP22 | | 3-03-0444A/D | GA | | | | | |
| VP23 | | 3-03-0432B/D | GA | | | | | |
| VP56 | | 3-03-0907A1 | GA | | | | | |
| VP57 | | 3-03-0934C/D | GA | | | | | |
| VP61 | | 3-03-1011D1 | GA | | | | | |
| VP63 | | 3-03-1057A/C | GA | | | | | |
| VP64 | | 3-03-1060A1 | GA | | | | | |
| VP65 | | 3-03-1074A/B | GA | | | | | |
| VP68 | | 3-03-10192A/B | GA | | | | | |
| VP70 | | 3-03-1114A/B | GA | X | | | | |
| VP71 | | 3-04-0014A1 | GA | | | | | |
| VP73 | | 3-04-0018A/B | GA | | | | | |
| VP74 | | 3-04-0041A/B | GA | X | | | | |
| VP77 | | 3-04-0051A/B | GA | X | | | | |
| VP78 | | no label | GA | | | | | |

TABLE 1-continued

Detection of HXV in Prostates (Masterlist)

| | | | | | | | | |
|---|---|---|---|---|---|---|---|---|
| VP97 | | 3-04-0460A/B | GA | | | | | |
| VP01 | | | GG | | | | | |
| VP02 | J1 | 3-03-0217A | GG | X | 6-110 | neg | 6-101 | neg |
| VP03 | J2 | 3-03-0235 | GG | X | 6-111 | neg | 6-102 | neg |
| VP06 | J5 | 3-03-0248A/D | GG | X | 6-114 | neg | 6-105 | neg |
| VP101 | | 3-04-0497A/B | GG | | | | | |
| VP102 | | 3-04-0522A/B | GG | | | | | |
| VP103 | | 3-04-0570A/B | GG | | | | | |
| VP105 | | no label | GG | | | | | |
| VP106 | | 3-04-0660A/B | GG | | | | | |
| VP109 | | 3-04-0705A/B | GG | | | | | |
| VP110 | | 3-04-0718A/B | GG | | | | | |
| VP113 | | 3-04-0770A/B | GG | | | | | |
| VP114 | | 3-04-0776A/B | GG | | | | | |
| VP116 | | 3-04-0791A/B | GG | | | | | |
| VP117 | | 3-04-0795A/B | GG | | | | | |
| VP118 | | 3-04-0803A/B | GG | | | | | |
| VP119 | | 3-04-0806A/B | GG | | | | | |
| VP12 | | 3-03-0312A/D | GG | | | | | |
| VP13 | | 3-03-0324A/D | GG | | | | | |
| VP16 | | 3-03-0357B/C | GG | | | | | |
| VP17 | | 3-03-0358A/D | GG | | | | | |
| VP19 | | 3-03-0362C/D | GG | | | | | |
| VP20 | | 3-03-0378A/D | GG | | | | | |
| VP21 | | 3-03-0389A/D | GG | | | | | |
| VP25 | | 3-03-0443A/D | GG | | | | | |
| VP26 | | 3-03-0455A/D | GG | | | | | |
| VP28 | | 3-03-0459A/D | GG | | | | | |
| VP30 | | 3-03-0487A/D | GG | X | 5-170 | neg | 5-175 | neg |
| VP32 | | 3-03-0497A/D | GG | | | | | |
| VP34 | | 3-03-0526A | GG | | | | | |
| VP36 | | 3-03-0528A | GG | | | | | |
| VP38 | | 3-03-0587A/D | GG | | | | | |
| VP39 | | 3-03-0589A/D | GG | | | | | |
| VP43 | | 3-03-0662A/D | GG | | | | | |
| VP47 | | no label | GG | ? | | | | |
| VP48 | | 3-03-0765A-D | GG | | | | | |
| VP50 | | 3-030817A/C | GG | X | 5-193 | neg | 5-198 | neg |
| VP51 | | 3-03-0820A/B | GG | X | 5-194 | neg | 5-199 | neg |
| VP52 | | 3-03-0834B/D | GG | | | | | |
| VP53 | | 3-03-0835B/D | GG | | | | | |

TABLE 1-continued

Detection of HXV in Prostates (Masterlist)

| | | | |
|---|---|---|---|
| VP54 | 3-03-0837C/D | GG | |
| VP58 | 3-03-0959C/D | GG | |
| VP59 | 3-03-0960C/D | GG | |
| VP60 | 3-03-0994A/B | GG | |
| VP66 | 3-03-1078A/B | GG | X |
| VP67 | 3-03-1090A/B | GG | |
| VP69 | 3-03-1105A1 | GG | |
| VP72 | 3-04-0007A/B | GG | X |
| VP75 | 3-04-0046A/B | GG | |
| VP76 | 3-04-0049A/B | GG | |
| VP80 | 3-04-0152A1 | GG | |
| VP84 | 3-04-0250A1 | GG | X |
| VP85 | 3-04-0248A/B | GG | |
| VP86 | 3-04-0256A/B | GG | X |
| VP87 | 3-04-0380A/B | GG | |
| VP91 | ? | GG | |
| VP93 | 3-04-0269A/B | GG | |
| VP95 | 3-04-0324A/B | GG | |
| VP96 | 3-04-0457A1 | GG | |
| VP98 | 3-04-0465A/B | GG | |
| VP99 | 3-04-0479A/B | GG | |

| Lab ID | RT PCR (7200F-227R) total RNA | RT PCR (7200F-227R) poly A RNA | Nested PCR (7600F-227R) template: RT PCR | Specific PCR LTR/env/pol murine type C retrovirus gen. DNA | Mouse GAPDH PCR Rdb total and polyA RNA | Nested Gag RT-PCR neg | Souther Blot of the nexted Gag RT-PCR (column O) |
|---|---|---|---|---|---|---|---|
| VP10 | pos | pos | pos | neg | | neg | pos |
| VP10 | neg | neg | neg | | | neg | neg |
| VP107 | neg | neg | neg | | | neg | neg |
| VP24 | | | pos | | | | |
| VP27 | | | neg | | | neg | neg |
| VP27 | | | pos | | neg | pos | pos |
| VP29 | | | pos | | neg | pos | pos |
| VP31 | | | neg | | neg | pos | pos |
| VP35 | | | neg | pos | neg | pos | pos |
| VP42 | | | pos | | | pos | pos |
| VP62 | | | pos | | | neg | neg |
| VP79 | | | pos | | | | |
| VP88 | | | | | | | |
| VP90 | | | | | | | |
| VP94 | | | | | | | |
| VP104 | | | | | | | |
| VP33 | | | | | | | |
| VP37 | | | | | | | |
| VP40 | | | | | | | |
| VP41 | | | | | | | |
| VP44 | | | | | | | |
| VP45 | neg | neg | neg | neg | neg | neg | neg |
| VP46 | neg | neg | neg | neg | neg | neg | neg |
| VP49 | neg | neg | neg | neg | neg | neg | neg |
| VP55 | | | | | | | |
| VP81 | | | | | | | |
| VP82 | | | | | | | |
| VP83 | | | | | | | |
| VP89 | | | | | | | |

TABLE 1-continued

Detection of HXV in Prostates (Masterlist)

| | | | | | | |
|---|---|---|---|---|---|---|
| VP92 | | | | | | |
| VP04 | | | | | | |
| VP05 | | | | | | |
| VP07 | | | | | | |
| VP08 | | | | | | |
| VP09 | | | | | | |
| VP100 | | | | | | |
| VP108 | | | | | | |
| VP11 | | | | | | |
| VP111 | | | | | | |
| VP112 | | | | | | |
| VP115 | | | | | | |
| VP14 | | | | | | |
| VP15 | | | | | | |
| VP18 | | | | | | |
| VP22 | | | | | | |
| VP23 | | | | | | |
| VP56 | | | | | | |
| VP57 | | | | | | |
| VP61 | | | | | | |
| VP63 | | | | | | |
| VP64 | | | | | | |
| VP65 | | | | | | |
| VP68 | | | | | | |
| VP70 | | neg | neg | | neg | neg |
| VP71 | | | | | | |
| VP73 | | | | | | |
| VP74 | | neg | neg | | neg | neg |
| VP77 | | neg | neg | | neg | neg |
| VP78 | | | | | | |
| VP97 | | | | | | |
| VP01 | | | | | | |
| VP02 | | | | | | |
| VP03 | | | | | | |
| VP06 | | | | | | |
| VP101 | | | | | | |
| VP102 | | | | | | |
| VP103 | | | | | | |
| VP105 | | | | | | |
| VP106 | | | | | | |
| VP109 | | | | | | |
| VP110 | | | | | | |
| VP113 | | | | | | |
| VP114 | | | | | | |
| VP116 | | | | | | |
| VP117 | | | | | | |
| VP118 | | | | | | |
| VP119 | | | | | | |
| VP12 | | | | | | |
| VP13 | | | | | | |
| VP16 | | | | | | |
| VP17 | | | | | | |
| VP19 | | | | | | |
| VP20 | | | | | | |
| VP21 | | | | | | |
| VP25 | | | | | | |
| VP26 | | | | | | |
| VP28 | | | | | | |
| VP30 | neg | neg | neg | neg | neg | neg |
| VP32 | | | | | | |
| VP34 | | | | | | |
| VP36 | | | | | | |
| VP38 | | | | | | |
| VP39 | | | | | | |
| VP43 | | | | | | |
| VP47 | | | | | | |
| VP48 | | | | | | |
| VP50 | neg | neg | neg | neg | neg | neg |
| VP51 | neg | neg | neg | neg | neg | neg |
| VP52 | | | | | | |
| VP53 | | | | | | |
| VP54 | | | | | | |
| VP58 | | | | | | |
| VP59 | | | | | | |
| VP60 | | | | | | |
| VP66 | | neg | neg | | neg | pos |
| VP67 | | | | | | |
| VP69 | | | | | | |

TABLE 1-continued

Detection of HXV in Prostates (Masterlist)

| | | | | | |
|---|---|---|---|---|---|
| VP72 | neg | neg | | neg | neg |
| VP75 | | | | | |
| VP76 | | | | | |
| VP80 | | | | | |
| VP84 | neg | neg | | neg | neg |
| VP85 | | | | | |
| VP86 | neg | neg | | pos | pos |
| VP87 | | | | | |
| VP91 | | | | | |
| VP93 | | | | | |
| VP95 | | | | | |
| VP96 | | | | | |
| VP98 | | | | | |
| VP99 | | | | | |

Legend:
MR = Murine Retrovirus

TABLE 2

Sequence of $HXV_{35}$.
>$HXV_{35}$: PCRV_complete_genome_from_RdB (Edit1, Jun. 30, 2004; Edit 2, Feb. 28, 2005)

GCGCCAGTCATCCGATAGACTGAGTCGCCCGGGTACCCGTGTTCCCAATAAAGCCTTTT

GCTGTTTGCATCCGAAGCGTGGCCTCGCTGTTCCTTGGGAGGGTCTCCTCAGAGTGATT

GACTACCCAGCTCGGGGGTCTTTCATTTGGGGGCTCGTCCGGGATTCGGAGACCCCCGC

CCAGGGACCACCGACCCACCGTCGGGAGGTAAGCCGGCCGGCGATCGTTTTGTCTTTGT

CTCTGTCTTTGTGCGTGTGTGTGTGCCGGCATCTAATCCTCGCGCCTGCGTCTGAAT

CTGTACTAGTTAGCTAACTAGATCTGTATCTGGCGGTTCCGCGGAAGAACTGACGAGTT

CGTATTCCCGGCCGCAGCCCAGGGAGACGTCCCAGCGGCCTCGGGGGCCCGTTTTGTGG

CCCATTCTGTATCAGTTAACCTACCCGAGTCGGACTCTTTGGAGTGGCTTTGTTGGGGG

ACGAGAGACAGAGACACTTCCCGCCCCCGTCTGAATTTTTGCTTTCGGTTTTACGCCGA

AACCGCGCCGCGCGTCTGATTTGTTTTGTTGTTCTTCTGTTCTTCGTTAGTTTTCTTCT

GTCTTTAAGTGTTCTCGAGATCATGGGACAGACCGTAACTACCCCTCTGAGTCTAACCT

TGCAGCACTGGGGAGATGTCCAGCGCATTGCATCCAACCAGTCTGTGGATGTCAAGAAG

AGGCGCTGGGTTACCTTCTGTTCCGCCGAATGGCCAACTTTCAATGTAGGATGGCCTCA

GGATGGTACTTTTAATTTAGGTGTTATCTCTCAGGTCAAGTCTAGAGTGTTTTGTCCTG

GTCCCCACGGACACCCGGATCAGGTCCCATATATCGTCACCTGGGAGGCACTTGCCTAT

GACCCCCCTCCGTGGGTCAAACCGTTTGTCTCTCCTAAACCCCCTCCTTTACCGACAGC

TCCCGTCCTCCCGCCCGGTCCTTCTGCGCAACCTCCGTCCCGATCTGCCCTTTACCCTG

CCCTTACCCTCTCTATAAAGTCCAAACCTCCTAAGCCCCAGGTTCTCCCTGATAGCGGC

GGACCTCTCATTGACCTTCTCACAGAGGATCCCCCGCCGTACGGAGTACAACCTTCCTC

CTCTGCCAGGGAGAACAATGAAGAAGAGGCGGCCACCACCTCCGAGGTTTCCCCCCCTT

CTCCCATGGTGTCTCGACTGCGGGGAAGGAGAGACCCTCCCGCAGCGGACTCCACCACC

TCCCAGGCATTCCCACTCCGCATGGGGGGAGATGGCCAGCTTCAGTACTGGCCGTTTTC

CTCCTCTGATTTATATAATTGGAAAAATAATAACCCTTCCTTTTCTGAAGATCCAGGTA

AATTGACGGCCTTGATTGAGTCCGTCCTCATCACCCACCAGCCCACCTGGGACGACTGT

CAGCAGTTGTTGGGGACCCTGCTGACCGGAGAAGAAAAGCAGCGGGTGCTCCTAGAGGC

TGGAAAGGCAGTCCGGGGCAATGATGGACGCCCCACTCAGTTGCCTAATGAAGTCAATG

TABLE 2-continued

| Sequence of $HXV_{35}$. >$HXV_{35}$: PCRV_complete_genome_from_RdB (Edit1, Jun. 30, 2004; Edit 2, Feb. 28, 2005) |
| --- |
| CTGCTTTTCCCCTTGAGCGCCCCGATTGGGATTACACCACTACAGAAGGTAGGAACCAC |
| CTAGTCCTCTACCGCCAGTTGCTCTTAGCGGGTCTCCAAAACGCGGGCAGGAGCCCCAC |
| CAATTTGGCCAAGGTAAAAGGGATAACCCAGGGACCTAATGAGTCTCCCTCAGCCTTTT |
| TAGAGAGACTCAAGGAGGCCTATCGCAGGTACACTCCTTATGACCCTGAGGACCCAGGG |
| CAAGAAACCAATGTGTCCATGTCATTCATCTGGCAGTCTGCCCCGGATATCGGGCGAAA |
| GTTAGAGCGGTTAGAAGATTTAAAGAGCAAGACCTTAGGAGACTTAGTGAGGGAAGCTG |
| AAAAGATCTTTAATAAGCGAGAAACCCCGGAAGAAAGAGAGGAACGTATCAGGAGAGAA |
| ATAGAGGAAAAAGAAGAACGCCGTAGGGCAGAGGATGAGCAGAGAGAGAGAGAAAGGGA |
| CCGCAGAAGACATAGAGAGATGAGCAAGCTCTTGGCCACTGTAGTTATTGGTCAGAGAC |
| AGGATAGACAGGGGGGAGAGCGGAGGAGGCCCCAACTTGATAAGGACCAATGCGCCTAC |
| TGCAAAGAAAAGGGACACTGGGCTAAGGACTGCCCAAAGAAGCCACGAGGGCCCCGAGG |
| ACCGAGGCCCCAGACCTCCCTCCTGACCTTAGGTGACTAGGGAGGTCAGGGTCAGGAGC |
| CCCCCCCTGAACCCAGGATAACCCTCAAAGTCGGGGGGCAACCCGTCACCTTCCTGGTA |
| GATACTGGGGCCCAACACTCCGTGCTGACCCAAAATCCTGGACCCCTAAGTGACAAGTC |
| TGCCTGGGTCCAAGGGGCTACTGGAGGAAAGCGGTATCGCTGGACCACGGATCGCAAAG |
| TACATCTGGCTACCGGTAAGGTCACCCACTCTTTCCTCCATGTACCAGACTGCCCCTAT |
| CCTCTGCTAGGAAGAGACTTGCTGACTAAACTAAAAGCCCAAATCCACTTCGAGGGATC |
| AGGAGCTCAGGTTGTGGGACCGATGGGACAGCCCCTGCAAGTGCTGACCCTAAACATAG |
| AAAATAAGTATCGGCTACATGAGACCTCAAAAGAGCCAGATGTTCCTCTAGGGTCCACA |
| TGGCTTTCTGATTTTCCCCAGGCCTGGGCGGAAACCGGGGGCATGGGACTGGCAGTTCG |
| CCAAGCTCCTCTGATCATACCTCTGAAGGCAACCTCTACCCCCGTGTCCATAAAACAAT |
| ACCCCATGTCACAAGAAGCCAGACTGGGGATCAAGCCCCACATACAGAGGCTGTTGGAC |
| CAGGGAATACTGGTACCCTGCCAGTCCCCCTGGAACACGCCCCTGCTACCCGTTAAGAA |
| ACCAGGGACTAATGATTATAGGCCTGTCCAGGATCTGAGAGAAGTCAACAAGCGGGTGG |
| AAGACATCCACCCCACCGTGCCCAACCCTTACAACCTCTTGAGCGGGCTCCCACCGTCC |
| CACCAGTGGTACACTGTGCTTGATTTAAAGGATGCCTTTTTCTGCCTGAGACTCCACCC |
| CACCAGTCAGCCTCTCTTCGCCTTTGAGTGGAGAGATCCAGAGATGGGAATCTCAGGAC |
| AACTGACCTGGACCAGACTCCCACAGGGTTTCAAAAACAGTCCCACCCTGTTTGATGAG |
| GCACTGCACAGAGACCTAGCAGATTTCCGGATCCAGCACCCAGACTTGATCCTGCTACA |
| GTACGTGGATGACTTACTGCTGGCCGCCACTTCTGAGCAAGACTGCCAACGAGGTACTC |
| GGGCCCTATTACAAACCCTAGGGAACCTCGGGTATCGGGCCTCGGCCAAGAAAGCCCAA |
| ATTTGCCAGAAACAGGTCAAGTATCTGGGGTATCTCCTAAAAGAGGGACAGAGATGGCT |
| GACTGAGGCCAGAAAAGAGACTGTGATGGGGCAGCCCACTCCGAAGACCCCTCGACAAC |
| TAAGGGAGTTCCTAGGGACGGCAGGCTTCTGTCGCCTCTGGATCCCTGGGTTTGCAGAA |
| ATGGCAGCCCCCTTGTACCCTCTTACCAAAACGGGGACTCTGTTTAATTGGGGCCCAGA |
| CCAGCAAAAGGCCTATCAAGAAATCAAACAGGCTCTTCTAACTGCCCCCGCCCTGGGAT |
| TGCCAGATTTGACTAAGCCCTTTGAACTCTTTGTCGACGAGAAGCAGGGCTACGCCAAA |
| GGCGTCCTAACGCAAAAACTGGGACCTTGGCGTCGGCCTGTGGCCTACCTGTCCAAAAA |

TABLE 2-continued

Sequence of HXV$_{35}$.
>HXV$_{35}$: PCRV_complete_genome_from_RdB (Edit1, Jun. 30, TABLE 2-continued

| Sequence of $HXV_{35}$.<br>>$HXV_{35}$: PCRV_complete_genome_from_RdB (Edit1, Jun. 30, 2004; Edit 2, Feb. 28, 2005) |
|---|
| AACCCGATATTGGAGATGGTTGCCGCTCTCCCGGGGGAAGAAAAAGGACAAGACTATAT |
| GATTTCTATGTTTGCCCCGGTCATACTGTATTAACAGGGTGTGGAGGGCCGAGAGAGGG |
| CTACTGTGGCAAATGGGGATGTGAGACCACTGGACAGGCATACTGGAAGCCATCATCAT |
| CATGGGACCTAATTTCCCTTAAGCGAGGAAACACTCCTAAGGGTCAGGGCCCCTGTTTT |
| GATTCCTCAGTGGGCTCCGGTAGCATCCAGGGTGCCACACCGGGGGGTCGATGCAACCC |
| CCTAGTCCTAGAATTCACTGACGCGGGTAAAAGGGCCAGCTGGGATGCCCCCAAAACAT |
| GGGGACTAAGACTGTATCGATCCACTGGGGCCGACCCGGTGACCCTGTTCTCTCTGACC |
| CGCCAGGTCCTCAATGTAGGGCCCCGCGTCCCCATTGGGCCTAATCCCGTGATCACTGA |
| ACAGCTACCCCCCTCCCAACCCGTGCAGATCATGCTCCCCAGGCCTCCTCGTCCTCCTC |
| CTTCAGGCGCGGCCTCTATGGTGCCTGGGGCTCCCCCGCCTTCTCAACAACCTGGGACG |
| GGAGACAGGCTGCTAAACCTGGTAGAAGGAGCCTACCAAGCCCTCAACCTCACCAGTCC |
| CGACAAAACCCAAGAGTGCTGGCTGTGTCTAGTATCGGGACCCCCCTACTACGAAGGGG |
| TGGCCGTCCTAGGTACTTACTCCAACCATACCTCTGCCCCGGCTAACTGCTCCGTGACC |
| TCCCAACACAAGCTGACCCTGTCCGAAGTGACCGGGCAGGGACTCTGCATAGGAGCAGT |
| TCCCAAAACCCATCAGGCCCTGTGTAATACCACCCAGAAGACGAGCGACGGGTCCTACT |
| ATTTGGCCTCTCCCGCCGGGACCATTTGGGCTTGCAGCACCGGGCTCACTCCCTGTCTA |
| TCTACTACTGTGCTTAACTTAACCACTGATTACTGTGTCCTGGTTGAACTCTGGCCAAA |
| GGTAACCTACCACTCCCCTAATTATGTTTATGGCCAGTTTGGAAAGAAAACTAAATATA |
| AAAGAGAGCCGGTGTCATTAACTCTGGCCCTGCTGTTGGGAGGACTTACTATGGGCGGC |
| ATAGCTGCAGGAGTTGGAACAGGGACTACAGCCCTAGTGGCCACCAAACAATTCGAGCA |
| GCTCCAGGCAGCCATACATACAGACCTTGGGGCCTTAGAAAAATCAGTCAGTGCCCTAG |
| AAAAGTCTCTGACCTCGTTGTCTGAGGTGGTCCTACAGAACCGGAGGGGATTAGATCTA |
| CTGTTCCTAAAAGAAGGAGGATTATGTGCTGCCCTAAAAAAAGAATGCTGTTTTTACGC |
| GGACCACACTGGCGTAGTAAGAGATAGCATGGCAAAGCTAAGAGAAAGGTTAAACCAGA |
| GACAAAAATTGTTCGAATCAGGACAAGGGTGGTTTGAGGGACTGTTTAACAGGTCCCCA |
| TGGTTCACGACCCTGATATCCACCATTATGGGCCCTCTGATAGTACTTTTATTAATCCT |
| ACTCTTCGGACCCTGTATTCTCAACCGCTTGGTCCAGTTTGTAAAAGACAGAATTTCGG |
| TAGTGCAGGCCCTGGTTCTGACCCAACAGTATCACCAACTCAAATCAATAGATCCAGAA |
| GAAGTGGAATCACGTGAATAAAAGATTTTATTCAGTTTCCAGAAAGAGGGGGGAATGAA |
| AGACCCCACCATAAGGCTTAGCACGCTAGCTACAGTAACGCCATTTTGCAAGGCATGGA |
| AAAGTACCAGAGCTGAGTTCTCAAAAGTTACAAGGAAGTTTAATTAAAGAATAAGGCTG |
| AATAACACTGGGACAGGGGCCAAACAGGATATCTGTAGTCAGGCACCTGGGCCCCGGCT |
| CAGGGCCAAGAACAGATGGTCCTCAGATAAAGCGAAACTAACAACAGTTTCTGGAAAGT |
| CCCACCTCAGTTTCAAGTTCCCCAAAAGACCGGGAAATACCCCAAGCCTTATTTAAACT |
| AACCAATCAGCTCGCTTCTCGCTTCTGTACCCGCGCTTTTTGCTCCCCAGTCCTAGCCC |
| TATAAAAAAGGGGTAAGAACTCCACACTCGGCGCGCCAGTCATCCGATAGACTGAGTCG |
| CCCGGGTACCCGTGTTCCCAATAAAGCCTTTTGCTGTTTGCAAAAA |

TABLE 3

Alignment of HXV35 and DG-75 Gag Polypeptides

Lipman-Pearson Protein Alignment
Ktuple: 2; Gap Penalty: 4; Gap Length Penalty: 12

| Seq1(1 > 536)<br>HXV35 gag | Seq2(1 > 536)<br>DG75 gag | Similarity<br>Index | Gap<br>Number | Gap<br>Length | Consensus<br>Length |
|---|---|---|---|---|---|
| (1 > 536) | (1 > 536) | 96.3 | 0 | 0 | 536 |
| (1 > 536) | (1 > 536) | 96.3 | 0 | 0 | 536 |

```
             v10       v20       v30       v40       v50       v60       v70       v80       v90      v100
    MGQTVTTPLSLTLQHWGDVQRIASNQSVDVKKRRWVTFCSAEWPTFNVGWPQDGTFNLGVISQVKSRVFCPGPHGHPDQVPYIVTWEALAYDPPPWVKPF

MGQTVTTPLSLTL:HWGDVQRIASNQSVDVKKRRWVTFCSAEWPTF:VGWPQDGTFNL::I QVKS:VF.PGPHGHPDQVPYIVTWEALAYDPPPWVKPF

MGQTVTTPLSLTLEHWGDVQRIASNQSVDVKKRRWVTFCSAEWPTFDVGWPQDGTFNLDIILQVKSKVFSPGPHGHPDQVPYIVTWEALAYDPPPWVKPF
            ^10       ^20       ^30       ^40       ^50       ^60       ^70       ^80       ^90      ^100 v110      v120      v130      v140      v150      v160      v170      v180      v190      v200
    VSPKPPPLPTAPVLPPGPSAQPPSRSALYPALTLSIKSKPPKPQVLPDSGGPLIDLLTEDPPPYGVQPSSSARENNEEEAATTSEVSPPSPMVSRLRGRR

VSPKPPPLPTAPVLPPGPSAQPPSRSALYPALT SIK:KPPKPQVLPD:GGPLIDLLTEDPPPYG.QPSSSAR.N.EEEAA:TSEVSPPSPMVSRLRGRR

VSPKPPPLPTAPVLPPGPSAQPPSRSALYPALTPSIKTKPPKPQVLPDNGGPLIDLLTEDPPPYGAQPSSSARGNDEEEAAATSEVSPPSPMVSRLRGRR
           ^110      ^120      ^130      ^140      ^150      ^160      ^170      ^180      ^190      ^200 v210      v220      v230      v240      v250      v260      v270      v280      v290      v300
    DPPAADSTTSQAFPLRMGGDGQLQYWPFSSSDLYNWKNNNPSFSEDPGKLTALIESVLITHQPTWDDCQQLLGTLLTGEEKQRVLLEAGKAVRGNDGRPT

DPPAADST:SQAFPLRMGGDGQLQYWPFSSSDLYNWKNNNPSFSEDPGKLTALIESVLITHQPTWDDCQQLLGTLLTGEEKQRVLLEA KAVRGNDGRPT

DPPAADSTSSQAFPLRMGGDGQLQYWPFSSSDLYNWKNNNPSFSEDPGKLTALIESVLITHQPTWDDCQQLLGTLLTGEEKQRVLLEARKAVRGNDGRPT
           ^210      ^220      ^230      ^240      ^250      ^260      ^270      ^280      ^290      ^300 v310      v320      v330      v340      v350      v360      v370      v380      v390      v400
    QLPNEVNAAFPLERPDWDYTTTEGRNHLVLYRQLLLAGLQNAGRSPTNLAKVKGITQGPNESPSAFLERLKEAYRRYTPYDPEDPGQETNVSMSFIWQSA

QLPNEVNAAFPLERPDWDYTTTEGRNHLVLYRQLLLAGLQNAGRSPTNLAKVKGITQGPNESPSAFLERLKEAYRRYTPYDPEDPGQETNVSMSFIWQSA

QLPNEVNAAFPLERPDWDYTTTEGRNHLVLYRQLLLAGLQNAGRSPTNLAKVKGITQGPNESPSAFLERLKEAYRRYTPYDPEDPGQETNVSMSFIWQSA
           ^310      ^320      ^330      ^340      ^350      ^360      ^370      ^380      ^390      ^400 v410      v420      v430      v440      v450      v460      v470      v480      v490      v500
    PDIGRKLERLEDLKSKTLGDLVREAEKIFNKRETPEEREERIRREIEEKEERRRAEDEQREREDRRRHREMSKLLATVVIGQRQDRQGGERRRPQLDKD

PDIGRKLERLEDLKSKTLGDLVREAEKIFNKRETPEEREERIRRE.EEKEERRRAEDEQRE:ERDR:RHREMSKLLATVV GQRQDRQGGERRRPQLDKD

PDIGRKLERLEDLKSKTLGDLVREAEKIFNKRETPEEREERIRRETEEKEERRRAEDEQREKERDRKRHREMSKLLATVVSGQRQDRQGGERRRPQLDKD
           ^410      ^420      ^430      ^440      ^450      ^460      ^470      ^480      ^490      ^500 v510      v520      v530
    QCAYCKEKGHWAKDCPKKKPRGPRGPRPQTSLLTLGD (SEQ ID NO: 3)

QCAYCKEKGHWAKDCPKKKPRGPRGPRPQTSLLTLGD (SEQ ID NO: 63)

QCAYCKEKGHWAKDCPKKKPRGPRGPRPQTSLLTLGD (SEQ ID NO: 64)
           ^510      ^520      ^530
```

TABLE 4

Alignment of HXV35 and DG-75 PRO-POL Polypeptides.

Lipman-Pearson Protein Alignment
Ktuple: 2; Gap Penalty: 4; Gap Length Penalty: 12

| Seq1(1 > 1196)<br>HXV35 pro-pol 2 2 8 05 | Seq2(1 > 1197)<br>DG75 pro-pol | Similarity<br>Index | Gap<br>Number | Gap<br>Length | Consensus<br>Length |
|---|---|---|---|---|---|
| (1 > 1196) | (2 > 1197) | 96.5 | 0 | 0 | 1196 |
| (1 > 1196) | (2 > 1197) | 96.5 | 0 | 0 | 1196 |

```
             v10       v20       v30       v40       v50       v60       v70       v80       v90      v100
    GGQGQEPPPEPRITLKVGGQPVTFLVDTGAQHSVLTQNPGPLSDKSAWVQGATGGKRYRWTTDRKVHLATGKVTHSFLHVPDCPYPLLGRDLLTKLKAQIHF

GGQGQEPPPEPRITLKVGGQPVTFLVDTGAQHSVLTQNPGPLSDKSAWVQGATGGKRYRWTTDRKVHLATGKVTHSFLHVPDCPYPLLGRDLLTKLKAQIHF

GGQGQEPPPEPRITLKVGGQPVTFLVDTGAQHSVLTQNPGPLSDKSAWVQGATGGKRYRWTTDRKVHLATGKVTHSFLHVPDCPYPLLGRDLLTKLKAQIHF
```

TABLE 4-continued

Alignment of HXV35 and DG-75 PRO-POL Polypeptides.

```
            ^10       ^20       ^30       ^40       ^50       ^60       ^70       ^80       ^90       ^100 v110      v120      v130      v140      v150      v160      v170      v180      v190      v200
     EGSGAQVVGPMGQPLQVLTLNIENKYRLHETSKEPDVPLGSTWLSDFPQAWAETGGMGLAVRQAPLIIPLKATSTPVSIKQYPMSQEARLGIKPHIQRLLD

EGSGAQVVGPMGQPLQVLTLNIE:,YRLHETS.EPDV:LGSTWLSDFPQAWAETG MGLAVRQAPLIIPLKATSTPVSIKQYPMSQEARLGIKPHIQRLLD

EGSGAQVVGPMGQPLQVLTLNIEDEYRLHETSTEPDVSLGSTWLSDFPQAWAETGGMGLAVRQAPLIIPLKATSTPVSIKQYPMSQEARLGIKPHIQRLLD
            ^110      ^120      ^130      ^140      ^150      ^160      ^170      ^180      ^190      ^200 v210      v220      v230      v240      v250      v260      v270      v280      v290      v300
     QGILVPCQSPWNTPLLPVKKPGTNDYRPVQDLREVNKRVEDIHPTVPNPYNLLSGLPPSHQWYTVLDLKDAFFCLRLHPTSQPLFAFEWRDPEMGISGQL

QGILVPCQSPWNTPLLPVKKPGTNDYRPVQDLREVNKRVEDIHPTVPNPYNLLSGLPPSHQWYTVLDLKDAFFCLRLHPTSQPLFAFEWRDPEMGISGQL

QGILVPCQSPWNTPLLPVKKPGTNDYRPVQDLREVNKRVEDIHPTVPNPYNLLSGLPPSHQWYTVLDLKDAFFCLRLHPTSQPLFAFEWRDPEMGISGQL
            ^210      ^220      ^230      ^240      ^250      ^260      ^270      ^280      ^290      ^300 v310      v320      v330      v340      v350      v360      v370      v380      v390      v400
     TWTRLPQGFKNSPTLFDEALHRDLADFRIQHPDLILLQYVDDLLLAATSEQDCQRGTRALLQTLGNLGYRASAKKAQICQKQVKYLGYLLKEGQRWLTEA

TWTRLPQGFKNSPTLFDEALHRDLADFRIQHPDLILLQYVDD:LLAATSE DCQ:GTRALL TLGNLGYRASAKKAQ:CQKQVKYLGYLLKEGQRWLTEA

TWTRLPQGFKNSPTLFDEALHRDLADFRIQHPDLILLQYVDDILLAATSELDCQQGTRALLLTLGNLGYRASAKKAQLCQKQVKYLGYLLKEGQRWLTEA
            ^310      ^320      ^330      ^340      ^350      ^360      ^370      ^380      ^390      ^400 v410      v420      v430      v440      v450      v460      v470      v480      v490      v500
     RKETVMGQPTPKTPRQLREFLGTAGFCRLWIPGFAEMAAPLYPLTKTGTLFNWGPDQQKAYQEIKQALLTAPALGLPDLTKPFELFVDEKQGYAKGVLTQ

RKETVMGQPTPKTPRQLREFLGTAGFCRLWIPGFAEMAAPLYPLTKTGTLFNWGPDQQKAYQEIKQALLTAPALGLPDLTKPFELFVDEKQGYAKGVLTQ

RKETVMGQPTPKTPRQLREFLGTAGFCRLWIPGFAEMAAPLYPLTKTGTLFNWGPDQQKAYQEIKQALLTAPALGLPDLTKPFELFVDEKQGYAKGVLTQ
            ^410      ^420      ^430      ^440      ^450      ^460      ^470      ^480      ^490      ^500 v510      v520      v530      v540      v550      v560      v570      v580      v590      v600
     KLGPWRRPVAYLSKKLDPVAAGWPPCLRMVAAIAVLTKDAGKLTMGQPLVILAPHAVEALVKQPPDRWLSNARMTHYQAMLLDTDRVQFGPVVALNPATL

KLGPWRRPVAYLSKKLDPVAA WPPCLRMVAAIAVLTKDAGKLTMGQPLVILAPHAVEALVKQPPDRWLSNARMTHYQAMLLDTDRVQFGPVVALNPATL

KLGPWRRPVAYLSKKLDPVAARWPPCLRMVAAIAVLTKDAGKLTMGQPLVILAPHAVEALVKQPPDRWLSNARMTHYQAMLLDTDRVQFGPVVALNPATL
            ^510      ^520      ^530      ^540      ^550      ^560      ^570      ^580      ^590      ^600 v610      v620      v630      v640      v650      v660      v670      v680      v690      v700
     LPLPEKEAPHDCLEILAETHGTRPDLTDQPIPDADYTWYTDGSSFLQEGQRRAGAAVTTETEVIWARALPAGTSAQRAELIALTQALKMAEGKKLNVYTD

LPLPEK.APHDCLEILAETHGTRPDLTDQPIPDAD.TWYTDGSSFLQEGQRRAGAAVTTETEVIWARALPAGTSAQRAELIALTQALKMAEGKKLNVYTD

LPLPEKGAPHDCLEILAETHGTRPDLTDQPIPDADHTWYTDGSSFLQEGQRRAGAAVTTETEVIWARALPAGTSAQRAELIALTQALKMAEGKKLNVYTD
            ^610      ^620      ^630      ^640      ^650      ^660      ^670      ^680      ^690      ^700 v710      v720      v730      v740      v750      v760      v770      v780      v790      v800
     SRYAFATAHVHGEIYRRRGLLTSEGREIKNKNEILALLKALFLPKRLSIIHCPGHQKGNSAEARGNRMADQAAREAAMKAVLETSTLLIEDSTPYTPPHF

SRYAFATAHVHGEIYRRRGLLTSEGREIKNK:EILALLKALFLPKRLSIIHCPGHQKGNSAEARGNRMADQAAREAA:::  ETSTLLIEDSTPYTP:HF

SRYAFATAHVHGEIYRRRGLLTSEGREIKNKSEILALLKALFLPKRLSIIHCPGHQKGNSAEARGNRMADQAAREAAIRTSPETSTLLIEDSTPYTPSHF
            ^710      ^720      ^730      ^740      ^750      ^760      ^770      ^780      ^790      ^800 v810      v820      v830      v840      v850      v860      v870      v880      v890      v900
     HYTETDLKRLRELGATYNQTKGYWVLQGKPVMPDQSVFELLDSLHRLTHPSPQKMKALLDDREESPYYMLNRDRTIQYVTETCTACAQVNASKAKIGAGV

HYTETDLKRLRELGATYNQ.KGYWVLQGKPVMPDQ VFELLDSLHRLTH SPQKMKALLDDREESPYYMLNRDRT:QYV:E:CTACAQVNASKAKIGAGV

HYTETDLKRLRELGATYNQIKGYWVLQGKPVMPDQFVFELLDSLHRLTLPSPQKMKALLDDREESPYYMLNRDRTLQYVAESCTACAQVNASKAKIGAGV
            ^810      ^820      ^830      ^840      ^850      ^860      ^870      ^880      ^890      ^900 v910      v920      v930      v940      v950      v960      v970      v980      v990      v1000
     RVRGHRPGTHWEVDFTEVKPGLYGYKYLLVFVDTFSGWVEAFPTKRETAKVVSKKLLEDIFPRFEMPQVLGSDNGPAFASQVSQSVADLLGIDWKLHCAY

R:RGHRPGTHWE:DFTEVKPGLYGYKYLLVFVDTFSGWVEAFPTKRETAKVV:KKLLE:IFPRF.MPQVLGSDNGPAF.SQVS:SVADLLGIDWKLHCAY

RIRGHRPGTHWEIDFTEVKPGLYGYKYLLVFVDTFSGWVEAFPTKRETAKVVTKKLLEEIFPRFGMPQVLGSDNGPAFVSQVSHSVADLLGIDWKLHCAY
            ^910      ^920      ^930      ^940      ^950      ^960      ^970      ^980      ^990      ^1000
```

TABLE 4-continued

Alignment of HXV35 and DG-75 PRO-POL Polypeptides.

```
            v1010      v1020      v1030      v1040      v1050      v1060      v1070      v1080      v1090      v1100
    KPQSSGQVERINKTIKETLTKLTLASGTKDWVLLLPLALYRARNTPGPHGLTPYEILYGAPPPLVNFHNPEMSKLTNSPSLQAHLQALQAVQQEVWKPLA

:PQSSGQVER:N:TIKETLTKLTLA:GT:DWVLLLPLALYRARNTPGPHGLTPYEILYGAPPPLVNFH:PEMSKLTNSPSLQAHLQALQAVQ:EVWKPLA

RPQSSGQVERMNRTIKETLTKLTLAAGTRDWVLLLPLALYRARNTPGPHGLTPYEILYGAPPPLVNFHDPEMSKLTNSPSLQAHLQALQAVQREVWKPLA
            ^1010      ^1020      ^1030      ^1040      ^1050      ^1060      ^1070      ^1080      ^1090      ^1100 v1110      v1120      v1130      v1140      v1150      v1160      v1170      v1180
    AAYQDQLDQPVIPHPFRVGDAVWVRRHQTKNLEPRWKGPYTVLLTTPTALKVDGISAWIHAAHVKAATTPPAGTAWKVQRSQNPL

AAYQDQLDQPVIPHPFRVGDAVWVRRHQTKNLEPRWKGPYTVLLTTPTALKVDGISAWIHAAHVKAATTPPAGTAWKVQRSQNPL

AAYQDQLDQPVIPHPFRVGDAVWVRRHQTKNLEPRWKGPYTVLLTTPTALKVDGISAWIHAAHVKAATTPPAGTAWKVQRSQNPL
            ^1110      ^1120      ^1130      ^1140      ^1150      ^1160      ^1170 v1190
    KIRLTRGAP (SEQ ID NO. 4)

KIRLTRGAP (SEQ ID NO. 65)

KIRLTRGAP (SEQ ID NO. 66)
            ^1180      ^1190
```

TABLE 5

Alignment of HXV35 and DG-75 ENV Polypeptides.

Lipman-Pearson Protein Alignment
Ktuple: 2; Gap Penalty: 4; Gap Length Penalty: 12

| Seq1(1 > 645) HXV35 env | Seq2(1 > 644) DG75 env | Similarity Index | Gap Number | Gap Length | Consensus Length |
|---|---|---|---|---|---|
| (1 > 645) | (1 > 644) | 93.8 | 1 | 1 | 645 |
| (1 > 645) | (1 > 644) | 93.8 | 1 | 1 | 645 |

```
            v10        v20        v30        v40        v50        v60        v70        v80        v90        v100
    MESPAFSKPLKDKINPWGPLIIMGILVRAGASVQRDSPHQVFNVTWKITNLMTGQTANATSLLGTMTDTFPKLYFDLCDLVGDNWDDPEPDIGDGCRSPG

ME:PAFSKPLKDKINPWGPLI:MGILVRAGASVQRDSPHQ:FNVTW::TNLMTGQTANATSLLGTMTDTFPKLYFDLCDLVGD WDDPEPDIGDGCR:PG

MEGPAFSKPLKDKINPWGPLIVMGILVRAGASVQRDSPHQIFNVTWRVTNLMTGQTANATSLLGTMTDTFPKLYFDLCDLVGDYWDDPEPDIGDGCRTPG
            ^10        ^20        ^30        ^40        ^50        ^60        ^70        ^80        ^90        ^100 v110       v120       v130       v140       v150       v160       v170       v180       v190       v200
    GRKRTRLTDFYVCPGHTVLTGCGGPREGYCGKWGCETTGQAYWKPSSSWDLISLKRGNTPKGQGPCFDSSVGSGSIQGATPGGRCNPLVLEFTDAGKRAS

GR:RTRLTDFYVCPGHTV .GCGGP EGYCGKWGCETTGQAYWKPSSSWDLISLKRGNTPK:QGPC:DSSV:SG :QGATPGGRCNPLVLEFTDAG::AS

GRKRTRLTDFYVCPGHTVPIGCGGPEGYCGKWGCETTGQAYWKPSSSWDLISLKRGNTPKDQGPCYDSSVSSG-VQGATPGGRCNPLVLEFTDAGRKAS
            ^110       ^120       ^130       ^140       ^150       ^160       ^170       ^180       ^190 v210       v220       v230       v240       v250       v260       v270       v280       v290       v300
    WDAPKTWGLRLYRSTGADPVTLFSLTRQVLNVGPRVPIGPNPVITEQLPPSQPVQIMLPRPPRPPPSGAASMVPGAPPPSQQPGTGDRLLNLVEGAYQAL

WDAPK.WGLRLYRSTGADPVT FSLTRQVLNVGPR:PIGPNPVIT:QLPPSQPVQIMLPRPP:PPPS:..SMVPGAPPPSQQPGTGDRLLNLVEGAYQAL

WDAPKVWGLRLYRSTGADPVTRFSLTRQVLNVGPRIPIGPNPVITDQLPPSQPVQIMLPRPPHPPPSDTVSMVPGAPPPSQQPGTGDRLLNLVEGAYQAL
            ^2ÔÔ       ^210       ^220       ^230       ^240       ^250       ^260       ^270       ^280       ^290 v310       v320       v330       v340       v350       v360       v370       v380       v390       v400
    NLTSPDKTQECWLCLVSGPPYYEGVAVLGTYSNHTSAPANCSVTSQHKLTLSEVTGQGLCIGAVPKTHQALCNTTQKTSDGSYYLASPAGTIWACSTGLT

NLTSPDKTQECWLCLVSGPPYYEGVAVLGTYSNHTSAPANCSV:SQHKLTLSEVTGQGLC:GAVPKTHQALCNTTQKTSDGSYYLA:PAGTIWAC:TGLT

NLTSPDKTQECWLCLVSGPPYYEGVAVLGTYSNHTSAPANCSVASQHKLTLSEVTGQGLCVGAVPKTHQALCNTTQKTSDGSYYLAAPAGTIWACNTGLT
            ^3ÔÔ       ^310       ^320       ^330       ^340       ^350       ^360       ^370       ^380       ^390
```

TABLE 5-continued

Alignment of HXV35 and DG-75 ENV Polypeptides.

```
         v410      v420      v430      v440      v450      v460      v470      v480      v490      v500
PCLSTTVLNLTTDYCVLVELWPKVTYHSPNYVYGQFGKKTKYKREPVSLTLALLLGGLTMGGIAAGVGTGTTALVATKQFEQLQAAIHTDLGALEKSVSA

PCLSTTVLNLTTDYCVLVELWPKVTYHSP.YVYGQF.:KTKYKREPVSLTLALLLGGLTMGGIAAGVGTGTTALVATKQFEQLQAAI .LGALEKSVSA

PCLSTTVLNLTTDYCVLVELWPKVTYHSPGYVYGQFERKTKYKREPVSLTLALLLGGLTMGGIAAGVGTGTTALVATKQFEQLQAAILQTLGALEKSVSA
^400      ^410      ^420      ^430      ^440      ^450      ^460      ^470      ^480      ^490 v510      v520      v530      v540      v550      v560      v570      v580      v590      v600
LEKSLTSLSEVVLQNRRGLDLLFLKEGGLCAALKKECCFYADHTGVVRDSMAKLRERLNQRQKLFESGQGWFEGLFNRSPWFTTLISTIMGPLIVLLLIL

LEKSLTSLSEVVLQNRRGLDLLFLKEGGLCAALK.ECCFYADHTGVVRDSMAKLRERLNQRQKLFESGQGWFEGLFNRSPWFTTLISTIMGPLIVLLLIL

LEKSLTSLSEVVLQNRRGLDLLFLKEGGLCAALKEECCFYADHTGVVRDSMAKLRERLNQRQKLFESGQGWFEGLFNRSPWFTTLISTIMGPLIVLLLIL
^500      ^510      ^520      ^530      ^540      ^550      ^560      ^570      ^580      ^590 v610      v620      v630      v640
LFGPCILNRLVQFVKDRISVVQALVLTQQYHQLKSIDPEEVESRE (SEQ ID NO. 5)

LFGPCILNRLVQFVK:RISVVQALVLTQQYHQLKSIDPE.VESRE (SEQ ID NO. 67)

LFGPCILNRLVQFVKGRISVVQALVLTQQYHQLKSIDPEAVESRE (SEQ ID NO. 68)
^600      ^610      ^620      ^630      ^640
```

TABLE 6

Primer-Binding Sites in HXV35 and DG-75

HXV35 PBS:        T G G G G G C T C G T C C G G G A T  (SEQ ID NO. 69)
proline tRNA DG-75 PBS (1):    T G G A G G T C C C A C C G A G A T  (SEQ ID NO. 70)
threonine tRNA

DG-75 PBS (2):    T G G A G G C C C C A G C G A G A T  (SEQ ID NO. 71)

TABLE 7

Variable Regions A and B in the SU proteins of different gammaretroviruses

| Variable Region A: | |
|---|---|
| HXV35 (xenotropic) | DnWDDpepdigd (SEQ ID NO. 72)........GCrTPggRrR (SEQ ID NO. 73) |
| DG-75 (xenotropic) | DyWDDpepdigd (SEQ ID NO. 74)........GCrTPggRrR (SEQ ID NO. 75) |
| MCF247 (polytropic) | DdWDEtgl (SEQ ID NO. 76)............GCrTPggRkR (SEQ ID NO. 77) |
| MKVENVA MLV (amphotropic) | EeWDPsdqepyvgy (SEQ ID NO. 78)......GCrTPggRqR (SEQ ID NO. 79) |
| M-MLV (ecotropic) | SyWGLeyqspfssppgppccsggsspgcsrdceepltsltpRCnTAwnRlK (SEQ ID NO. 80) |
| Variable Region B: | |
| HXV35 (xenotropic) | trlyd(SEQ ID NO. 81)[ . . . ]FYVCPGhtvltG (SEQ ID NO. 82) |
| DG-75 (xenotropic) | trlyd(SEQ ID NO. 83)[ . . . ]FYVCPGhtvpiG (SEQ ID NO. 84) |
| MCF247 (polytropic) | artfd(SEQ ID NO. 85)[ . . . ]FYVCPGhtvptG (SEQ ID NO. 86) |
| MKVENVA MLV (amphotropic) | trtfd(SEQ ID NO. 87)[ . . . ]FYVCPGhtvskG (SEQ ID NO. 88) |
| M-MLV (ecotropic) | ldgtthksnegFYVCPGphrprEsks (SEQ ID NO. 89) |

TABLE 8

Alignment of partial sequence of LNCap derived virus.

Sequence from LNCap RNA RTPCR product. (7084-7750bp)

AAAAGAGAGCCCGGTGTCATTAACTCTGGCCCTGTCTGTTGGGAGGACTTACTATGGGCGGCATAGCTCCAGGAGTTGGAACAGGGACTACAGCCCTAGTGGC

ACCAAACAATTCGAGCAGCTCCAGGCAGCCTACATACAGACCTTGGGGCCTTAGAAAAAATCAGTCAGTGCCCTAGAAAAGTCTCTGACCTCGTTGTCTGAGG

TGGTCCTACAGAACCGGAGGGGATTAGATCTACTGTTCCTAAAAGAAGGAGGATTATGTGCTGCCCTAAAAGAAAGAATGCTGTTTTTACGCGGACCACACTG

GCGTAGTAAGAGATAGCATGGCAAAGCTAAGAGAAAGGTTAAACCAGAGACAAAAATTGTTCGAATCAGGACAAGGGTGGTTTGAGGGACTGTTTAACAGGTC

CCCATGGTTCACGACCCTGATATCCACCACCATTATGGGCCCTCTGATAGTACTTTTATTAATCCTACTTTTCGGACCCTGTATTCTCAACCGCTTGGTCCAG

TTTGTAAAAGACACAGAATTTCGGTAGTGCAGGCCCTGGTTCTGACCCAGCAGTATCACCAACTCAAATCAATAGATCCAGAAGAAGTGGAATCACGTGAATA

AAAGATTTTATTCAGTTTCCAGAAAGAGGGGGGAATGAAAGACCCCCCCATAAGGC (SEQ ID NO. 6)

Lipman-Pearson Protein Alignment
Ktuple: 2; Gap Penalty: 4; Gap Length Penalty: 12

| Seq1(1 > 127) LNCAP env seq | Seq2(1 > 645) HXV35 env | Similarity Index | Gap Number | Gap Length | Consensus Length |
|---|---|---|---|---|---|
| (2 > 123) | (496 > 616) | 97.6 | 1 | 1 | 122 |
| (2 > 123) | (496 > 616) | 97.6 | 1 | 1 | 122 |

```
         v10       v20       v30       v40       v50       v60       v70       v80
KSVSALEKSLTSLSEVVLQNRRGLDLLFLKEGGLCAALKEECCFYADHTGVVRDSMAKLRERLNQRQKLFESGQGWFEGLFNRSPWFTTL

KSVSALEKSLTSLSEVVLQNRRGLDLLFLKEGGLCAALK.ECCFYADHTGVVRDSMAKLRERLNQRQKLFESGQGWFEGLFNRSPWFTTL

KSVSALEKSLTSLSEVVLQNRRGLDLLFLKEGGLCAALKKECCFYADHTGVVRDSMAKLRERLNQRQKLFESGQGWPEGLFNRSPWFTTL
         ^500      ^510      ^520      ^530      ^540      ^550      ^560      ^570 v90       v100      v110      v120
ISTTIMGPLIVLLLILLFGPCILNRLVQFVKD (SEQ ID NO. 90)

IST IMGPLIVLLLILLFGPCILNRLVQFVKD (SEQ ID NO. 91)

IST-IMGPLIVLLLILLFGPCILNRLVQFVKD (SEQ ID NO. 92)
         ^580      ^590      ^600      ^610
```

Lipman-Pearson Protein Alignment
Ktuple: 2; Gap Penalty: 4; Gap Length Penalty: 12

| Seq1(1 > 127) LNCAP env seq | Seq2(1 > 644) DG-75 env | Similarity Index | Gap Number | Gap Length | Consensus Length |
|---|---|---|---|---|---|
| (2 > 123) | (495 > 615) | 97.6 | 1 | 1 | 122 |
| (2 > 123) | (495 > 615) | 97.6 | 1 | 1 | 122 |

```
         v10       v20       v30       v40       v50       v60       v70       v60       v90
KSVSALEKSLTSLSEVVLQNRRGLDLLPLKEGGLCAALKEECCFYADHTGVVRDSMAXLRERLNQRQKLFESGQGWFEGLFNRSPWFTTLIST

KSVSALEKSLTSLSEVVLQNRRGLDLLPLKEGGLCAALKEECCFYADHTGVVRDSMAKLRERLNQRQKLFESGQGWFEGLFNRSPWFTTLIST

KSVSALEKSLTSLSEVVLQNRRGLDLLFLKEGGLCAALKEECCFYADHTGVVRDSMAKLRERLNQRQKLFESGQGWFEGLFNRSPWFTTLIST
         ^500      ^510      ^520      ^530      ^540      ^550      ^560      ^570      ^580 v100      v110      v120
TIMGPLIVLLLILLFGPCILNRLVQFVXD (SEQ ID NO. 90)

IMGPLIVLLLILLFGPCILNRLVQFVK: (SEQ ID NO. 93)

-IMGPLIVLLLILLFGPCILNRLVQFVKG (SEQ ID NO. 94)
         ^590      ^600      ^610
```

TABLE 9

Presence of HXV in prostates as determined by RT-PCR and FISH.

| VP# | RNL genotype | HXV by RT-PCR | FISH (+) cells | Cells counted | % FISH (+) cells | HXV by FISH |
|---|---|---|---|---|---|---|
| VP 29 | AA | yes | 7 | 659 | 1.062 | ++ |
| VP 42 | AA | yes | 6 | 530 | 1.132 | ++ |
| VP 62 | AA | yes | 10 | 904 | 1.106 | ++ |
| VP 88 | AA | yes | 5 | 408 | 1.225 | ++ |
| VP 31 | AA | no | 6 | 526 | 1.141 | ++ |
| VP 79 | AA | yes | 2 | 464 | 0.431 | +/− |

TABLE 9-continued

Presence of HXV in prostates as determined by RT-PCR and FISH.

| VP# | RNL genotype | HXV by RT-PCR | FISH (+) cells | Cells counted | % FISH (+) cells | HXV by FISH |
|---|---|---|---|---|---|---|
| VP 10 | AA | yes | 1 | 872 | 0.115 | − |
| VP 35 | AA | yes | 1 | 849 | 0.118 | − |
| VP 90 | AA | yes | 1 | 843 | 0.119 | − |
| VP 27 | AA | no | 0 | 762 | 0.000 | − |
| VP 45 | AG | no | 0 | 987 | 0.000 | − |
| VP 46 | AG | no | 0 | 794 | 0.000 | − |
| VP 30 | GG | no | 1 | 661 | 0.151 | − |
| VP 50 | GG | no | 1 | 787 | 0.127 | − |
| VP 51 | GG | no | 0 | 842 | 0.000 | − |

<1/500 = −;
1-2/500 = +/−;
3-4/500 +;
5-6/500 ++

TABLE 10

XMRV screening by gag nested RT-PCR.

| | Genotype[a] | | | |
|---|---|---|---|---|
| | QQ | RQ | RR | Total |
| PCR+ | 8 | 0 | 1 | 9 |
| PCR− | 12 | 14 | 51 | 77 |
| Total | 20 | 14 | 52 | 86 |

[a]RNASEL genotypes are as follows: QQ-homozygous R462Q variant; RQ-heterozygous; RR-homozygous wild-type.

TABLE 11

PCR primers used for sequencing of XMRV genomes.

| Primer | Sequence | Fragment size (bp) | XMRV nucleotide positions |
|---|---|---|---|
| 1F | 5'-GCGCCAGTCATCCGATAGACT(SEQ ID NO: 95) | 642 | 1-642 |
| NA3-136R | 5'-CCCAGTGCTGCAAGGTTAGA(SEQ ID NO: 96) | | |
| 550F | 5'-CGCCGAAACCGCGCCGCGCGT(SEQ ID NO: 97) | 968 | 526-1494 |
| 1500R | 5'-TCGTCGCCCCGGACTGCCTTTCTG(SEQ ID NO: 98) | | |
| 1470F | 5'-GACAGGAGAAGAAAAGCAGCG(SEQ ID NO: 99) | 1280 | 1440-2720 |
| 2730R | 5'-GCTTGGCGAACTGCCAGTCCC(SEQ ID NO: 100) | | |
| 2670F | 5'-AGCCGGATGTTTCTCTAGGGT(SEQ ID NO: 101) | 1228 | 2631-3859 |
| 3870R | 5'-GCTTGCCTGCATCTTTTGTC(SEQ ID NO: 102) | | |
| 3810F | 5'-AGACCCAGTGGCAGCCGGGT(SEQ ID NO: 103) | 1400 | 3780-5180 |
| 5190R | 5'-TGACTTACCTGGGAGACGAAG(SEQ ID NO: 104) | | |
| 5100F | 5'-AACTGCCAAGGTTGTGACCAA(SEQ ID NO: 105) | 748 | 5071-5819 |
| 5842R | 5'-AACTATTGGGGGCCCCACGGGTTA(SEQ ID NO: 106) | | |
| NA7-F | 5'-CATGGAAAGTCCAGCGTTCT(SEQ ID NO: 107) | 1448 | 5753-7201 |
| C9-R | 5'-AGCTGCTCGAATTGTTTGGT(SEQ ID NO. 108) | | |
| 7200F | 5'-CTAGTGGCCACCAAACAATTC(SEQ ID NO: 40) | 997 | 7175-8172 |
| K1-R | 5'-AAGGCTTTATTGGGAACACG(SEQ ID NO: 109) | | |
| 7600F | 5'-CGCTTGGTCCAGTTTGTAAAA(SEQ ID NO: 38) | 411 | 7578-7989 |
| 227R | 5'-TGGGGAACTTGAAACTGAGG(SEQ ID NO: 39) | | |
| 100F | 5'-AGGGGCCAAACAGGATAACT(SEQ ID NO: 110) | 127 | 7862-7989 |
| 227R | 5'-TGGGGAACTTGAAACTGAGG(SEQ ID NO: 111) | | |
| B7-F | 5'-TCTGGAAAGTCCCACCTCAG(SEQ ID NO: 112) | 216 | 7956-8172 |
| K1-R | 5'-AAGGCTTTATTGGGAACACG(SEQ ID NO: 109) | | |

TABLE 12

Computational viral species predictions using E-Predict for the Virochip microarrays shown in FIGS. 22A-22B.

| Sample | Array ID | Top prediction (p < 0.05)[a] | NCBI Taxonomy ID | p-value |
|---|---|---|---|---|
| VP10 | MegaViroP7-244 | NA | | |
| VP27 | MegaViroP7-245 | NA | | |
| VP29 | MegaViroP5-174 | Spleen focus-forming virus | 11819 | 1.3E−05 |
| VP31 | MegaViroP5-176 | NA | | |

TABLE 12-continued

Computational viral species predictions using E-Predict
for the Virochip microarrays shown in FIGS. 22A-22B.

| Sample | Array ID | Top prediction (p < 0.05)[a] | NCBI Taxonomy ID | p-value |
|---|---|---|---|---|
| VP35 | MegaViroP5-177 | Spleen focus-forming virus | 11819 | 1.0E−05 |
| VP42 | MegaViroP5-178 | Murine osteosarcoma virus | 11830 | 1.5E−05 |
| VP62 | MegaViroP8-037 | Spleen focus-forming virus | 11819 | 2.0E−05 |
| VP79 | MegaViroP8-030 | Murine type C retrovirus | 44561 | 2.9E−03 |
| VP88 | MegaViroP8-031 | Spleen focus-forming virus | 11819 | 1.4E−05 |
| VP90 | MegaViroP8-032 | Spleen focus-forming virus | 11819 | 2.4E−04 |
| VP107 | MegaViroP7-246 | NA | | |
| VP45 | MegaViroP5-195 | NA | | |
| VP46 | MegaViroP5-196 | NA | | |
| VP49 | MegaViroP5-197 | NA | | |
| VP30 | MegaViroP5-175 | NA | | |
| VP50 | MegaViroP10-128 | NA | | |
| VP51 | MegaViroP5-199 | NA | | |
| VP66 | MegaViroP8-035 | NA | | |
| VP86 | MegaViroP8-036 | Spleen focus-forming virus | 11819 | 8.2E−04 |
| HeLa | MegaViroP5-179 | Human papillomavirus type 18 | 10582 | 1.0E−06 |

[a]Microarrays were analyzed using E-Predict as described previously (Urisman, A., et al. (2005), Genome Biol 6: R78).

TABLE 13

Frequency of XMRV infected prostatic cells determined by FISH.

| Patient | RNASEL Amino Acid Residue 462[a] | Total # Cells Counted[b] | FISH/XMRV Positive Cells (%) | XMRV FISH[c] | XMRV gag RT-PCR[d] |
|---|---|---|---|---|---|
| VP 88 | QQ | 408 | 5 | ++ | + |
| VP 31 | QQ | 526 | 6 | ++ | − |
| VP 42 | QQ | 530 | 6 | ++ | + |
| VP 62 | QQ | 904 | 10 | ++ | + |
| VP 29 | QQ | 659 | 7 | ++ | + |
| VP 79 | QQ | 464 | 2 | + | + |
| VP 10 | QQ | 872 | 1 | +/− | − |
| VP 35 | QQ | 849 | 1 | +/− | + |
| VP 90 | QQ | 843 | 1 | +/− | + |
| VP 45 | RQ | 987 | 0 | − | − |
| VP 46 | RQ | 794 | 0 | − | − |
| VP 30 | RR | 661 | 1 | +/− | − |
| VP 50 | RR | 787 | 1 | +/− | − |
| VP 51 | RR | 842 | 0 | − | − |

[a]SNP nt1385 "A" results in glutamine (Q) at amino acid 462,
[b]and SNP nt1385 "G" correspond to an arginine (R) at residue 462; includes all types of prostatic cells;
[c]+/− = 0.1-0.2% 1 + = 02-1%; ++ = >1%;
[d]see Urisman, A., et al., (2005), PLOS Pathogens.

All of the references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated virus comprising a nucleic acid sequence having at least 94% identity to SEQ ID No: 1 or a complement thereof.

2. The isolated virus of claim 1 wherein the nucleic acid sequence comprises SEQ ID No: 1 or a complement thereof.

3. A vector comprising the nucleic acid sequence of claim 1.

4. An isolated cell comprising the vector of claim 3.

5. A method of producing Xenotropic Murine Leukemia Virus Related Virus (XMRV) comprising maintaining the cell of claim 3 under conditions in which XMRV is produced.

6. The isolated virus of claim 5 wherein the nucleic acid sequence comprises the nucleic acid sequence of deposited virus A.T.C.C. No. PTA-6650 or a complement thereof.

* * * * *

UNITED STATES PATENT AND TRADEMARK OFFICE
CERTIFICATE OF CORRECTION

| | | |
|---|---|---|
| PATENT NO. | : 8,263,085 B2 | |
| APPLICATION NO. | : 11/903756 | |
| DATED | : September 11, 2012 | |
| INVENTOR(S) | : Robert H. Silverman et al. | |

It is certified that error appears in the above-identified patent and that said Letters Patent is hereby corrected as shown below:

In Claim 6, column 198, line 39, please delete "claim 5" and insert -- claim 1 --

Signed and Sealed this
Twenty-seventh Day of November, 2012

David J. Kappos
*Director of the United States Patent and Trademark Office*

SEQUENCE LISTING

<160> NUMBER OF SEQ ID NOS: 113

<210> SEQ ID NO 1
<211> LENGTH: 8188
<212> TYPE: DNA
<213> ORGANISM: Unknown
<220> FEATURE:
<223> OTHER INFORMATION: HXV35 genomic sequence

<400> SEQUENCE: 1

```
gcgccagtca tccgatagac tgagtcgccc gggtacccgt gttcccaata aagccttttg     60
ctgtttgcat ccgaagcgtg gcctcgctgt tccttgggag ggtctcctca gagtgattga    120
ctacccagct cgggggtctt tcatttgggg gctcgtccgg gattcggaga cccccgccca    180
gggaccaccg acccaccgtc gggaggtaag ccggccggcg atcgttttgt ctttgtctct    240
```

```
gtctttgtgc gtgtgtgtgt gtgccggcat ctaatcctcg cgcctgcgtc tgaatctgta    300
ctagttagct aactagatct gtatctggcg gttccgcgga agaactgacg agttcgtatt    360
cccggccgca gcccagggag acgtcccagc ggcctcgggg gcccgttttg tggcccattc    420
tgtatcagtt aacctacccg agtcggactc tttggagtgg ctttgttggg ggacgagaga    480
cagagacact tcccgccccc gtctgaattt ttgctttcgg ttttacgccg aaaccgcgcc    540
gcgcgtctga tttgttttgt tgttcttctg ttcttcgtta gttttcttct gtctttaagt    600
gttctcgaga tcatgggaca gaccgtaact accccctctga gtctaacctt gcagcactgg    660
ggagatgtcc agcgcattgc atccaaccag tctgtggatg tcaagaagag cgctggggtt    720
accttctgtt ccgccgaatg gccaactttc aatgtaggat ggcctcagga tggtactttt    780
aatttaggtg ttatctctca ggtcaagtct agagtgtttt gtcctggtcc ccacggacac    840
ccggatcagg tcccatatat cgtcacctgg gaggcacttg cctatgaccc ccctccgtgg    900
gtcaaaccgt ttgtctctcc taaaccccct cctttaccga cagctcccgt cctcccgccc    960
ggtccttctg cgcaacctcc gtcccgatct gccctttacc ctgcccttac cctctctata   1020
aagtccaaac ctcctaagcc ccaggttctc cctgatagcg gcggacctct cattgacctt   1080
ctcacagagg atccccgcc gtacggagta caaccttcct cctctgccag ggagaacaat   1140
gaagaagagg cggccaccac ctccgaggtt tcccccccttt ctcccatggt gtctcgactg   1200
cggggaagga gagaccctcc cgcagcggac tccaccacct cccaggcatt cccactccgc   1260 atgggggggag atggccagct tcagtactgg ccgttttcct cctctgattt atataattgg   1320
aaaaataata acccttcctt ttctgaagat ccaggtaaat tgacggcctt gattgagtcc   1380
gtcctcatca cccaccagcc cacctgggac gactgtcagc agttgttggg gaccctgctg   1440
accggagaag aaaagcagcg ggtgctccta gaggctggaa aggcagtccg gggcaatgat   1500
ggacgcccca ctcagttgcc taatgaagtc aatgctgctt ttccccttga gcgccccgat   1560
tgggattaca ccactacaga aggtaggaac cacctagtcc tctaccgcca gttgctctta   1620
gcgggtctcc aaaacgcggg caggagcccc accaatttgg ccaaggtaaa agggataacc   1680
cagggaccta atgagtctcc ctcagccttt ttagagagac tcaaggaggc ctatcgcagg   1740
tacactcctt atgaccctga ggacccaggg caagaaacca atgtgtccat gtcattcatc   1800
tggcagtctg ccccggatat cgggcgaaag ttagagcggt tagaagattt aaagagcaag   1860
accttaggag acttagtgag ggaagctgaa aagatcttta ataagcgaga accccggaa    1920 gaaagagagg aacgtatcag gagagaaata gaggaaaaag aagaacgccg tagggcagag   1980
gatgagcaga gagagagaga aagggaccgc agaagacata gagagatgag caagctcttg   2040
gccactgtag ttattggtca gagacaggat agacaggggg gagagcggag gaggccccaa   2100
cttgataagg accaatgcgc ctactgcaaa gaaaagggac actgggctaa ggactgccca   2160
aagaagccac gagggccccg aggaccgagg ccccagacct ccctcctgac cttaggtgac   2220
tagggaggtc agggtcagga gccccccccct gaacccagga taaccctcaa agtcgggggg   2280
caacccgtca ccttcctggt agatactggg gcccaacact ccgtgctgac ccaaaatcct   2340 ggaccctaa gtgacaagtc tgcctgggtc caaggggcta ctggaggaaa gcggtatcgc   2400
tggaccacgg atcgcaaagt acatctggct accggtaagg tcacccactc tttcctccat   2460
gtaccagact gcccctatcc tctgctagga agagacttgc tgactaaact aaaagcccaa   2520
atccacttcg agggatcagg agctcaggtt gtgggaccga tgggacagcc cctgcaagtg   2580
ctgaccctaa acatagaaaa taagtatcgg ctacatgaga cctcaaaaga gccagatgtt   2640
```

```
cctctagggt ccacatggct ttctgatttt ccccaggcct gggcggaaac cggggggcatg    2700 ggactggcag ttcgccaagc tcctctgatc atacctctga aggcaacctc taccccgtg     2760 tccataaaac aatacccat gtcacaagaa gccagactgg ggatcaagcc ccacatacag     2820
aggctgttgg accagggaat actggtaccc tgccagtccc cctggaacac gcccctgcta    2880
cccgttaaga aaccagggac taatgattat aggcctgtcc aggatctgag agaagtcaac    2940
aagcgggtga agacatcca ccccaccgtg cccaacccett acaacctctt gagcgggctc    3000
ccaccgtccc accagtggta cactgtgctt gatttaaagg atgcctttt ctgcctgaga     3060 ctccaccca ccagtcagcc tctcttcgcc tttgagtgga gagatccaga gatgggaatc     3120
tcaggacaac tgacctggac cagactccca cagggtttca aaaacagtcc caccctgttt    3180
gatgaggcac tgcacagaga cctagcagat ttccggatcc agcacccaga cttgatcctg    3240
ctacagtacg tggatgactt actgctggcc gccacttctg agcaagactg ccaacgaggt    3300
actcgggccc tattacaaac cctagggaac ctcgggtatc gggcctcggc caagaaagcc    3360
caaatttgcc agaaacaggt caagtatctg gggtatctcc taaaagaggg acagagatgg    3420
ctgactgagg ccagaaaaga gactgtgatg gggcagccca ctccgaagac ccctcgacaa    3480
ctaagggagt tcctagggac ggcaggcttc tgtcgcctct ggatccctgg gtttgcagaa    3540
atggcagccc ccttgtaccc tcttaccaaa acggggactc tgtttaattg gggcccagac    3600
cagcaaaagg cctatcaaga aatcaaacag gctcttctaa ctgcccccgc cctgggattg    3660
ccagatttga ctaagccctt tgaactcttt gtcgacgaga agcagggcta cgccaaaggc    3720
gtcctaacgc aaaaactggg accttggcgt cggcctgtgg cctacctgtc caaaaagcta    3780
gacccagtgg cagctgggtg gccccccttgc ctacggatgg tagcagccat tgccgttctg    3840
acaaaggatg caggcaagct aactatggga cagccgctag tcattctggc cccccatgcg    3900
gtagaagcac tggtcaaaca accccctgac cgttggctat ccaatgcccg catgacccac    3960
tatcaggcaa tgctcctgga tacagaccgg gttcagttcg gaccggtggt ggccctcaac    4020
ccggccaccc tgctcccct accggaaaag gaagccccc atgactgcct cgagatcttg     4080
gctgagacgc acggaaccag accggacctc acggaccagc ccatcccaga cgctgattac    4140
acttggtaca cagatggaag cagcttccta caagaaggac aacggagagc tggagcagcg    4200
gtgactactg agaccgaggt aatctgggcg agggctctgc cggctggaac atccgcccaa    4260
cgagccgaac tgatagcact cacccaagcc ttaaagatgg cagaaggtaa gaagctaaat    4320
gtttacactg atagccgcta tgccttcgcc acggcccatg tccatggaga aatatatagg    4380
aggcgagggt tgctgacctc agaaggcaga gaaattaaaa acaagaacga gatcttggcc    4440
ttgctaaaag ctctcttct gcccaaacga cttagtataa ttcactgtcc aggacatcaa    4500
aaaggaaaca gtgctgaggc cagaggcaac cgtatggcag atcaagcagc ccgagaggca    4560
gccatgaagg cagttctaga aacctctaca ctcctcatag aggactcaac cccgtatacg    4620 cctcccatt tccattacac cgaaacagat ctcaaaagac tacgggaact gggagccacc    4680
tacaatcaga caaaaggata ttgggtccta caaggcaaac ctgtgatgcc cgatcagtcc    4740
gtgtttgaac tgttagactc cctacacaga ctcacccatc cgagccctca aagatgaag     4800 gcactcctcg acagagaaga aagccccctac tacatgttaa accgggacag aactatccag    4860
tatgtgactg agacctgcac cgcctgtgcc caagtaaatg ccagcaaagc caaaattggg    4920
gcaggggtgc gagtacgcgg acatcggcca ggcacccatt gggaagttga tttcacggaa    4980
gtaaagccag gactgtatgg gtacaagtac ctcctagtgt ttgtagacac cttctctggc    5040
```

```
tgggtagagg cattcccgac caagcgggaa actgccaagg tcgtgtccaa aaagctgtta   5100
gaagacattt ttccgagatt tgaaatgccg caggtattgg gatctgataa cgggcctgcc   5160
ttcgcctccc aggtaagtca gtcagtggcc gatttactgg gaatcgattg gaagttacat   5220
tgtgcttata aacccagag ttcaggacag gtagaaagaa taaataaaac aattaaggag    5280
actttaacca aattaacgct tgcatctggc actaaagact gggtactcct actccccttta  5340 gccctctacc gagcccggaa tactccgggc ccccacggac tgactccgta tgaaattctg   5400 tatgggcac ccccgcccct tgtcaattt cataatcctg aaatgtcaaa gttaactaat     5460
agtccctctc tccaagctca cttacaggcc tccaagcag tacaacaaga ggtctggaag    5520
ccgctggccg ctgcttatca ggaccagcta gatcagccag tgataccaca ccccttccgt   5580
gtcggtgacg ccgtgtgggt acgccggcac cagactaaga acttagaacc tcgctggaaa   5640
ggaccctaca ccgtcctgct gacaaccccc accgctctca agtagacgg catctctgcg    5700 tggatacacg ccgctcacgt aaaggcgcg acaactcctc cggccggaac agcatggaaa    5760
gtccagcgtt ctcaaaaccc cttaaagata agattaaccc gtggggcccc ctgataatta   5820 tgggatctt ggtgagggca ggagcctcag tacaacgtga cagccctcac caggtctttta  5880 atgtcacttg gaaaattacc aacctaatga caggacaaac agctaatgct acctccctcc   5940
tggggacgat gacagacact ttccctaaac tatattttga cttgtgtgat ttagttggag   6000
acaactggga tgacccggaa cccgatattg gagatggttg ccgctctccc ggggaagaa    6060 aaaggacaag actatatgat ttctatgttt gccccggtca tactgtatta acaggtgtg   6120 gagggccgag agagggctac tgtggcaaat ggggatgtga gaccactgga caggcatact   6180
ggaagccatc atcatcatgg gacctaattt cccttaagcg aggaaacact cctaagggtc   6240
agggcccctg ttttgattcc tcagtgggct ccggtagcat ccagggtgcc acaccgggg    6300 gtcgatgcaa ccccctagtc ctagaattca ctgacgcggg taaaagggcc agctgggatg   6360 ccccccaaaac atgggggacta agactgtatc gatccactgg ggccgacccg gtgaccctgt 6420
tctctctgac ccgccaggtc ctcaatgtag ggccccgcgt ccccattggg cctaatcccg   6480
tgatcactga acagctaccc ccctcccaac ccgtgcagat catgctcccc aggcctcctc   6540
gtcctcctcc ttcaggcgcg gcctctatgg tgcctggggc tccccgcct tctcaacaac    6600 ctgggacggg agacaggctg ctaaacctgg tagaaggagc ctaccaagcc ctcaacctca   6660
ccagtcccga caaaacccaa gagtgctggc tgtgtctagt atcgggaccc ccctactacg   6720
aaggggtggc cgtcctaggt acttactcca accataccctc tgccccggct aactgctccg   6780
tgacctccca acacaagctg accctgtccg aagtgaccgg gcagggactc tgcataggag   6840
cagttcccaa aacccatcag gccctgtgta ataccacca gaagacgagc gacgggtcct    6900
actatttggc ctctcccgcc gggaccattt gggcttgcag caccgggctc actccctgtc   6960
tatctactac tgtgcttaac ttaaccactg attactgtgt cctggttgaa ctctggccaa   7020
aggtaaccta ccactccct aattatgttt atggccagtt tggaaagaaa actaaatata    7080
aaagagagcc ggtgtcatta actctggccc tgctgttggg aggacttact atgggcggca   7140
tagctgcagg agttggaaca gggactacag ccctagtggc caccaaacaa ttcgagcagc   7200
tccaggcagc catacataca gaccttgggg ccttagaaaa atcagtcagt gccctagaaa   7260
agtctctgac ctcgttgtct gaggtggtcc tacagaaccg gagggattaa gatctactgt   7320
tcctaaaaga aggaggatta tgtgctgccc taaaaaaaga atgctgtttt tacgcggacc   7380
acactggcgt agtaagagat agcatggcaa agctaagaga aaggttaaac cagagacaaa   7440
```

-continued

```
aattgttcga atcaggacaa gggtggtttg agggactgtt taacaggtcc ccatggttca    7500
cgaccctgat atccaccatt atgggccctc tgatagtact tttattaatc ctactcttcg    7560
gaccctgtat tctcaaccgc ttggtccagt ttgtaaaaga cagaatttcg gtagtgcagg    7620
ccctggttct gacccaacag tatcaccaac tcaaatcaat agatccagaa gaagtggaat    7680
cacgtgaata aaagatttta ttcagtttcc agaagagggg gggaatgaaa gaccccacca    7740
taaggcttag cacgctagct acagtaacgc cattttgcaa ggcatggaaa agtaccagag    7800
ctgagttctc aaaagttaca aggaagttta attaaagaat aaggctgaat aacactggga    7860
caggggccaa acaggatatc tgtagtcagg cacctgggcc ccggctcagg gccaagaaca    7920
gatggtcctc agataaagcg aaactaacaa cagtttctgg aaagtcccac ctcagtttca    7980
agttccccaa aagaccggga aatacccaa gccttattta aactaaccaa tcagctcgct     8040
tctcgcttct gtacccgcgc tttttgctcc ccagtcctag ccctataaaa aagggggtaag   8100 aactccacac tcggcgcgcc agtcatccga tagactgagt cgcccgggta cccgtgttcc    8160
caataaagcc ttttgctgtt tgcaaaaa                                        8188
```

<210> SEQ ID NO 2
<211> LENGTH: 2377
<212> TYPE: PRT
<213> ORGANISM: Unknown
<220> FEATURE:
<223> OTHER INFORMATION: HXV35 amino acid sequence

<400> SEQUENCE: 2

```
Met Gly Gln Thr Val Thr Thr Pro Leu Ser Leu Thr Leu Gln His Trp
1               5                   10                  15

Gly Asp Val Gln Arg Ile Ala Ser Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Gln Asp Gly Thr Phe Asn Leu Gly Val Ile Ser Gln Val
    50                  55                  60

Lys Ser Arg Val Phe Cys Pro Gly Pro His Gly His Pro Asp Gln Val
65                  70                  75                  80

Pro Tyr Ile Val Thr Trp Glu Ala Leu Ala Tyr Asp Pro Pro Pro Trp
                85                  90                  95

Val Lys Pro Phe Val Ser Pro Lys Pro Pro Leu Pro Thr Ala Pro
            100                 105                 110

Val Leu Pro Pro Gly Pro Ser Ala Gln Pro Pro Ser Arg Ser Ala Leu
        115                 120                 125

Tyr Pro Ala Leu Thr Leu Ser Ile Lys Ser Lys Pro Pro Lys Pro Gln
    130                 135                 140

Val Leu Pro Asp Ser Gly Gly Pro Leu Ile Asp Leu Leu Thr Glu Asp
145                 150                 155                 160

Pro Pro Pro Tyr Gly Val Gln Pro Ser Ser Ala Arg Glu Asn Asn
                165                 170                 175

Glu Glu Glu Ala Ala Thr Thr Ser Glu Val Ser Pro Ser Pro Met
            180                 185                 190

Val Ser Arg Leu Arg Gly Arg Arg Asp Pro Pro Ala Ala Asp Ser Thr
        195                 200                 205

Thr Ser Gln Ala Phe Pro Leu Arg Met Gly Gly Asp Gly Gln Leu Gln
    210                 215                 220

Tyr Trp Pro Phe Ser Ser Ser Asp Leu Tyr Asn Trp Lys Asn Asn Asn
225                 230                 235                 240
```

```
Pro Ser Phe Ser Glu Asp Pro Gly Lys Leu Thr Ala Leu Ile Glu Ser
            245                 250                 255

Val Leu Ile Thr His Gln Pro Thr Trp Asp Asp Cys Gln Gln Leu Leu
            260                 265                 270

Gly Thr Leu Leu Thr Gly Glu Lys Gln Arg Val Leu Leu Glu Ala
            275                 280                 285

Gly Lys Ala Val Arg Gly Asn Asp Gly Arg Pro Thr Gln Leu Pro Asn
290                 295                 300

Glu Val Asn Ala Ala Phe Pro Leu Glu Arg Pro Asp Trp Asp Tyr Thr
305                 310                 315                 320

Thr Thr Glu Gly Arg Asn His Leu Val Leu Tyr Arg Gln Leu Leu Leu
                325                 330                 335

Ala Gly Leu Gln Asn Ala Gly Arg Ser Pro Thr Asn Leu Ala Lys Val
            340                 345                 350

Lys Gly Ile Thr Gln Gly Pro Asn Glu Ser Pro Ser Ala Phe Leu Glu
            355                 360                 365

Arg Leu Lys Glu Ala Tyr Arg Arg Tyr Thr Pro Tyr Asp Pro Glu Asp
    370                 375                 380

Pro Gly Gln Glu Thr Asn Val Ser Met Ser Phe Ile Trp Gln Ser Ala
385                 390                 395                 400

Pro Asp Ile Gly Arg Lys Leu Glu Arg Leu Glu Asp Leu Lys Ser Lys
            405                 410                 415

Thr Leu Gly Asp Leu Val Arg Glu Ala Glu Lys Ile Phe Asn Lys Arg
            420                 425                 430

Glu Thr Pro Glu Glu Arg Glu Arg Ile Arg Arg Glu Ile Glu Glu
    435                 440                 445

Lys Glu Glu Arg Arg Ala Glu Asp Gln Arg Glu Arg Glu Arg
    450                 455                 460

Asp Arg Arg Arg His Arg Glu Met Ser Lys Leu Leu Ala Thr Val Val
465                 470                 475                 480

Ile Gly Gln Arg Gln Asp Arg Gln Gly Gly Glu Arg Arg Pro Gln
            485                 490                 495

Leu Asp Lys Asp Gln Cys Ala Tyr Cys Lys Glu Lys Gly His Trp Ala
            500                 505                 510

Lys Asp Cys Pro Lys Lys Pro Arg Gly Pro Arg Gly Pro Arg Pro Gln
            515                 520                 525

Thr Ser Leu Leu Thr Leu Gly Asp Gly Gly Gln Gly Gln Glu Pro Pro
            530                 535                 540

Pro Glu Pro Arg Ile Thr Leu Lys Val Gly Gly Gln Pro Val Thr Phe
545                 550                 555                 560

Leu Val Asp Thr Gly Ala Gln His Ser Val Leu Thr Gln Asn Pro Gly
            565                 570                 575

Pro Leu Ser Asp Lys Ser Ala Trp Val Gln Gly Ala Thr Gly Gly Lys
            580                 585                 590

Arg Tyr Arg Trp Thr Thr Asp Arg Lys Val His Leu Ala Thr Gly Lys
    595                 600                 605

Val Thr His Ser Phe Leu His Val Pro Asp Cys Pro Tyr Pro Leu Leu
            610                 615                 620

Gly Arg Asp Leu Leu Thr Lys Leu Lys Ala Gln Ile His Phe Glu Gly
625                 630                 635                 640

Ser Gly Ala Gln Val Val Gly Pro Met Gly Gln Pro Leu Gln Val Leu
            645                 650                 655

Thr Leu Asn Ile Glu Asn Lys Tyr Arg Leu His Glu Thr Ser Lys Glu
```

```
                660                 665                 670
Pro Asp Val Pro Leu Gly Ser Thr Trp Leu Ser Asp Phe Pro Gln Ala
            675                 680                 685
Trp Ala Glu Thr Gly Gly Met Gly Leu Ala Val Arg Gln Ala Pro Leu
            690                 695                 700
Ile Ile Pro Leu Lys Ala Thr Ser Thr Pro Val Ser Ile Lys Gln Tyr
705                 710                 715                 720
Pro Met Ser Gln Glu Ala Arg Leu Gly Ile Lys Pro His Ile Gln Arg
            725                 730                 735
Leu Leu Asp Gln Gly Ile Leu Val Pro Cys Gln Ser Pro Trp Asn Thr
            740                 745                 750
Pro Leu Leu Pro Val Lys Lys Pro Gly Thr Asn Asp Tyr Arg Pro Val
            755                 760                 765
Gln Asp Leu Arg Glu Val Asn Lys Arg Val Glu Asp Ile His Pro Thr
            770                 775                 780
Val Pro Asn Pro Tyr Asn Leu Leu Ser Gly Leu Pro Pro Ser His Gln
785                 790                 795                 800
Trp Tyr Thr Val Leu Asp Leu Lys Asp Ala Phe Phe Cys Leu Arg Leu
            805                 810                 815
His Pro Thr Ser Gln Pro Leu Phe Ala Phe Glu Trp Arg Asp Pro Glu
            820                 825                 830
Met Gly Ile Ser Gly Gln Leu Thr Trp Thr Arg Leu Pro Gln Gly Phe
            835                 840                 845
Lys Asn Ser Pro Thr Leu Phe Asp Glu Ala Leu His Arg Asp Leu Ala
            850                 855                 860
Asp Phe Arg Ile Gln His Pro Asp Leu Ile Leu Leu Gln Tyr Val Asp
865                 870                 875                 880
Asp Leu Leu Leu Ala Ala Thr Ser Glu Gln Asp Cys Gln Arg Gly Thr
            885                 890                 895
Arg Ala Leu Leu Gln Thr Leu Gly Asn Leu Gly Tyr Arg Ala Ser Ala
            900                 905                 910
Lys Lys Ala Gln Ile Cys Gln Lys Gln Val Lys Tyr Leu Gly Tyr Leu
            915                 920                 925
Leu Lys Glu Gly Gln Arg Trp Leu Thr Glu Ala Arg Lys Glu Thr Val
            930                 935                 940
Met Gly Gln Pro Thr Pro Lys Thr Pro Arg Gln Leu Arg Glu Phe Leu
945                 950                 955                 960
Gly Thr Ala Gly Phe Cys Arg Leu Trp Ile Pro Gly Phe Ala Glu Met
            965                 970                 975
Ala Ala Pro Leu Tyr Pro Leu Thr Lys Thr Gly Thr Leu Phe Asn Trp
            980                 985                 990
Gly Pro Asp Gln Gln Lys Ala Tyr Gln Glu Ile Lys Gln Ala Leu Leu
            995                 1000                1005
Thr Ala Pro Ala Leu Gly Leu Pro Asp Leu Thr Lys Pro Phe Glu Leu
            1010                1015                1020
Phe Val Asp Glu Lys Gln Gly Tyr Ala Lys Gly Val Leu Thr Gln Lys
1025                1030                1035                1040
Leu Gly Pro Trp Arg Arg Pro Val Ala Tyr Leu Ser Lys Lys Leu Asp
            1045                1050                1055
Pro Val Ala Ala Gly Trp Pro Pro Cys Leu Arg Met Val Ala Ala Ile
            1060                1065                1070
Ala Val Leu Thr Lys Asp Ala Gly Lys Leu Thr Met Gly Gln Pro Leu
            1075                1080                1085
```

-continued

```
Val Ile Leu Ala Pro His Ala Val Glu Ala Leu Val Lys Gln Pro Pro
    1090                1095                1100

Asp Arg Trp Leu Ser Asn Ala Arg Met Thr His Tyr Gln Ala Met Leu
1105                1110                1115                1120

Leu Asp Thr Asp Arg Val Gln Phe Gly Pro Val Val Ala Leu Asn Pro
            1125                1130                1135

Ala Thr Leu Leu Pro Leu Pro Glu Lys Glu Ala Pro His Asp Cys Leu
        1140                1145                1150

Glu Ile Leu Ala Glu Thr His Gly Thr Arg Pro Asp Leu Thr Asp Gln
    1155                1160                1165

Pro Ile Pro Asp Ala Asp Tyr Thr Trp Tyr Thr Asp Gly Ser Ser Phe
    1170                1175                1180

Leu Gln Glu Gly Gln Arg Arg Ala Gly Ala Ala Val Thr Thr Glu Thr
1185                1190                1195                1200

Glu Val Ile Trp Ala Arg Ala Leu Pro Ala Gly Thr Ser Ala Gln Arg
            1205                1210                1215

Ala Glu Leu Ile Ala Leu Thr Gln Ala Leu Lys Met Ala Glu Gly Lys
        1220                1225                1230

Lys Leu Asn Val Tyr Thr Asp Ser Arg Tyr Ala Phe Ala Thr Ala His
    1235                1240                1245

Val His Gly Glu Ile Tyr Arg Arg Arg Gly Leu Leu Thr Ser Glu Gly
    1250                1255                1260

Arg Glu Ile Lys Asn Lys Asn Glu Ile Leu Ala Leu Leu Lys Ala Leu
1265                1270                1275                1280

Phe Leu Pro Lys Arg Leu Ser Ile Ile His Cys Pro Gly His Gln Lys
            1285                1290                1295

Gly Asn Ser Ala Glu Ala Arg Gly Asn Arg Met Ala Asp Gln Ala Ala
            1300                1305                1310

Arg Glu Ala Ala Met Lys Ala Val Leu Glu Thr Ser Thr Leu Leu Ile
        1315                1320                1325

Glu Asp Ser Thr Pro Tyr Thr Pro Pro His Phe His Tyr Thr Glu Thr
    1330                1335                1340

Asp Leu Lys Arg Leu Arg Glu Leu Gly Ala Thr Tyr Asn Gln Thr Lys
1345                1350                1355                1360

Gly Tyr Trp Val Leu Gln Gly Lys Pro Val Met Pro Asp Gln Ser Val
            1365                1370                1375

Phe Glu Leu Leu Asp Ser Leu His Arg Leu Thr His Pro Ser Pro Gln
            1380                1385                1390

Lys Met Lys Ala Leu Leu Asp Arg Glu Glu Ser Pro Tyr Tyr Met Leu
        1395                1400                1405

Asn Arg Asp Arg Thr Ile Gln Tyr Val Thr Glu Thr Cys Thr Ala Cys
    1410                1415                1420

Ala Gln Val Asn Ala Ser Lys Ala Lys Ile Gly Ala Gly Val Arg Val
1425                1430                1435                1440

Arg Gly His Arg Pro Gly Thr His Trp Glu Val Asp Phe Thr Glu Val
            1445                1450                1455

Lys Pro Gly Leu Tyr Gly Tyr Lys Tyr Leu Leu Val Phe Val Asp Thr
            1460                1465                1470

Phe Ser Gly Trp Val Glu Ala Phe Pro Thr Lys Arg Glu Thr Ala Lys
        1475                1480                1485

Val Val Ser Lys Lys Leu Leu Glu Asp Ile Phe Pro Arg Phe Glu Met
    1490                1495                1500

Pro Gln Val Leu Gly Ser Asp Asn Gly Pro Ala Phe Ala Ser Gln Val
1505                1510                1515                1520
```

```
Ser Gln Ser Val Ala Asp Leu Leu Gly Ile Asp Trp Lys Leu His Cys
            1525                1530                1535

Ala Tyr Lys Pro Gln Ser Ser Gly Gln Val Glu Arg Ile Asn Lys Thr
            1540                1545                1550

Ile Lys Glu Thr Leu Thr Lys Leu Thr Leu Ala Ser Gly Thr Lys Asp
            1555                1560                1565

Trp Val Leu Leu Pro Leu Ala Leu Tyr Arg Ala Arg Asn Thr Pro
    1570                1575                1580

Gly Pro His Gly Leu Thr Pro Tyr Glu Ile Leu Tyr Gly Ala Pro Pro
1585                1590                1595                1600

Pro Leu Val Asn Phe His Asn Pro Glu Met Ser Lys Leu Thr Asn Ser
            1605                1610                1615

Pro Ser Leu Gln Ala His Leu Gln Ala Leu Gln Ala Val Gln Gln Glu
            1620                1625                1630

Val Trp Lys Pro Leu Ala Ala Ala Tyr Gln Asp Gln Leu Asp Gln Pro
            1635                1640                1645

Val Ile Pro His Pro Phe Arg Val Gly Asp Ala Val Trp Val Arg Arg
            1650                1655                1660

His Gln Thr Lys Asn Leu Glu Pro Arg Trp Lys Gly Pro Tyr Thr Val
1665                1670                1675                1680

Leu Leu Thr Thr Pro Thr Ala Leu Lys Val Asp Gly Ile Ser Ala Trp
            1685                1690                1695

Ile His Ala Ala His Val Lys Ala Ala Thr Thr Pro Ala Gly Thr
            1700                1705                1710

Ala Trp Lys Val Gln Arg Ser Gln Asn Pro Leu Lys Ile Arg Leu Thr
            1715                1720                1725

Arg Gly Ala Pro Met Glu Ser Pro Ala Phe Ser Lys Pro Leu Lys Asp
            1730                1735                1740

Lys Ile Asn Pro Trp Gly Pro Leu Ile Ile Met Gly Ile Leu Val Arg
1745                1750                1755                1760

Ala Gly Ala Ser Val Gln Arg Asp Ser Pro His Gln Val Phe Asn Val
            1765                1770                1775

Thr Trp Lys Ile Thr Asn Leu Met Thr Gly Gln Thr Ala Asn Ala Thr
            1780                1785                1790

Ser Leu Leu Gly Thr Met Thr Asp Thr Phe Pro Lys Leu Tyr Phe Asp
            1795                1800                1805

Leu Cys Asp Leu Val Gly Asp Asn Trp Asp Asp Pro Glu Pro Asp Ile
            1810                1815                1820

Gly Asp Gly Cys Arg Ser Pro Gly Gly Arg Lys Arg Thr Arg Leu Tyr
1825                1830                1835                1840

Asp Phe Tyr Val Cys Pro Gly His Thr Val Leu Thr Gly Cys Gly Gly
            1845                1850                1855

Pro Arg Glu Gly Tyr Cys Gly Lys Trp Gly Cys Glu Thr Thr Gly Gln
            1860                1865                1870

Ala Tyr Trp Lys Pro Ser Ser Ser Trp Asp Leu Ile Ser Leu Lys Arg
            1875                1880                1885

Gly Asn Thr Pro Lys Gly Gln Gly Pro Cys Phe Asp Ser Ser Val Gly
            1890                1895                1900

Ser Gly Ser Ile Gln Gly Ala Thr Pro Gly Gly Arg Cys Asn Pro Leu
1905                1910                1915                1920

Val Leu Glu Phe Thr Asp Ala Gly Lys Arg Ala Ser Trp Asp Ala Pro
            1925                1930                1935

Lys Thr Trp Gly Leu Arg Leu Tyr Arg Ser Thr Gly Ala Asp Pro Val
```

-continued

```
                1940            1945            1950
Thr Leu Phe Ser Leu Thr Arg Gln Val Leu Asn Val Gly Pro Arg Val
        1955            1960            1965
Pro Ile Gly Pro Asn Pro Val Ile Thr Glu Gln Leu Pro Pro Ser Gln
        1970            1975            1980
Pro Val Gln Ile Met Leu Pro Arg Pro Pro Arg Pro Pro Pro Ser Gly
1985            1990            1995            2000
Ala Ala Ser Met Val Pro Gly Ala Pro Pro Ser Gln Gln Pro Gly
            2005            2010            2015
Thr Gly Asp Arg Leu Leu Asn Leu Val Glu Gly Ala Tyr Gln Ala Leu
            2020            2025            2030
Asn Leu Thr Ser Pro Asp Lys Thr Gln Glu Cys Trp Leu Cys Leu Val
        2035            2040            2045
Ser Gly Pro Pro Tyr Tyr Glu Gly Val Ala Val Leu Gly Thr Tyr Ser
    2050            2055            2060
Asn His Thr Ser Ala Pro Ala Asn Cys Ser Val Thr Ser Gln His Lys
2065            2070            2075            2080
Leu Thr Leu Ser Glu Val Thr Gly Gln Gly Leu Cys Ile Gly Ala Val
            2085            2090            2095
Pro Lys Thr His Gln Ala Leu Cys Asn Thr Thr Gln Lys Thr Ser Asp
            2100            2105            2110
Gly Ser Tyr Tyr Leu Ala Ser Pro Ala Gly Thr Ile Trp Ala Cys Ser
            2115            2120            2125
Thr Gly Leu Thr Pro Cys Leu Ser Thr Thr Val Leu Asn Leu Thr Thr
            2130            2135            2140
Asp Tyr Cys Val Leu Val Glu Leu Trp Pro Lys Val Thr Tyr His Ser
2145            2150            2155            2160
Pro Asn Tyr Val Tyr Gly Gln Phe Gly Lys Lys Thr Lys Tyr Lys Arg
            2165            2170            2175
Glu Pro Val Ser Leu Thr Leu Ala Leu Leu Leu Gly Gly Leu Thr Met
            2180            2185            2190
Gly Gly Ile Ala Ala Gly Val Gly Thr Gly Thr Thr Ala Leu Val Ala
        2195            2200            2205
Thr Lys Gln Phe Glu Gln Leu Gln Ala Ala Ile His Thr Asp Leu Gly
        2210            2215            2220
Ala Leu Glu Lys Ser Val Ser Ala Leu Glu Lys Ser Leu Thr Ser Leu
2225            2230            2235            2240
Ser Glu Val Val Leu Gln Asn Arg Arg Gly Leu Asp Leu Leu Phe Leu
            2245            2250            2255
Lys Glu Gly Gly Leu Cys Ala Ala Leu Lys Lys Glu Cys Cys Phe Tyr
            2260            2265            2270
Ala Asp His Thr Gly Val Val Arg Asp Ser Met Ala Lys Leu Arg Glu
        2275            2280            2285
Arg Leu Asn Gln Arg Gln Lys Leu Phe Glu Ser Gly Gln Gly Trp Phe
            2290            2295            2300
Glu Gly Leu Phe Asn Arg Ser Pro Trp Phe Thr Thr Leu Ile Ser Thr
2305            2310            2315            2320
Ile Met Gly Pro Leu Ile Val Leu Leu Leu Ile Leu Leu Phe Gly Pro
                2325            2330            2335
Cys Ile Leu Asn Arg Leu Val Gln Phe Val Lys Asp Arg Ile Ser Val
            2340            2345            2350
Val Gln Ala Leu Val Leu Thr Gln Gln Tyr His Gln Leu Lys Ser Ile
            2355            2360            2365
```

-continued

```
Asp Pro Glu Val Glu Ser Arg Glu
    2370                2375
```

<210> SEQ ID NO 3
<211> LENGTH: 536
<212> TYPE: PRT
<213> ORGANISM: Unknown
<220> FEATURE:
<223> OTHER INFORMATION: HXV35 Gag

<400> SEQUENCE: 3

```
Met Gly Gln Thr Val Thr Thr Pro Leu Ser Leu Thr Leu Gln His Trp
1               5                   10                  15

Gly Asp Val Gln Arg Ile Ala Ser Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Gln Asp Gly Thr Phe Asn Leu Gly Val Ile Ser Gln Val
    50                  55                  60

Lys Ser Arg Val Phe Cys Pro Gly Pro His Gly His Pro Asp Gln Val
65                  70                  75                  80

Pro Tyr Ile Val Thr Trp Glu Ala Leu Ala Tyr Asp Pro Pro Pro Trp
                85                  90                  95

Val Lys Pro Phe Val Ser Pro Lys Pro Pro Leu Pro Thr Ala Pro
            100                 105                 110

Val Leu Pro Pro Gly Pro Ser Ala Gln Pro Pro Ser Arg Ser Ala Leu
        115                 120                 125

Tyr Pro Ala Leu Thr Leu Ser Ile Lys Ser Lys Pro Pro Lys Pro Gln
    130                 135                 140

Val Leu Pro Asp Ser Gly Gly Pro Leu Ile Asp Leu Leu Thr Glu Asp
145                 150                 155                 160

Pro Pro Pro Tyr Gly Val Gln Pro Ser Ser Ser Ala Arg Glu Asn Asn
                165                 170                 175

Glu Glu Glu Ala Ala Thr Thr Ser Glu Val Ser Pro Pro Ser Pro Met
            180                 185                 190

Val Ser Arg Leu Arg Gly Arg Arg Asp Pro Pro Ala Ala Asp Ser Thr
        195                 200                 205

Thr Ser Gln Ala Phe Pro Leu Arg Met Gly Gly Asp Gly Gln Leu Gln
    210                 215                 220

Tyr Trp Pro Phe Ser Ser Ser Asp Leu Tyr Asn Trp Lys Asn Asn Asn
225                 230                 235                 240

Pro Ser Phe Ser Glu Asp Pro Gly Lys Leu Thr Ala Leu Ile Glu Ser
                245                 250                 255

Val Leu Ile Thr His Gln Pro Thr Trp Asp Asp Cys Gln Gln Leu Leu
            260                 265                 270

Gly Thr Leu Leu Thr Gly Glu Glu Lys Gln Arg Val Leu Leu Glu Ala
        275                 280                 285

Gly Lys Ala Val Arg Gly Asn Asp Gly Arg Pro Thr Gln Leu Pro Asn
    290                 295                 300

Glu Val Asn Ala Ala Phe Pro Leu Glu Arg Pro Asp Trp Asp Tyr Thr
305                 310                 315                 320

Thr Thr Glu Gly Arg Asn His Leu Val Leu Tyr Arg Gln Leu Leu Leu
                325                 330                 335

Ala Gly Leu Gln Asn Ala Gly Arg Ser Pro Thr Asn Leu Ala Lys Val
            340                 345                 350

Lys Gly Ile Thr Gln Gly Pro Asn Glu Ser Pro Ser Ala Phe Leu Glu
```

```
                    355                 360                 365
Arg Leu Lys Glu Ala Tyr Arg Arg Tyr Thr Pro Tyr Asp Pro Glu Asp
        370                 375                 380

Pro Gly Gln Glu Thr Asn Val Ser Met Ser Phe Ile Trp Gln Ser Ala
385                 390                 395                 400

Pro Asp Ile Gly Arg Lys Leu Glu Arg Leu Glu Asp Leu Lys Ser Lys
                405                 410                 415

Thr Leu Gly Asp Leu Val Arg Glu Ala Glu Lys Ile Phe Asn Lys Arg
            420                 425                 430

Glu Thr Pro Glu Glu Arg Glu Arg Ile Arg Arg Glu Ile Glu Glu
            435                 440                 445

Lys Glu Glu Arg Arg Ala Glu Asp Glu Gln Arg Glu Arg Glu Arg
    450                 455                 460

Asp Arg Arg Arg His Arg Glu Met Ser Lys Leu Leu Ala Thr Val Val
465                 470                 475                 480

Ile Gly Gln Arg Gln Asp Arg Gln Gly Gly Glu Arg Arg Pro Gln
                485                 490                 495

Leu Asp Lys Asp Gln Cys Ala Tyr Cys Lys Glu Lys Gly His Trp Ala
                500                 505                 510

Lys Asp Cys Pro Lys Lys Pro Arg Gly Pro Arg Gly Pro Arg Pro Gln
            515                 520                 525

Thr Ser Leu Leu Thr Leu Gly Asp
    530                 535

<210> SEQ ID NO 4
<211> LENGTH: 1196
<212> TYPE: PRT
<213> ORGANISM: Unknown
<220> FEATURE:
<223> OTHER INFORMATION: HXV35 Pro-Pol

<400> SEQUENCE: 4

Gly Gly Gln Gly Gln Glu Pro Pro Glu Pro Arg Ile Thr Leu Lys
1               5                   10                  15

Val Gly Gly Gln Pro Val Thr Phe Leu Val Asp Thr Gly Ala Gln His
            20                  25                  30

Ser Val Leu Thr Gln Asn Pro Gly Pro Leu Ser Asp Lys Ser Ala Trp
        35                  40                  45

Val Gln Gly Ala Thr Gly Gly Lys Arg Tyr Arg Trp Thr Thr Asp Arg
    50                  55                  60

Lys Val His Leu Ala Thr Gly Lys Val Thr His Ser Phe Leu His Val
65                  70                  75                  80

Pro Asp Cys Pro Tyr Pro Leu Leu Gly Arg Asp Leu Leu Thr Lys Leu
                85                  90                  95

Lys Ala Gln Ile His Phe Glu Gly Ser Gly Ala Gln Val Val Gly Pro
            100                 105                 110

Met Gly Gln Pro Leu Gln Val Leu Thr Leu Asn Ile Glu Asn Lys Tyr
        115                 120                 125

Arg Leu His Glu Thr Ser Lys Glu Pro Asp Val Pro Leu Gly Ser Thr
    130                 135                 140

Trp Leu Ser Asp Phe Pro Gln Ala Trp Ala Glu Thr Gly Gly Met Gly
145                 150                 155                 160

Leu Ala Val Arg Gln Ala Pro Leu Ile Ile Pro Leu Lys Ala Thr Ser
                165                 170                 175

Thr Pro Val Ser Ile Lys Gln Tyr Pro Met Ser Gln Glu Ala Arg Leu
            180                 185                 190
```

Gly Ile Lys Pro His Ile Gln Arg Leu Leu Asp Gln Gly Ile Leu Val
        195                 200                 205

Pro Cys Gln Ser Pro Trp Asn Thr Pro Leu Leu Pro Val Lys Lys Pro
    210                 215                 220

Gly Thr Asn Asp Tyr Arg Pro Val Gln Asp Leu Arg Glu Val Asn Lys
225                 230                 235                 240

Arg Val Glu Asp Ile His Pro Thr Val Pro Asn Pro Tyr Asn Leu Leu
                245                 250                 255

Ser Gly Leu Pro Pro Ser His Gln Trp Tyr Thr Val Leu Asp Leu Lys
            260                 265                 270

Asp Ala Phe Phe Cys Leu Arg Leu His Pro Thr Ser Gln Pro Leu Phe
        275                 280                 285

Ala Phe Glu Trp Arg Asp Pro Glu Met Gly Ile Ser Gly Gln Leu Thr
    290                 295                 300

Trp Thr Arg Leu Pro Gln Gly Phe Lys Asn Ser Pro Thr Leu Phe Asp
305                 310                 315                 320

Glu Ala Leu His Arg Asp Leu Ala Asp Phe Arg Ile Gln His Pro Asp
                325                 330                 335

Leu Ile Leu Leu Gln Tyr Val Asp Asp Leu Leu Leu Ala Ala Thr Ser
            340                 345                 350

Glu Gln Asp Cys Gln Arg Gly Thr Arg Ala Leu Leu Gln Thr Leu Gly
        355                 360                 365

Asn Leu Gly Tyr Arg Ala Ser Ala Lys Lys Ala Gln Ile Cys Gln Lys
    370                 375                 380

Gln Val Lys Tyr Leu Gly Tyr Leu Leu Lys Glu Gly Gln Arg Trp Leu
385                 390                 395                 400

Thr Glu Ala Arg Lys Glu Thr Val Met Gly Gln Pro Thr Pro Lys Thr
                405                 410                 415

Pro Arg Gln Leu Arg Glu Phe Leu Gly Thr Ala Gly Phe Cys Arg Leu
            420                 425                 430

Trp Ile Pro Gly Phe Ala Glu Met Ala Ala Pro Leu Tyr Pro Leu Thr
        435                 440                 445

Lys Thr Gly Thr Leu Phe Asn Trp Gly Pro Asp Gln Gln Lys Ala Tyr
    450                 455                 460

Gln Glu Ile Lys Gln Ala Leu Leu Thr Ala Pro Ala Leu Gly Leu Pro
465                 470                 475                 480

Asp Leu Thr Lys Pro Phe Glu Leu Phe Val Asp Glu Lys Gln Gly Tyr
                485                 490                 495

Ala Lys Gly Val Leu Thr Gln Lys Leu Gly Pro Trp Arg Arg Pro Val
            500                 505                 510

Ala Tyr Leu Ser Lys Lys Leu Asp Pro Val Ala Ala Gly Trp Pro Pro
        515                 520                 525

Cys Leu Arg Met Val Ala Ala Ile Ala Val Leu Thr Lys Asp Ala Gly
    530                 535                 540

Lys Leu Thr Met Gly Gln Pro Leu Val Ile Leu Ala Pro His Ala Val
545                 550                 555                 560

Glu Ala Leu Val Lys Gln Pro Pro Asp Arg Trp Leu Ser Asn Ala Arg
                565                 570                 575

Met Thr His Tyr Gln Ala Met Leu Leu Asp Thr Asp Arg Val Gln Phe
            580                 585                 590

Gly Pro Val Val Ala Leu Asn Pro Ala Thr Leu Leu Pro Leu Pro Glu
        595                 600                 605

Lys Glu Ala Pro His Asp Cys Leu Glu Ile Leu Ala Glu Thr His Gly

```
                610                 615                 620
Thr Arg Pro Asp Leu Thr Asp Gln Pro Ile Pro Asp Ala Asp Tyr Thr
625                 630                 635                 640

Trp Tyr Thr Asp Gly Ser Ser Phe Leu Gln Glu Gly Gln Arg Ala
                645                 650                 655

Gly Ala Ala Val Thr Thr Glu Thr Glu Val Ile Trp Ala Arg Ala Leu
                660                 665                 670

Pro Ala Gly Thr Ser Ala Gln Arg Ala Glu Leu Ile Ala Leu Thr Gln
                675                 680                 685

Ala Leu Lys Met Ala Glu Gly Lys Lys Leu Asn Val Tyr Thr Asp Ser
690                 695                 700

Arg Tyr Ala Phe Ala Thr Ala His Val His Gly Glu Ile Tyr Arg Arg
705                 710                 715                 720

Arg Gly Leu Leu Thr Ser Glu Gly Arg Glu Ile Lys Asn Lys Asn Glu
                725                 730                 735

Ile Leu Ala Leu Leu Lys Ala Leu Phe Leu Pro Lys Arg Leu Ser Ile
                740                 745                 750

Ile His Cys Pro Gly His Gln Lys Gly Asn Ser Ala Glu Ala Arg Gly
                755                 760                 765

Asn Arg Met Ala Asp Gln Ala Ala Arg Glu Ala Ala Met Lys Ala Val
                770                 775                 780

Leu Glu Thr Ser Thr Leu Leu Ile Glu Asp Ser Thr Pro Tyr Thr Pro
785                 790                 795                 800

Pro His Phe His Tyr Thr Glu Thr Asp Leu Lys Arg Leu Arg Glu Leu
                805                 810                 815

Gly Ala Thr Tyr Asn Gln Thr Lys Gly Tyr Trp Val Leu Gln Gly Lys
                820                 825                 830

Pro Val Met Pro Asp Gln Ser Val Phe Glu Leu Leu Asp Ser Leu His
                835                 840                 845

Arg Leu Thr His Pro Ser Pro Gln Lys Met Lys Ala Leu Leu Asp Arg
                850                 855                 860

Glu Glu Ser Pro Tyr Tyr Met Leu Asn Arg Asp Arg Thr Ile Gln Tyr
865                 870                 875                 880

Val Thr Glu Thr Cys Thr Ala Cys Ala Gln Val Asn Ala Ser Lys Ala
                885                 890                 895

Lys Ile Gly Ala Gly Val Arg Val Arg Gly His Arg Pro Gly Thr His
                900                 905                 910

Trp Glu Val Asp Phe Thr Glu Val Lys Pro Gly Leu Tyr Gly Tyr Lys
                915                 920                 925

Tyr Leu Leu Val Phe Val Asp Thr Phe Ser Gly Trp Val Glu Ala Phe
930                 935                 940

Pro Thr Lys Arg Glu Thr Ala Lys Val Val Ser Lys Lys Leu Leu Glu
945                 950                 955                 960

Asp Ile Phe Pro Arg Phe Glu Met Pro Gln Val Leu Gly Ser Asp Asn
                965                 970                 975

Gly Pro Ala Phe Ala Ser Gln Val Ser Gln Ser Val Ala Asp Leu Leu
                980                 985                 990

Gly Ile Asp Trp Lys Leu His Cys Ala Tyr Lys Pro Gln Ser Ser Gly
                995                 1000                1005

Gln Val Glu Arg Ile Asn Lys Thr Ile Lys Glu Thr Leu Thr Lys Leu
                1010                1015                1020

Thr Leu Ala Ser Gly Thr Lys Asp Trp Val Leu Leu Leu Pro Leu Ala
1025                1030                1035                1040
```

```
Leu Tyr Arg Ala Arg Asn Thr Pro Gly Pro His Gly Leu Thr Pro Tyr
                1045                1050                1055

Glu Ile Leu Tyr Gly Ala Pro Pro Pro Leu Val Asn Phe His Asn Pro
            1060                1065                1070

Glu Met Ser Lys Leu Thr Asn Ser Pro Ser Leu Gln Ala His Leu Gln
        1075                1080                1085

Ala Leu Gln Ala Val Gln Gln Glu Val Trp Lys Pro Leu Ala Ala Ala
    1090                1095                1100

Tyr Gln Asp Gln Leu Asp Gln Pro Val Ile Pro His Pro Phe Arg Val
1105                1110                1115                1120

Gly Asp Ala Val Trp Val Arg Arg His Gln Thr Lys Asn Leu Glu Pro
                1125                1130                1135

Arg Trp Lys Gly Pro Tyr Thr Val Leu Leu Thr Thr Pro Thr Ala Leu
            1140                1145                1150

Lys Val Asp Gly Ile Ser Ala Trp Ile His Ala Ala His Val Lys Ala
        1155                1160                1165

Ala Thr Thr Pro Pro Ala Gly Thr Ala Trp Lys Val Gln Arg Ser Gln
    1170                1175                1180

Asn Pro Leu Lys Ile Arg Leu Thr Arg Gly Ala Pro
1185                1190                1195

<210> SEQ ID NO 5
<211> LENGTH: 645
<212> TYPE: PRT
<213> ORGANISM: Unknown
<220> FEATURE:
<223> OTHER INFORMATION: HXV35 ENV

<400> SEQUENCE: 5

Met Glu Ser Pro Ala Phe Ser Lys Pro Leu Lys Asp Lys Ile Asn Pro
1               5                   10                  15

Trp Gly Pro Leu Ile Ile Met Gly Ile Leu Val Arg Ala Gly Ala Ser
            20                  25                  30

Val Gln Arg Asp Ser Pro His Gln Val Phe Asn Val Thr Trp Lys Ile
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Asn Trp Asp Asp Pro Glu Pro Asp Ile Gly Asp Gly Cys
                85                  90                  95

Arg Ser Pro Gly Gly Arg Lys Arg Thr Arg Leu Tyr Asp Phe Tyr Val
            100                 105                 110

Cys Pro Gly His Thr Val Leu Thr Gly Cys Gly Gly Pro Arg Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Gly Gln Gly Pro Cys Phe Asp Ser Ser Val Gly Ser Gly Ser Ile
                165                 170                 175

Gln Gly Ala Thr Pro Gly Gly Arg Cys Asn Pro Leu Val Leu Glu Phe
            180                 185                 190

Thr Asp Ala Gly Lys Arg Ala Ser Trp Asp Ala Pro Lys Thr Trp Gly
        195                 200                 205

Leu Arg Leu Tyr Arg Ser Thr Gly Ala Asp Pro Val Thr Leu Phe Ser

```
            210                 215                 220
Leu Thr Arg Gln Val Leu Asn Val Gly Pro Arg Val Pro Ile Gly Pro
225                 230                 235                 240

Asn Pro Val Ile Thr Glu Gln Leu Pro Pro Ser Gln Pro Val Gln Ile
                245                 250                 255

Met Leu Pro Arg Pro Arg Pro Pro Ser Gly Ala Ala Ser Met
                260                 265                 270

Val Pro Gly Ala Pro Pro Ser Gln Gln Pro Gly Thr Gly Asp Arg
                275                 280                 285

Leu Leu Asn Leu Val Glu Gly Ala Tyr Gln Ala Leu Asn Leu Thr Ser
                290                 295                 300

Pro Asp Lys Thr Gln Glu Cys Trp Leu Cys Leu Val Ser Gly Pro Pro
305                 310                 315                 320

Tyr Tyr Glu Gly Val Ala Val Leu Gly Thr Tyr Ser Asn His Thr Ser
                325                 330                 335

Ala Pro Ala Asn Cys Ser Val Thr Ser Gln His Lys Leu Thr Leu Ser
                340                 345                 350

Glu Val Thr Gly Gln Gly Leu Cys Ile Gly Ala Val Pro Lys Thr His
                355                 360                 365

Gln Ala Leu Cys Asn Thr Thr Gln Lys Thr Ser Asp Gly Ser Tyr Tyr
370                 375                 380

Leu Ala Ser Pro Ala Gly Thr Ile Trp Ala Cys Ser Thr Gly Leu Thr
385                 390                 395                 400

Pro Cys Leu Ser Thr Thr Val Leu Asn Leu Thr Thr Asp Tyr Cys Val
                405                 410                 415

Leu Val Glu Leu Trp Pro Lys Val Thr Tyr His Ser Pro Asn Tyr Val
                420                 425                 430

Tyr Gly Gln Phe Gly Lys Lys Thr Lys Tyr Lys Arg Glu Pro Val Ser
                435                 440                 445

Leu Thr Leu Ala Leu Leu Leu Gly Gly Leu Thr Met Gly Gly Ile Ala
                450                 455                 460

Ala Gly Val Gly Thr Gly Thr Thr Ala Leu Val Ala Thr Lys Gln Phe
465                 470                 475                 480

Glu Gln Leu Gln Ala Ala Ile His Thr Asp Leu Gly Ala Leu Glu Lys
                485                 490                 495

Ser Val Ser Ala Leu Glu Lys Ser Leu Thr Ser Leu Ser Glu Val Val
                500                 505                 510

Leu Gln Asn Arg Arg Gly Leu Asp Leu Leu Phe Leu Lys Glu Gly Gly
                515                 520                 525

Leu Cys Ala Ala Leu Lys Lys Glu Cys Cys Phe Tyr Ala Asp His Thr
530                 535                 540

Gly Val Val Arg Asp Ser Met Ala Lys Leu Arg Glu Arg Leu Asn Gln
545                 550                 555                 560

Arg Gln Lys Leu Phe Glu Ser Gly Gln Gly Trp Phe Glu Gly Leu Phe
                565                 570                 575

Asn Arg Ser Pro Trp Phe Thr Thr Leu Ile Ser Thr Ile Met Gly Pro
                580                 585                 590

Leu Ile Val Leu Leu Leu Ile Leu Leu Phe Gly Pro Cys Ile Leu Asn
                595                 600                 605

Arg Leu Val Gln Phe Val Lys Asp Arg Ile Ser Val Val Gln Ala Leu
                610                 615                 620

Val Leu Thr Gln Gln Tyr His Gln Leu Lys Ser Ile Asp Pro Glu Glu
625                 630                 635                 640
```

Val Glu Ser Arg Glu
            645

<210> SEQ ID NO 6
<211> LENGTH: 675
<212> TYPE: DNA
<213> ORGANISM: Unknown
<220> FEATURE:
<223> OTHER INFORMATION: LNCaP RTPCR product, 7084-7750 bp

<400> SEQUENCE: 6

```
aaaagagagc ccggtgtcat taactctggc cctgtctgtt gggaggactt actatgggcg    60
gcatagctcc aggagttgga acagggacta cagccctagt ggccaccaaa caattcgagc   120
agctccaggc agccatacat acagaccttg gggccttaga aaaaatcagt cagtgcccta   180
gaaaagtctc tgacctcgtt gtctgaggtg gtcctacaga accggagggg attagatcta   240
ctgttcctaa agaaggagg attatgtgct gccctaaaag aagaatgctg ttttacgcg    300
gaccacactg gcgtagtaag agatagcatg gcaaagctaa gagaaggtt aaaccagaga   360
caaaaattgt tcgaatcagg acaagggtgg tttgagggac tgtttaacag gtccccatgg   420
ttcacgaccc tgtatccac caccattatg ggccctctga tagtactttt attaatccta   480
cttttcggac cctgtattct caaccgcttg gtccagtttg taaaagacac agaatttcgg   540
tagtgcaggc cctggttctg acccagcagt atcaccaact caaatcaata gatccagaag   600
aagtggaatc acgtgaataa agatttttat tcagtttcca gaaagagggg ggaatgaaag   660
accccccccat aaggc                                                    675
```

<210> SEQ ID NO 7
<211> LENGTH: 14
<212> TYPE: PRT
<213> ORGANISM: Unknown
<220> FEATURE:
<223> OTHER INFORMATION: HXV gag antigenic candidate

<400> SEQUENCE: 7

Asp Val Lys Lys Arg Arg Trp Val Thr Phe Cys Ser Ala Glu
1               5                   10

<210> SEQ ID NO 8
<211> LENGTH: 16
<212> TYPE: PRT
<213> ORGANISM: Unknown
<220> FEATURE:
<223> OTHER INFORMATION: HXV gag antigenic candidate

<400> SEQUENCE: 8

Glu Ala Gly Lys Ala Val Arg Gly Asn Asp Gly Arg Pro Thr Gln Leu
1               5                   10                  15

<210> SEQ ID NO 9
<211> LENGTH: 14
<212> TYPE: PRT
<213> ORGANISM: Unknown
<220> FEATURE:
<223> OTHER INFORMATION: HXV gag antigenic candidate

<400> SEQUENCE: 9

Lys Asp Cys Pro Lys Lys Pro Arg Gly Pro Arg Gly Pro Arg
1               5                   10

<210> SEQ ID NO 10
<211> LENGTH: 117
<212> TYPE: PRT

-continued

```
<213> ORGANISM: Unknown
<220> FEATURE:
<223> OTHER INFORMATION: SU glycoprotein variable region (VRA & VRB) of
      VP35

<400> SEQUENCE: 10

Leu Cys Asp Leu Val Gly Asp Asn Trp Asp Asp Pro Glu Pro Asp Ile
1               5                   10                  15

Gly Asp Gly Cys Arg Ser Pro Gly Gly Arg Lys Arg Thr Arg Leu Tyr
                20                  25                  30

Asp Phe Tyr Val Cys Pro Gly His Thr Val Leu Thr Gly Cys Gly Gly
            35                  40                  45

Pro Arg Glu Gly Tyr Cys Gly Lys Trp Gly Cys Glu Thr Thr Gly Gln
        50                  55                  60

Ala Tyr Trp Lys Pro Ser Ser Ser Trp Asp Leu Ile Ser Leu Lys Arg
65                  70                  75                  80

Gly Asn Thr Pro Lys Gly Gln Gly Pro Cys Phe Asp Ser Ser Val Gly
                85                  90                  95

Ser Gly Ser Ile Gln Gly Ala Thr Pro Gly Gly Arg Cys Asn Pro Leu
            100                 105                 110

Val Leu Glu Phe Thr
        115

<210> SEQ ID NO 11
<211> LENGTH: 117
<212> TYPE: PRT
<213> ORGANISM: Unknown
<220> FEATURE:
<223> OTHER INFORMATION: SU glycoprotein variable region (VRA & VRB) of
      VP42

<400> SEQUENCE: 11

Leu Cys Asp Leu Val Gly Asp Asn Trp Asp Asp Pro Glu Pro Asp Ile
1               5                   10                  15

Gly Asp Gly Cys Arg Ser Pro Gly Gly Arg Lys Arg Thr Arg Leu Tyr
                20                  25                  30

Asp Phe Tyr Val Cys Pro Gly His Thr Val Leu Thr Gly Cys Gly Gly
            35                  40                  45

Pro Arg Glu Gly Tyr Cys Gly Lys Trp Gly Cys Glu Thr Thr Gly Gln
        50                  55                  60

Ala Tyr Trp Lys Pro Ser Ser Ser Trp Asp Leu Ile Ser Leu Lys Arg
65                  70                  75                  80

Gly Asn Thr Pro Lys Gly Gln Gly Pro Cys Phe Asp Ser Ser Val Gly
                85                  90                  95

Ser Gly Ser Ile Gln Gly Ala Thr Pro Gly Gly Arg Cys Asn Pro Leu
            100                 105                 110

Val Leu Glu Phe Thr
        115

<210> SEQ ID NO 12
<211> LENGTH: 116
<212> TYPE: PRT
<213> ORGANISM: Unknown
<220> FEATURE:
<223> OTHER INFORMATION: SU glycoprotein variable region (VRA & VRB) of
      DG-75

<400> SEQUENCE: 12

Leu Cys Asp Leu Val Gly Asp Tyr Trp Asp Asp Pro Glu Pro Asp Ile
1               5                   10                  15
```

```
Gly Asp Gly Cys Arg Thr Pro Gly Gly Arg Arg Thr Arg Leu Tyr
            20                  25                  30

Asp Phe Tyr Val Cys Pro Gly His Thr Val Pro Ile Gly Cys Gly Gly
        35                  40                  45

Pro Gly Glu Gly Tyr Cys Gly Lys Trp Gly Cys Glu Thr Thr Gly Gln
50                  55                  60

Ala Tyr Trp Lys Pro Ser Ser Trp Asp Leu Ile Ser Leu Lys Arg
65                  70                  75                  80

Gly Asn Thr Pro Lys Asp Gln Gly Pro Cys Tyr Asp Ser Ser Val Ser
                85                  90                  95

Ser Gly Val Gln Gly Ala Thr Pro Gly Gly Arg Cys Asn Pro Leu Val
                100                 105                 110

Leu Glu Phe Thr
        115

<210> SEQ ID NO 13
<211> LENGTH: 116
<212> TYPE: PRT
<213> ORGANISM: Unknown
<220> FEATURE:
<223> OTHER INFORMATION: SU glycoprotein variable region (VRA & VRB) of
      NZB-9-1

<400> SEQUENCE: 13

Leu Cys Asp Leu Val Gly Asp Tyr Trp Asp Pro Glu Pro Asp Ile
1               5                   10                  15

Gly Asp Gly Cys Arg Thr Pro Gly Gly Arg Arg Arg Thr Arg Leu Tyr
            20                  25                  30

Asp Phe Tyr Val Cys Pro Gly His Thr Val Pro Ile Gly Cys Gly Gly
        35                  40                  45

Pro Gly Glu Gly Tyr Cys Gly Lys Trp Gly Cys Glu Thr Thr Gly Gln
50                  55                  60

Ala Tyr Trp Lys Pro Ser Ser Trp Asp Leu Ile Ser Leu Lys Arg
65                  70                  75                  80

Gly Asn Thr Pro Lys Asp Gln Gly Pro Cys Tyr Asp Ser Ser Val Ser
                85                  90                  95

Ser Gly Val Gln Gly Ala Thr Pro Gly Gly Arg Cys Asn Pro Leu Val
                100                 105                 110

Leu Glu Phe Thr
        115

<210> SEQ ID NO 14
<211> LENGTH: 116
<212> TYPE: PRT
<213> ORGANISM: Unknown
<220> FEATURE:
<223> OTHER INFORMATION: SU glycoprotein variable region (VRA & VRB) of
      MTCR

<400> SEQUENCE: 14

Leu Cys Asp Leu Val Gly Asp His Trp Asp Pro Glu Pro Asp Ile
1               5                   10                  15

Gly Asp Gly Cys Arg Ser Pro Gly Gly Arg Lys Arg Thr Arg Leu Tyr
            20                  25                  30

Asp Phe Tyr Val Cys Pro Gly His Thr Val Pro Ile Gly Cys Gly Gly
        35                  40                  45

Pro Gly Glu Gly Tyr Cys Gly Lys Trp Gly Cys Glu Thr Thr Gly Gln
50                  55                  60

Ala Tyr Trp Lys Pro Ser Ser Ser Trp Asp Leu Ile Ser Leu Lys Arg
```

```
                  65                  70                  75                  80
Gly Asn Thr Pro Lys Asp Gln Gly Pro Cys Tyr Asp Ser Ser Val Ser
                    85                  90                  95

Ser Gly Val Gln Gly Ala Thr Pro Gly Gly Arg Cys Asn Pro Leu Val
                    100                 105                 110

Leu Glu Phe Thr
            115

<210> SEQ ID NO 15
<211> LENGTH: 113
<212> TYPE: PRT
<213> ORGANISM: Unknown
<220> FEATURE:
<223> OTHER INFORMATION: SU glycoprotein variable region (VRA & VRB) of
      MCF1233

<400> SEQUENCE: 15

Leu Cys Asp Leu Ile Gly Asp Asp Trp Asp Glu Thr Gly Leu Gly Cys
1               5                   10                  15

Arg Thr Pro Gly Gly Arg Lys Arg Ala Arg Thr Phe Asp Phe Tyr Val
                20                  25                  30

Cys Pro Gly His Thr Val Pro Thr Gly Cys Gly Gly Pro Arg Glu Gly
                35                  40                  45

Tyr Cys Gly Lys Trp Gly Cys Glu Thr Thr Gly Gln Ala Tyr Trp Lys
            50                  55                  60

Pro Ser Ser Ser Trp Asp Leu Ile Ser Leu Lys Arg Gly Asn Thr Pro
65              70                  75                  80

Gln Asn Gln Gly Pro Cys Tyr Asp Ser Ser Ala Val Ser Ser Asp Ile
                85                  90                  95

Lys Gly Ala Thr Pro Gly Gly Arg Cys Asn Pro Leu Val Leu Glu Phe
                100                 105                 110

Thr

<210> SEQ ID NO 16
<211> LENGTH: 148
<212> TYPE: PRT
<213> ORGANISM: Unknown
<220> FEATURE:
<223> OTHER INFORMATION: SU glycoprotein variable region (VRA & VRB) of
      Friend

<400> SEQUENCE: 16

Leu Cys Met Leu Ala Leu Ser Gly Pro Pro His Trp Gly Leu Glu Tyr
1               5

Gln Ala Val Gln Val Cys Lys Asp Asn Lys Trp Cys Asn Pro Leu Ala
            130                 135                 140

Ile Arg Phe Thr
145

<210> SEQ ID NO 17
<211> LENGTH: 148
<212> TYPE: PRT
<213> ORGANISM: Unknown
<220> FEATURE:
<223> OTHER INFORMATION: SU glycoprotein variable region (VRA & VRB) of
      Rauscher

<400> SEQUENCE: 17

Leu Cys Met Leu Ala Leu His Gly Pro Pro His Trp Gly Leu Glu Tyr
1               5                   10                  15

Gln Ala Pro Tyr Ser Ser Pro Gly Pro Cys Cys Ser Gly Ser
            20                  25                  30

Gly Gly Ser Ser Pro Gly Cys Ser Arg Asp Cys Asn Glu Pro Leu Thr
            35                  40                  45

Ser Leu Thr Pro Arg Cys Asn Thr Ala Trp Asn Arg Leu Lys Leu Asp
50                  55                  60

Gln Val Thr His Lys Ser Ser Glu Gly Phe Tyr Val Cys Pro Gly Ser
65                  70                  75                  80

His Arg Pro Arg Glu Ala Lys Ser Cys Gly Gly Pro Asp Ser Phe Tyr
                85                  90                  95

Cys Ala Ser Trp Gly Cys Glu Thr Thr Gly Arg Ala Tyr Trp Lys Pro
            100                 105                 110

Ser Ser Ser Trp Asp Tyr Ile Thr Val Asp Asn Asn Leu Thr Thr Asn
            115                 120                 125

Gln Ala Val Gln Val Cys Lys Asp Asn Lys Trp Cys Asn Pro Leu Ala
            130                 135                 140

Ile Gln Phe Thr
145

<210> SEQ ID NO 18
<211> LENGTH: 146
<212> TYPE: PRT
<213> ORGANISM: Unknown
<220> FEATURE:
<223> OTHER INFORMATION: SU glycoprotein variable region (VRA & VRB) of
      Moloney

<400> SEQUENCE: 18

Leu Cys Met Leu Ala His His Gly Pro Ser Tyr Trp Gly Leu Glu Tyr
1               5                   10                  15

Gln Ser Pro Phe Ser Ser Pro Gly Pro Cys Cys Ser Gly Gly
            20                  25                  30

Ser Ser Pro Gly Cys Ser Arg Asp Cys Glu Glu Pro Leu Thr Ser Leu
            35                  40                  45

Thr Pro Arg Cys Asn Thr Ala Trp Asn Arg Leu Lys Leu Asp Gln Thr
            50                  55                  60

Thr His Lys Ser Asn Glu Gly Phe Tyr Val Cys Pro Gly Pro His Arg
65                  70                  75                  80

Pro Arg Glu Ser Lys Ser Cys Gly Gly Pro Asp Ser Phe Tyr Cys Ala
                85                  90                  95

Tyr Trp Gly Cys Glu Thr Thr Gly Arg Ala Tyr Trp Lys Pro Ser Ser
            100                 105                 110

Ser Trp Asp Phe Ile Thr Val Asn Asn Asn Leu Thr Ser Asp Gln Ala

```
              115                 120                 125
Val Gln Val Cys Lys Asp Asn Lys Trp Cys Asn Pro Leu Val Ile Arg
        130                 135                 140

Phe Thr
145

<210> SEQ ID NO 19
<211> LENGTH: 148
<212> TYPE: PRT
<213> ORGANISM: Unknown
<220> FEATURE:
<223> OTHER INFORMATION: SU glycoprotein variable region (VRA & VRB)
      of Akv

<400> SEQUENCE: 19

Leu Cys Met Leu Ala Leu His Gly Pro Ser Tyr Trp Gly Leu Glu Tyr
1               5                   10                  15

Arg Ala Pro Phe Ser Pro Pro Gly Pro Pro Cys Cys Ser Gly Ser
            20                  25                  30

Ser Asp Ser Thr Pro Gly Cys Ser Arg Asp Cys Glu Glu Pro Leu Thr
        35                  40                  45

Ser Tyr Thr Pro Arg Cys Asn Thr Ala Trp Asn Arg Leu Lys Leu Ser
    50                  55                  60

Lys Val Thr His Ala His Asn Gly Gly Phe Tyr Val Cys Pro Gly Pro
65                  70                  75                  80

His Arg Pro Arg Trp Ala Arg Ser Cys Gly Gly Pro Glu Ser Phe Tyr
                85                  90                  95

Cys Ala Ser Trp Gly Cys Glu Thr Thr Gly Arg Ala Ser Trp Lys Pro
            100                 105                 110

Ser Ser Ser Trp Asp Tyr Ile Thr Val Ser Asn Leu Thr Ser Asp
        115                 120                 125

Gln Ala Thr Pro Val Cys Lys Gly Asn Glu Trp Cys Asn Ser Leu Thr
    130                 135                 140

Ile Arg Phe Thr
145

<210> SEQ ID NO 20
<211> LENGTH: 271
<212> TYPE: DNA
<213> ORGANISM: Unknown
<220> FEATURE:
<223> OTHER INFORMATION: 5' gag leader sequence from VP35

<400> SEQUENCE: 20
ctgacgagtt cgtattcccg gccgcagccc agggagacgt cccagcggcc tcggggGCCC   60
gttttgtggc ccattctgta tcagttaacc tacccgagtc ggactctttg gagtggcttt  120 gttggggac gagagacaga gacacttccc gccccgtct gaattttgc tttcggtttt    180 acgccgaaac cgcgccgcgc gtctgatttg ttttgttgtt cttctgttct cgttagttt   240 tcttctgtct ttaagtgttc tcgagatcat g                                 271

<210> SEQ ID NO 21
<211> LENGTH: 271
<212> TYPE: DNA
<213> ORGANISM: Unknown
<220> FEATURE:
<223> OTHER INFORMATION: 5' gag leader sequence from VP42

<400> SEQUENCE: 21
ctgacgagtt cgtattcccg gccgcagccc tgggagacgt cccagcggcc tcggggGCCC   60
```

```
gttttgtggc ccattctgta tcagttaacc tacccgagtc ggacttttg gagtggcttt      120 gttggggac gagagacaga gacacttccc gccccgtct gaattttgc tttcggtttt       180 acgccgaaac cgcgccgcgc gtctgatttg ttttgttgtt cttctgttct tcgttagttt    240
tcttctgtct ttaagtgttc tcgagatcat g                                   271

<210> SEQ ID NO 22
<211> LENGTH: 296
<212> TYPE: DNA
<213> ORGANISM: Unknown
<220> FEATURE:
<223> OTHER INFORMATION: 5' gag leader sequence from MTCR

<400> SEQUENCE: 22
ctgacgagtt cgtattcccg accgcagccc tgggagacgt ctcagaggca tcaggggccc     60
gctgggtggc ccgatcagta agtccgagtc ctgaccgatt cggactattt ggagcccctc   120
ctttgtcgga gggggacgtg gttctttag gagacgagag gtccaagccc tcgccgcctc   180
catctgaatt tttgctttcg ttttttcgcc gaaaccgcgc gcgcgtctt gtctgtctca    240 gtgttgtttt gtcatttgtc tgttcgttat tgttttggac cgtttctaaa aatatg        296

<210> SEQ ID NO 23
<211> LENGTH: 296
<212> TYPE: DNA
<213> ORGANISM: Unknown
<220> FEATURE:
<223> OTHER INFORMATION: 5' gag leader sequence from MCF1233

<400> SEQUENCE: 23
ctgacgagtt cgtattcccg accgcagccc tgggagacgt ctcagaggca tcggggccc      60 gctgggtggc ccaatcagta agtccgagtc ctgaccgatt cggactattt ggagcccctc   120
ctttgtcgga ggggtacgtg gttctttag gagacgagag gtccaagccc tcgccgcctc   180
catctgaatt tttgctttcg ttttttcgcc gaaaccgcgc gcgcgtctt gtctgtctta    240 gtgttgtttt gtcatttgtc tgttcgttat tgttttggac cgtttctaaa aatatg        296

<210> SEQ ID NO 24
<211> LENGTH: 296
<212> TYPE: DNA
<213> ORGANISM: Unknown
<220> FEATURE:
<223> OTHER INFORMATION: 5' gag leader sequence from DG-75

<400> SEQUENCE: 24
ctgacgagtt catattcccg gccgcagccc tgggagacgt ctcagaggca tcggggcca      60 tctttgtggc ccaatctgta tctgagaacc cgacccgtct cggactcttt ggagcctctc   120
ctttgaccga gggatacgtg gttctgttgg gcggcgaggg gccgaaacgc tcctctcccc   180
catctgaatt tttgttttcg ttttccgcc gaaaccgcgc cgcacgtctt gtctgtctct    240
gtgttgtttt gtcatttgtc ggttcgttat tgttttggat cgtttctaaa aatatg        296

<210> SEQ ID NO 25
<211> LENGTH: 296
<212> TYPE: DNA
<213> ORGANISM: Unknown
<220> FEATURE:
<223> OTHER INFORMATION: 5' gag leader sequence from Friend

<400> SEQUENCE: 25
ctgacgagtt cgggataccc ggccgcaacc ctgggagacg tcccagggac ttcggggcc      60
```

| | |
|---|---|
| atttttgtgg cccggccaga gtccaactat cccgatcgtt ttggactctt tggcgcaccc | 120 |
| cccttagagg aggggtatgt gattctggta ggggacggaa ggtaaaacgg tttccgcccc | 180 |
| cgtctgagtt tttgctttcg gtttggagcc gaagccgcgc cgcgcgtcct gtctgctgca | 240 |
| gcatcgttct gtgttgtttc tgtttgactg ttttttctgta tttgtctgaa aacatg | 296 |

<210> SEQ ID NO 26
<211> LENGTH: 8185
<212> TYPE: DNA
<213> ORGANISM: Unknown
<220> FEATURE:
<223> OTHER INFORMATION: XMRV VP35 complete nucleotide sequence

<400> SEQUENCE: 26
gcgccagtca tccgatagac tgagtcgccc gggtacccgt gttcccaata aagccttttg 60
ctgtttgcat ccgaagcgtg gcctcgctgt tccttgggag ggtctcctca gagtgattga 120
ctacccagct cgggggtctt tcatttgggg gctcgtccgg gattcggaga cccccgccca 180
gggaccaccg acccaccgtc gggaggtaag ccggccggcg atcgttttgt ctttgtctct 240
gtctttgtgc gtgtgtgtgt gtgccggcat ctaatcctcg cgcctgcgtc tgaatctgta 300
ctagttagct aactagatct gtatctggcg gttccgcgga agaactgacg agttcgtatt 360
cccggccgca gcccagggag acgtcccagc ggcctcgggg gcccgttttg tggcccattc 420
tgtatcagtt aacctacccg agtcggactc tttggagtgg ctttgttggg ggacgagaga 480
cagagacact tcccgccccc gtctgaattt ttgctttcgg ttttacgccg aaaccgcgcc 540
gcgcgtctga tttgttttgt tgttcttctg ttcttcgtta gtttcttct gtctttaagt 600 gttctcgaga tcatgggaca gaccgtaact acccctctga gtctaacctt gcagcactgg 660
ggagatgtcc agcgcattgc atccaaccag tctgtggatg tcaagaagag gcgctgggtt 720
accttctgtt ccgccgaatg gccaactttc aatgtaggat ggcctcagga tggtactttt 780
aatttaggtg ttatctctca ggtcaagtct agagtgtttt gtcctggtcc ccacggacac 840
ccggatcagg tcccatatat cgtcacctgg gaggcacttg cctatgaccc ccctccgtgg 900
gtcaaaccgt ttgtctctcc taaacccct cctttaccga cagctcccgt cctcccgccc 960
ggtccttctg cgcaacctcc gtcccgatct gccctttacc ctgcccttac cctctctata 1020
aagtccaaac ctcctaagcc ccaggttctc cctgatagcg gcggacctct cattgacctt 1080
ctcacagagg atcccccgcc gtacggagta caaccttcct cctctgccag ggagaacaat 1140
gaagaagagg cggccaccac ctccgaggtt tcccccctt ctcccatggt gtctcgactg 1200
cggggaagga gagaccctcc cgcagcggac tccaccacct cccaggcatt cccactccgc 1260 atgggggag atggccagct tcagtactgg ccgttttcct cctctgattt atataattgg 1320
aaaaataata acccttcctt ttctgaagat ccaggtaaat tgacggcctt gattgagtcc 1380
gtcctcatca cccaccagcc cacctgggac gactgtcagc agttgttggg gaccctgctg 1440
accggagaag aaaagcagcg ggtgctccta gaggctggaa aggcagtccg gggcaatgat 1500
ggacgcccca ctcagttgcc taatgaagtc aatgctgctt ttccccttga gcgccccgat 1560
tgggattaca ccactacaga aggtaggaac cacctagtcc tctaccgcca gttgctctta 1620
gcgggtctcc aaaacgcggg caggagcccc accaatttgg ccaaggtaaa agggataacc 1680
cagggaccta atgagtctcc ctcagccttt ttagagagac tcaaggaggc ctatcgcagg 1740
tacactcctt atgaccctga ggacccaggg caagaaacca atgtgtccat gtcattcatc 1800
tggcagtctg ccccggatat cgggcgaaag ttagagcggt tagaagattt aaagagcaag 1860

```
accttaggag acttagtgag ggaagctgaa aagatctta ataagcgaga aaccccggaa    1920
gaaagagagg aacgtatcag gagagaaata gaggaaaaag aagaacgccg tagggcagag    1980
gatgagcaga gagagagaga aagggaccgc agaagacata gagagatgag caagctcttg    2040
gccactgtag ttattggtca gagacaggat agacagggg gagagcggag gaggcccaa      2100 cttgataagg accaatgcgc ctactgcaaa gaaaagggac actgggctaa ggactgccca    2160
aagaagccac gagggccccg aggaccgagg ccccagacct ccctcctgac cttaggtgac    2220
tagggaggtc agggtcagga gccccccct gaacccagga taaccctcaa agtcgggggg     2280
caacccgtca ccttcctggt agatactggg gcccaacact ccgtgctgac ccaaaatcct    2340
ggacccctaa gtgacaagtc tgcctgggtc caagggcta ctggaggaaa gcggtatcgc     2400
tggaccacgg atcgcaaagt acatctggct accggtaagg tcacccactc tttcctccat    2460
gtaccagact gccctatcc tctgctagga agagacttgc tgactaaact aaaagcccaa     2520
atccacttcg agggatcagg agctcaggtt gtgggaccga tgggacagcc cctgcaagtg    2580 ctgacccta acatagaaaa taagtatcgg ctacatgaga cctcaaaaga gccagatgtt     2640
cctctagggt ccacatggct ttctgatttt ccccaggcct gggcggaaac cgggggcatg    2700
ggactggcag ttcgccaagc tcctctgatc atacctctga aggcaacctc taccccccgtg  2760 tccataaaac ataccccat gtcacaagaa gccagactgg ggatcaagcc ccacatacag     2820
aggctgttgg accagggaat actggtaccc tgccagtccc cctggaacac gccctgcta    2880 cccgttaaga aaccagggac taatgattat aggcctgtcc aggatctgag agaagtcaac    2940
aagcgggtgg aagacatcca ccccaccgtg cccaacccctt acaacctctt gagcgggctc   3000
ccaccgtccc accagtggta cactgtgctt gattaaagg atgcctttt ctgcctgaga      3060 ctccacccca ccagtcagcc tctcttcgcc tttgagtgga gagatccaga gatgggaatc    3120
tcaggacaac tgacctggac cagactccca caggttttca aaaacagtcc caccctgttt    3180
gatgaggcac tgcacagaga cctagcagat ttccggatcc agcacccaga cttgatcctg    3240
ctacagtacg tggatgactt actgctggcc gccacttctg agcaagactg ccaacgaggt    3300
actcgggccc tattacaaac cctagggaac ctcgggtatc gggcctcggc caagaaagcc    3360
caaatttgcc agaaacaggt caagtatctg gggtatctcc taaaagaggg acagagatgg    3420
ctgactgagg ccagaaaaga gactgtgatg gggcagccca ctccgaagac ccctcgacaa    3480
ctaagggagt tcctagggac ggcaggcttc tgtcgcctct ggatccctgg gttttgcagaa   3540 atggcagccc ccttgtaccc tcttaccaaa acggggactc tgtttaattg ggggcccagac   3600 cagcaaaagg cctatcaaga aatcaaacag gctcttctaa ctgcccccgc cctgggattg    3660
ccagatttga ctaagcccctt tgaactcttt gtcgacgaga agcagggcta cgccaaaggc    3720
gtcctaacgc aaaaactggg accttggcgt cggcctgtgg cctacctgtc caaaaagcta    3780
gacccagtgg cagctgggtg gccccccttgc ctacggatgg tagcagccat tgccgttctg   3840
acaaaggatg caggcaagct aactatggga cagccgctag tcattctggc cccccatgcg    3900
gtagaagcac tggtcaaaca accccctgac cgttggctat ccaatgcccg catgacccac    3960
tatcaggcaa tgctcctgga tacagaccgg gttcagttcg gaccggtggt ggccctcaac    4020
ccggccaccc tgctcccct accggaaaag gaagcccccc atgactgcct cgagatcttg     4080
gctgagacgc acggaaccag accggacctc acggaccagc ccatcccaga cgctgattac    4140
acttggtaca cagatggaag cagcttccta caagaaggaa aacggagagc tggagcagcg    4200
gtgactactg agaccgaggt aatctgggcg agggctctgc cggctggaac atccgcccaa    4260
```

```
cgagccgaac tgatagcact cacccaagcc ttaaagatgg cagaaggtaa gaagctaaat   4320
gtttacactg atagccgcta tgccttcgcc acggcccatg tccatggaga aatatatagg   4380
aggcgagggt tgctgacctc agaaggcaga gaaattaaaa acaagaacga gatcttggcc   4440
ttgctaaaag ctctctttct gcccaaacga cttagtataa ttcactgtcc aggacatcaa   4500
aaaggaaaca gtgctgaggc cagaggcaac cgtatggcag atcaagcagc ccgagaggca   4560
gccatgaagg cagttctaga aacctctaca ctcctcatag aggactcaac cccgtatacg   4620 cctcccatt tccattacac cgaaacagat ctcaaaagac tacgggaact gggagccacc   4680
tacaatcaga caaaaggata ttgggtccta caaggcaaac ctgtgatgcc cgatcagtcc   4740
gtgtttgaac tgttagactc cctacacaga ctcacccatc cgagccctca aaagatgaag   4800
gcactcctcg acagagaaga aagcccctac tacatgttaa accgggacag aactatccag   4860
tatgtgactg agacctgcac cgcctgtgcc caagtaaatg ccagcaaagc caaaattggg   4920
gcaggggtgc gagtacgcgg acatcggcca ggcacccatt gggaagttga tttcacggaa   4980
gtaaagccag gactgtatgg gtacaagtac ctcctagtgt ttgtagacac cttctctggc   5040
tgggtagagg cattcccgac caagcgggaa actgccaagg tcgtgtccaa aaagctgtta   5100
gaagacattt ttccgagatt tgaaatgccg caggtattgg gatctgataa cgggcctgcc   5160
ttcgcctccc aggtaagtca gtcagtggcc gatttactgg gaatcgattg gaagttacat   5220
tgtgcttata aaccccagag ttcaggacag gtagaaagaa taaataaaac aattaaggag   5280
actttaacca aattaacgct tgcatctggc actaaagact gggtactcct actccccta   5340 gccctctacc gagcccggaa tactccgggc ccccacggac tgactccgta tgaaattctg   5400 tatgggcac ccccgcccct tgtcaattt cataatcctg aaatgtcaaa gttaactaat   5460 agtccctct ccaagctca cttacaggcc ctccaagcag tacaacaaga ggtctggaag   5520
ccgctggccg ctgcttatca ggaccagcta gatcagccag tgataccaca ccccttccgt   5580
gtcggtgacg ccgtgtgggt acgccggcac cagactaaga acttagaacc tcgctggaaa   5640
ggaccctaca ccgtcctgct gacaaccccc accgctctca agtagacgg catctctgcg   5700 tggatacacg ccgctcacgt aaaggcggcg acaactcctc cggccggaac agcatggaaa   5760
gtccagcgtt ctcaaaaccc cttaaagata agattaaccc gtggggcccc ctgataatta   5820
tggggatctt ggtgagggca ggagcctcag tacaacgtga cagccctcac caggtcttta   5880
atgtcacttg gaaaattacc aacctaatga caggacaaac agctaatgct acctccctcc   5940
tggggacgat gacagacact ttccctaaac tatattttga cttgtgtgat ttagttggag   6000
acaactggga tgaccggaa cccgatattg gagatggttg ccgctctccc ggggaagaa   6060 aaaggacaag actatatgat ttctatgttt gccccggtca tactgtatta acagggtgtg   6120
gagggccgag agagggctac tgtggcaaat ggggatgtga gaccactgga caggcatact   6180
ggaagccatc atcatcatgg gacctaatttt cccttaagcg aggaaacact cctaagggtc   6240
agggcccctg tttgattcc tcagtgggct ccggtagcat ccagggtgcc acaccggggg   6300
gtcgatgcaa cccctagtc ctagaattca ctgacgcggg taaaagggcc agctgggatg   6360 cccccaaaaac atgggaacta agactgtatc gatccactgg ggccgacccg gtgaccctgt   6420
tctctctgac ccgccaggtc ctcaatgtag ggccccgcgt ccccattggg cctaatcccg   6480
tgatcactga acagctaccc ccctcccaac ccgtgcagat catgctcccc aggcctcctc   6540
gtcctcctcc ttcaggcgcg gcctctatgg tgcctgggc tccccgcct tctcaacaac   6600 ctgggacggg agacaggctg ctaaacctgg tagaaggagc ctaccaagcc ctcaacctca   6660
```

-continued

```
ccagtcccga caaaacccaa gagtgctggc tgtgtctagt atcgggaccc ccctactacg    6720
aaggggtggc cgtcctaggt acttactcca accatacctc tgccccggct aactgctccg    6780
tgacctccca acacaagctg accctgtccg aagtgaccgg gcagggactc tgcataggag    6840
cagttcccaa aacccatcag gccctgtgta ataccaccca gaagacgagc gacgggtcct    6900
actatttggc ctctcccgcc gggaccattt gggcttgcag caccgggctc actccctgtc    6960
tatctactac tgtgcttaac ttaaccactg attactgtgt cctggttgaa ctctggccaa    7020
aggtaaccta ccactcccct aattatgttt atggccagtt tggaaagaaa actaaatata    7080
aaagagagcc ggtgtcatta actctggccc tgctgttggg aggacttact atgggcggca    7140
tagctgcagg agttggaaca gggactacag ccctagtggc caccaaacaa ttcgagcagc    7200
tccaggcagc catacataca gaccttgggg ccttagaaaa atcagtcagt gccctagaaa    7260
agtctctgac ctcgttgtct gaggtggtcc tacagaaccg gaggggatta gatctactgt    7320
tcctaaaaga aggaggatta tgtgctgccc taaaaaaaga atgctgtttt tacgcggacc    7380
acactggcgt agtaagagat agcatggcaa agctaagaga aaggttaaac cagagacaaa    7440
aattgttcga atcaggacaa gggtggtttg agggactgtt taacaggtcc ccatggttca    7500
cgaccctgat atccaccatt atgggccctc tgatagtact tttattaatc ctactcttcg    7560
gaccctgtat tctcaaccgc ttggtccagt ttgtaaaaga cagaatttcg gtagtgcagg    7620
ccctggttct gacccaacag tatcaccaac tcaaatcaat agatccagaa gaagtggaat    7680
cacgtgaata aaagatttta ttcagtttcc agaaagaggg gggaatgaaa gaccccacca    7740
taaggcttag cacgctagct acagtaacgc cattttgcaa ggcatggaaa agtaccagag    7800
ctgagttctc aaaagttaca aggaagttta attaaagaat aaggctgaat aacactggga    7860
caggggccaa acaggatatc tgtagtcagg cacctgggcc ccggctcagg gccaagaaca    7920
gatggtcctc agataaagcg aaactaacaa cagtttctgg aaagtcccac ctcagtttca    7980
agttccccaa aagaccggga aatacccccaa gccttattta aactaaccaa tcagctcgct    8040
tctcgcttct gtaccgcgc ttttgctcc ccagtcctag ccctataaaa aaggggtaag    8100
aactccacac tcggcgcgcc agtcatccga tagactgagt cgcccgggta cccgtgttcc    8160
caataaagcc ttttgctgtt tgcaa    8185
```

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 271
<212> TYPE: PRT
<213> ORGANISM: Unknown
<220> FEATURE:

<223> OTHER INFORMATION: XMRV - LNCaP RV gag

<400> SEQUENCE: 30

```
Cys Thr Gly Ala Cys Gly Ala Gly Thr Thr Cys Gly Thr Ala Thr
1               5                   10                  15
Cys Cys Cys Gly Gly Cys Cys Gly Cys Ala Gly Cys Cys Thr Gly
            20                  25                  30
Gly Gly Ala Gly Ala Cys Gly Thr Cys Cys Ala Gly Cys Gly Gly
        35                  40                  45
Cys Cys Thr Cys Gly Gly Gly Gly Cys Cys Gly Thr Thr Thr
        50                  55                  60
Thr Gly Thr Gly Gly Cys Cys Ala Thr Thr Cys Thr Gly Thr Ala
65                  70                  75                  80
Thr Cys Ala Gly Thr Thr Ala Ala Cys Cys Thr Ala Cys Cys Gly
            85                  90                  95
Ala Gly Thr Cys Gly Gly Ala Cys Thr Thr Thr Thr Gly Gly Ala
            100                 105                 110
Gly Thr Gly Gly Cys Thr Thr Thr Gly Thr Gly Gly Gly Gly
        115                 120                 125
Ala Cys Gly Ala Gly Ala Gly Ala Cys Ala Gly Ala Cys Ala
    130                 135                 140
Cys Thr Thr Cys Cys Gly Cys Cys Cys Cys Gly Thr Cys Thr
145                 150                 155                 160
Gly Ala Ala Thr Thr Thr Thr Gly Cys Thr Thr Thr Cys Gly Gly
            165                 170                 175
Thr Thr Thr Thr Ala Cys Gly Cys Cys Gly Ala Ala Ala Cys Cys Gly
            180                 185                 190
Cys Gly Cys Cys Gly Cys Gly Cys Gly Thr Cys Thr Gly Ala Thr Thr
        195                 200                 205
Thr Gly Thr Thr Thr Thr Gly Thr Thr Gly Thr Thr Cys Thr Thr Cys
    210                 215                 220
Thr Gly Thr Thr Cys Thr Thr Cys Gly Thr Thr Ala Gly Thr Thr Thr
225                 230                 235                 240
Thr Cys Thr Thr Cys Thr Thr Gly Thr Thr Cys Thr Thr Ala Ala Gly Thr
            245                 250                 255
Gly Thr Thr Cys Thr Cys Gly Ala Gly Ala Thr Cys Ala Thr Gly
            260                 265                 270
```

<210> SEQ ID NO 31
<211> LENGTH: 32
<212> TYPE: DNA
<213> ORGANISM: Unknown
<220> FEATURE:
<223> OTHER INFORMATION: XMRV LNCaP-R integration site, chromosome
     10q11.22

<400> SEQUENCE: 31 ggggggtcttt cagttcttgt gctctcagag gt                                          32

<210> SEQ ID NO 32
<211> LENGTH: 32
<212> TYPE: DNA
<213> ORGANISM: Unknown
<220> FEATURE:
<223> OTHER INFORMATION: XMRV LNCaP-R integration site, chromosome 7q22

<400> SEQUENCE: 32 ggggggtcttt caacaagagc cggaatcgcc gt                                          32

```
<210> SEQ ID NO 33
<211> LENGTH: 32
<212> TYPE: DNA
<213> ORGANISM: Unknown
<220> FEATURE:
<223> OTHER INFORMATION: XMRV LNCaP-R integration site, chromosome 7p15

<400> SEQUENCE: 33
gggggtcttt cagttgtata tttcaactga ag                                32

<210> SEQ ID NO 34
<211> LENGTH: 20
<212> TYPE: DNA
<213> ORGANISM: Unknown
<220> FEATURE:
<223> OTHER INFORMATION: PCRV - Gag - Outside Forward Primer

<400> SEQUENCE: 34
cgcgtctgat ttgttttgtt                                              20

<210> SEQ ID NO 35
<211> LENGTH: 20
<212> TYPE: DNA
<213> ORGANISM: Unknown
<220> FEATURE:
<223> OTHER INFORMATION: PCRV - Gag - Outside Reverse Primer

<400> SEQUENCE: 35
ccgcctcttc ttcattgttc                                              20

<210> SEQ ID NO 36
<211> LENGTH: 20
<212> TYPE: DNA
<213> ORGANISM: Unknown
<220> FEATURE:
<223> OTHER INFORMATION: PCRV - Gag - Inside Forward Primer

<400> SEQUENCE: 36
tctcgagatc atgggacaga                                              20

<210> SEQ ID NO 37
<211> LENGTH: 20
<212> TYPE: DNA
<213> ORGANISM: Unknown
<220> FEATURE:
<223> OTHER INFORMATION: PCRV - Gag - Outside Reverse Primer

<400> SEQUENCE: 37
agagggtaag ggcagggtaa                                              20

<210> SEQ ID NO 38
<211> LENGTH: 21
<212> TYPE: DNA
<213> ORGANISM: Unknown
<220> FEATURE:
<223> OTHER INFORMATION: Env 7600 Outside Forward Primer

<400> SEQUENCE: 38
cgcttggtcc agtttgtaaa a                                            21

<210> SEQ ID NO 39
<211> LENGTH: 20
<212> TYPE: DNA
<213> ORGANISM: Unknown
<220> FEATURE:
<223> OTHER INFORMATION: Env 227 Reverse Primer
```

```
<400> SEQUENCE: 39
tggggaactt gaaactgagg                                                   20

<210> SEQ ID NO 40
<211> LENGTH: 21
<212> TYPE: DNA
<213> ORGANISM: Unknown
<220> FEATURE:
<223> OTHER INFORMATION: Env 7200 Inside Forward Primer

<400> SEQUENCE: 40
ctagtggcca ccaaacaatt c                                                 21

<210> SEQ ID NO 41
<211> LENGTH: 20
<212> TYPE: DNA
<213> ORGANISM: Unknown
<220> FEATURE:
<223> OTHER INFORMATION: Forward primer for HXV conserved 700 bp region

<400> SEQUENCE: 41
gtttatggcc agtttggaaa                                                   20

<210> SEQ ID NO 42
<211> LENGTH: 20
<212> TYPE: DNA
<213> ORGANISM: Unknown
<220> FEATURE:
<223> OTHER INFORMATION: Reverse primer for HXV conserved 700 bp region

<400> SEQUENCE: 42
gccttatggt ggggtctttc                                                   20

<210> SEQ ID NO 43
<211> LENGTH: 20
<212> TYPE: DNA
<213> ORGANISM: Unknown
<220> FEATURE:
<223> OTHER INFORMATION: Virus 2345 forward primer

<400> SEQUENCE: 43
acccctaagt gacaagtctg                                                   20

<210> SEQ ID NO 44
<211> LENGTH: 20
<212> TYPE: DNA
<213> ORGANISM: Unknown
<220> FEATURE:
<223> OTHER INFORMATION: Virus 4495 reverse primer

<400> SEQUENCE: 44
ctggacagtg aattatacta                                                   20

<210> SEQ ID NO 45
<211> LENGTH: 70
<212> TYPE: DNA
<213> ORGANISM: Unknown
<220> FEATURE:
<223> OTHER INFORMATION: oligonucleotide 9628654_317 rc derived from
      MTCR

<400> SEQUENCE: 45
ttcgctttat ctgagtacca tctgttcttg gccctgagcc ggggcccagg tgctcgacca       60
cagatatcct                                                              70
```

```
<210> SEQ ID NO 46
<211> LENGTH: 70
<212> TYPE: DNA
<213> ORGANISM: Unknown
<220> FEATURE:
<223> OTHER INFORMATION: oligonucleotide 9626955_16 rc derived from
      spleen focus-forming virus

<400> SEQUENCE: 46
tcggatgcaa tcagcaagag gctttattgg gaacacgggt acccgggcga ctcagtctgt      60
cggaggactg                                                             70

<210> SEQ ID NO 47
<211> LENGTH: 7
<212> TYPE: DNA
<213> ORGANISM: Unknown
<220> FEATURE:
<223> OTHER INFORMATION: conserved splice donor site position 204,
      involved in generation of env subgenomic RNAs

<400> SEQUENCE: 47 aggtaag                                                                 7

<210> SEQ ID NO 48
<211> LENGTH: 9
<212> TYPE: DNA
<213> ORGANISM: Unknown
<220> FEATURE:
<223> OTHER INFORMATION: conserved splice acceptor site, position 5479
      involved in generation of env subgenomic RNAs

<400> SEQUENCE: 48 cacttacag                                                               9

<210> SEQ ID NO 49
<211> LENGTH: 5
<212> TYPE: DNA
<213> ORGANISM: Unknown
<220> FEATURE:
<223> OTHER INFORMATION: CCAAT box in U3 of XMRV

<400> SEQUENCE: 49 ccaat                                                                   5

<210> SEQ ID NO 50
<211> LENGTH: 7
<212> TYPE: DNA
<213> ORGANISM: Unknown
<220> FEATURE:
<223> OTHER INFORMATION: AATAAA box in U3 of XMRV

<400> SEQUENCE: 50 tataaaa                                                                 7

<210> SEQ ID NO 51
<211> LENGTH: 6
<212> TYPE: DNA
<213> ORGANISM: Unknown
<220> FEATURE:
<223> OTHER INFORMATION: polyadenylation signal in U3 of XMRV

<400> SEQUENCE: 51 aataaa                                                                  6

<210> SEQ ID NO 52
<211> LENGTH: 15
<212> TYPE: DNA
```

<213> ORGANISM: Unknown
<220> FEATURE:
<223> OTHER INFORMATION: glucocorticoid response element in U3 of XMRV

<400> SEQUENCE: 52
agaacagatg gtcct                                                          15

<210> SEQ ID NO 53
<211> LENGTH: 14
<212> TYPE: PRT
<213> ORGANISM: Unknown
<220> FEATURE:
<223> OTHER INFORMATION: conserved MuLV NC peptide

<400> SEQUENCE: 53

Lys Asp Cys Pro Lys Lys Pro Arg Gly Pro Arg Gly Pro Arg
1               5                   10

<210> SEQ ID NO 54
<211> LENGTH: 20
<212> TYPE: DNA
<213> ORGANISM: Unknown
<220> FEATURE:
<223> OTHER INFORMATION: GAPDH exon 8 specific forward primer

<400> SEQUENCE: 54
tgccatcact gccacccaga                                                     20

<210> SEQ ID NO 55
<211> LENGTH: 20
<212> TYPE: DNA
<213> ORGANISM: Unknown
<220> FEATURE:
<223> OTHER INFORMATION: GAPDH exon 8 specific reverse primer

<400> SEQUENCE: 55
cttgacaaag tggtcgttga                                                     20

<210> SEQ ID NO 56
<211> LENGTH: 20
<212> TYPE: DNA
<213> ORGANISM: Unknown
<220> FEATURE:
<223> OTHER INFORMATION: forward primer - 4915

<400> SEQUENCE: 56
aaattggggc aggggtgcga                                                     20

<210> SEQ ID NO 57
<211> LENGTH: 20
<212> TYPE: DNA
<213> ORGANISM: Unknown
<220> FEATURE:
<223> OTHER INFORMATION: reverse primer - 6755

<400> SEQUENCE: 57
ttggagtaag tacctaggac                                                     20

<210> SEQ ID NO 58
<211> LENGTH: 23
<212> TYPE: DNA
<213> ORGANISM: Unknown
<220> FEATURE:
<223> OTHER INFORMATION: biotinylated primer B-7151F

<400> SEQUENCE: 58
tgggagttgg aacagggact aca                                                 23

-continued

<210> SEQ ID NO 59
<211> LENGTH: 35
<212> TYPE: DNA
<213> ORGANISM: Unknown
<220> FEATURE:
<223> OTHER INFORMATION: Link A

<400> SEQUENCE: 59
cggatcccgc atcatatctc caggtgtgac agttt                               35

<210> SEQ ID NO 60
<211> LENGTH: 30
<212> TYPE: DNA
<213> ORGANISM: Unknown
<220> FEATURE:
<223> OTHER INFORMATION: Link - Nsp - S

<400> SEQUENCE: 60
aacctggaga tatgatgcgg gatccgcatg                                     30

<210> SEQ ID NO 61
<211> LENGTH: 20
<212> TYPE: DNA
<213> ORGANISM: Unknown
<220> FEATURE:
<223> OTHER INFORMATION: Forward Primer V38F

<400> SEQUENCE: 61
cgtgttccca ataaagcctt                                                20

<210> SEQ ID NO 62
<211> LENGTH: 23
<212> TYPE: DNA
<213> ORGANISM: Unknown
<220> FEATURE:
<223> OTHER INFORMATION: Reverse Primer NspL-R

<400> SEQUENCE: 62
taacctggag atatgatgcg gga                                            23

<210> SEQ ID NO 63
<211> LENGTH: 284
<212> TYPE: PRT
<213> ORGANISM: Unknown
<220> FEATURE:
<223> OTHER INFORMATION: consensus sequence between HXV35 gag and DG75
      gag

<400> SEQUENCE: 63

Met Gly Gln Thr Val Thr Thr Pro Leu Ser Leu Thr Leu His Trp Gly
1               5                   10                  15

Asp Val Gln Arg Ile Ala Ser Asn Gln Ser Val Asp Val Lys Lys Arg
            20                  25                  30

Arg Trp Val Thr Phe Cys Ser Ala Glu Trp Pro Thr Phe Val Gly Trp
        35                  40                  45

Pro Gln Asp Gly Thr Phe Asn Leu Ile Gln Val Lys Ser Val Phe Pro
    50                  55                  60

Gly Pro His Gly His Pro Asp Gln Val Pro Tyr Ile Val Thr Trp Glu
65                  70                  75                  80

Ala Leu Ala Tyr Asp Pro Pro Pro Trp Val Lys Pro Phe Val Ser Pro
                85                  90                  95

Lys Pro Pro Pro Leu Pro Thr Ala Pro Val Leu Pro Pro Gly Pro Ser
            100                 105                 110

Ala Gln Pro Pro Ser Arg Ser Ala Leu Tyr Pro Ala Leu Thr Ser Ile
            115                 120                 125

Lys Lys Pro Pro Lys Pro Gln Val Leu Pro Asp Gly Pro Leu Ile
    130                 135                 140

Asp Leu Leu Thr Glu Asp Pro Pro Tyr Gly Gln Pro Ser Ser Ser
145                 150                 155                 160

Ala Arg Asn Glu Glu Glu Ala Ala Thr Ser Glu Val Ser Pro Ser
                165                 170                 175

Pro Met Val Ser Arg Leu Arg Gly Arg Arg Asp Pro Pro Ala Ala Asp
            180                 185                 190

Ser Thr Ser Gln Ala Phe Pro Leu Arg Met Gly Gly Asp Gly Gln Leu
            195                 200                 205

Gln Tyr Trp Pro Phe Ser Ser Asp Leu Tyr Asn Trp Lys Asn Asn
    210                 215                 220

Asn Pro Ser Phe Ser Glu Asp Pro Gly Lys Leu Thr Ala Leu Ile Glu
225                 230                 235                 240

Ser Val Leu Ile Thr His Gln Pro Thr Trp Asp Asp Cys Gln Gln Leu
                245                 250                 255

Leu Gly Thr Leu Leu Thr Gly Glu Glu Lys Gln Arg Val Leu Leu Glu
            260                 265                 270

Ala Lys Ala Val Arg Gly Asn Asp Gly Arg Pro Thr
    275                 280

<210> SEQ ID NO 64
<211> LENGTH: 537
<212> TYPE: PRT
<213> ORGANISM: Unknown
<220> FEATURE:
<223> OTHER INFORMATION: DG75 gag

<400> SEQUENCE: 64

Met Gly Gln Thr Val Thr Thr Pro Leu Ser Leu Thr Leu Glu His Trp
1               5                   10                  15

Gly Asp Val Gln Arg Ile Ala Ser Asn Gln Ser Val Asp Val Lys Lys
            20                  25                  30

Arg Arg Trp Val Thr Phe Cys Ser Ala Glu Trp Pro Thr Phe Asp Val
        35                  40                  45

Gly Trp Pro Gln Asp Gly Thr Phe Asn Leu Asp Ile Ile Leu Gln Val
    50                  55                  60

Lys Ser Lys Val Phe Ser Pro Gly Pro His Gly His Pro Asp Gln Val
65              70                  75                  80

Pro Tyr Ile Val Thr Trp Glu Ala Leu Ala Tyr Asp Pro Pro Trp
            85                  90                  95

Val Lys Pro Phe Val Ser Pro Lys Pro Pro Leu Pro Thr Ala Pro
                100                 105                 110

Val Leu Pro Pro Gly Pro Ser Ala Gln Pro Pro Ser Arg Ser Ala Leu
            115                 120                 125

Tyr Pro Ala Leu Thr Pro Ser Ile Lys Thr Lys Pro Pro Lys Pro Gln
    130                 135                 140

Val Leu Pro Asp Asn Gly Gly Pro Leu Ile Asp Leu Leu Thr Glu Asp
145                 150                 155                 160

Pro Pro Pro Tyr Gly Ala Gln Pro Ser Ser Ser Ala Arg Gly Asn Asp
                165                 170                 175

Glu Glu Glu Ala Ala Thr Ser Glu Val Ser Pro Ser Pro Met
            180                 185                 190

```
Val Ser Arg Leu Arg Gly Arg Arg Asp Pro Ala Ala Asp Ser Thr
    195                 200                 205

Ser Ser Gln Ala Phe Pro Leu Arg Met Gly Gly Asp Gly Gln Leu Gln
    210                 215                 220

Tyr Trp Pro Phe Ser Ser Asp Leu Tyr Asn Trp Lys Asn Asn
225                 230                 235                 240

Pro Ser Phe Ser Glu Asp Pro Gly Lys Leu Thr Ala Leu Ile Glu Ser
                245                 250                 255

Val Leu Ile Thr His Gln Pro Thr Trp Asp Asp Cys Gln Gln Leu Leu
                260                 265                 270

Gly Thr Leu Leu Thr Gly Glu Glu Lys Gln Arg Val Leu Leu Glu Ala
                275                 280                 285

Arg Lys Ala Val Arg Gly Asn Asp Gly Arg Pro Thr Gln Leu Pro Asn
290                 295                 300

Glu Val Asn Ala Ala Phe Pro Leu Glu Arg Pro Asp Trp Asp Tyr Thr
305                 310                 315                 320

Thr Thr Glu Gly Arg Asn His Leu Val Leu Tyr Arg Gln Leu Leu Leu
                325                 330                 335

Ala Gly Leu Gln Asn Ala Gly Arg Ser Pro Thr Asn Leu Ala Lys Val
                340                 345                 350

Lys Gly Ile Thr Gln Gly Pro Asn Glu Ser Pro Ser Ala Phe Leu Glu
                355                 360                 365

Arg Leu Lys Glu Ala Tyr Arg Arg Tyr Thr Pro Tyr Asp Pro Glu Asp
                370                 375                 380

Pro Gly Gln Glu Thr Asn Val Ser Met Ser Phe Ile Trp Gln Ser Ala
385                 390                 395                 400

Pro Asp Ile Gly Arg Lys Leu Glu Arg Leu Glu Asp Leu Lys Ser Lys
                405                 410                 415

Thr Leu Gly Asp Leu Val Arg Glu Ala Glu Lys Ile Phe Asn Lys Arg
                420                 425                 430

Glu Thr Pro Glu Glu Arg Glu Arg Ile Arg Arg Glu Thr Glu Glu
                435                 440                 445

Lys Glu Glu Arg Arg Ala Glu Asp Glu Gln Arg Glu Lys Glu Arg
450                 455                 460

Asp Arg Lys Arg His Arg Glu Met Ser Lys Leu Leu Ala Thr Val Val
465                 470                 475                 480

Ser Gly Gln Arg Gln Asp Arg Gln Gly Gly Glu Arg Arg Pro Gln
                485                 490                 495

Leu Asp Lys Asp Gln Cys Ala Tyr Cys Lys Glu Lys Gly His Trp Ala
                500                 505                 510

Lys Asp Cys Pro Lys Lys Pro Arg Gly Pro Arg Gly Pro Arg Pro
                515                 520                 525

Gln Thr Ser Leu Leu Thr Leu Gly Asp
    530                 535

<210> SEQ ID NO 65
<211> LENGTH: 1157
<212> TYPE: PRT
<213> ORGANISM: Unknown
<220> FEATURE:
<223> OTHER INFORMATION: consensus sequence between HXV35 pro-pol and
      DG75 pro-pol

<400> SEQUENCE: 65

Gly Gly Gln Gly Gln Glu Pro Pro Glu Pro Arg Ile Thr Leu Lys
1               5                   10                  15
```

```
Val Gly Gly Gln Pro Val Thr Phe Leu Val Asp Thr Gly Ala Gln His
         20                  25                  30

Ser Val Leu Thr Gln Asn Pro Gly Pro Leu Ser Asp Lys Ser Ala Trp
         35                  40                  45

Val Gln Gly Ala Thr Gly Gly Lys Arg Tyr Arg Trp Thr Thr Asp Arg
 50                  55                  60

Lys Val His Leu Ala Thr Gly Lys Val Thr His Ser Phe Leu His Val
 65                  70                  75                  80

Pro Asp Cys Pro Tyr Pro Leu Leu Gly Arg Asp Leu Leu Thr Lys Leu
                 85                  90                  95

Lys Ala Gln Ile His Phe Glu Gly Ser Gly Ala Gln Val Val Gly Pro
                100                 105                 110

Met Gly Gln Pro Leu Gln Val Leu Thr Leu Asn Ile Glu Tyr Arg Leu
         115                 120                 125

His Glu Thr Ser Glu Pro Asp Val Leu Gly Ser Thr Trp Leu Ser Asp
     130                 135                 140

Phe Pro Gln Ala Trp Ala Glu Thr Gly Met Gly Leu Ala Val Arg Gln
145                 150                 155                 160

Ala Pro Leu Ile Ile Pro Leu Lys Ala Thr Ser Thr Pro Val Ser Ile
                165                 170                 175

Lys Gln Tyr Pro Met Ser Gln Glu Ala Arg Leu Gly Ile Lys Pro His
            180                 185                 190

Ile Gln Arg Leu Leu Asp Gln Gly Ile Leu Val Pro Cys Gln Ser Pro
        195                 200                 205

Trp Asn Thr Pro Leu Leu Pro Val Lys Lys Pro Gly Thr Asn Asp Tyr
    210                 215                 220

Arg Pro Val Gln Asp Leu Arg Glu Val Asn Lys Arg Val Glu Asp Ile
225                 230                 235                 240

His Pro Thr Val Pro Asn Pro Tyr Asn Leu Leu Ser Gly Leu Pro Pro
                245                 250                 255

Ser His Gln Trp Tyr Thr Val Leu Asp Leu Lys Asp Ala Phe Phe Cys
            260                 265                 270

Leu Arg Leu His Pro Thr Ser Gln Pro Leu Phe Ala Phe Glu Trp Arg
        275                 280                 285

Asp Pro Glu Met Gly Ile Ser Gly Gln Leu Thr Trp Thr Arg Leu Pro
    290                 295                 300

Gln Gly Phe Lys Asn Ser Pro Thr Leu Phe Asp Glu Ala Leu His Arg
305                 310                 315                 320

Asp Leu Ala Asp Phe Arg Ile Gln His Pro Asp Leu Ile Leu Leu Gln
                325                 330                 335

Tyr Val Asp Asp Leu Leu Ala Ala Thr Ser Glu Asp Cys Gln Gly Thr
            340                 345                 350

Arg Ala Leu Leu Thr Leu Gly Asn Leu Gly Tyr Arg Ala Ser Ala Lys
        355                 360                 365

Lys Ala Gln Cys Gln Lys Gln Val Lys Tyr Leu Gly Tyr Leu Leu Lys
    370                 375                 380

Glu Gly Gln Arg Trp Leu Thr Glu Ala Arg Lys Glu Thr Val Met Gly
385                 390                 395                 400

Gln Pro Thr Pro Lys Thr Pro Arg Gln Leu Arg Glu Phe Leu Gly Thr
                405                 410                 415

Ala Gly Phe Cys Arg Leu Trp Ile Pro Gly Phe Ala Glu Met Ala Ala
            420                 425                 430

Pro Leu Tyr Pro Leu Thr Lys Thr Gly Thr Leu Phe Asn Trp Gly Pro
        435                 440                 445
```

```
Asp Gln Gln Lys Ala Tyr Gln Glu Ile Lys Gln Ala Leu Leu Thr Ala
    450                 455                 460
Pro Ala Leu Gly Leu Pro Asp Leu Thr Lys Pro Phe Glu Leu Phe Val
465                 470                 475                 480
Asp Glu Lys Gln Gly Tyr Ala Lys Gly Val Leu Thr Gln Lys Leu Gly
                485                 490                 495
Pro Trp Arg Arg Pro Val Ala Tyr Leu Ser Lys Lys Leu Asp Pro Val
            500                 505                 510
Ala Ala Trp Pro Pro Cys Leu Arg Met Val Ala Ala Ile Ala Val Leu
        515                 520                 525
Thr Lys Asp Ala Gly Lys Leu Thr Met Gly Gln Pro Leu Val Ile Leu
    530                 535                 540
Ala Pro His Ala Val Glu Ala Leu Val Lys Gln Pro Pro Asp Arg Trp
545                 550                 555                 560
Leu Ser Asn Ala Arg Met Thr His Tyr Gln Ala Met Leu Leu Asp Thr
                565                 570                 575
Asp Arg Val Gln Phe Gly Pro Val Val Ala Leu Asn Pro Ala Thr Leu
            580                 585                 590
Leu Pro Leu Pro Glu Lys Ala Pro His Asp Cys Leu Glu Ile Leu Ala
        595                 600                 605
Glu Thr His Gly Thr Arg Pro Asp Leu Thr Asp Gln Pro Ile Pro Asp
    610                 615                 620
Ala Asp Thr Trp Tyr Thr Asp Gly Ser Ser Phe Leu Gln Glu Gly Gln
625                 630                 635                 640
Arg Arg Ala Gly Ala Ala Val Thr Thr Glu Thr Glu Val Ile Trp Ala
                645                 650                 655
Arg Ala Leu Pro Ala Gly Thr Ser Ala Gln Arg Ala Glu Leu Ile Ala
            660                 665                 670
Leu Thr Gln Ala Leu Lys Met Ala Glu Gly Lys Lys Leu Asn Val Tyr
        675                 680                 685
Thr Asp Ser Arg Tyr Ala Phe Ala Thr Ala His Val His Gly Glu Ile
    690                 695                 700
Tyr Arg Arg Arg Gly Leu Leu Thr Ser Glu Gly Arg Glu Ile Lys Asn
705                 710                 715                 720
Lys Glu Ile Leu Ala Leu Leu Lys Ala Leu Phe Leu Pro Lys Arg Leu
                725                 730                 735
Ser Ile Ile His Cys Pro Gly His Gln Lys Gly Asn Ser Ala Glu Ala
            740                 745                 750
Arg Gly Asn Arg Met Ala Asp Gln Ala Ala Arg Glu Ala Ala Glu Thr
        755                 760                 765
Ser Thr Leu Leu Ile Glu Asp Ser Thr Pro Tyr Thr Pro His Phe His
    770                 775                 780
Tyr Thr Glu Thr Asp Leu Lys Arg Leu Arg Glu Leu Gly Ala Thr Tyr
785                 790                 795                 800
Asn Gln Lys Gly Tyr Trp Val Leu Gln Gly Lys Pro Val Met Pro Asp
                805                 810                 815
Gln Val Phe Glu Leu Leu Asp Ser Leu His Arg Leu Thr His Ser Pro
            820                 825                 830
Gln Lys Met Lys Ala Leu Leu Asp Asp Arg Glu Glu Ser Pro Tyr Tyr
        835                 840                 845
Met Leu Asn Arg Asp Arg Thr Gln Tyr Val Glu Cys Thr Ala Cys Ala
    850                 855                 860
Gln Val Asn Ala Ser Lys Ala Lys Ile Gly Ala Gly Val Arg Arg Gly
```

```
                865                 870                 875                 880
His Arg Pro Gly Thr His Trp Glu Asp Phe Thr Glu Val Lys Pro Gly
                    885                 890                 895

Leu Tyr Gly Tyr Lys Tyr Leu Leu Val Phe Val Asp Thr Phe Ser Gly
            900                 905                 910

Trp Val Glu Ala Phe Pro Thr Lys Arg Glu Thr Ala Lys Val Val Lys
        915                 920                 925

Lys Leu Leu Glu Ile Phe Pro Arg Phe Met Pro Gln Val Leu Gly Ser
    930                 935                 940

Asp Asn Gly Pro Ala Phe Ser Gln Val Ser Ser Val Ala Asp Leu Leu
945                 950                 955                 960

Gly Ile Asp Trp Lys Leu His Cys Ala Tyr Pro Gln Ser Ser Gly Gln
                965                 970                 975

Val Glu Arg Asn Thr Ile Lys Glu Thr Leu Thr Lys Leu Thr Leu Ala
            980                 985                 990

Gly Thr Asp Trp Val Leu Leu Pro Leu Ala Leu Tyr Arg Ala Arg
        995                 1000                1005

Asn Thr Pro Gly Pro His Gly Leu Thr Pro Tyr Glu Ile Leu Tyr Gly
    1010                1015                1020

Ala Pro Pro Leu Val Asn Phe His Pro Glu Met Ser Lys Leu Thr
1025                1030                1035                1040

Asn Ser Pro Ser Leu Gln Ala His Leu Gln Ala Leu Gln Ala Val Gln
                1045                1050                1055

Glu Val Trp Lys Pro Leu Ala Ala Ala Tyr Gln Asp Gln Leu Asp Gln
            1060                1065                1070

Pro Val Ile Pro His Pro Phe Arg Val Gly Asp Ala Val Trp Val Arg
        1075                1080                1085

Arg His Gln Thr Lys Asn Leu Glu Pro Arg Trp Lys Gly Pro Tyr Thr
    1090                1095                1100

Val Leu Leu Thr Thr Pro Thr Ala Leu Lys Val Asp Gly Ile Ser Ala
1105                1110                1115                1120

Trp Ile His Ala Ala His Val Lys Ala Ala Thr Thr Pro Pro Ala Gly
                1125                1130                1135

Thr Ala Trp Lys Val Gln Arg Ser Gln Asn Pro Leu Lys Ile Arg Leu
            1140                1145                1150

Thr Arg Gly Ala Pro
        1155

<210> SEQ ID NO 66
<211> LENGTH: 1197
<212> TYPE: PRT
<213> ORGANISM: Unknown
<220> FEATURE:
<223> OTHER INFORMATION: DG75 pro-pol

<400> SEQUENCE: 66

Gly Gly Gln Gly Gln Glu Pro Pro Glu Pro Arg Ile Thr Leu Lys
1               5                   10                  15

Val Gly Gly Gln Pro Val Thr Phe Leu Val Asp Thr Gly Ala Gln His
            20                  25                  30

Ser Val Leu Thr Gln Asn Pro Gly Pro Leu Ser Asp Lys Ser Ala Trp
        35                  40                  45

Val Gln Gly Ala Thr Gly Gly Lys Arg Tyr Arg Trp Thr Thr Asp Arg
    50                  55                  60

Lys Val His Leu Ala Thr Gly Lys Val Thr His Ser Phe Leu His Val
65                  70                  75                  80
```

-continued

```
Pro Asp Cys Pro Tyr Pro Leu Leu Gly Arg Asp Leu Leu Thr Lys Leu
                85                  90                  95

Lys Ala Gln Ile His Phe Glu Gly Ser Gly Ala Gln Val Val Gly Pro
            100                 105                 110

Met Gly Gln Pro Leu Gln Val Leu Thr Leu Asn Ile Glu Asp Glu Tyr
            115                 120                 125

Arg Leu His Glu Thr Ser Thr Glu Pro Asp Val Ser Leu Gly Ser Thr
        130                 135                 140

Trp Leu Ser Asp Phe Pro Gln Ala Trp Ala Glu Thr Gly Met Gly
145                 150                 155                 160

Leu Ala Val Arg Gln Ala Pro Leu Ile Ile Pro Leu Lys Ala Thr Ser
                165                 170                 175

Thr Pro Val Ser Ile Lys Gln Tyr Pro Met Ser Gln Glu Ala Arg Leu
            180                 185                 190

Gly Ile Lys Pro His Ile Gln Arg Leu Leu Asp Gln Gly Ile Leu Val
        195                 200                 205

Pro Cys Gln Ser Pro Trp Asn Thr Pro Leu Leu Pro Val Lys Lys Pro
    210                 215                 220

Gly Thr Asn Asp Tyr Arg Pro Val Gln Asp Leu Arg Glu Val Asn Lys
225                 230                 235                 240

Arg Val Glu Asp Ile His Pro Thr Val Pro Asn Pro Tyr Asn Leu Leu
                245                 250                 255

Ser Gly Leu Pro Pro Ser His Gln Trp Tyr Thr Val Leu Asp Leu Lys
            260                 265                 270

Asp Ala Phe Phe Cys Leu Arg Leu His Pro Thr Ser Gln Pro Leu Phe
        275                 280                 285

Ala Phe Glu Trp Arg Asp Pro Glu Met Gly Ile Ser Gly Gln Leu Thr
    290                 295                 300

Trp Thr Arg Leu Pro Gln Gly Phe Lys Asn Ser Pro Thr Leu Phe Asp
305                 310                 315                 320

Glu Ala Leu His Arg Asp Leu Ala Asp Phe Arg Ile Gln His Pro Asp
                325                 330                 335

Leu Ile Leu Leu Gln Tyr Val Asp Asp Ile Leu Leu Ala Ala Thr Ser
            340                 345                 350

Glu Leu Asp Cys Gln Gln Gly Thr Arg Ala Leu Leu Leu Thr Leu Gly
        355                 360                 365

Asn Leu Gly Tyr Arg Ala Ser Ala Lys Lys Ala Gln Leu Cys Gln Lys
    370                 375                 380

Gln Val Lys Tyr Leu Gly Tyr Leu Leu Lys Glu Gly Gln Arg Trp Leu
385                 390                 395                 400

Thr Glu Ala Arg Lys Glu Thr Val Met Gly Pro Thr Pro Lys Thr
                405                 410                 415

Pro Arg Gln Leu Arg Glu Phe Leu Gly Thr Ala Gly Phe Cys Arg Leu
            420                 425                 430

Trp Ile Pro Gly Phe Ala Glu Met Ala Ala Pro Leu Tyr Pro Leu Thr
        435                 440                 445

Lys Thr Gly Thr Leu Phe Asn Trp Gly Pro Asp Gln Gln Lys Ala Tyr
    450                 455                 460

Gln Glu Ile Lys Gln Ala Leu Leu Thr Ala Pro Ala Leu Gly Leu Pro
465                 470                 475                 480

Asp Leu Thr Lys Pro Phe Glu Leu Phe Val Asp Glu Lys Gln Gly Tyr
                485                 490                 495

Ala Lys Gly Val Leu Thr Gln Lys Leu Gly Pro Trp Arg Arg Pro Val
```

```
                500             505             510
Ala Tyr Leu Ser Lys Lys Leu Asp Pro Val Ala Ala Arg Trp Pro Pro
            515                 520                 525
Cys Leu Arg Met Val Ala Ala Ile Ala Val Leu Thr Lys Asp Ala Gly
            530                 535                 540
Lys Leu Thr Met Gly Gln Pro Leu Val Ile Leu Ala Pro His Ala Val
545                 550                 555                 560
Glu Ala Leu Val Lys Gln Pro Pro Asp Arg Trp Leu Ser Asn Ala Arg
            565                 570                 575
Met Thr His Tyr Gln Ala Met Leu Leu Asp Thr Asp Arg Val Gln Phe
            580                 585                 590
Gly Pro Val Val Ala Leu Asn Pro Ala Thr Leu Leu Pro Leu Pro Glu
            595                 600                 605
Lys Gly Ala Pro His Asp Cys Leu Glu Ile Leu Ala Glu Thr His Gly
            610                 615                 620
Thr Arg Pro Asp Leu Thr Asp Gln Pro Ile Pro Asp Ala Asp His Thr
625                 630                 635                 640
Trp Tyr Thr Asp Gly Ser Ser Phe Leu Gln Glu Gly Gln Arg Arg Ala
            645                 650                 655
Gly Ala Ala Val Thr Thr Glu Thr Glu Val Ile Trp Ala Arg Ala Leu
            660                 665                 670
Pro Ala Gly Thr Ser Ala Gln Arg Ala Glu Leu Ile Ala Leu Thr Gln
            675                 680                 685
Ala Leu Lys Met Ala Glu Gly Lys Lys Leu Asn Val Tyr Thr Asp Ser
            690                 695                 700
Arg Tyr Ala Phe Ala Thr Ala His Val His Gly Glu Ile Tyr Arg Arg
705                 710                 715                 720
Arg Gly Leu Leu Thr Ser Glu Gly Arg Glu Ile Lys Asn Lys Ser Glu
            725                 730                 735
Ile Leu Ala Leu Leu Lys Ala Leu Phe Leu Pro Lys Arg Leu Ser Ile
            740                 745                 750
Ile His Cys Pro Gly His Gln Lys Gly Asn Ser Ala Glu Ala Arg Gly
            755                 760                 765
Asn Arg Met Ala Asp Gln Ala Ala Arg Glu Ala Ala Ile Arg Thr Ser
            770                 775                 780
Pro Glu Thr Ser Thr Leu Leu Ile Glu Asp Ser Thr Pro Tyr Thr Pro
785                 790                 795                 800
Ser His Phe His Tyr Thr Glu Thr Asp Leu Lys Arg Leu Arg Glu Leu
            805                 810                 815
Gly Ala Thr Tyr Asn Gln Ile Lys Gly Tyr Trp Val Leu Gln Gly Lys
            820                 825                 830
Pro Val Met Pro Asp Gln Phe Val Phe Glu Leu Leu Asp Ser Leu His
            835                 840                 845
Arg Leu Thr Leu Pro Ser Pro Gln Lys Met Lys Ala Leu Leu Asp Asp
            850                 855                 860
Arg Glu Glu Ser Pro Tyr Tyr Met Leu Asn Arg Asp Arg Thr Leu Gln
865                 870                 875                 880
Tyr Val Ala Glu Ser Cys Thr Ala Cys Ala Gln Val Asn Ala Ser Lys
            885                 890                 895
Ala Lys Ile Gly Ala Gly Val Arg Ile Arg Gly His Arg Pro Gly Thr
            900                 905                 910
His Trp Glu Ile Asp Phe Thr Glu Val Lys Pro Gly Leu Tyr Gly Tyr
            915                 920                 925
```

```
Lys Tyr Leu Leu Val Phe Val Asp Thr Phe Ser Gly Trp Val Glu Ala
            930                 935                 940

Phe Pro Thr Lys Arg Glu Thr Ala Lys Val Val Thr Lys Lys Leu Leu
945                 950                 955                 960

Glu Glu Ile Phe Pro Arg Phe Gly Met Pro Gln Val Leu Gly Ser Asp
                965                 970                 975

Asn Gly Pro Ala Phe Val Ser Gln Val Ser His Ser Val Ala Asp Leu
            980                 985                 990

Leu Gly Ile Asp Trp Lys Leu His Cys Ala Tyr Arg Pro Gln Ser Ser
        995                1000                1005

Gly Gln Val Glu Arg Met Asn Arg Thr Ile Lys Glu Thr Leu Thr Lys
           1010                1015                1020

Leu Thr Leu Ala Ala Gly Thr Arg Asp Trp Val Leu Leu Pro Leu
1025                1030                1035                1040

Ala Leu Tyr Arg Ala Arg Asn Thr Pro Gly Pro His Gly Leu Thr Pro
               1045                1050                1055

Tyr Glu Ile Leu Tyr Gly Ala Pro Pro Leu Val Asn Phe His Asp
               1060                1065                1070

Pro Glu Met Ser Lys Leu Thr Asn Ser Pro Ser Leu Gln Ala His Leu
           1075                1080                1085

Gln Ala Leu Gln Ala Val Gln Arg Glu Val Trp Lys Pro Leu Ala Ala
        1090                1095                1100

Ala Tyr Gln Asp Gln Leu Asp Gln Pro Val Ile Pro His Pro Phe Arg
1105                1110                1115                1120

Val Gly Asp Ala Val Trp Val Arg Arg His Gln Thr Lys Asn Leu Glu
               1125                1130                1135

Pro Arg Trp Lys Gly Pro Tyr Thr Val Leu Leu Thr Thr Pro Thr Ala
           1140                1145                1150

Leu Lys Val Asp Gly Ile Ser Ala Trp Ile His Ala Ala His Val Lys
        1155                1160                1165

Ala Ala Thr Thr Pro Pro Ala Gly Thr Ala Trp Lys Val Gln Arg Ser
        1170                1175                1180

Gln Asn Pro Leu Lys Ile Arg Leu Thr Arg Gly Ala Pro
1185                1190                1195

<210> SEQ ID NO 67
<211> LENGTH: 606
<212> TYPE: PRT
<213> ORGANISM: Unknown
<220> FEATURE:
<223> OTHER INFORMATION: consensus sequence between HXV35 env and DG75
      env

<400> SEQUENCE: 67

Met Glu Pro Ala Phe Ser Lys Pro Leu Lys Asp Lys Ile Asn Pro Trp
1               5                  10                  15

Gly Pro Leu Ile Met Gly Ile Leu Val Arg Ala Gly Ala Ser Val Gln
            20                  25                  30

Arg Asp Ser Pro His Gln Phe Asn Val Thr Trp Thr Asn Leu Met Thr
        35                  40                  45

Gly Gln Thr Ala Asn Ala Thr Ser Leu Leu Gly Thr Met Thr Asp Thr
    50                  55                  60

Phe Pro Lys Leu Tyr Phe Asp Leu Cys Asp Leu Val Gly Asp Trp Asp
65                  70                  75                  80

Asp Pro Glu Pro Asp Ile Gly Asp Gly Cys Arg Pro Gly Gly Arg Arg
                85                  90                  95
```

```
Thr Arg Leu Thr Asp Phe Tyr Val Cys Pro Gly His Thr Val Gly Cys
            100                 105                 110
Gly Gly Pro Glu Gly Tyr Cys Gly Lys Trp Gly Cys Glu Thr Thr Gly
        115                 120                 125
Gln Ala Tyr Trp Lys Pro Ser Ser Ser Trp Asp Leu Ile Ser Leu Lys
    130                 135                 140
Arg Gly Asn Thr Pro Lys Gln Gly Pro Cys Asp Ser Ser Val Ser Gly
145                 150                 155                 160
Gln Gly Ala Thr Pro Gly Gly Arg Cys Asn Pro Leu Val Leu Glu Phe
                165                 170                 175
Thr Asp Ala Gly Ala Ser Trp Asp Ala Pro Lys Trp Gly Leu Arg Leu
            180                 185                 190
Tyr Arg Ser Thr Gly Ala Asp Pro Val Thr Phe Ser Leu Thr Arg Gln
        195                 200                 205
Val Leu Asn Val Gly Pro Arg Pro Ile Gly Pro Asn Pro Val Ile Thr
    210                 215                 220
Gln Leu Pro Pro Ser Gln Pro Val Gln Ile Met Leu Pro Arg Pro Pro
225                 230                 235                 240
Pro Pro Pro Ser Ser Met Val Pro Gly Ala Pro Pro Pro Ser Gln Gln
                245                 250                 255
Pro Gly Thr Gly Asp Arg Leu Leu Asn Leu Val Glu Gly Ala Tyr Gln
            260                 265                 270
Ala Leu Asn Leu Thr Ser Pro Asp Lys Thr Gln Glu Cys Trp Leu Cys
        275                 280                 285
Leu Val Ser Gly Pro Pro Tyr Tyr Glu Gly Val Ala Val Leu Gly Thr
    290                 295                 300
Tyr Ser Asn His Thr Ser Ala Pro Ala Asn Cys Ser Val Ser Gln His
305                 310                 315                 320
Lys Leu Thr Leu Ser Glu Val Thr Gly Gln Gly Leu Cys Gly Ala Val
                325                 330                 335
Pro Lys Thr His Gln Ala Leu Cys Asn Thr Thr Gln Lys Thr Ser Asp
            340                 345                 350
Gly Ser Tyr Tyr Leu Ala Pro Ala Gly Thr Ile Trp Ala Cys Thr Gly
        355                 360                 365
Leu Thr Pro Cys Leu Ser Thr Thr Val Leu Asn Leu Thr Thr Asp Tyr
    370                 375                 380
Cys Val Leu Val Glu Leu Trp Pro Lys Val Thr Tyr His Ser Pro Tyr
385                 390                 395                 400
Val Tyr Gly Gln Phe Lys Thr Lys Tyr Lys Arg Glu Pro Val Ser Leu
                405                 410                 415
Thr Leu Ala Leu Leu Leu Gly Gly Leu Thr Met Gly Gly Ile Ala Ala
            420                 425                 430
Gly Val Gly Thr Gly Thr Thr Ala Leu Val Ala Thr Lys Gln Phe Glu
        435                 440                 445
Gln Leu Gln Ala Ala Ile Leu Gly Ala Leu Glu Lys Ser Val Ser Ala
    450                 455                 460
Leu Glu Lys Ser Leu Thr Ser Leu Ser Glu Val Val Leu Gln Asn Arg
465                 470                 475                 480
Arg Gly Leu Asp Leu Leu Phe Leu Lys Glu Gly Gly Leu Cys Ala Ala
                485                 490                 495
Leu Lys Glu Cys Cys Phe Tyr Ala Asp His Thr Gly Val Val Arg Asp
            500                 505                 510
Ser Met Ala Lys Leu Arg Glu Arg Leu Asn Gln Arg Gln Lys Leu Phe
        515                 520                 525
```

Glu Ser Gly Gln Gly Trp Phe Glu Gly Leu Phe Asn Arg Ser Pro Trp
    530                 535                 540

Phe Thr Thr Leu Ile Ser Thr Ile Met Gly Pro Leu Ile Val Leu Leu
545                 550                 555                 560

Leu Ile Leu Leu Phe Gly Pro Cys Ile Leu Asn Arg Leu Val Gln Phe
                565                 570                 575

Val Lys Arg Ile Ser Val Val Gln Ala Leu Val Leu Thr Gln Gln Tyr
            580                 585                 590

His Gln Leu Lys Ser Ile Asp Pro Glu Val Glu Ser Arg Glu
        595                 600                 605

<210> SEQ ID NO 68
<211> LENGTH: 644
<212> TYPE: PRT
<213> ORGANISM: Unknown
<220> FEATURE:
<223> OTHER INFORMATION: DG75 env

<400> SEQUENCE: 68

Met Glu Gly Pro Ala Phe Ser Lys Pro Leu Lys Asp Lys Ile Asn Pro
1               5                   10                  15

Trp Gly Pro Leu Ile Val Met Gly Ile Leu Val Arg Ala Gly Ala Ser
            20                  25                  30

Val Gln Arg Asp Ser Pro His Gln Ile Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Tyr Trp Asp Asp Pro Glu Pro Asp Ile Gly Asp Gly Cys
                85                  90                  95

Arg Thr Pro Gly Gly Arg Lys Arg Thr Arg Leu Thr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175

Gly Ala Thr Pro Gly Gly Arg Cys Asn Pro Leu Val Leu Glu Phe Thr
            180                 185                 190

Asp Ala Gly Arg Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Pro Arg Ile Pro Ile Gly Pro Asn
225                 230                 235                 240

Pro Val Ile Thr Asp Gln Leu Pro Pro Ser Gln Pro Val Gln Ile Met
                245                 250                 255

Leu Pro Arg Pro Pro His Pro Pro Pro Ser Asp Thr Val Ser Met Val
            260                 265                 270

Pro Gly Ala Pro Pro Pro Ser Gln Gln Pro Gly Thr Gly Asp Arg Leu
        275                 280                 285

-continued

```
Leu Asn Leu Val Glu Gly Ala Tyr Gln Ala Leu Asn Leu Thr Ser Pro
            290                 295                 300

Asp Lys Thr Gln Glu Cys Trp Leu Cys Leu Val Ser Gly Pro Pro Tyr
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
                340                 345                 350

Val Thr Gly Gln Gly Leu Cys Val Gly Ala Val Pro Lys Thr His Gln
            355                 360                 365

Ala Leu Cys Asn Thr Thr Gln Lys Thr Ser Asp Gly Ser Tyr Tyr Leu
        370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asn Leu Thr Thr Asp Tyr Cys Val Leu
                405                 410                 415

Val Glu Leu Trp Pro Lys Val Thr Tyr His Ser Pro Gly Tyr Val Tyr
            420                 425                 430

Gly Gln Phe Glu Arg Lys Thr Lys Tyr Lys Arg Glu Pro Val Ser Leu
        435                 440                 445

Thr Leu Ala Leu Leu Leu Gly Gly Leu Thr Met Gly Gly Ile Ala Ala
450                 455                 460

Gly Val Gly Thr Gly Thr Thr Ala Leu Val Ala Thr Lys Gln Phe Glu
465                 470                 475                 480

Gln Leu Gln Ala Ala Ile Leu Gln Thr Leu Gly Ala Leu Glu Lys Ser
                485                 490                 495

Val Ser Ala Leu Glu Lys Ser Leu Thr Ser Leu Ser Glu Val Val Leu
            500                 505                 510

Gln Asn Arg Arg Gly Leu Asp Leu Leu Phe Leu Lys Glu Gly Gly Leu
        515                 520                 525

Cys Ala Ala Leu Lys Glu Glu Cys Cys Phe Tyr Ala Asp His Thr Gly
        530                 535                 540

Val Val Arg Asp Ser Met Ala Lys Leu Arg Glu Arg Leu Asn Gln Arg
545                 550                 555                 560

Gln Lys Leu Phe Glu Ser Gly Gln Gly Trp Phe Glu Gly Leu Phe Asn
                565                 570                 575

Arg Ser Pro Trp Phe Thr Thr Leu Ile Ser Thr Ile Met Gly Pro Leu
                580                 585                 590

Ile Val Leu Leu Leu Ile Leu Leu Phe Gly Pro Cys Ile Leu Asn Arg
            595                 600                 605

Leu Val Gln Phe Val Lys Gly Arg Ile Ser Val Val Gln Ala Leu Val
        610                 615                 620

Leu Thr Gln Gln Tyr His Gln Leu Lys Ser Ile Asp Pro Glu Ala Val
625                 630                 635                 640

Glu Ser Arg Glu
```

<210> SEQ ID NO 69
<211> LENGTH: 18
<212> TYPE: DNA
<213> ORGANISM: Unknown
<220> FEATURE:
<223> OTHER INFORMATION: primer binding site in HXV35

<400> SEQUENCE: 69 tgg ggg ctc gtc cgg gat                18

```
<210> SEQ ID NO 70
<211> LENGTH: 18
<212> TYPE: DNA
<213> ORGANISM: Unknown
<220> FEATURE:
<223> OTHER INFORMATION: primer binding site in DG-75

<400> SEQUENCE: 70
tggaggtccc accgagat                                                 18

<210> SEQ ID NO 71
<211> LENGTH: 18
<212> TYPE: DNA
<213> ORGANISM: Unknown
<220> FEATURE:
<223> OTHER INFORMATION: primer binding site in DG-75

<400> SEQUENCE: 71
tggaggcccc agcgagat                                                 18

<210> SEQ ID NO 72
<211> LENGTH: 12
<212> TYPE: PRT
<213> ORGANISM: Unknown
<220> FEATURE:
<223> OTHER INFORMATION: peptide in HXV35 variable region A

<400> SEQUENCE: 72

Asp Asn Trp Asp Asp Pro Glu Pro Asp Ile Gly Asp
1               5                   10

<210> SEQ ID NO 73
<211> LENGTH: 10
<212> TYPE: PRT
<213> ORGANISM: Unknown
<220> FEATURE:
<223> OTHER INFORMATION: peptide in HXV35 variable region A

<400> SEQUENCE: 73

Gly Cys Arg Thr Pro Gly Gly Arg Arg Arg
1               5                   10

<210> SEQ ID NO 74
<211> LENGTH: 12
<212> TYPE: PRT
<213> ORGANISM: Unknown
<220> FEATURE:
<223> OTHER INFORMATION: peptide in DG-75 variable region A

<400> SEQUENCE: 74

Asp Tyr Trp Asp Asp Pro Glu Pro Asp Ile Gly Asp
1               5                   10

<210> SEQ ID NO 75
<211> LENGTH: 10
<212> TYPE: PRT
<213> ORGANISM: Unknown
<220> FEATURE:
<223> OTHER INFORMATION: peptide in DG-75 variable region A

<400> SEQUENCE: 75

Gly Cys Arg Thr Pro Gly Gly Arg Arg Arg
1               5                   10

<210> SEQ ID NO 76
<211> LENGTH: 8
<212> TYPE: PRT
```

-continued

```
<213> ORGANISM: Unknown
<220> FEATURE:
<223> OTHER INFORMATION: peptide in MCF247 variable region A

<400> SEQUENCE: 76

Asp Asp Trp Asp Glu Thr Gly Leu
1               5

<210> SEQ ID NO 77
<211> LENGTH: 10
<212> TYPE: PRT
<213> ORGANISM: Unknown
<220> FEATURE:
<223> OTHER INFORMATION: peptide in MCF247 variable region A

<400> SEQUENCE: 77

Gly Cys Arg Thr Pro Gly Gly Arg Lys Arg
1               5                   10

<210> SEQ ID NO 78
<211> LENGTH: 14
<212> TYPE: PRT
<213> ORGANISM: Unknown
<220> FEATURE:
<223> OTHER INFORMATION: peptide in MKVENVA MLV variable region A

<400> SEQUENCE: 78

Glu Glu Trp Asp Pro Ser Asp Gln Glu Pro Tyr Val Gly Tyr
1               5                   10

<210> SEQ ID NO 79
<211> LENGTH: 10
<212> TYPE: PRT
<213> ORGANISM: Unknown
<220> FEATURE:
<223> OTHER INFORMATION: peptide in MKVENVA MLV variable region A

<400> SEQUENCE: 79

Gly Cys Arg Thr Pro Gly Gly Arg Gln Arg
1               5                   10

<210> SEQ ID NO 80
<211> LENGTH: 51
<212> TYPE: PRT
<213> ORGANISM: Unknown
<220> FEATURE:
<223> OTHER INFORMATION: peptide in M-MLV variable region A

<400> SEQUENCE: 80

Ser Tyr Trp Gly Leu Glu Tyr Gln Ser Pro Phe Ser Ser Pro Pro Gly
1               5                   10                  15

Pro Pro Cys Cys Ser Gly Gly Ser Ser Pro Gly Cys Ser Arg Asp Cys
            20                  25                  30

Glu Glu Pro Leu Thr Ser Leu Thr Pro Arg Cys Asn Thr Ala Trp Asn
        35                  40                  45

Arg Leu Lys
    50

<210> SEQ ID NO 81
<211> LENGTH: 5
<212> TYPE: PRT
<213> ORGANISM: Unknown
<220> FEATURE:
<223> OTHER INFORMATION: peptide region in HXV35 variable region B

<400> SEQUENCE: 81
```

Thr Arg Leu Tyr Asp
1               5

<210> SEQ ID NO 82
<211> LENGTH: 12
<212> TYPE: PRT
<213> ORGANISM: Unknown
<220> FEATURE:
<223> OTHER INFORMATION: peptide region in HXV35 variable region B

<400> SEQUENCE: 82

Phe Tyr Val Cys Pro Gly His Thr Val Leu Thr Gly
1               5                   10

<210> SEQ ID NO 83
<211> LENGTH: 5
<212> TYPE: PRT
<213> ORGANISM: Unknown
<220> FEATURE:
<223> OTHER INFORMATION: peptide region in DG-75 variable region B

<400> SEQUENCE: 83

Thr Arg Leu Tyr Asp
1               5

<210> SEQ ID NO 84
<211> LENGTH: 12
<212> TYPE: PRT
<213> ORGANISM: Unknown
<220> FEATURE:
<223> OTHER INFORMATION: peptide region in DG-75 variable region B

<400> SEQUENCE: 84

Phe Tyr Val Cys Pro Gly His Thr Val Pro Ile Gly
1               5                   10

<210> SEQ ID NO 85
<211> LENGTH: 5
<212> TYPE: PRT
<213> ORGANISM: Unknown
<220> FEATURE:
<223> OTHER INFORMATION: peptide region in MCF247 variable region B

<400> SEQUENCE: 85

Ala Arg Thr Phe Asp
1               5

<210> SEQ ID NO 86
<211> LENGTH: 12
<212> TYPE: PRT
<213> ORGANISM: Unknown
<220> FEATURE:
<223> OTHER INFORMATION: peptide region in MCF247 variable region B

<400> SEQUENCE: 86

Phe Tyr Val Cys Pro Gly His Thr Val Pro Thr Gly
1               5                   10

<210> SEQ ID NO 87
<211> LENGTH: 5
<212> TYPE: PRT
<213> ORGANISM: Unknown
<220> FEATURE:
<223> OTHER INFORMATION: peptide region in MKVENVA MLV variable region B

<400> SEQUENCE: 87

Thr Arg Thr Phe Asp
1               5

<210> SEQ ID NO 88
<211> LENGTH: 12
<212> TYPE: PRT
<213> ORGANISM: Unknown
<220> FEATURE:
<223> OTHER INFORMATION: peptide region in MKVENVA MLV variable region B

<400> SEQUENCE: 88

Phe Tyr Val Cys Pro Gly His Thr Val Ser Lys Gly
1               5                   10

<210> SEQ ID NO 89
<211> LENGTH: 26
<212> TYPE: PRT
<213> ORGANISM: Unknown
<220> FEATURE:
<223> OTHER INFORMATION: peptide region in M-MLV variable region B

<400> SEQUENCE: 89

Leu Asp Gly Thr Thr His Lys Ser Asn Glu Gly Phe Tyr Val Cys Pro
1               5                   10                  15

Gly Pro His Arg Pro Arg Glu Ser Lys Ser
            20                  25

<210> SEQ ID NO 90
<211> LENGTH: 122
<212> TYPE: PRT
<213> ORGANISM: Unknown
<220> FEATURE:
<223> OTHER INFORMATION: LNCAP env

<400> SEQUENCE: 90

Lys Ser Val Ser Ala Leu Glu Lys Ser Leu Thr Ser Leu Ser Glu Val
1               5                   10                  15

Val Leu Gln Asn Arg Arg Gly Leu Asp Leu Leu Phe Leu Lys Glu Gly
            20                  25                  30

Gly Leu Cys Ala Ala Leu Lys Glu Glu Cys Cys Phe Tyr Ala Asp His
        35                  40                  45

Thr Gly Val Val Arg Asp Ser Met Ala Lys Leu Arg Glu Arg Leu Asn
    50                  55                  60

Gln Arg Gln Lys Leu Phe Glu Ser Gly Gln Gly Trp Phe Glu Gly Leu
65                  70                  75                  80

Phe Asn Arg Ser Pro Trp Phe Thr Thr Leu Ile Ser Thr Ile Met
                85                  90                  95

Gly Pro Leu Ile Val Leu Leu Ile Leu Leu Phe Gly Pro Cys Ile
            100                 105                 110

Leu Asn Arg Leu Val Gln Phe Val Lys Asp
        115                 120

<210> SEQ ID NO 91
<211> LENGTH: 120
<212> TYPE: PRT
<213> ORGANISM: Unknown
<220> FEATURE:
<223> OTHER INFORMATION: HXV35 env

<400> SEQUENCE: 91

Lys Ser Val Ser Ala Leu Glu Lys Ser Leu Thr Ser Leu Ser Glu Val
1               5                   10                  15

Val Leu Gln Asn Arg Arg Gly Leu Asp Leu Leu Phe Leu Lys Glu Gly
            20                  25                  30

```
Gly Leu Cys Ala Ala Leu Lys Glu Cys Cys Phe Tyr Ala Asp His Thr
            35                  40                  45

Gly Val Val Arg Asp Ser Met Ala Lys Leu Arg Glu Arg Leu Asn Gln
    50                  55                  60

Arg Gln Lys Leu Phe Glu Ser Gly Gln Gly Trp Phe Glu Gly Leu Phe
65                  70                  75                  80

Asn Arg Ser Pro Trp Phe Thr Thr Leu Ile Ser Thr Ile Met Gly Pro
                85                  90                  95

Leu Ile Val Leu Leu Leu Ile Leu Leu Phe Gly Pro Cys Ile Leu Asn
                100                 105                 110

Arg Leu Val Gln Phe Val Lys Asp
            115                 120

<210> SEQ ID NO 92
<211> LENGTH: 121
<212> TYPE: PRT
<213> ORGANISM: Unknown
<220> FEATURE:
<223> OTHER INFORMATION: consensus sequence between LNCAP env and
      HXV35 env

<400> SEQUENCE: 92

Lys Ser Val Ser Ala Leu Glu Lys Ser Leu Thr Ser Leu Ser Glu Val
1               5                   10                  15

Val Leu Gln Asn Arg Arg Gly Leu Asp Leu Leu Phe Leu Lys Glu Gly
            20                  25                  30

Gly Leu Cys Ala Ala Leu Lys Lys Glu Cys Cys Phe Tyr Ala Asp His
            35                  40                  45

Thr Gly Val Val Arg Asp Ser Met Ala Lys Leu Arg Glu Arg Leu Asn
    50                  55                  60

Gln Arg Gln Lys Leu Phe Glu Ser Gly Gln Gly Trp Pro Glu Gly Leu
65                  70                  75                  80

Phe Asn Arg Ser Pro Trp Phe Thr Thr Leu Ile Ser Thr Ile Met Gly
                85                  90                  95

Pro Leu Ile Val Leu Leu Leu Ile Leu Leu Phe Gly Pro Cys Ile Leu
                100                 105                 110

Asn Arg Leu Val Gln Phe Val Lys Asp
            115                 120

<210> SEQ ID NO 93
<211> LENGTH: 120
<212> TYPE: PRT
<213> ORGANISM: Unknown
<220> FEATURE:
<223> OTHER INFORMATION: DG75 env

<400> SEQUENCE: 93

Lys Ser Val Ser Ala Leu Glu Lys Ser Leu Thr Ser Leu Ser Glu Val
1               5                   10                  15

Val Leu Gln Asn Arg Arg Gly Leu Asp Leu Leu Pro Leu Lys Glu Gly
            20                  25                  30

Gly Leu Cys Ala Ala Leu Lys Glu Glu Cys Cys Phe Tyr Ala Asp His
            35                  40                  45

Thr Gly Val Val Arg Asp Ser Met Ala Lys Leu Arg Glu Arg Leu Asn
    50                  55                  60

Gln Arg Gln Lys Leu Phe Glu Ser Gly Gln Gly Trp Phe Glu Gly Leu
65                  70                  75                  80

Phe Asn Arg Ser Pro Trp Phe Thr Thr Leu Ile Ser Thr Ile Met Gly
                85                  90                  95
```

Pro Leu Ile Val Leu Leu Ile Leu Leu Phe Gly Pro Cys Ile Leu
            100                 105                 110

Asn Arg Leu Val Gln Phe Val Lys
        115                 120

<210> SEQ ID NO 94
<211> LENGTH: 121
<212> TYPE: PRT
<213> ORGANISM: Unknown
<220> FEATURE:
<223> OTHER INFORMATION: consensus sequence between LNCAP env and DG75
      env

<400> SEQUENCE: 94

Lys Ser Val Ser Ala Leu Glu Lys Ser Leu Thr Ser Leu Ser Glu Val
1               5                   10                  15

Val Leu Gln Asn Arg Arg Gly Leu Asp Leu Leu Phe Leu Lys Glu Gly
            20                  25                  30

Gly Leu Cys Ala Ala Leu Lys Glu Glu Cys Cys Phe Tyr Ala Asp His
        35                  40                  45

Thr Gly Val Val Arg Asp Ser Met Ala Lys Leu Arg Glu Arg Leu Asn
    50                  55                  60

Gln Arg Gln Lys Leu Phe Glu Ser Gly Gln Gly Trp Phe Glu Gly Leu
65                  70                  75                  80

Phe Asn Arg Ser Pro Trp Phe Thr Thr Leu Ile Ser Thr Ile Met Gly
                85                  90                  95

Pro Leu Ile Val Leu Leu Ile Leu Leu Phe Gly Pro Cys Ile Leu
            100                 105                 110

Asn Arg Leu Val Gln Phe Val Lys Gly
        115                 120

<210> SEQ ID NO 95
<211> LENGTH: 21
<212> TYPE: DNA
<213> ORGANISM: Unknown
<220> FEATURE:
<223> OTHER INFORMATION: Primer 1F used for sequencing XMRV gene

<400> SEQUENCE: 95
gcgccagtca tccgatagac t                                         21

<210> SEQ ID NO 96
<211> LENGTH: 20
<212> TYPE: DNA
<213> ORGANISM: Unknown
<220> FEATURE:
<223> OTHER INFORMATION: Primer NA3-136R used for sequencing XMRV gene

<400> SEQUENCE: 96
cccagtgctg caaggttaga                                           20

<210> SEQ ID NO 97
<211> LENGTH: 21
<212> TYPE: DNA
<213> ORGANISM: Unknown
<220> FEATURE:
<223> OTHER INFORMATION: Primer 550F used for sequencing XMRV gene

<400> SEQUENCE: 97
cgccgaaacc gcgccgcgcg t                                         21

<210> SEQ ID NO 98

```
<211> LENGTH: 24
<212> TYPE: DNA
<213> ORGANISM: Unknown
<220> FEATURE:
<223> OTHER INFORMATION: Primer 1500 used for sequencing XMRV gene

<400> SEQUENCE: 98
tcgtcgcccc ggactgcctt tctg                                          24

<210> SEQ ID NO 99
<211> LENGTH: 21
<212> TYPE: DNA
<213> ORGANISM: Unknown
<220> FEATURE:
<223> OTHER INFORMATION: Primer 1470R used for sequencing XMRV gene

<400> SEQUENCE: 99
gacaggagaa gaaaagcagc g                                             21

<210> SEQ ID NO 100
<211> LENGTH: 21
<212> TYPE: DNA
<213> ORGANISM: Unknown
<220> FEATURE:
<223> OTHER INFORMATION: Primer 2703R used for sequencing XMRV gene

<400> SEQUENCE: 100
gcttggcgaa ctgccagtcc c                                             21

<210> SEQ ID NO 101
<211> LENGTH: 21
<212> TYPE: DNA
<213> ORGANISM: Unknown
<220> FEATURE:
<223> OTHER INFORMATION: Primer 2670F used for sequencing XMRV gene

<400> SEQUENCE: 101
agccggatgt ttctctaggg t                                             21

<210> SEQ ID NO 102
<211> LENGTH: 20
<212> TYPE: DNA
<213> ORGANISM: Unknown
<220> FEATURE:
<223> OTHER INFORMATION: Primer 3870R used for sequencing XMRV gene

<400> SEQUENCE: 102
gcttgcctgc atcttttgtc                                               20

<210> SEQ ID NO 103
<211> LENGTH: 20
<212> TYPE: DNA
<213> ORGANISM: Unknown
<220> FEATURE:
<223> OTHER INFORMATION: Primer 3810F used for sequencing XMRV gene

<400> SEQUENCE: 103
agacccagtg gcagccgggt                                               20

<210> SEQ ID NO 104
<211> LENGTH: 21
<212> TYPE: DNA
<213> ORGANISM: Unknown
<220> FEATURE:
<223> OTHER INFORMATION: Primer 5190R used for sequencing XMRV gene

<400> SEQUENCE: 104
```

```
tgacttacct gggagacgaa g                                              21
```

<210> SEQ ID NO 105
<211> LENGTH: 21
<212> TYPE: DNA
<213> ORGANISM: Unknown
<220> FEATURE:
<223> OTHER INFORMATION: Primer 5100F used for sequencing XMRV gene

<400> SEQUENCE: 105

```
aactgccaag gttgtgacca a                                              21
```

<210> SEQ ID NO 106
<211> LENGTH: 24
<212> TYPE: DNA
<213> ORGANISM: Unknown
<220> FEATURE:
<223> OTHER INFORMATION: Primer 5842R used for sequencing XMRV gene

<400> SEQUENCE: 106

```
aactattggg ggccccacgg gtta                                           24
```

<210> SEQ ID NO 107
<211> LENGTH: 20
<212> TYPE: DNA
<213> ORGANISM: Unknown
<220> FEATURE:
<223> OTHER INFORMATION: Primer NA7-F used for sequencing XMRV gene

<400> SEQUENCE: 107

```
catggaaagt ccagcgttct                                                20
```

<210> SEQ ID NO 108
<211> LENGTH: 20
<212> TYPE: DNA
<213> ORGANISM: Unknown
<220> FEATURE:
<223> OTHER INFORMATION: Primer C9-R used for sequencing XMRV gene

<400> SEQUENCE: 108

```
agctgctcga attgtttggt                                                20
```

<210> SEQ ID NO 109
<211> LENGTH: 20
<212> TYPE: DNA
<213> ORGANISM: Unknown
<220> FEATURE:
<223> OTHER INFORMATION: Primer K1-R used for sequencing XMRV gene

<400> SEQUENCE: 109

```
aaggctttat tgggaacacg                                                20
```

<210> SEQ ID NO 110
<211> LENGTH: 20
<212> TYPE: DNA
<213> ORGANISM: Unknown
<220> FEATURE:
<223> OTHER INFORMATION: Primer 100F used for sequencing XMRV gene

<400> SEQUENCE: 110

```
aggggccaaa caggataact                                                20
```

<210> SEQ ID NO 111
<211> LENGTH: 20
<212> TYPE: DNA
<213> ORGANISM: Unknown
<220> FEATURE:

-continued

```
<223> OTHER INFORMATION: Primer 227R used for sequencing XMRV gene

<400> SEQUENCE: 111
tggggaactt gaaactgagg                                                    20

<210> SEQ ID NO 112
<211> LENGTH: 20
<212> TYPE: DNA
<213> ORGANISM: Unknown
<220> FEATURE:
<223> OTHER INFORMATION: Primer B7-F used for sequencing XMRV gene

<400> SEQUENCE: 112
tctggaaagt cccacctcag                                                    20

<210> SEQ ID NO 113
<211> LENGTH: 53
<212> TYPE: PRT
<213> ORGANISM: Unknown
<220> FEATURE:
<223> OTHER INFORMATION: VP35 leader sequence

<400> SEQUENCE: 113

Met Thr Ser Ser Tyr Ser Arg Pro Gln Pro Trp Glu Thr Ser Gln Arg
1               5                   10                  15

Pro Arg Gly Pro Val Leu Trp Pro Ile Leu Tyr Gln Leu Thr Tyr Pro
            20                  25                  30

Ser Arg Thr Phe Trp Ser Gly Phe Val Gly Gly Arg Glu Thr Glu Thr
        35                  40                  45

Leu Pro Ala Pro Val
    50
```